United States Patent [19]
Blanc et al.

[11] Patent Number: 5,891,695
[45] Date of Patent: Apr. 6, 1999

[54] POLYPEPTIDES INVOLVED IN THE BIOSYNTHESIS OF STREPTOGRAMINS, NUCLEOTIDE SEQUENCES CODING FOR THESE POLYPEPTIDES AND THEIR USE

[75] Inventors: Veronique Blanc; Francis Blanche; Joel Crouzet; Nathalie Jacques, all of Paris; Patricia Lacroix, Bry-sur-Marne; Denis Thibaut; Monique Zagorec, both of Paris; Laurent Debussche, Athis Mons; Valerie De Crecy-Lagard, Grosrouvre, all of France

[73] Assignee: Rhone-Poulenc Rorer S.A., Antony, France

[21] Appl. No.: 403,852

[22] PCT Filed: Sep. 25, 1993

[86] PCT No.: PCT/FR93/00923

§ 371 Date: May 10, 1995

§ 102(e) Date: May 10, 1995

[87] PCT Pub. No.: WO94/08014

PCT Pub. Date: Apr. 14, 1994

[30] Foreign Application Priority Data

Sep. 25, 1992 [FR] France .................................. 92 11441

[51] Int. Cl.$^6$ ............................... C12N 9/00; C12N 1/20; C07H 21/04
[52] U.S. Cl. ........................... 435/183; 435/41; 435/189; 435/252.33; 435/320.1; 435/69.1; 530/350; 536/23.1; 536/23.2; 536/23.7
[58] Field of Search ......................... 435/41, 69.1, 70.1, 435/120, 119, 252.3, 252.35, 252.8, 320.1, 172.3, 183; 536/23.1, 23.2, 23.7

[56] References Cited

U.S. PATENT DOCUMENTS 5,252,474 10/1993 Gewain et al. ..................... 435/172.3
5,591,614 1/1997 Blanche et al. ......................... 435/120

OTHER PUBLICATIONS

Spyrou et al. "Characterization of the flavin reductase gene (fre) of *Escherichia coli* and construction of a plasmid of over production of the enzyme" J. Bacteriol. 173, 3673–3679, Jun. 1991.

Francis et al. "Biosynthesis of chloramphenicol in streptomyces species 3022a: the nature of arylamine synthetase system" Can. J. Microbiol. 25, 1408–1515, 1979.

Biotechnology; vol. 8; Feb. 1990; NY, US; pp. 115–121, Chater et al.; "The improving prospects for yield increase by genetic engineering . . . ".

Gene; vol. 74; 1988; Amsterdam, NL; pp. 305–320; Hallam et al.; "Nucleotide sequence transcription and deduced function of a gene . . . ".

Chemical Abstracts; vol. 115; No. 23; Dec. 1991; abstract No. 251978n; Funane, Kazumi et al.; "Isolation and properties of IM factor . . . ".

Drugs and the Pharmaceutical Sciences; vol. 22; 1984; pp. 695–720; A. M. Biot; "Virginiamycin: properties, biosynthesis and fermentation".

Biotechnology Letters; vol. 14; No. 11; Nov. 1992; pp. 1065–1070; Paquet et al; "Induction of pristinamycins production in Streptomyces".

Database WPI; Sec. CH; Week 8420; Apr. 1984; Derwent Publ.; London GB; Class B02, AN 84–123313; "Selective production of neoviridogrisein . . . ", Abstract.

Folia Microbiologica; vol. 35; No. 6; 1990; Prague; p. 494; "Abstract" M. Blumauerova; Physiological and genetic aspects of Virginiamycin . . .

Biotechnology and Bioindustry; vol. 2; 1988; pp. 20–21; V. Prykrylova "Strain development in *Streptomyces virginiae*, a producer of . . . ".

*Primary Examiner*—Keith D. Hendricks
*Assistant Examiner*—Nashaat T. Nashed
*Attorney, Agent, or Firm*—Finnegan, Henderson, Farabow, Garrett & Dunner, L.L.P.

[57] ABSTRACT

The invention concerns nucleotide sequences coding for a polypeptide involved in Streptogramin biosynthesis, recombinant cells containing said sequences, and use thereof.

11 Claims, 33 Drawing Sheets

| FORMULA I | FORMULA II |
|---|---|
| PRISTINAMYCIN IIA | PRISTINAMYCIN IIB |
| MIKAMYCIN A | |
| OSTREOGRYCIN A | OSTREOGRYCIN G |
| STREPTOGRAMIN A | |
| SYNERGISTIN A-I | |
| VERNAMYCIN A | |
| VIRGINIAMYCIN $M_1$ | VIRGINIAMYCIN $M_2$ |

A

GRISEOVIRIDIN

MADUMYCIN I

B

VIRGINIAMYCIN $S_1$

VERNAMYCIN C

ETAMYCIN

Phe(pNH2)  : paraaminophenylalanine
Phe(pNMe)  : paramethylaminophenylalanine
Phe(pNMe2) : paradimethylaminophenylalanine

POLYPEPTIDES INVOLVED IN THE BIOSYNTHESIS OF STREPTOGRAMINS, NUCLEOTIDE SEQUENCES CODING FOR THESE POLYPEPTIDES AND THEIR USE

This is U.S. national stage application of PCT/FR93/00923, filed Sep. 25, 1993 (WO/08014).

FIELD OF THE INVENTION

The present invention relates to novel polypeptides involved in the biosynthesis of streptogramins, and also comprises the isolation and identification of genes for the biosynthesis of the A and B components of streptogramins, the expression of these genes with the object of increasing the levels of production and their use for the construction of blocked mutants capable of leading to the synthesis of novel antibiotics or to derived forms of streptogramins.

BACKGROUND OF THE INVENTION

Streptogramins form a homogeneous group of antibiotics, consisting of a combination of two types of molecules which are chemically different; on the one hand polyunsaturated macrolactones (A-group components, two examples of structures of which are presented in FIG. 1), and on the other hand depsipeptides (B-group components, three examples of the structure of which are presented in FIG. 2). This group comprises many antibiotics (see Table 1 and FIG. 3), which are known by different names in accordance with their origin, including pristinamycins, mikamycins and virginiamycins (for a review, see Cocito 1979, 1983).

The A and B components have a synergistic antibacterial activity which can reach 100 times that of the separate components and which, in contrast to that of each component, is bactericidal (Cocito 1979). This activity is more especially effective against Gram-positive bacteria such as staphylococci and streptococci (Cocito 1979, Videau 1982). The A and B components inhibit protein synthesis by binding to the 50S subunit of the ribosome (Cocito 1979; for a review, see Di Giambattista et al. 1989).

Streptogramins are chiefly produced by actinomycetes, including many streptomycetes, presented in Table 1. In addition, streptogramins are also synthesized by eukaryotes such as Micromonospora which synthesizes vernamycins. Actinomycetes constitute a very important group of microorganisms on account of the large amount of secondary metabolites they produce, including many antibiotics (beta-lactams, tetracyclines, macrolides, aminoglycosides, polyacetates and the like), herbicides, anticancer agents, antifungal agents, immunomodulators and enzyme inhibitors. Many biosynthesis pathways relating to antibiotics belonging to miscellaneous classes as well as other secondary metabolites such as pigments (for a review, Chater 1990) have already been studied at the present time in actinomycetes. An important aspect of this group of bacteria is that the genes involved in the same biosynthesis pathway, structural genes and also resistance gene(s) and regulatory gene (s), are grouped together physically on the chromosome, constituting clusters which can reach more than 100 kb (Hopwood et al. 1986a, Hopwood et al. 1986b, Hallam et al. 1988, Anzai et al. 1987, Ohnuki et al. 1985). To date, no example has been found to contradict this observation. Such a structural organization is of great interest in the development of strategies for cloning biosynthesis genes. In effect, it is possible, starting from a single gene previously cloned by various techniques, a biosynthesis, resistance or regulatory gene, to walk along the chromosome and thus to isolate the set of genes of the biosynthesis cluster.

Our knowledge of the biosynthesis pathways of each of the components of streptogramins is still very incomplete, but the origin of the different parts of each molecule has been identified by radioactive labelling (Kingston et al. 1983). Thus, the A-type components are made up of two regions originating from the condensation of acetates and several amino acids such as serine and glycine, for example. As regards the B-type components, studies have shown that all the amino acids present in the peptide chain are derived from natural amino acids (Hook and Vining 1973). However, no polypeptide involved in these pathways has, to date, been purified in sufficient amounts to permit its molecular characterization, and no biosynthesis gene has been described. In the process of biosynthesis of the B-type components, two parts may be distinguished:

1) Synthesis of the precursors, or of their analogues, of the macrocycle: 3-hydroxypicolinic acid (3-hPic), L-2-aminobutyric acid (L-Abu), p-dimethylamino-L-phenylalanine, 4-oxo-L-pipecolic acid (4-oPIP), L-phenylglycine (L-Phg).

2) Formation of the macrocycle from the precursors mentioned above, L-threonine and L-proline, or their analogues, with possible modification of these precursors or peptide N-methylation.

To date, only the probable metabolic origin of the precursors of the macrocycle of the B-type components has been determined by studies using labelled isotopes (Reed et al., 1986, Molinero et al., 1989, Reed et al., 1989).

DESCRIPTION OF THE INVENTION

The present invention results from the purification of polypeptides participating in the biosynthesis of streptogramins, as well as from the cloning of genes whose product participates in the biosynthesis of streptogramins. The term biosynthesis of streptogramins is understood to comprise the regulatory genes and the genes conferring resistance on the producing microorganisms. Thus, the present invention makes it possible to increase the levels of production of these metabolites by means of recombinant DNA techniques. Another benefit of the present invention lies in the possibility, by construction of mutants blocked in the different steps of this biosynthesis, of producing synthesis intermediates for each of the two components. These intermediates may serve as substrates for further modification for chemical, biochemical, enzymatic or microbiological means. Similarly, isolation of the biosynthesis genes makes it possible, by gene transfer between producing strains, to manufacture hybrid antibiotics having pharmacologically advantageous properties (Hopwood et al., 1985a, Hopwood et al., 1985b, Hutchinson et al. 1989). Another benefit of the present invention lies in the fact that it provides a better knowledge of the biosynthesis pathways of the metabolites classed as streptogramins. In effect, the invention enables bacterial or fungal strains to be constructed in which one or more proteins participating in the biosynthesis of streptogramins is/are expressed under the control of suitable expression signals. Such strains may then be used to carry out bioconversions. These bioconversions may be carried out either using whole cells, or using acellular extracts of the said cells. These bioconversions may enable a streptogramin to be converted to a derived form with an enzyme of a biosynthesis pathway. For example, pristinamycin IIB may be converted in this manner to pristinamycin IIA. The same reasoning may be applied to any biosynthesis intermediate.

A first subject of the invention hence relates to a nucleotide sequence coding for a polypeptide involved in the biosynthesis of streptogramins.

More especially, several genes whose product participates in the biosynthesis of streptogramins have been isolated from *Streptomyces pristinaespiralis*. Since the streptogramins produced by this strain are more commonly designated by the term pristinamycins (see Table 1), in what follows, reference will be made in some cases to genes for the biosynthesis of pristinamycins. However, it is clear that the results obtained apply to all the streptogramins. Pristinamycins I and II correspond, respectively, to the B and A components of streptogramins. Molecules of the pristinamycin II family and of the pristinamycin I family hence designate in what follows the A and B components of streptogramins, respectively.

The present invention describes in particular the isolation and characterization of the snaA, snaB, snaC, snaD, papA, papM, samS, snbA, snbC, snbD, snbE and snbR genes. These genes were isolated from a library of genomic DNA of *S.pristinaespiralis*. This library was obtained by partial digestion of genomic DNA *S.pristinaespiralis* with the restriction enzyme Sau3A. Large DNA fragments, from 40 to 50 kb on average, were cloned into cosmid pHC79 (Hohn, B., and Collins, J. F., 1980). After in vitro encapsidation, *E.coli* strains HB101 (Boyer et Roulland-Dussoix, 1969) and DH1 (Low, 1968) were transfected. The DNA library of *S.pristinaespiralis* thus occurs in two different strains of *E.coli*.

The snaA, snaB and samS (initially designated SnaC genes are present on cosmid pIBV1 (FIG. 4). The product of the snaA and snaB genes, corresponding to the polypeptides SnaA and SnaB, participates in the final step of biosynthesis of the II component of pristinamycins (conversion of pristinamycin IIB to pristinamycin IIA), corresponding to the oxidation of the 2,3 bond of D-proline. These two polypeptides constitute the two subunits of pristinamycin IIA synthase, the purification of which is described in the present invention. The product of the samS gene is considered to participate in the synthesis of SAM (methyl group donor) from ATP and methionine. The A component of most streptogramins is, in effect, methylated at C-4 (FIG. 1), and this methyl has been described (Kingston et al., 1983) as being derived from the methyl of methionine, very probably via a methylation reaction with SAM. The samS gene is hence considered to code for a SAM synthase (SamS; EC. 2.5.1.6) which is specific to the biosynthesis pathway of pristinamycins.

The snbA, snbR, papA and papM genes are present on cosmid pIBV2 (FIG. 5). The snbA gene corresponds, on the basis of the biochemical studies presented in Example 5, to the first step for synthesis of pristinamycins I. This comprises activation of the first acid of the chain, 3-hydroxypicolinic acid, by adenylation. The snbR gene might participate in the transport of molecules of the pristinamycin I (or possibly pristinamycin II) family out of the cell after synthesis, thereby conferring a resistance to this component on the producing strain. The papA gene corresponds, on the basis of sequence analyses (Example 8.8) and the study of a mutant disrupted in this gene (Example 9.3), to a gene for the biosynthesis of para-aminophenylalanine from chorismate. para-Aminophenylalanine is then dimethylated by the product of the papM gene, an N-methyltransferase described in the present invention, to form para-dimethylaminophenylalanine, which is then incorporated in pristinamycin IA. The papA and papM genes hence participate in the synthesis of one of the precursors of pristinamycin IA.

The snaA, snaD, snbC, snbD and snbE genes are present on cosmid pIBV3 (FIG. 6), which hence adjoins cosmid pIBV1 on which the snaA gene is already present. The snaD gene codes, on the basis of analysis of its sequence (Example 8.9) and the study of a mutant disrupted in this gene (Example 9.5), for a peptide synthase involved in the biosynthesis of pristinamycin II. The snbC gene, whose product is described in the present invention, participates in the incorporation of threonine and aminobutyric acid residues in the peptide chain of pristinamycin IA. The snbD gene, whose product is also described in the present invention, is involved in the incorporation of proline and para-dimethylaminophenylalanine residues in the peptide chain of pristinamycin IA. It also governs the N-methylation of the peptide bond between these 2 residues. Lastly, the snbE gene, whose product is also described in the present invention, participates in the incorporation of the last two residues of pristinamycin IA, namely phenylglycine and 4-oxopipecolic acid.

The snaC gene is present on cosmid pIBV4 (FIG. 7). It codes for an FMN:NADH oxidoreductase, also designated FMN reductase, described in the present invention and which supplies pristinamycin IIA synthase with $FMNH_2$ from FMN and NADH. The snaC gene hence participates in the final step of the biosynthesis of pristinamycin IIA.

These different genes were subcloned from their cosmid of origin and their nucleic acid sequences were determined. The snaA, snaB and samS genes were subcloned on a 6-kb BamHI-BamHI fragment, a portion of which was sequenced (SEQ ID no. 1). The snbA gene was subcloned in a 5.5-kb EcoRI-BglII fragment, a portion of which was sequenced (SEQ ID no. 5). The snbR gene was subcloned in a 4.6-kb BglII-BglII fragment, a portion of which was sequenced (SEQ ID no. 6). A portion of the papA gene was subcloned in a 3.4-kb XhoI-XhoI fragment, a portion of which was sequenced (SEQ ID no. 9). The papM gene was subcloned in a 4.1-kb PstI-PstI fragment, a portion of which was sequenced (SEQ ID no. 10). A portion of the snaD gene was subcloned in a 1.5-kb BamHI-SstI fragment, a portion of which was sequenced (SEQ ID no. 8). A portion of the snbC gene was subcloned on a 6.2-kb SphI-SphI fragment, 2 regions of which were sequences (SEQ ID nos. 11 and 12). A portion of the snbD gene was subcloned on an 8.4-kb SphI-SphI fragment, 2 regions of which were sequenced (SEQ ID Nos. 13 and 14). A portion of the snbE gene was subcloned on a 6.6-kb SphI-SphI fragment, 2 regions of which were sequenced (SEQ ID Nos. 15 and 16). The snaC gene was subcloned in a 4-kb BamHI-BamHI fragment, a portion of which was sequenced (SEQ ID no. 7).

The proximity of the snaA, snaB, snaD, samS, snbC, snbD and snbE genes on the one hand, as well as the snbA, snbR, papA and papM genes, confirms the cluster localization of the genes for biosynthesis of the A and B components of streptogramins. Furthermore, the 4 cosmids described in the present invention are grouped together in a region of the chromosome whose size is estimated at 200 kb by pulsed-field electrophoresis, equivalent to 3% of the total genome (7500 kb) of *Streptomyces pristinaespiralis* (Example 13). It is hence obvious that the regions surrounding the genes identified in the present invention (snaA, snaB, snaD, samS, snbC, snbD and snbE; snbA, snbR, papA and papM; snaC) contain the other genes of the pristinamycin biosynthesis cluster, and that these genes may be used to localize the other genes for the biosynthesis of streptogramins.

Preferably, the subject of the invention is a nucleotide sequence chosen from:

(a) all or part of the snaA (SEQ ID no. 2), snaB (SEQ ID no. 3), snaC (SEQ ID no. 7), snaD (SEQ ID no. 8), papA (SEQ ID no. 9), papM (SEQ ID no. 10), samS (SEQ ID no. 4), snbA (SEQ ID no. 5), snbC (SEQ ID nos. 11 and 12), snbD (SEQ ID nos. 13 and 14), snbE (SEQ ID nos. 15 and 16) and snbR (SEQ ID no. 6) genes, (b) the sequences adjacent to the genes (a) constituting the biosynthesis clusters and coding for the polypeptides involved in the biosynthesis of streptogramins, (c) the sequences which hybridize with all or part of the genes (a) or (b) and which code for a polypeptide involved in the biosynthesis of streptogramins, and (d) the sequences derived from the sequences (a), (b) and (c) owing to the degeneracy of the genetic code.

Still more preferably, the subject of the invention is the nucleotide sequences represented by the snaA (SEQ ID no. 2), snaB (SEQ ID no. 3), snaC (SEQ ID no. 7), snaD (SEQ ID no. 8), papA (SEQ ID no. 9), papM (SEQ ID no. 10), samS (SEQ ID no. 4), snbA (SEQ ID no. 5), snbC (SEQ ID nos. 11 and 12), snbD (SEQ ID nos. 13 and 14), snbE (SEQ ID nos. 15 and 16) and snbR (SEQ ID no. 6) genes.

Another subject of the invention relates to any recombinant DNA comprising a gene for the biosynthesis of streptogramins. More preferably, this is a recombinant DNA comprising all or part of cosmids pIBV1, pIBV2, pIBV3 or pIBV4 as shown in FIGS. 4 to 7, or all or part of sequences which hybridize with cosmids pIBV1 to pIBV4 or with fragments of these latter.

In a preferred embodiment of the invention, the nucleotide sequences defined above form part of an expression vector, which can be autonomously replicating or integrative.

As stated above, although the invention is more especially illustrated with the genes for the biosynthesis of pristinamycin, it is clear that the results obtained apply to all streptogramins.

More especially, the techniques developed in the present invention for purifying proteins or cloning genes for the biosynthesis of streptogramins from *S. pristinaespiralis* may be applied to other microorganisms producing streptogramins (see Table 1).

Thus, the purification of an enzymatic activity from *S. pristinaespiralis* makes it possible to purify the same activity from another strain producing streptogramin. The present invention may hence by applied to the cloning of genes for the biosynthesis of streptogramins from any producing microorganism, by purification of a protein participating in the biosynthesis and then, using the $NH_2$-terminal sequence thereof, synthesis of an oligonucleotide probe which enables the corresponding gene to be cloned. Chromosome walking then enables the whole biosynthesis cluster to be identified.

Furthermore, from the genes identified in the present application, it is possible, by hybridization, to clone the genes for the biosynthesis of streptogramins directly from the DNA of another producing microorganism. In effect, the genes for the biosynthesis of pristinamycins hybridize strongly with those for the other streptogramins. It is thus possible to clone, by hybridization, the genes for the biosynthesis of streptogramins using as a probe the sna, snb or pap genes, or fragments of the latter, or fragments adjacent to these containing, as is shown in the present invention, other sna and snb genes. This is due to the fact that: 1) the streptogramins produced by the different microorganisms have identical or similar structures (see FIG. 3), 2) the genes for the biosynthesis of streptogramins are organized in clusters, and 3) the enzyme systems responsible for this biosynthesis do not have an absolute specificity for their substrates.

Moreover, the cloning of genes involved in the biosynthesis of streptogramins may also be carried out using degenerate oligonucleotides, prepared from the sequences of the sna or snb genes mentioned above, or fragments of these genes, or fragments adjacent to these genes. It is thus possible to take one's pick of the genes for the biosynthesis of the A and B components of the different strains producing streptogramins. These strains can belong to the genus Streptomyces, and also to other genera (see Table 1). In addition, if the genomic DNA of the starting strains used has a G+C composition different from that observed in Streptomyces, the probes used may be synthesized with a codon bias specific to the genus or species from which it is desired to isolate the DNA.

Another subject of the present invention relates to the polypeptides resulting from the expression of the nucleotide sequences defined above. More especially, the present invention relates to polypeptides comprising all or part of the polypeptides SnaA (SEQ ID NO:17), SnaB (SEQ ID NO:18), SnaC (SEQ ID NO:22), SnaD (SEQ ID NO:23), PapA (SEQ ID NO:24), PapM (SEQ ID NO:25), SamS (SEQ ID NO:19), SnbA (SEQ ID NO: 20), SnbC (SEQ ID NO:26 and SEQ ID NO:27), SnbD (SEQ ID NO:28 and SEQ ID NO:29), SnbE (SEQ ID no. 15 and 16) and SnbR (SEQ ID NO:21) or of derivatives of these. Within the meaning used in the present invention, the term derivative denotes any molecule obtained by modification of a genetic and/or chemical nature of the peptide sequence. Modification of a genetic and/or chemical nature is understood to mean any mutation, substitution, deletion, addition and/or modification of one or more residues. Such derivatives may be generated for different purposes, such as, in particular, that of increasing the affinity of the peptide for its substrate (s), that of improving its levels of production, that of increasing its resistance to proteases, that of increasing and/or modifying its activity, or that of endowing it with novel biological properties. Among derivatives resulting from an addition, there may be mentioned, for example, chimeric polypeptides containing an additional heterologous portion attached to one end. The term derivative also comprises polypeptides homologous to the polypeptides described in the present invention and originating from other cell sources, and in particular from strains producing streptogramins.

The subject of the invention is also any recombinant cell containing a nucleotide sequence or a vector as defined above. The recombinant cells according to the invention can equally well be eukaryotic cells or prokaryotic cells. Among eukaryotic cells which are suitable, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127 cells, Xenopus eggs, and the like, may be mentioned. Among fungi, special mention may be made of Micromonospora, *Aspergillus ssp.* or *Trichoderma ssp.* As prokaryotic cells, it is preferable to use the following bacteria: Actinomycetes, and Streptomyces in particular, *E. coli* (Example 11), Bacillus. Preferably, the recombinant cells of the invention are chosen from cells producing streptogramins (see Table 1). The recombinant cells of the invention may be obtained by any method which enables a foreign nucleotide sequence to be introduced into a cell. It can be, in particular, transformation, electroporation, conjugation, protoplast fusion or any other technique known to a person skilled in the art.

A further subject of the invention is a method for producing a polypeptide involved in the biosynthesis of streptogramins, according to which a recombinant cell as defined above is cultured and the polypeptide produced is recovered.

The subject of the invention is also the use of a recombinant cell as defined above, expressing at least one polypeptide involved in the biosynthesis of streptogramins, in a bioconversion reaction. In particular, these cells can enable a streptogramin to be converted into a derived form. For example, pristinamycin IIB can be converted in this manner to pristinamycin IIA. The same reasoning may be applied to any biosynthesis intermediate. These cells can also enable hybrid antibiotics having advantageous pharmacological properties to be manufactured (Hopwood et al. 1985a, Hopwood et al. 1985b, Hutchinson et al. 1989). These bioconversions may be carried out either using whole cells, or using acellular extracts of the said cells.

Another subject of the invention relates to the use of a nucleotide sequence as defined above for amplifying streptogramin production. The invention also relates to a method for producing streptogramins, according to which one or more nucleotide sequences according to the invention is/are introduced and/or amplified in a cell producing streptogramins or which is potentially a producer of streptogramins, the said cell is cultured under conditions of streptogramin production, and the streptogramins produced are recovered.

The overexpression of certain genes involved in the biosynthesis can enable the streptogramin A and/or B production of the producing strains to be increased. This overproduction may be carried out in several strains: either strains which produce only molecules of the streptogramin A family, or strains which produce only molecules of the streptogramin B family, or strains which produce both the A and B components. These overexpressions can result from an increase in the level of synthesis, and hence in the productivity, of the A and/or B components, either in an Erlenmeyer, or in small fermenters, or in large industrial fermenters. Moreover, the specific overexpression of a gene involved in the biosynthesis of an A or B component also makes it possible to vary the % of A and B components produced by the strain, and thus to obtain a better synergy between these molecules. In addition, the biosynthesis genes isolated from a microorganism producing streptogramins may be used to amplify production in another producing microorganism.

Another subject of the invention relates to a method for preparing cells blocked in a step of the pathway of biosynthesis of streptogramins, according to which a mutagenesis is performed on at least one gene of the biosynthesis pathway, on a cell producing streptogramins.

Preferably, the mutagenesis is performed in vitro or in situ, by suppression, substitution, deletion and/or addition of one or more bases in the gene in question, or by gene disruption.

Another aspect of the present invention lies, in effect, in the construction of mutants blocked in certain steps of biosynthesis of streptogramins. The value lies, on the one hand in the study of the functionality of the mutated proteins, and on the other hand in the production of strains producing biosynthesis intermediates. These intermediates may be modified, where appropriate after separation, either by adding particular components to the production media, or by introducing into the strains thus mutated other genes capable of modifying the intermediate by acting as a substrate for them. These intermediates may thus be modified by chemical, biochemical, enzymatic and/or microbiological means. In this context, the mutant SP92::pVRC505 of *S. pristinaespiralis* strain SP92 was constructed: *S. pristinaespiralis* SP92::pVRC505 was isolated by homologous integration in the snaA gene of a suicide plasmid pVRC505, constructed from the vector pDH5 and a fragment internal to the snaA gene. The following mutants were also constructed: SP92 samS::ΩamR; SP92::pVRC508; SP92::pVRC404 and SP92::pVRC1000 (Example 9).

The invention hence also relates to a method for preparing an intermediate of the biosynthesis of streptogramins, according to which:

a cell blocked in a step of the pathway of biosynthesis of streptogramins is prepared as described above, the said cell is cultured, and the accumulated intermediate is recovered.

The invention also relates to a method for preparing a molecule derived from streptogramins, according to which:

a cell blocked in a step of the pathway of biosynthesis of streptogramins is prepared as described above, the said cell is cultured, and the intermediate accumulated by this cell is modified, where appropriate after separation of the culture medium.

EXAMPLES

The present invention is illustrated by means of the examples and figures which follow, which are to be considered as illustrative and non-limiting.

MATERIALS

Figure 1:
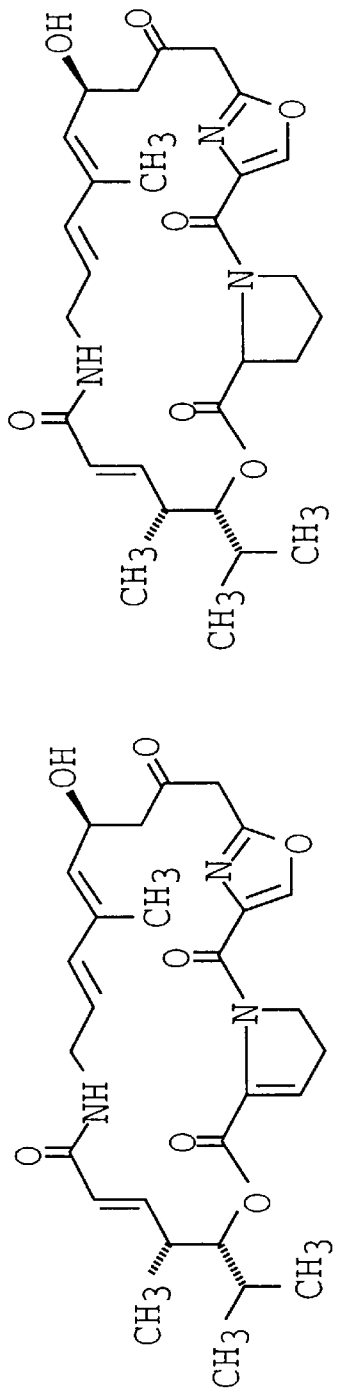
FIG. 1: Example of structure of the A components of streptogramins.

Bio-Sil SEC 125 and 250 columns (Bio-Rad) MonoQ HR 5/5, 10/10 and 16/10 columns (Pharmacia)
PD-10 column (Pharmacia)
Superose 6 HR 10/30 column (Pharmacia)
Superdex 200 Hi-Load 16/60 and 75 HR 10/30 column (Pharmacia)
Superose 12 prep grade column (Pharmacia)
Vydac C4 and C18 columns (The Separations Group)
Nucleosil 5-C18 column (Macherey-Nagel)
Phenyl Superose HR 10/10 column (Pharmacia)
TSK G2000 SW column (Tosoh, Japan)
Phenyl Sepharose (Pharmacia)
FMN-agarose (Sigma)
Q Sepharose Fast Flow (Pharmacia)
Sephadex G-25 Fine (Pharmacia)
Centricon 10 or 30 (Amicon)
Centriprep 10 or 30 (Amicon)
Centrilutor (Amicon)

Example 1

Isolation of total DNA of *Streptomyces pristinaespiralis* strain SP92

This example illustrates how *S. pristinaespiralis* SP92 DNA may be purified.

*S. pristinaespiralis* strain SP92 is derived from *S. pristinaespiralis* strain DS5647 (ATCC25486).

50 ml of YEME medium (34% sucrose, 5 mM $MgCl_2$, 0.25% glycine (D. Hopwood et al. 1985)) are inoculated with $10^8$ *S.pristinaespiralis* SP92 spores, and the culture is incubated for 40 hours at 30° C. with stirring at 280 rpm.

The mycelium is harvested and washed with 15 ml of 10.3% sucrose. Approximately 1 g of the mycelium pellet is taken up with 5 ml of TE supplemented with 34% of sucrose, to which are added 1 ml of lysozyme at a concentration of 50 mg/ml in 10 mM Tris-HCl solution pH 8.0 and 1 ml of 0.25M EDTA pH 8.0. After incubation at 30° C. for a period of 30 to 60 min, the mixture is clarified by adding 0.8 ml of 10% sarkosyl. 2 ml of 0.25M EDTA pH 8.0, 10 ml of TE, 18 g of CsCl and 1.2 ml of ETB at a concentration 10 mg/ml are then added. The preparation is ultracentrifuged overnight at 55,000 rpm at 20° C.

The chromosomal DNA, present in the CsCl gradient in the form of a band, is recovered using a Pasteur pipette. The ETB is removed by several washes with a solution of isopropanol saturated with TE buffer, 5M NaCl. The DNA is precipitated by adding 3 volumes of TE and 4 volumes of isopropanol. After washing with 70% ethanol, the DNA is taken up in a suitable volume of TE. The total amount of DNA obtained varies between 250 and 500 μg per g of mycelium.

Example 2

Isolation of *E. coli* Plasmid DNA

This example illustrates how *E. coli* plasmid DNA is prepared from recombinant strains of *E. coli*.

2.1. Preparation of *E.coli* Plasmid DNA in Large Amounts

This example illustrates how maxi preparations of plasmid DNA are produced in *E. coli*.

This preparation is performed using a 500 ml culture in LB medium containing 150 μg/ml of ampicillin. The extraction protocol is derived from the methods described by Birnboim and Doly (1979) and Ish-Horowicz and Burke (1981), and is described in Maniatis et al. (1989).

After this extraction, the plasmid DNA is purified using a CsCl gradient as described by Maniatis et al. (1989). The plasmid DNA is then precipitated by adding 3 volumes of TE and 4 volumes of isopropanol. After centrifugation, the pellet is taken up in 0.5 to 1 ml of TE.

2.2. Preparation of *E. coli* Plasmid DNA in Small Amounts

This example illustrates how minipreparations of plasmid DNA are produced in *E. coli*.

This preparation is carried out using 1.5 ml of culture in LB medium containing 150 μg/ml of ampicillin. The procedure is that described by Birnboim and Doly (1979).

Example 3

Construction of the Genomic DNA Library of *S. pristinaespiralis* SP92 in *E. coli* and Preparation of Hybridization Membranes This example illustrates how a genomic DNA library of *S. pristinaespiralis* SP92 is produced in *E. coli*.

3.1. Preparation of Genomic DNA Fragments

This example illustrates how high molecular weight genomic DNA fragments may be prepared.

Total DNA of the strain SP92, prepared as described in Example 1, is partially digested with Sau3A (New England Biolabs, Beverly, Mass. 01915-5510 USA) in the buffer recommended by the supplier: 100 mM NaCl, 10 mM Tris-HCl (pH7.5), 10 mM $MgCl_2$, 100 μg/ml BSA. The amount of enzyme used to obtain high molecular weight DNA fragments was determined empirically. Approximately 0.025 enzyme units are used to digest 1 μg of total DNA for 20 min at 37° C. The reaction is then stopped by incubation for 15 min at 65° C., and the enzyme is removed by adding an equal volume of phenol/chloroform. After centrifugation, the supernatant containing the partially digested total DNA is precipitated by adding 0.3M final sodium acetate and 2.5 volumes of ethanol.

Approximately 100 μg of total DNA are digested in this way, and DNA fragments between 30 and 50 kb in size are isolated with a 10–40% sucrose gradient. Their size is verified by electrophoresis on 0.4% agarose gel.

3.2. Preparation of Cosmid pHC79

This example illustrates how cosmid pHC79 is prepared from *E. coli*.

Cosmid pHC79 (Hohn, B. and Collins, 1980) comprises a portion of pBR322 (Bolivar, F. et al., 1977), the cro-cII region of λ and the region containing the cos sequence of Charon 4A (Blattner, F. R. et al., 1977).

Extraction of the cosmid was carried out as described in Example 2.1., from an *E. coli* strain TG1 (K12, Δ(lac-pro) supE thi hsd DS F' traD36 proA⁺B⁺ lacIq LacZ ΔM15, Gibson, 1984).

500 ng of cosmid pHC79 are digested with BamHI (New England Biolabs, Beverly, Mass. 01915–5510 USA) in 20 μl of buffer comprising 150 mM NaCl, 6 mM Tris-HCl pH 7.9, 6 mM $MgCl_2$, 6 mM 2-mercaptoethanol, 100 μg/ml BSA.

3.3. Ligation of the DNA Fragments and the Cosmid

This example illustrates how the fragments of the *S. pristinaespiralis* SP92 genome originating from an Sau3A digestion may be ligated with the BamHI-linearized vector pHC79.

Approximately 150 ng of cosmid linearized as described above were precipitated by means of ethanol with 350 ng of fragments of total DNA of *S. pristinaespiralis* SP92 prepared as described in Example 3.2. The pellet was taken up in 10 μl of ligation buffer: 50 mM Tris-HCl pH 7.8, 10 mM $MgCl_2$, 20 mM DTT, 1 Mm ATP, 50 μg/ml of BSA, and 0.5 μl of T4 DNA ligase at a concentration of 400,000 units per ml (New England Biolabs, Beverly, Mass. 01915-5510 USA) were added. Incubation was carried out overnight at 15° C.

3.4. Carrying Out Encapsidation in vitro

This example illustrates how the cosmids constructed in 3.3 are encapsidated in vitro.

Encapsidation of the hybrid cosmids after ligation was carried out using the Gigapack II Gold kit developed by Stratagene (Stratagene Cloning Systems, La Jolla, Calif. 92037, USA).

2×4 μl of ligation mixture, equivalent to 2×70 ng of hybrid cosmids, were encapsidated in vitro according to the procedure described by the supplier.

3.5. Transfection of *E. coli* Strains DH1 and HB101

This example illustrates how the cosmids are introduced into *E. coli*.

Two transfections were carried out in parallel with *E. coli* strains DH1 (F⁻ gyrA96 recA1 relA1 endA1 thi-1 hsdR17 supE44L-, Low 1968) and HB101 (F⁻ supE44 hsdS20(rB⁻ mB⁻) recA13 ara-14 proA2 lacY1 galK2 rpsL20 xyl-5 mtl-1, Boyer and Roulland-Dussoix 1969).

The cells were prepared according to the following protocol: a 100-ml preculture is produced in LB medium supplemented with 0.2% maltose and 10 mM $MgSO_4$ for 4 to 5 hours until the $OD_{600}$ reaches a value of 0.8. The culture is then centrifuged, and the pellet is taken up in 40 ml of 10 mM $MgSO_4$ and diluted to $OD_{600}$=0.5 in the same solution. 200 μl of the cell suspension thus prepared are mixed with 100 μl of encapsidation mixture. After 20 min of contact at 37° C., 1 ml of LB is added and the whole is incubated for 1 hour at 37° C. The transfectants are then selected on solid LB medium containing 150 μg/ml of ampicillin. The number of transfectants obtained is approximately $10^4$ per μg of recombinant cosmid.

3.6. Storage of Genomic DNA Libraries of *S. pristinaespiralis* SP92

This example illustrates how the genomic DNA libraries of *S. pristinaespiralis* SP92 are stored.

After verification of the average size of the fragments inserted into cosmid pHC79, approximately 1500 colonies originating from each of the transfections carried out with the strains HB101 and DH1 are subcultured in 96-well microtitration plates containing 200 μl of Hogness medium (LB medium supplemented with 8.8% glycerol, 3 mM sodium acetate, 55 mM $K_2HPO_4$, 26 mM $KH_2PO_4$, 1 mM $MgSO_4$, 15 mM $(NH_4)_2SO_4$, 150 μg/ml ampicillin). These plates are incubated overnight at 37° C. and then stored at −80° C.

3.7. Preparation of Hybridization Membranes from Genomic Libraries of *S. pristinaespiralis* SP92

This example illustrates how the DNA of the colonies constituting the genomic libraries of *S. pristinaespiralis* SP92 is transferred onto a hybridization membrane.

These hybridization membranes were produced in duplicate for each of the 2 libraries according to the following protocol:

The 15 microtitration plates of each library are replicated using a replica plater on LB agar medium containing 150 μg/ml of ampicillin. After growth overnight at 37° C., colony transfer is performed onto a Biohylon $Z^+$ membrane (Bioprope System) according to the following protocol: the membrane is cut to the appropriate size and left in contact with the colonies for 1 min. Denaturation is then performed by soaking the membrane with 0.5M NaOH, 1.5M NaCl solution for 5 min, followed by neutralization by soaking the membrane in 3M sodium acetate solution for 5 min. The DNA is fixed to the membrane by exposure under a UV lamp for 5 min.

Example 4

4.1. Preparation of Chromosomal DNA of *S. pristinaespiralis* Strain SP92 and Strains Derived from SP92 in the Form of Inserts for Pulsed-Field Electrophoresis This example illustrates how DNA of *S. pristinaespiralis* strain SP92 and strains derived from SP92 is prepared in the form of inserts for pulsed-field electrophoresis.

This preparation is made from a mycelium culture obtained in the following manner: 30 ml of YEME medium containing 0.25% of glycine are inoculated with $10^8$ spores of the strain under study, and the culture is incubated for 48 hours at 30° C. and stirred at 280 rpm in 250-ml Erlenmeyers. The mycelium is then harvested by centrifugation for 10 min at 3800 rpm and washed twice with 10% sucrose. The mycelium pellet is then resuspended in 5 ml of solution I (250 mM EDTA pH 8.0, 20.6% sucrose). To 200 Ml of mycelium thereby obtained, 400 Ml of a lysozyme solution at a concentration of 50 mg/ml in solution I together with 800 Ml of 1% LMP agarose in 25 mM EDTA pH 8 and 10.3% sucrose, maintained at 42° C., are added. The mixture maintained at 42° C. is then poured into the wells of special combs, which are closed with adhesive tape and kept for 30 min at 4° C. The mixture solidifies, and the 30 to 40 inserts thereby obtained and contained in the wells are carefully removed from the moulds.

The inserts are first rinsed for 30 min at 4° C. in a solution containing 25 mM EDTA and 10.3% sucrose. They are then soaked in a solution of 500 mM EDTA, 1% lauryl sarcosyl and 1 mg/ml of proteinase K for twice 24 hours at 50° C., stirring from time to time. The inserts are then washed for 3 times one hour in TE containing 1 mM PMSF, changing the solution after each wash. The inserts thereby obtained are stored at 4° C. for not more than 4 months in 0.5M EDTA pH 8.0.

4.2. Digestion of Inserts of DNA of *S. pristinaespiralis* Strain SP92 and Strains Derived from SP92 and Analysis by Pulsed-Field Electrophoresis This example illustrates how chromosomal DNA of *S. pristinaespiralis* strain SP92 and strains derived from SP92, prepared in the form of inserts as described in Example 4.1., is cut with different restriction enzymes for pulsed-field electrophoresis.

4.2.1. Digestion of Chromosomal DNA in the Form of Inserts

The inserts are first washed six times in TE, and then incubated twice for one hour in the buffer of the chosen restriction enzyme. Each insert is then placed in the lid of an Eppendorf tube containing 160 Ml of buffer of the restriction enzyme and 40 units of enzyme. The whole is covered with Parafilm, and the Eppendorf is closed to hold in place the Parafilm which enables any evaporation of the buffer to be avoided. The tubes are incubated at the desired temperature in an incubator overnight.

4.2.2. Analysis of Digested DNA by Pulsed-Field Electrophoresis

The pulsed-field electrophoresis technique chosen for this study is that of the CHEF (Clamped Homogenous Electric Field) system developed by Chu et al. (1986), which makes it possible to obtain two homogeneous alternating fields oriented at 120° with respect to one another and linear trajectories for the DNA molecules. The apparatus used is the "Pulsafor System" marketed by Pharmacia-LKB.

The electrophoretic migration paratmeters, such as the pulse time and the migration period, were varied so as to obtain an optimal separation of DNA fragments ranging in size between 10 and 2500 kb. The three migration conditions used are as follows: to separate large fragments from 200 to 1700 kb in size, the chosen migration is 40 hours with a pulse time of 90 seconds; to separate fragments from 50 to 400 kb in size, the chosen migration is 20 hours with a pulse time of 10 seconds followed by 20 hours with a pulse time of 30 seconds; lastly, to separate smaller fragments from 10 kb to 200 kb in size, the chosen migration is 24 hours with a pulse time of 10 seconds. For these three migration conditions, the voltage is set at a constant 150 volts, the temperature is maintained at 13° C. and the electrophoresis gels contain 1.3% of agarose.

The inserts containing chromosomal DNA of *S. pristinaespiralis* strain SP92 and strains derived from SP92 are digested with the restriction enzymes as described above and are placed in the wells of the electrophoresis gel using two scalpel blades. The molecular weight markers used are "Yeast chromosome PFG marker" and "Lambda Ladder PFG marker" marketed by the company New England Biolabs. Migration is performed under one of the conditions described above and the gel is then stained in a bath of ETB (ethidium bromide) at a concentration of 4 Mg/ml for 20 min and thereafter decolorized in water for 20 min. After the gel is photographed, the DNA fragments are transferred onto a nylon membrane and then hybridized with [$\alpha$-$^{32}$P]dCTP-labelled probes as described in Example 9.1.

Example 5

Isolation of Cosmids Carrying the Genes Coding for Purified Proteins Involved in the Biosynthesis of Streptogramins This example describes how, starting from a purified protein participating in biosynthesis of pristinamycins and whose NH$_2$-terminal sequence or an internal sequence has been established, it is possible to isolate a cosmid carrying the structural gene for this same protein from the genomic libraries produced above, or alternatively to identify the corresponding structural gene from among the genes carried by the cosmids and which have already been sequenced.

5.1. Isolation of Cosmids pIBV1 and pIBV3 Carrying One or Both Structural Genes for the Two Subunits of Pristinamycin IIA Synthase

5.1.1. Identification and Purification of One of the Proteins Involved in the Final Step of the Synthesis of Pristinamycins II: Pristinamycin IIA Synthase As stated in the introduction, the final step of synthesis of pristinamycin IIA corresponds to an oxidation of the 2,3 bond of D-proline to dehydroproline. The protein responsible for this activity has been purified to homogeneity, as illustrated by this example.

5.1.1.A. Assay of Pristinamycin IIA Synthase Activity

Figure 8:
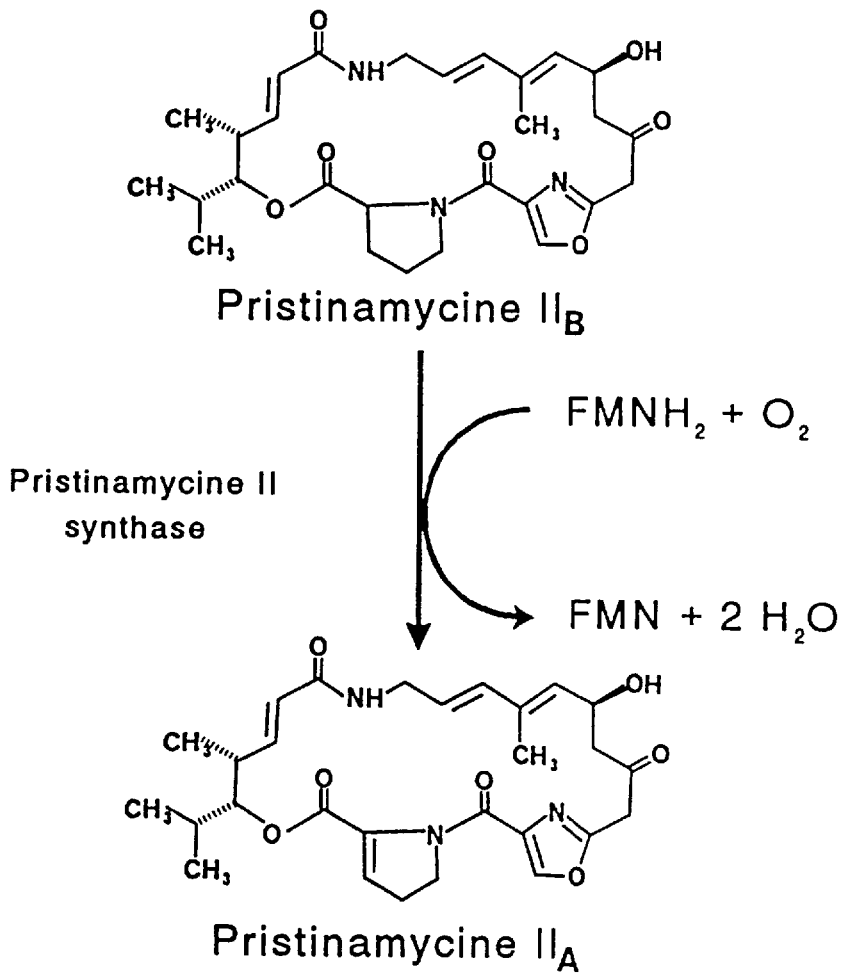
FIG. 8: Reaction catalysed by pristinamycin IIA synthase.

This example illustrates the assay of an activity of the biosynthesis pathway of pristinamycin IIA which has never before been described and which possesses the noteworthy property of being expressed only during the period of production of pristinamycins. The enzyme in question is pristinamycin IIA synthase, which catalyses the conversion of pristinamycin IIB to pristinamycin IIA by oxidation of the D-proline residue of pristinamycin IIB to a 2,3-dehydroproline residue (FIG. 8) in the presence of molecular oxygen and FMNH$_2$. The enzyme fractions to be assayed (0.002 to 0.005 units) are incubated for 1 h at 27° C. in a total volume of 500 ml of 50 mM bis-tris propane buffer pH 6.8 containing NADH (500 $\mu$M), FMN (5 $\mu$M), pristinamycin IIB (20 $\mu$M) and 0.02 units of FMN reductase (Boehringer Mannheim).

The pristinamycin IIA formed is assayed by HPLC after incubation is stopped by adding 500 $\mu$l of 0.1N hydrochloric acid and 500 $\mu$l of acetonitrile and centrifugation of the sample for 5 min at 5000 g. 150 $\mu$l of the centrifugation supernatant are injected onto a 15-cm Nucleosil 5-C8 column eluted with a mixture of 34% of acetonitrile and 66% of 0.1M phosphate buffer pH 2.9. Pristinamycins IIA and IIB are detected by means of their UV absorbance at 206 nm.

The unit of enzymatic activity is defined as the amount of enzyme needed to synthesize 1 $\mu$mol of pristinamycin IIA per hour under the conditions described.

5.1.1.B. Purification of *S. pristinaespiralis* SP92 Pristinamycin IIA Synthase This experiment illustrates how an enzyme of *S. pristinaespiralis* SP92 participating in the biosynthesis pathway of pristinamycin IIA may be purified.

Using the assay described above in Example 5.1.1.A, the purification of pristinamycin IIA synthase is carried out as described below taking care to freeze and store the active fractions at -30° C. between successive steps if necessary.

150 g of a centrifugation pellet, washed with 0.1M phosphate buffer pH 7.2 containing 10% v/v of glycerol, of an *S. pristinaespiralis* SP92 culture harvested at the beginning of the pristinamycin production phase are taken up with 450 ml of 50 mM bis-tris propane buffer pH 6.8 containing 5 mM DTT and 0.2 mg/ml of lysozyme. The suspension thereby obtained is incubated for 45 minutes at 27° C. and then centrifuged at 50,000 g for 1 hour. The crude extract thereby collected is fractionated by ammonium sulphate precipitation. The protein fraction precipitating at between 40 and 55% saturation is desalted on a column of Sephadex G-25 Fine, and then injected (100 mg per injection) in pH 6.8 50 mM bis-tris propane buffer, 1 mM DTT onto a monoQ HR 10/10 column. The proteins are eluted with a linear KCl gradient (0 to 0.5M). The fractions containing the enzymatic activity (detected by means of the test described in Example 5.1.1.A) are pooled and concentrated to 20 ml on Centriprep 10. After dilution with one volume of pH 6.8 50 mM bis-tris propane buffer, 1 mM DTT containing 2M ammonium sulphate, the proteins are chromatographed (22.5 mg per injection) on a Phenyl Superose HR 10/10 column with a decreasing ammonium sulphate gradient (1.0M to 0M). The best fractions containing the desired activity are pooled, reconcentrated to 1 ml on Centriprep 10 and then applied (200 μl per injection) to a Bio-Sil SEC 250 column. The activity peak is detected in this technique at a molecular weight centred at 77,000. The fraction containing the activity is injected onto a MonoQ HR 5/5 column in pH 6.8 50 mM bis-tris propane buffer, DTT 1 mM eluted with a linear KCl gradient (0 to 0.5M).

After this step, the enzyme is pure and, in SDS-PAGE electrophoresis, two subunits of molecular weight estimated at 35,000 and 50,000 are detected. They are separated on a 25-cm Vydac C4 column eluted with a linear gradient of from 30 to 50% of acetonitrile in water containing 0.07% of trifluoroacetic acid.

TABLE 2

Purification of pristinamycin IIA synthase

| Purification Step | Vol. (ml) | Protein (mg) | Sp.Act. μmol/h/mg | Yield (%) | Purification factor |
|---|---|---|---|---|---|
| Crude extract | 490 | 1690 | 0.14 | 100 | 1 |
| 40–45% A.S. | 60 | 1050 | 0.19 | 85 | 1.4 |
| MonoQ 10/10 | 95 | 45 | 3.0 | 58 | 21 |
| Phenyl Superose | 8 | 2.8 | 12 | 14 | 86 |
| Bio-Sil SEC | 5 | 1.3 | 19 | 14 | 130 |
| MonoQ 5/5 | 10 | 0.7 | 23 | 10 | 160 |

The purification factor is calculated from the increase in specific activity of the fractions during the purification.

5.1.2. Production of Oligonucleotides from the Protein Sequences

This example describes how, starting from the NH$_2$-terminal sequences of the two subunits of pristinamycin IIA synthase purified as described in Example 5.1.1.B., it is possible to synthesize oligonucleotides. The two subunits of pristinamycin IIA synthase are referred to as SnaA and SnaB, and correspond to polypeptides of molecular weights 50,000 and 35,000, respectively, as descibed in Example 5.1.1.B.

The NH$_2$-terminal sequences of the proteins SnaA and SnaB, corresponding to the subunits of pristinamycin IIA synthase, were deduced by microsequencing. This is carried out by the Edman degradation technique, using an automated sequencer (Applied Biosystems model 407A) coupled to an HPLC apparatus for identification of the phenylthiohydantoin derivatives. About thirty residues were determined for each of them.

Protein SnaA: (see residues 2 to 29 on SEQ ID NO:17)
T A P(R) (R,W)R I T L A G I I D G P G G H V A A(W)R H P (A) T
Protein SnaB: (see residues 2 to 31 on SEQ ID NO:18)
T A P I L V A T L D T R G P A A T L G T I T(R)A V(R)A A E A Moreover, sequences internal to these two polypeptides were determined after trypsin digestion of SnaA and SnaB and purification of the fragments obtained on a Vydac C18 HPLC column. The following internal sequences were found:

Protein SnaA: (see residues 365 to 384 on SEQ ID NO:17)
G A D G F N I D F P Y L P G S A D D F V
Protein SnaB: (see residues 122 to 136 on SEQ ID No. 3)
G L(-)D S F D D D A F V H D R From the underlined regions in each of the sequences of the fragments internal to the proteins SnaA and SnaB, and in accordance with the degeneracy of the genetic code specific to Streptomyces (see Example 8), the following mixtures of oligonucleotides were synthesized with a Biosearch 8600 automated synthesizer. They were then purified by the technique already described (Sawadogo M. and Von Dyke M. W., 1991). The snaA and snaB genes denote the structural genes for the proteins SnaA and SnaB, respectively.

Mixture Corresponding to the Underlined Portion of the Internal Sequence of SnaA ATC GAC TTC CCC TAC CTC CCC GG
 T    T    G    T    G    G
                 A
                 T (SEQ ID NO: 32)

Mixture Corresponding to Underlined Portion of the Internal Sequence of SnaB

TTC GAC GAT GAT GCA TTC GTC CAT GAC
        C   C   T         G   C
                 C
                 G (SEQ ID NO: 33)

5.1.3. Labelling of the Mixtures of Synthetic Oligonucleotides and Hybridization with the Genomic DNA Libraries of the Strain SP92

This example describes how oligonucleotides specific for a gene for the biosynthesis of pristinamycins may be radioactively labelled and then hybridized with membranes onto which DNA of genomic libraries of *S. pristinaespiralis* SP92 has been transferred.

Labelling of the oligonucleotides is carried out by transfer at the 5'-terminal position of the [γ-$^{32}$P]phosphate group of ATP with T4 polynucleotide kinase. This labelling is carried out as described in Maniatis et al. (1989). After labelling, the oligonucleotides are used without purification.

Approximately 2×500 ng of each mixture of oligonucleotides were labelled in this way with $^{32}$P and were used to hybridize each of the two libraries.

Hybridization of the membranes of each library is carried out according to a protocol derived from those developed by Meinkoth, J. and Wahl, G. (1984) and Hames, B. D. and Higgins, S. J. (1985): the 15 membranes are prehybridized for 3 hours at 50° C. in 40 ml of a solution containing: Denhardt (×5) [Denhardt (×100): 2% (w/v) Ficoll, 2% (w/v) polyvinylpyrrolidone, 2% (w/v) BSA)], SSC (×5) [SSC (×20): 3M NaCl, 0.3M sodium citrate), 50 mM NaPO$_4$ pH 6.5, 0.1% SDS, 250 μg/ml salmon sperm DNA].

Hybridization is then carried out overnight at 50° C. in 20 ml of the same solution to which the 500 ng of labelled oligonucleotides are added.

The filters are then washed in a solution of SSC (×6) and 0.5% SDS, twice for 30 min at room temperature and then empirically at gradually higher temperatures (50° to 65° C.). The temperature of these latter washes is gradually increased after successive autoradiographic exposures in order to determine the specificity of the hybridizing clones with the mixtures of oligonucleotides.

5.1.4. Isolation of Cosmids pIBV1 and pIBV3 and Determination of the Regions Containing the snaA and snaB Genes This example illustrates how it is possible to isolate cosmids constructed as described in Example 3 containing genes for the biosynthesis of pristinamycins.

Cosmids pIBV1 and pIBV3 were isolated from two clones originating, respectively, from the library produced in the strain HB101 and from the library produced in the strain DH1 which hybridized with both mixtures of oligonucleotides simultaneously for pIBV1 and with the mixture of oligonucleotides originating from the internal sequence of the protein SnaA for pIBV3.

Figure 4:
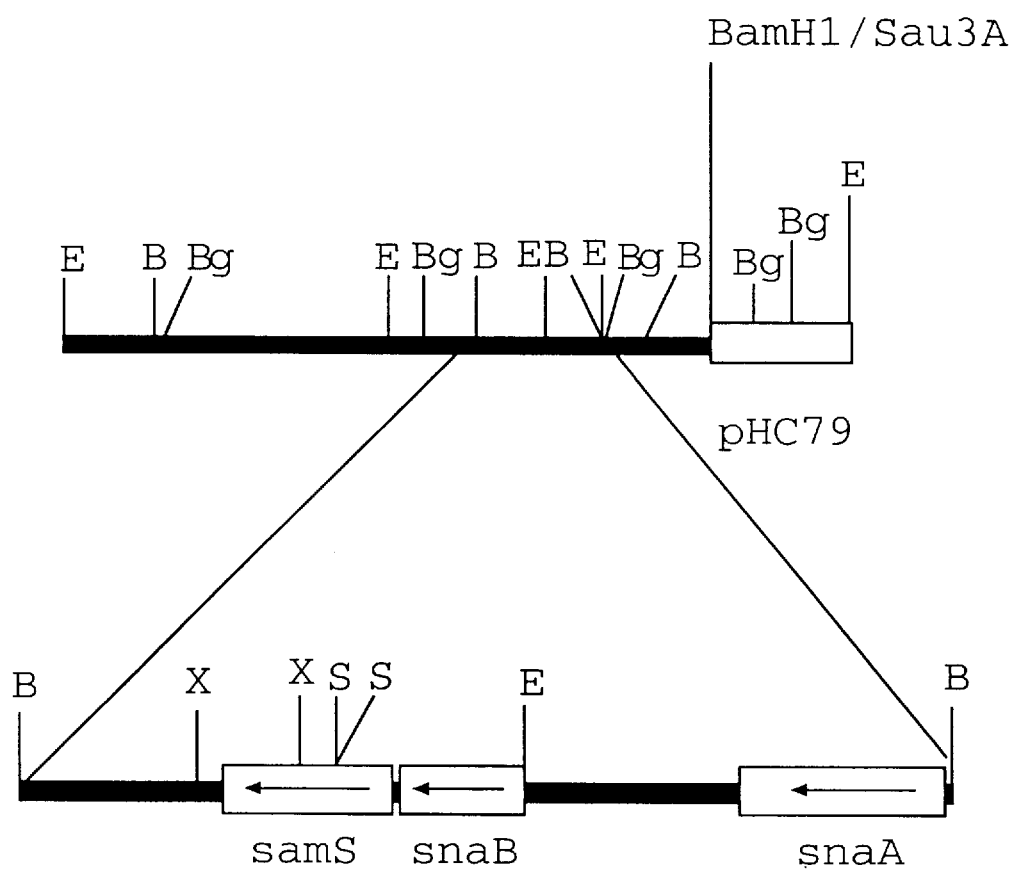
FIG. 4: Diagram of cosmid pIBV1.
Figure 6:
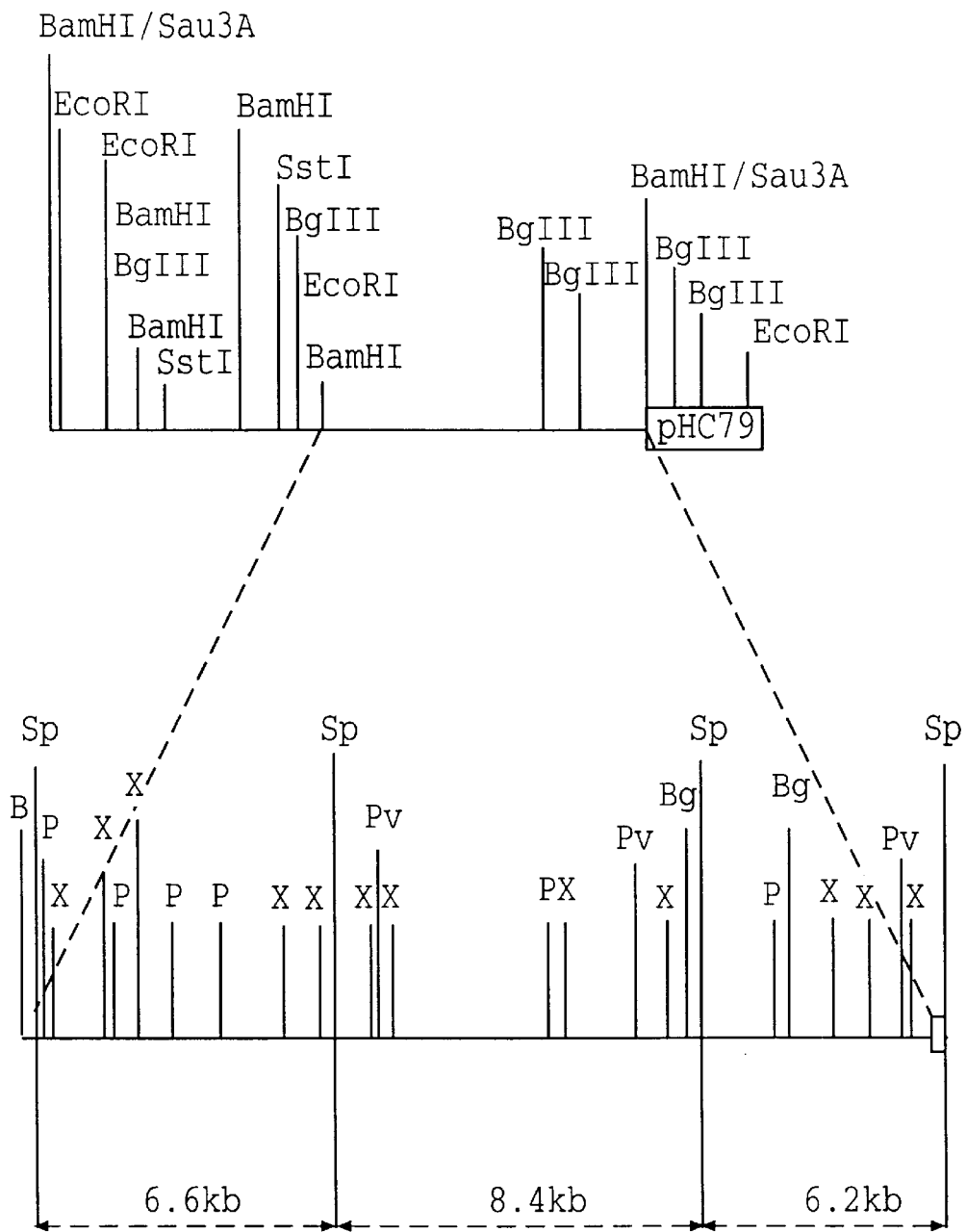
FIG. 6: Diagram of cosmid pIBV3.

These cosmids were purified as described in Example 2. Cosmids pIBV1 and pIBV3 contain, respectively, a genomic DNA insert of *S. pristinaespiralis* SP92 whose sizes were estimated, respectively, at 30 kb and 34 kb. Maps (FIGS. 4 and 6) were established from digestions with different restriction enzymes, according to the protocols of the supplier (New England Biolabs, Beverly, Mass. 01915-5510 USA).

Southern hybridizations of pIBV1 and pIBV3 DNA, digested by means of different enzymes, with the mixtures of oligonucleotides enabled the region of this cosmid containing the snaA and/or snaB genes to be identified.

Southern hybridization was carried out as described in Maniatis et al. (1989). After separation of the restriction fragments by electrophoresis on 0.8% agarose gel, the DNA is transferred onto a Biohylon Z$^+$ membrane (Bioprope System). Hybridization of the DNA thus transferred onto the membranes with the mixtures of oligonucleotides was carried out as described in Example 5.1.3.

These Southern hybridizations enabled it to be shown that cosmid pIBV1 possessed a 6-kb BamHI fragment containing the sequences homologous to the probes synthesized in Example 5.1.2 (originating from the proteins SnaA and SnaB), as well as a 2.5-kb EcoRI fragment internal to the BamHI fragment containing the sequences homologous to the probes originating exclusively from the protein SnaA. Furthermore, the hybridization signals obtained with cosmid pIBV3 showed that it possessed only the 2.5-kb EcoRI fragment containing the sequences homologous to probes originating exclusively from the protein SnaA.

5.2. Isolation of Cosmid pIBV2 Containing the Structural Gene for 3-hydroxypicolinic acid:AMP Ligase (snbA)

This example illustrates how it is possible to obtain a cosmid as constructed in Example 3 containing at least one gene for the biosynthesis of pristinamycins I.

5.2.1. Identification and Purification of the Protein Involved in the Activation of 3-hydroxypicolinic Acid This example illustrates how the protein responsible for the activation of 3-hydroxypicolinic acid may be purified to homogeneity from *S. pristinaespiralis* SP92.

5.2.1.A. Assay of 3-hydroxypicolinic acid:AMP Ligase

Figure 9:
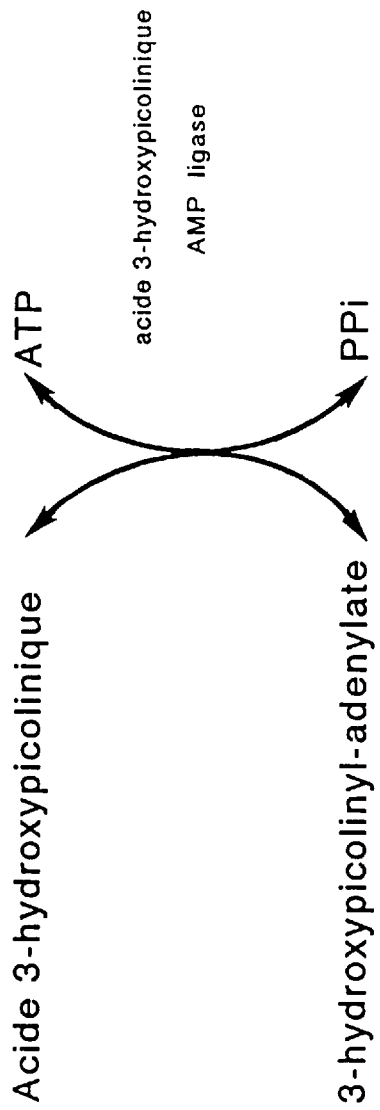
FIG. 9: Reaction catalysed by 3-hydroxypicolinic acid:AMP ligase.

This example illustrates the assay of an activity of the biosynthesis pathway of pristinamycin IA which has never before been described and which possesses the noteworthy property of being expressed only during the period of production of pristinamycins. The enzyme in question is 3-hydroxypicolinic acid:AMP ligase, which catalyses the formation of the adenylate of 3-hydroxypicolinic acid (FIG. 9) from this free acid and ATP in the presence of $MgCl_2$.

The enzyme fractions to be assayed (0.002 to 0.020 units) are incubated for 15 min at 27° C. in a total volume of 250 µl of pH 6.8 50 mM bis-tris propane buffer, 1 mM DTT, 10% v/v glycerol, in the presence of 3-hydroxypicolinic acid (1 mM), ATP (2 mM), $MgCl_2$ (5 mM) and tetrasodium pyrophosphate labelled with the radioactive isotope 32 of the phosphorus atom (200 µM).

The reaction is stopped by adding 1 ml of a suspension of activated charcoal at a concentration of 10 g/l in a mixture of 75% of 0.1M tetrasodium pyrophosphate and 25% of 14% perchloric acid. After stirring, the charcoal is collected and washed with twice 1 ml of the pyrophosphate/perchloric acid mixture. The radioactive organic molecules are then eluted with three times 1 ml of a mixture of 50% of methanol and 50% of N ammonia solution into a counting vial containing 12 ml of water. The radioactivity is measured by the Cerenkov effect with a scintillation counter (PACKARD Minaxi TriCarb 4000).

The unit of enzymatic activity is defined as the amount of enzyme needed to incorporate 1 µmol of pyrophosphate into ATP in the course of 1 hour under the conditions described above.

5.2.1.B. Purification of *S. pristinaespiralis* SP92 3-hydroxypicolinic acid:AMP Ligase This experiment illustrates how an enzyme of *S. pristinaespiralis* SP92 participating in the biosynthesis pathway of pristinamycin IA may be purified.

Using the assay described above in Example 5.2.1.A, the purification of 3-hydroxypicolinic acid:AMP ligase is carried out as described below, taking care to freeze the active fractions at −70° C. and store them at −30° C. between successive steps if necessary.

234 g of a centrifugation pellet, washed with 0.1M phosphate buffer pH 7.2 containing 10% v/v of glycerol, of an *S. pristinaespiralis* SP92 culture harvested at the beginning of the pristinamycin production phase are taken up with 234 ml of pH 8.0 100 mM Tris-HCl buffer containing 4 mM DTE, 1 mM benzamidine, 1 mM PMSF, 15% v/v glycerol and 0.6 mg/ml of lysozyme. The suspension thereby obtained is incubated for 30 minutes at 27° C. and then centrifuged at 50,000 g for 1 hour. The crude extract thereby collected is injected in pH 8.0 100 mM Tris-HCl buffer, 4 mM DTE, 1 mM benzamidine, 1 mM PMSF, 15% v/v glycerol onto a column (80 ml) of Q Sepharose Fast Flow. The proteins are eluted with a linear KCl gradient (0 to 0.4M). The fractions containing the enzymatic activity (detected by means of the test described in Example 5.2.1.A) are pooled and diluted with one volume of pH 8.0 100 mM Tris-HCl buffer, 1 mM benzamidine, 1 mM PMSF, 15% v/v glycerol containing 2M ammonium sulphate. The proteins are then chromatographed on a column (50 ml) of Phenyl Sepharose with a decreasing ammonium sulphate gradient (1.0M to 0M) in pH 8.0 100 mM Tris-HCl buffer, 1 mM benzamidine, 1 mM PMSF, 15% v/v glycerol. After the addition of 4 mM DTE, the active fractions are pooled, concentrated to 5 ml on Centriprep 10 and then applied to a column (100 ml) of Superose 12 prep grade. The fractions containing the desired activity are pooled and injected in pH 8.0 100 mM Tris-HCl buffer, 4 mM DTE, 1 mM benzamidine, 1 mM PMSF, 15% v/v glycerol (approximately 6 mg per injection) onto a column of MonoQ HR 5/5 eluted with a linear KCl gradient (0 to 0.4M). The active fractions are pooled, concentrated to 1 ml on Centricon 10, diluted with 3 volumes of pH 6.8 50 mM bis-tris propane buffer, 4 mM DTE, 1 mM benzamidine, 1 mM PMSF, 15% v/v glycerol, and then injected (2 mg per injection) in the latter buffer onto a column of MonoQ HR 5/5 eluted with a linear KCl gradient (0 to 0.3M). The best fractions containing the desired ligase are pooled and then applied in pH 6.8 20 mM sodium phosphate buffer, 50 mM sodium sulphate to a Bio-Sil SEC 250 column. The activity peak is detected in this technique at a molecular weight centred at 60,000.

The protein possessing the activity of activation of 3-hydroxypicolinic acid is hereinafter designated SnbA.

After this step, the enzyme is pure and, in SDS-PAGE electrophoresis, its molecular weight is estimated at approximately 67,000.

TABLE 3

Purification of 3-hydroxypicolinic acid:AMP ligase

| Purification Step | Vol. (ml) | Protein (mg) | Sp.Act. μmol/h/mg[a] | Yield (%) | Purification factor |
|---|---|---|---|---|---|
| Crude extract | 246 | 2050 | (0.06) | | |
| Q Sepharoae | 40 | 188 | 0.47 | 100 | 1 |
| Phenyl Sepharose | 70 | 35 | 2.21 | 88 | 4.7 |
| Superose 12 | 16 | 17 | 2.03 | 39 | 4.3 |
| MonoQ pH 8.0 | 4.5 | 9.0 | 2.09 | 21 | 4.5 |
| MonoQ pH 6.8 | 1.0 | 2.0 | 2.9 | 6.6 | 6.2 |
| Bio-Sil 250 | 2.5 | 0.23 | 12.4 | 3.2 | 26 |

[a]The activity in the crude extract cannot be measured accurately owing to exchanges between pyro-phosphate and ATP which are not specific to 3-hydroxy-picolinic acid.

The purification factor is calculated from the increase in specific activity of the fractions during the purification.

5.2.2. Production of Oligonucleotides from the Protein Sequence

This example describes how, starting from the NH$_2$-terminal and internal sequences of the protein 3-hydroxypicolinic:AMP ligase, it is possible to synthesize oligonucleotides.

The NH$_2$-terminal sequence of the protein SnbA was deduced by microsequencing as described in Example 5.1.2. About twenty residues were identified in this way.

A sequence of approximately 20 amino acids internal to the protein SnbA was also identified after trypsin hydrolysis and purification of the fragments obtained on a Vydac C18 HPLC column.

NH$_2$-terminal Sequence of the Protein 3-hydroxypicolinic:AMP Ligase (See residues 1 to 21 on SEQ ID NO:20)
M L D G S <u>V P W P E D V A A K Y</u> R A A G Y Internal Sequence of the Protein 3-hydroxypicolinic:AMP Ligase (See residues 448 to 467 on SEQ ID NO:20)
V S A (–) <u>E V E G H L G A H P D V Q Q</u> A A From the underlined regions in each of the sequences, and in accordance with the degeneracy of the genetic code specific to Streptomyces (see Example 8), the following mixtures of oligonucleotides were synthesized:

Mixture Corresponding to the Underlined Portion of the NH$_2$-terminal Sequence of the Protein 3-hydroxypicolinic:AMP Ligase

```
5'                                                              3'
GTC CCC TGG CCC GAG GAC GTC GCC GCC AAG TAC
 G   G       G           G   G   G
(SEQ ID NO: 34)
```

Mixture Corresponding to the Underlined Portion of the Internal Sequence of the Protein 3-hydroxypicolinic:AMP Ligase

```
5'                                                                              3'
GAG GTC GAG GGC CAC CTC GGC GCC CAC CCC GAC GTC CAG CAG GC
 G       G       G   G   G       G
(SEQ ID NO: 35)
```

5.2.3. Labelling of the Mixtures of Synthetic Oligonucleotides and Hybridization of the Genomic DNA Libraries of S. pristinaespiralis SP92

This example describes how oligonucleotides specific for a gene for the biosynthesis of pristinamycins may be radioactively labelled and then hybridized with membranes onto which DNA of genomic libraries of S. pristinaespiralis has been transferred.

Labelling the oligonucleotides is carried out by transfer at the 5'-terminal position of the [$\gamma$-$^{32}$P]phosphate group of ATP with T4 polynucleotide kinase, as described in Example 5.1.3.

Approximately 2×500 ng of each mixture of oligonucleotides were labelled in this way with $^{32}$P and were used to hybridize each of the two libraries.

Hybridization of the membranes of each library was carried out as described in Example 5.1.3.

5.2.4. Isolation of Cosmid pIBV2 and Determination of the Region Containing the Structural Gene for 3-hydroxypicolinic acid:AMP Ligase This example illustrates how it is possible to obtain a cosmid as constructed in Example 3 containing at least the structural gene for 3-hydroxypicolinic acid:AMP ligase.

Cosmid pIBV2 was isolated from a clone of the library produced in E. coli strain DH1 which hybridized with both mixtures of oligonucleotides simultaneously.

Figure 5:
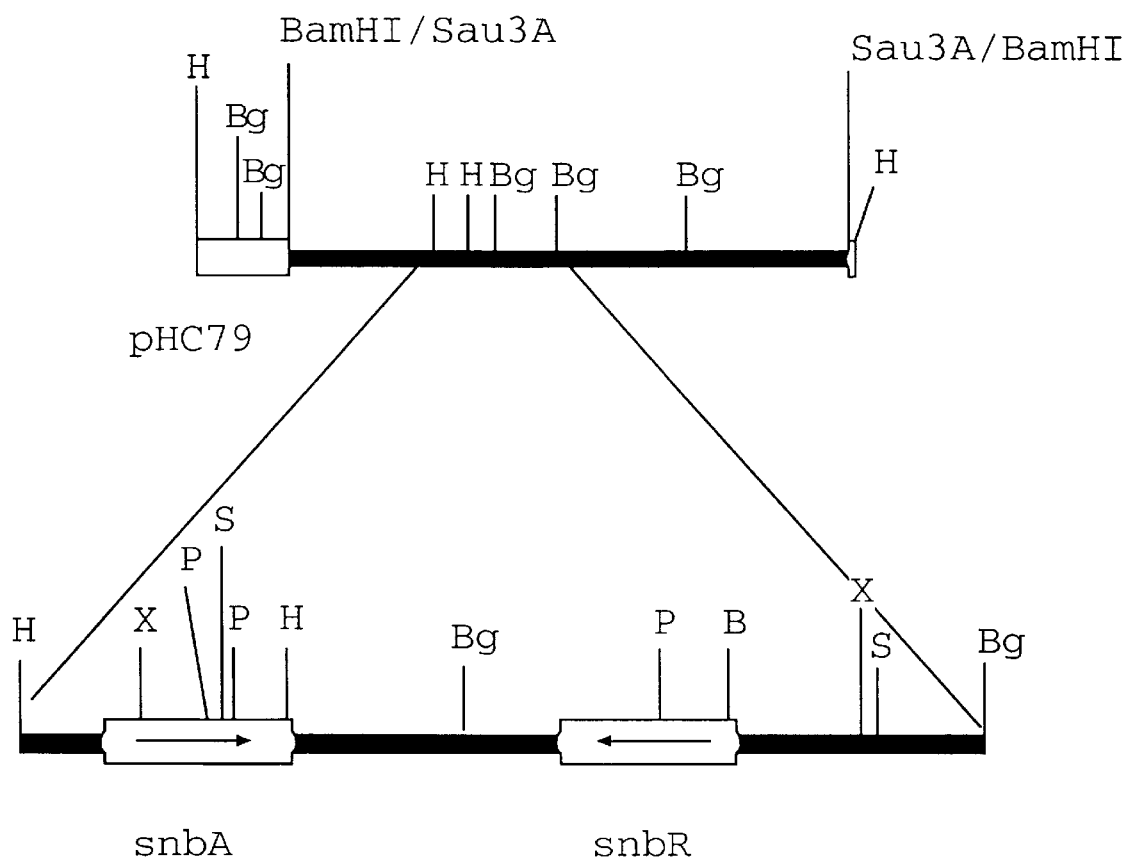
FIG. 5: Diagram of cosmid pIBV2.

This cosmid was purified as described in Example 2. It contains a genomic DNA insert of S. pristinaespiralis SP92 whose size was estimated at 47 kb. A map (FIG. 5) was established from digestions with different restriction enzymes, as described in Example 5.1.4.

Southern hybridizations of pIBV2 DNA, digested by means of different enzymes, with the mixtures of oligonucleotides enabled the region containing the structural gene for 3-hydroxypicolinic acid:AMP ligase to be identified. Southern blotting and hybridizations were carried out as described in Example 5.1.4.

The hybridization results enabled it to be shown that cosmid pIBV2 possessed a 5.5-kb EcoRI-BglII fragment containing the sequence homologous to the probes synthesized in Example 5.2.2.

5.3. Demonstration of the Presence of a Portion of the Structural Gene for Pristinamycin I Synthase II (SnbC) on Cosmid pIBV3

This example illustrates how it is possible to identify the presence of genes for the biosynthesis of pristinamycins I on a cosmid which has already been isolated (Example 5.1).

5.3.1. Identification of Pristinamycin I Synthase II Involved in the Incorporation of Threonine and Aminobutyric Acid Residues into the Peptide Chain Pristinamycin IA This example illustrates how the protein responsible for the incorporation of threonine and aminobutyric acid residues into the peptide chain of pristinamycin IA may be purified to homogeneity from S. pristinaespiralis SP92.

5.3.1.A. Assay of the Partial Activities of Pristinamycin I Synthase II

Figure 10:
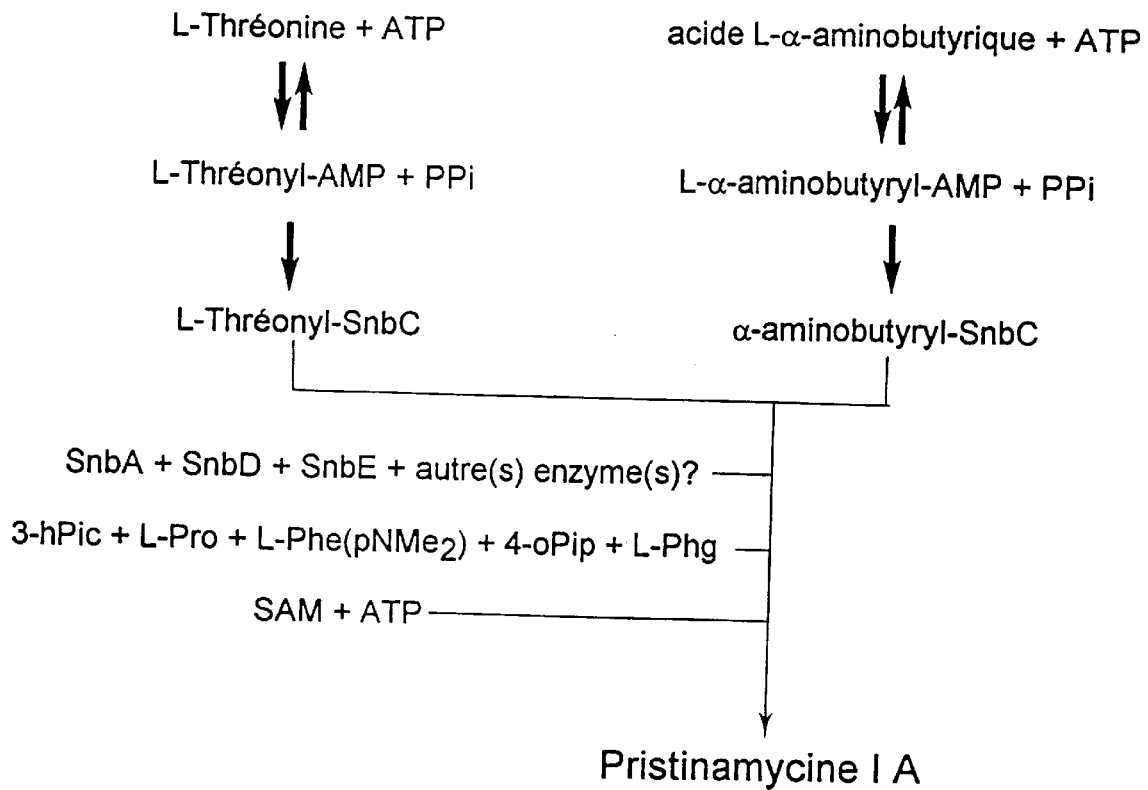
FIG. 10: Reaction catalysed by SnbC.

This example illustrates the assay of activities of the biosynthesis pathway of pristinamycin IA which have never before been described and which possess the noteworth property of being expressed only during the period of production of pristinamycins. The activities in question are the partial activities of the peptide synthase responsible for the incorporation of threonine and aminobutyric acid residues into the peptide chain of pristinamycin IA (FIG. 10) in the presence of ATP and MgCl$_2$.

The threonine:AMP ligase and aminobutyric acid:AMP ligase activities are measured in an enzymatic test of ATP-pyrophosphate exchange similar to that described in 5.2.1.A for 3-hydroxypicolinic acid:AMP ligase.

The aminoacylation reactions of the enzyme with threonine or alanine (an analogue of aminobutyric acid which is found in pristinamycin IC) enable the peptide synthase to be differentiated from other enzymes which may effect an ATP-pyrophosphate exchange, and in particular aminoacyl-tRNA synthetases. The test of aminoacylation of the enzyme with tritium-labelled threonine described below is hence the one which was used in this example.

The enzyme fractions to be assayed (0.2 to 2 units) are incubated for 15 min at 27° C. in a total volume of 250 $\mu$l of pH 6.8 50 mM bis-tris propane buffer, 1 mM DTT, 10% v/v glycerol in the presence of 1 $\mu$Ci of [3-$^3$H]-L-threonine (15 Ci/mmol), ATP (2 mM) and MgCl$_2$ (5 mM).

The reaction is stopped by adding 150 $\mu$l of 25% trichloroacetic acid solution. The precipitated proteins are collected on a microfilter and washed with 3 times 400 $\mu$l of 7% trichloroacetic acid, before being eluted with twice 400 $\mu$l of N sodium hydroxide into a counting vial containing 1 ml of N HCl and 12 ml of scintillation cocktail (Beckmann Readygel). The amount of radioactivity contained in this vial is measured with a scintillation counter (PACKARD Minaxi TriCarb 4000). It represents the amount of threonine bound covalently to the desired peptide synthase.

The unit of enzymatic activity is defined as the amount of enzyme needed to bind 1 picomole of threonine covalently in 15 min under the conditions described above.

5.3.1.B. Purification of Pristinamycin I Synthase II

This experiment illustrates how an enzyme of S. pristinaespiralis SP92 participating in the biosynthesis pathway of pristinamycin IA may be purified.

Using the acid described above in Example 5.3.1.A., purification of the peptide synthase responsible for the incorporation of threonine and aminobutyric acid residues into the peptide chain of pristinamycin IA is carried out as described below, taking care to work at 4° C. and to store the active fractions at −70° C.

150 g of a centrifugation pellet, washed with 0.1M phosphate buffer pH 7.2 containing 10% v/v of glycerol, of an S. pristinaespiralis SP92 culture harvested at the beginning of the pristinamycin production phase are taken up with 450 ml of pH 8.0 100 mM Tris-HCl buffer containing 4 mM DTE, 1 mM benzamidine, 1 mM PMSF, 1 mM EDTA, 1 mM EGTA, 15% v/v glycerol. The suspension thereby obtained is ground using a French Press adjusted to a pressure of 5000 psi, and then centrifuged at 50,000 g for 1 hour. The crude extract thereby collected is injected in pH 8 100 mM Tris-HCl buffer, 4 mM DTE, 2 mM benzamidine, 2 mg/l leupeptin, 1 mg/l E-64, 15% v/v glycerol onto a column (200 ml) of Q Sepharose Fast Flow. The proteins are eluted with a linear KCl gradient (0 to 0.6M). At outflow from the column, each fraction is treated with one-tenth of its volume of a solution of 1 mM PMSF, 5 mM EDTA, 5 mM EGTA. The fractions containing the enzymatic activity (detected by means of the test described in Example 5.3.1.A) are pooled and reconcentrated by ultrafiltration on Centriprep 30 to a final volume of 28 ml. This concentrate is injected in 4-ml aliquots onto a Superdex 200 Hi-Load 16/60 permeation column equilibrated in pH 6.8 50 mM bis-tris propane buffer, 1 mM benzamidine, 4 mM DTE, 0.2 mM Pefabloc, 1 mM EDTA, 0.1M KCl, 20% v/v glycerol. After assaying, the active fractions are pooled and reconcentrated to 15 ml on Centriprep 30, then desalted on PD-10 in pH 8.0 100 mM Tris-HCl buffer, 4 mM DTE, 2 mM benzamidine, 2 mg/l leupeptin, 1 mg/l E-64, 20% v/v glycerol and applied in two portions to a MonoQ HR 10/10 column equilibrated and eluted with a linear gradient of from 0.4M KCl in this same buffer. The fractions containing the desired activity are pooled, reconcentrated on Centriprep 30 and then Centricon 30 to a final volume of 1 ml and injected in five portions onto a column of Superose 6 HR 10/30 in pH 6.8 50 mM bis-tris propane buffer, 1 mM benzamidine, 4 mM DTE, 0.2 mM Pefabloc, 1 mM EDTA, 0.1M KCl, 20% v/v glycerol. The activity peak is detected in this technique at a molecular weight centred at 450,000.

After this step the enzyme is pure and, in SDS-PAGE electophoresis, its molecular weight is estimated at approximately 240,000. This band also contains all radioactivity of the protein labelled by aminoacylation with tritiated threonine.

At this stage, the maximal activity of the enzyme using a concentration of 100 µCi/ml of threonine (15 ci/mmol) amounts to 3670 units/mg; the enzyme is also capable of forming adenylates with L-aminobutyric acid or L-alanine; an aminoacylation reaction of the enzyme with tritiated alanine is detected, and the maximal activity in the presence of 200 µCi/ml of [2,3-$^3$H]-L-alanine (15 Ci/mmol) is 2290 pmol/mg in 15 min.

TABLE 4

Purification of pristinamycin I synthase II

| Purification step | Vol. (ml) | Protein (mg) | Sp.Act.$^a$ (units/mg) | Yield (%) | Purification factor |
|---|---|---|---|---|---|
| Crude extract | 445 | 4700 | (1) | — | — |
| Q Sepharose | 308 | 834 | 7 | 100 | 1 |
| Superdex 200 | 120 | 105 | 22 | 40 | 3.1 |
| MonoQ HR | 15 | 11.5 | 96 | 19 | 14 |
| Superose 6 | 7.5 | 2.8 | 122 | 6 | 17 |

$^a$: The activity in the crude extract cannot be measured accurately.

The purification factor is calculated from the increase in specific activity of the fractions during the purification.

5.3.2. Production of Oligonucleotides from the Protein Sequence

This example describes how, starting from internal sequences of pristinamycin I synthase II, it is possible to synthesize oligonucleotides.

The internal sequences of the peptide synthase which is responsible for the incorporation of threonine and aminobutyric acid residues into the peptide chain of pristinamycin IA were deduced by microsequencing as described in Example 5.1.2. after trypsin hydrolysis and purification of the fragments obtained on a Vydac C18 column.

Sequences Internal to the Protein Pristinamycin I Synthase II (See residues 49 to 61 on SEQ ID NO: 27)

```
1     5      10
L A A F N D T A R P V P R
1     5      10      15     20
V P A A F V P L D A L P L T G N G V L D
```
(SEQ ID NO: 36)

From the underlined regions in these sequences, and in accordance with the degeneracy of the genetic code specific to Streptomyces (see Example 8), the following mixtures of oligonucleotides were snythesized:

Mixture Corresponding to the Underlined Portion of the Sequence 1 Internal to the Protein Pristinamycin I Synthase II

```
5'                                              3'
  GCC GCC TTC AAC GAC ACC GCC CGC CC
   G   G               G   G   G
```
(SEQ ID NO: 37)

Mixture Corresponding to the Underlined Portion of Sequence 2 Internal to the Protein Pristinamycin I Synthase II

```
5'                                              3'
  TTC GTC CCC CTC GAC GCC CTC CCC CT
   G   G   G       G   G   G
```
(SEQ ID NO: 38)

5.3.3. Labelling of the Mixtures of Synthetic Oligonucleotides and Southern Hybridization of Cosmid PIBV3 DNA This example describes how oligonucleotides specific for a gene for the biosynthesis of pristinamycins I may be radioactively labelled and then hybridized with a membrane onto which cosmid pIBV3 DNA has been transferred.

Labelling of the oligonucleotides is carried out by transfer at the 5'-terminal position of the [γ-$^{32}$P]phosphate group of ATP with T4 polynucleotide kinase, as described in 5.1.3.

Approximately 500 ng of the mixture of oligonucleotides were labelled in this way with $^{32}$P, and were used for Southern hybridization of pIBV3 DNA digested with different enzymes. These hybridizations enabled it to be shown that a portion of the structural gene for pristinamycin I synthase II was carried by cosmid pIBV3, and enabled the region containing this gene to be identified. Southern blotting and hybridization were carried out as described in Example 5.1.4.

The hybridization results enabled it to be shown that cosmid pIBV3 possessed a 6.2-kb SphI fragment containing the sequence homologous to the probes synthesized in Example 5.3.2.

5.4. Demonstration of the Presence of a Portion of the Structural Gene for Pristinamycin I Synthase III (SnbD) on Cosmid pIBV3

This example illustrates how it is possible to identify the presence of genes for the biosynthesis of pristinamycins I on a cosmid which has already been isolated (Example 5.1).

5.4.1. Identification of Pristinamycin I Synthase III Involved in the Incorporation of Proline and p-dimethylaminophenylalanine Residues into the Peptide Chain of Pristinamycin IA This example illustrates how the protein responsible for the incorporation of proline and p-dimethylaminophenylalanine residues into the peptide chain of pristinamycin IA may be purified to homogeneity from *S. pristinaespiralis* SP92.

5.4.1.A. Assay of Partial Activities of Pristinamycin I Synthase III

Figure 11:
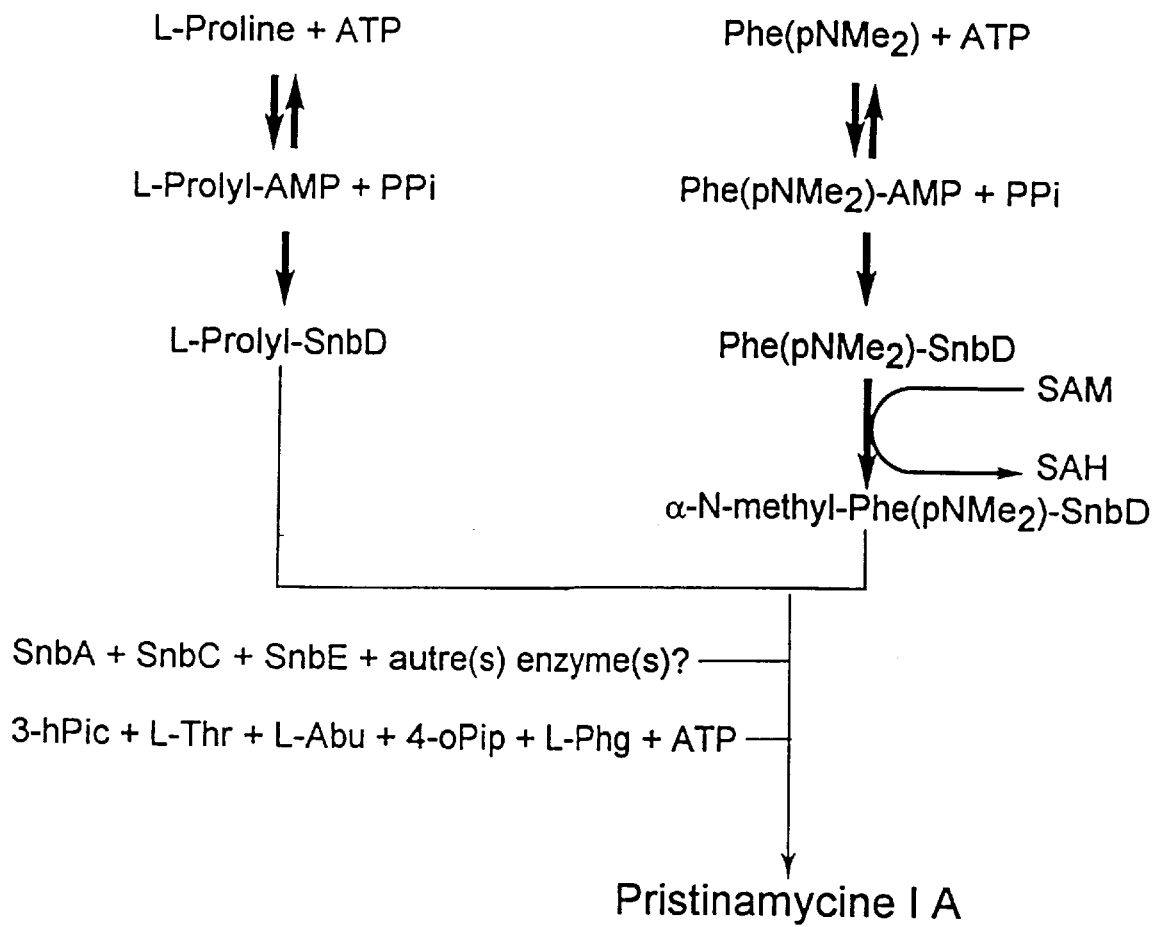
FIG. 11: Reaction catalysed by SnbD.

This example illustrates the assay of activities of the biosynthesis pathway of pristinamycin IA which have never before been described and which possess the noteworthy property of being expressed only during the period of production of pristinamycins. The activities in question are partial activities of the peptide synthase responsible for the incorporation of proline and para-dimethylaminophenylalanine residues into the peptide chain of pristinamycin IA (FIG. 11) in the presence of SAM, ATP and $MgCl_2$.

The proline:AMP ligase and p-dimethylaminophenylalanine:AMP ligase activities are measured in an enzymatic test of ATP-pyrophosphate exchange similar to that described in 5.2.1.A. for 3-hydroxypicolinic acid:AMP ligase.

The aminoacylation reactions of the enzyme with proline and p-dimethylaminophenylalanine make it possible to differentiate the peptide synthase from other enzymes which may perform a ATP-pyrophosphate exchange, and in particular aminoacyl-tRNA synthases. The same applies to the N-methylation of the α-amino function of p-dimethylaminophenylalanine acylated on the enzyme. The latter test characteristic of N-methylation is hence the one which was used in this example.

The enzyme fractions to be assayed (0.2 to 2 units) are incubated for 15 min at 27° C. in a total volume of 250 µl of pH 6.8 50 mM bis-tris propane buffer, 1 mM DTT, 10% v/v glycerol in the presence of 1 µCi of [methyl-$^3$H]-SAM (15 Ci/mmol), para-dimethylamino-L-phenylalanine (1 mM), ATP (2 mM) and $MgCl_2$ (5 mM).

The reaction is stopped by adding 150 µl of 25% trichloroacetic acid solution. The precipitated proteins are collected on a microfilter and washed with 3 times 400 µl of 7% trichloroacetic acid, before being eluted with twice 400 µl of N sodium hydroxide into a counting vial containing 1 ml N HCl and 12 ml of scintillation cocktail (Beckmann Readygel). The amount of radioactivity contained in this vial is measured with a scintillation counter (PACKARD Minaxi TriCarb 4000). It represents the amount of N-methylated para-dimethylaminophenylalanine bound covalently to the desired peptide synthase.

The unit of enzymatic activity is defined as the amount of enzyme needed to bind 1 picomole of N-methylated p-dimethylaminophenylalanine covalently in 15 min under the conditions described above.

5.4.1.B. Purification of Pristinamycin I Synthase III

This experiment illustrates how an enzyme of *S. pristinaespiralis* SP92 participating in the biosynthesis pathway of pristinamycin IA may be purified.

Using the assay described above in Example 5.4.1.A, purification of the peptide synthase responsible for the incorporation of proline and para-dimethylaminophenylalanine residues into the peptide chain of pristinamycin IA is carried out as described below, taking care to work at 4° C. and to store the active fractions at −70° C.

250 g of a centrifugation pellet, washed with 0.1M phosphate buffer pH 7.2, 1 mM PMSF, 5 mM EDTA, 5 mM EGTA, 0.5M KCl, 10% v/v glycerol, of an *S. pristinaespiralis* SP92 culture harvested at the beginning of the pristinamycin production phase are taken up with 750 ml of pH 8.0 100 mM Tris-HCl buffer containing 4 mM DTE, 5 mM benzamidine, 0.2 mM Pefabloc, 1 mM EDTA, 1 mM EGTA, 2 mg/l leupeptin, 2 mg/l STI, 2 mg/l aprotinin, 1 mg/l E-64, 20% v/v glycerol. The suspension thereby obtained is ground using a French Press adjusted to a pressure of 5000 psi, and then centrifuged at 50,000 g for 1 h. The crude extract thereby collected is fractionated by ammonium sulphate precipitation. The protein fraction coming out at between 0 and 35% ammonium sulphate saturation is redissolved in the disruption buffer and desalted on a column of Sephadex G 25 Fine equilibrated and eluted in this same buffer. The proteins thus prepared are injected in pH 8.0 100 mM Tris-HCl buffer, 4 mM DTE, 2 mM benzamidine, 2 mg/l leupeptin, 1 mg/l E-64, 20% v/v glycerol onto a column (200 ml) of Q Sepharose Fast Flow, and are then eluted with a linear KCl gradient (0 to 0.6M). At outflow from the column, each fraction is treated with one-tenth of its volume of a solution of 2 mM Pefabloc, 5 mM EDTA, 5 mM EGTA, 5 mM benzamidine. The fractions containing the enzymatic activity (detected by means of the test described in Example 5.4.1.A) are pooled and precipitated with ammonium sulphate at 80% saturation. The proteins which have come out are redissolved in pH 6.8 50 mM bis-tris propane buffer, 1 mM benzamidine, 1 mM DTE, 0.2 mM Pefabloc, 1 mM EDTA, 1 mM EGTA, 2 mg/l leupeptin, 0.15M NaCl, 20% v/v glycerol, and injected in 5 4-ml aliquot portions onto a Superdex 200 Hi-Load 16/60 permeation column equilibrated and eluted in this same buffer. After assay, the active fractions are pooled and reconcentrated to 3 ml on Centriprep 30, then rediluted to 20 ml with pH 8.0 100 mM Tris-HCl buffer, 4 mM DTE, 1 mM benzamidine, 1 mM PMSF, 20% v/v glycerol and applied in two portions to a MonoQ HR 10/10 column equilibrated and eluted with a linear gradient from 0.4M KCl in this same buffer. The best fractions containing the desired activity are pooled and used as material for characterization of the activities of the enzyme and for its microsequencing.

After this step, the enzyme is pure and, in SDS-PAGE electrophoresis, its molecular weight is estimated at approximately 250,000. This band also contains all the radioactivity of the protein labelled by aminoacylation with tritiated SAM and para-dimethylaminophenylalanine. In permeation on Superose 6 HR 10/30, the native molecular weight of the enzyme is estimated at 700,000.

At this stage, the enzyme is also capable of forming adenylates with proline; an aminoacylation reaction of the enzyme with tritiated proline is detected, and the maximal activity in the presence of 200 µCi/ml of [5-$^3$H]-L-proline (34 Ci/mmol) is 2490 pmol/mg in 15 min.

TABLE 5

Purification of pristinamycin I synthase III

| Purification Step | Vol. (ml) | Protein (mg) | Sp.Act.[a] (units/mg) | Yield (%) | Purification factor |
|---|---|---|---|---|---|
| Crude extract | 800 | 8100 | (4) | — | — |
| 35% A.S. | 200 | 4000 | (6) | — | — |
| Q Sepharcae | 132 | 498 | 46 | 100 | 1 |
| Superdex 200 | 45 | 39.5 | 417 | 71 | 9 |
| MonoQ HR | 9 | 5.3 | 1070 | 25 | 23 |

[a]: The activity in the crude extract and after ammonium sulphate precipitation cannot be measured accurately.

The purification factor is calculated from the increase in specific activity of the fractions during the purification.

5.4.2. Production of Oligonucleotides from the Protein Sequence

This example describes how, starting from internal sequences of pristinamycin I synthase III, it is possible to synthesize oligonucleotides.

An internal sequence of the peptide synthase responsible for the incorporation of proline and para-dimethylaminophenylalanine residues into the peptide chain of pristinamycin IA was deduced by micro-sequencing as described in Example 5.1.2. after cyanogen bromide treatment and purification of the fragments obtained on a Vydac C18 HPLC column.

Sequence Internal to the Protein Pristinamycin I Synthase III 1 (see residues 2 to 20 on SEQ ID NO: 28)
1     5     10     15     20
P—V T P Y R A Y A L A H L A G—D D D From the underlined region in this sequence, and in accordance with the degeneracy of the genetic code specific to Streptomyces (see Example 8), the following mixture of oligonucleotides was synthesized:

Mixture Corresponding to the Underlined Portion of the Sequence Internal to the Protein Pristinamycin I Synthase III

```
5'                                    3'
GTC  ACC  CCG  TAC  CGC  GCC  TAC
 G    G    C          G    G
(SEQ ID NO: 39)
```

5.4.3. Labelling of the Mixtures of Synthetic Oligonucleotides and Southern Hybridization of Cosmid pIBV3 DNA This example describes how oligonucleotides specific for a gene for the biosynthesis of pristinamycins I may be radioactively labelled and then hybridized with a membrane onto which cosmid pIBV3 DNA has been transferred.

Labelling of the oligonucleotides is carried out by transfer at the 5'-terminal position of the [$\gamma$-$^{32}$P]phosphate group of ATP with T4 polynucleotide kinase, as described in 5.1.3.

Approximately 500 ng of the mixture of oligonucleotides were labelled in this way with $^{32}$P, and were used for Southern hybridization of pIBV3 DNA digested with different enzymes. These hybridizations enabled it to be shown that a portion of the structural gene for pristinamycin I synthase III was carried by cosmid pIBV3, and enabled the region containing this gene to be identified. Southern blotting and hybridization were carried out as described in Example 5.1.4.

The hybridization results enabled it to be shown that cosmid pIBV3 possessed an 8.4-kb SphI fragment containing the sequence homologous to the probes synthesized in Example 5.4.2.

5.5. Demonstration of the Presence of a Portion of the Structural Gene for Pristinamycin I Synthase IV (SnbE) on Cosmid pIBV3

This example illustrates how it is possible to identify the presence of genes for the biosynthesis of pristinamycins I on a cosmid which has already been isolated (Example 5.1).

5.5.1. Identification of the Peptide Synthase (Referred to as Pristinamycin I Synthase IV) Responsible for the Incorporation of the Phenylglycine Residue into the Peptide Chain of Pristinamycin IA

Figure 12:
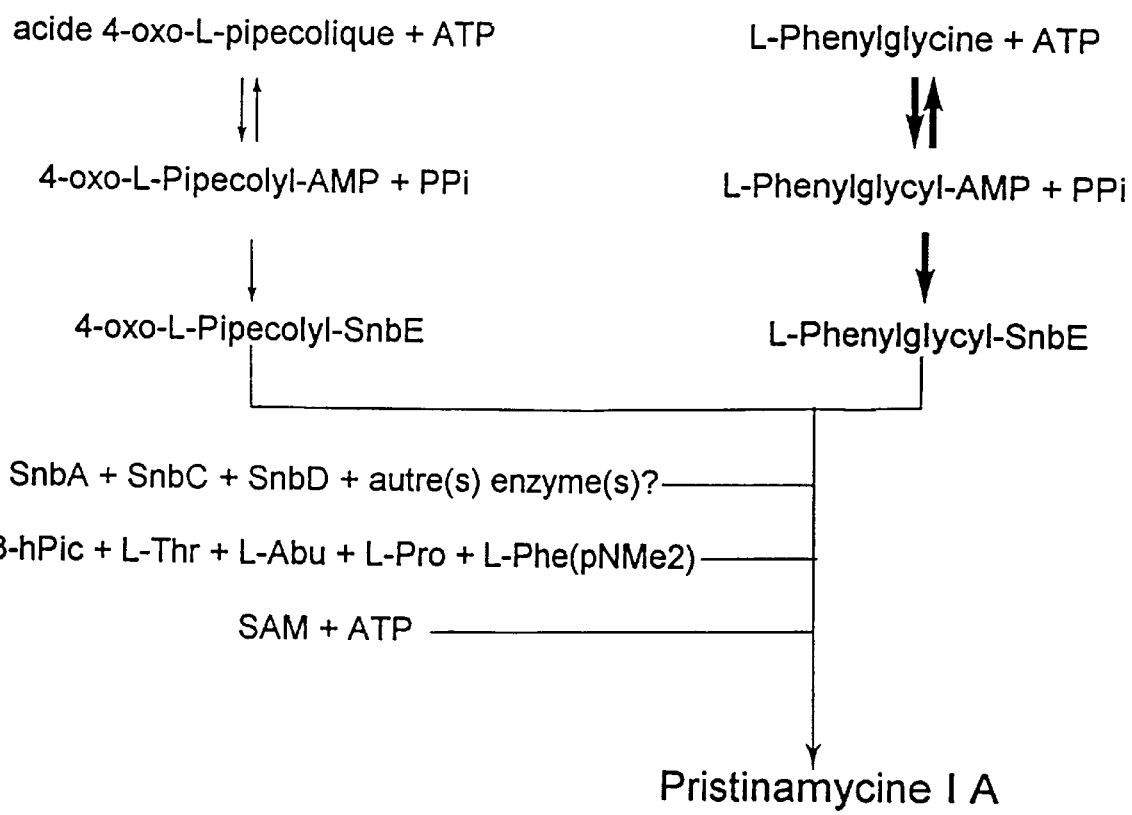
FIG. 12: Reaction catalysed by SnbE.

5.5.1.A. Assay of Enzymatic Activities Carried by the Peptide Synthase (Pristinamycin I Synthase IV) Responsible for the Incorporation of the Phenylglycine Residue into the Peptide Chain of Pristinamycin IA This example illustrates the assay of an enzymatic activity of the biosynthesis pathway of pristinamycin IA which has not been described hitherto and which possesses the noteworthy property of being expressed only during the period of production of pristinamycins in the wild-type microorganism. The activity in question is that of the peptide synthase (pristinamycin I synthase IV) responsible for the incorporation of the L-phenylglycine residue into the peptide chain (FIG. 12) in the presence of ATP and $MgCl_2$. The phenylglycine:AMP ligase activity of pristinamycin I synthase IV is measured in an enzymatic test of ATP-pyrophosphate exchange similar to that described in 5.2.1.A. for 3-hydroxypicolinic acid:AMP ligase activity, in the presence of L-phenylglycine (1 mM) and KCl (50 mM) in the incubation buffer.

5.5.1.B. Purification of the Peptide Synthase Responsible for the Incorporation of the Phenylglycine Residue (Pristinamycin I Synthase IV) into the Peptide Chain of Pristinamycin IA This example illustrates how an enzyme of *S. pristinaespiralis* SP92 participating in the biosynthesis pathway of pristinamycin IA may be purified. Using the assay described above in Example 5.5.1.A. The purification of pristinamycin I synthase IV is carried out as described below. All the operations are performed at 4° C. The fractions containing the activity are frozen immediately and stored at −70° C.

70 g of wet cells, harvested as described in Example 5.2.1.B., are resuspended in 250 ml of cell lysis buffer (100 mM Tris-HCl pH 8.0 containing 25% of glycerol, 4 mM DTE, 1 mM EGTA, 1 mM EDTA, 1 mM PMSF, 1 mg/l E-64, 2 mg/l STI, 2 mg/l $\alpha_2$-macroglobulin, 1 mg/l leupeptin, 2 mg/l aprotinin, 5 mM benzamidine, 0.6 mg/ml lysozyme. The solution thereby obtained is kept stirring at 4° C. for 1 h and then centrifuged at 50,000 g for 1 h. The supernatant is then injected in the cell lysis buffer onto a column of Sephadex G-25, and the excluded fraction (approximately 250 mg of protein injected in each chromatographic run) is injected onto a column of Mono Q HR 16/10 (Pharmacia) equilibrated with 100 mM Tris-HCl buffer pH 8.0, 4 mM DTE, 1 mM EGTA, 1 mM EDTA, 1 mg/l E-64, 2 mg/l STI, 20% glycerol. The proteins are eluted with a linear gradient of from 0 to 0.6M KCl and, at outflow from the column, each fraction is treated with one-tenth of its volume of a solution of 2 mM Pefabloc, 5 mM EGTA, 5 mM EDTA. The fractions containing the activity are pooled and then mixed with 1 volume of 100 mM Tris-HCl pH 8.0, 15% glycerol, 1 mM PMSF, 1 mM benzamidine, 4 mM DTT, 3.4M ammonium sulphate per 3 volumes of fraction. The solution is injected onto a column of Phenyl Superose HR 10/10 (one-fifth of the solution is injected at each chromatographic run), and the proteins are eluted with a decreasing linear gradient of from 0.9 to 0M ammonium sulphate. The fractions containing the activity are pooled. The solution is concentrated to 3500 μl in a Centriprep 30 and injected in two portions onto a Superdex 200 Hi-Load 16/60 column equilibrated and eluted with 50 mM bis-tris propane buffer pH 6.8 containing 20% of glycerol, 0.15M NaCl, 4 mM DTT, 1 mM PMSF, 1 mM benzamidine, 1 mM EDTA. The active fraction is diluted with 9 volumes of 50 mM bis-tris propane buffer pH 6.8 containing 25% of glycerol, 4 mM DTT, 1 mM PMSF, 1 mM benzamidine, and then injected onto a column of Mono Q HR 5/5 equilibrated in the same buffer. The desired activity is eluted with a linear gradient of from 0 to 0.4M KCl and concentrated to 630 μl in a Centricon-30. The desired protein is then purified by electrophoresis on 6% polyacrylamide gel after denaturation of the sample by heating for 10 min at 80° C. with an SDS/mercaptoethanol mixture. After electrophoresis and staining of the gel with Coomassie blue, the gel band containing the protein is cut out and the protein is electroeluted from the gel in a Centrilutor.

Note: the band corresponding to pristinamycin I synthase IV is identified by comparison with a tritiated (by covalent binding to tritiated phenylglycine; see description in Example 5.5.2.) pristinamycin I synthase IV standard.

After this step, the enzyme is pure in electrophoresis (SDS-PAGE). Its molecular weight is estimated at approximately 170,000.

5.5.2. Labelling of Pristinamycin I Synthase IV by Thioesterification of Radioactive Phenylglycine on the Enzyme After activation in the form of an adenylate through phenylglycine:AMP ligase activity, phenylglycine is transferred to a thiol group of the active site of the enzyme before being incorporated into the peptide chain during elongation (general process of biosynthesis of peptide antibiotics known by the name of "thiotemplate mechanism"). Generally speaking, radioactive labelling of the protein effecting the activation of amino acid may hence be performed by preparing the thioester derivative with a radioactive form of the amino acid.

As an example, the radioactive labelling of pristinamycin I synthase IV is accomplished by incubating 50 μg of the protein (active fraction emerging from the Mono Q HR 5/5 chromatography column; see above in Example 55.1.B.) for 1 hour at 27° C. with 100 μCi of (RS)-2-phenyl[2-$^3$H] glycine (18 Ci/mmol; Amersham) in 70 μl of 50 mM bis-tris propane buffer pH 6.8 containing 20% of glycerol, 25 mM MgCl$_2$, 5 mM ATP, 0.15M NaCl, 4 mM DTT, 1 mM PMSF, 1 mM benzamidine, 1 mM EDTA. After denaturation (SDS alone without mercaptoethanol), the proteins are separated by electrophoresis (SDS-PAGE, 6% gel) and visualized with Coomassie blue. Analysis of the radioactivity profile by counting the protein bands as well as by autoradiography (Hyperfilm MP; fluorography after impregnation of the gel with Amersham Amplify) discloses a single radioactive band with a molecular weight of 170,000.

TABLE 6

Purification of pristinamycin I synthase IV

| Purification Step | Protein (mg) | Sp.Act. (cmp/mg)[a] | Protein (mg) | Purification factor |
|---|---|---|---|---|
| Crude extract | 2200 | 3.6 | — | — |
| Mono Q 16/10 | 136 | 58 | 100 | 16 |
| Phenyl Superose | 32.6 | 175 | 72 | 49 |
| Superdex 200 | 3.1 | 870 | 34 | 240 |
| Mono Q 515 | 2.0 | 1000 | 25 | 280 |
| Electroelution SDS-PAGE | 0.1 | — | — | — |

[a]The specific activity cannot be measured accurately in the crude extract owing to the high level of non-phenylglycine-dependent ATP-pyrophosphate exchange. The specific activity value was calculated from the number of units present at emergence from the first chromatographic step expressed with reference to the amount of protein in the crude extract.

5.5.3. Other Activities Carried by Pristinamycin I Synthase IV

Purification of the peptide synthase responsible for the incorporation of phenylglycine, described in Example 5.5.2., led to a pure protein of molecular weight 170,000. This protein does not activate the other amino acids tested, especially pipecolic acid or 4-oxopipecolic acid. A second preparation of this protein, performed under the conditions described in 5.5.1.B. eliminating, however, the Phenyl Superose step, starting from another culture of *S. pristinaespiralis* SP92, the crude extract of which was prepared in a French Press as described in 5.4.1B, led to a protein which, at emergence from the Mono Q HR 5/5 step, was equivalent in purity to that obtained at the same step in the example described in 5.5.1.B., but possessed a molecular weight of approximately 250,000 in SDS-PAGE. This new preparation was competent for the activation and thioesterification of phenylglycine, but possessed, in addition, an ATP-pyrophosphate exchange activity with L-pipecolic acid (1 mM) in the exchange test similar to that described in 5.2.1.A. for 3-hydroxypicolinic acid. Moreover, it could be shown that the 170,000 protein does not possess ATP-pyrophosphate exchange activity with L-pipecolic acid even in preparations of the protein that are still very impure. It should be noted that *S. pristinaespiralis* SP92 naturally produces small amounts of a pristinamycin IA analogue having a pipecolic acid residue in place of 4-oxopipecolic acid. Hence this demonstrates that the peptide synthase responsible for the incorporation of phenylglycine (pristinamycin I synthase IV) also catalyses the incorporation of the preceding residue (probably pipecolic acid). The difference in molecular weight obtained for pristinamycin I synthase IV in the two preparations (170,000 and 250,000) is attributed to a phenomenon of partial proteolytic cleavage in the first case, leading to loss of the activity of activation of L-pipecolic acid.

5.5.4. Synthesis of Oligonucleotides from the Protein Sequence

This example describes how, starting from an internal sequence of pristinamycin I synthase IV, it is possible to set about testing for the corresponding gene using suitably chosen oligonucleotides.

An internal sequence of pristinamycin I synthase IV of 15 amino acids was identified after cyanogen bromide cleavage of the purified protein and purification of the fragments obtained on a Vydac C18 HPLC column.

Sequence Internal to the Protein Pristinamycin I Synthase IV (See residues 82 to 98 on SEQ ID NO: 31)
1    5    10    15
V T V F L N N T R L I O N F R P R—F—G D From the underlined region in this sequence, and in accordance with the degeneracy of the genetic code specific to Streptomyces (see Example 8), the following mixture of oligonucleotides was synthesized:

Mixture corresponding to the underlined portion of the internal sequence of the protein pristinamycin I synthase IV:

```
5'                                              3'
    ACG  CGC  CTC  ATC  CAG  AAC  TTC  CGC  CC
         C    G    G                        G
              T                   T
(SEQ ID NO: 40)
```

5.5.5. Labelling of the Mixtures of Synthetic Oligonucleotides and Southern Hybridization of Cosmid pIBV3 DNA This example describes how oligonucleotides specific for a gene for the biosynthesis of pristinamycins I may be radioactively labelled and then hybridized with a membrane onto which cosmid pIBV3 DNA has been transferred.

Labelling of the oligonucleotides is carried out by transfer at the 5'-terminal position of the [γ-$^{32}$P]phosphate group of ATP with T4 polynucleotide kinase, as described in 5.1.3.

Approximately 500 ng of the mixture of oligonucleotides were labelled in this way with $^{32}$P, and were used for Southern hybridization of pIBV3 DNA digested with different enzymes. These hybridizations enabled it to be shown that a portion of the structural gene for pristinamycin I synthase II was carried by cosmid pIBV3, and enabled the region containing this gene to be identified. Southern blotting and hybridization were carried out as described in Example 5.1.4.

The hybridization results enabled it to be shown that cosmid pIBV3 possessed a 6.6-kb SphI fragment containing the sequence homologous to the probes synthesized in Example 5.5.4.

5.6. Isolation of Cosmid pIBV4 Containing the Structural Gene for FMN Reductase (snaC)

This example illustrates how it is possible to obtain a cosmid as constructed in Example 3 containing at least one gene for the biosynthesis of PII.

5.6.1. Identification of FMN Reductase Associated with Pristinamycin IIA Synthase This example illustrates how the protein responsible for reduction of FMN by NADH to form the FMNH$_2$ needed for the reaction catalysed by pristinamycin IIA synthase may be purified to homogeneity from S. pristinaespiralis SP92.

5.6.1.A. Assay of FMN Reductase Activity

Figure 13:
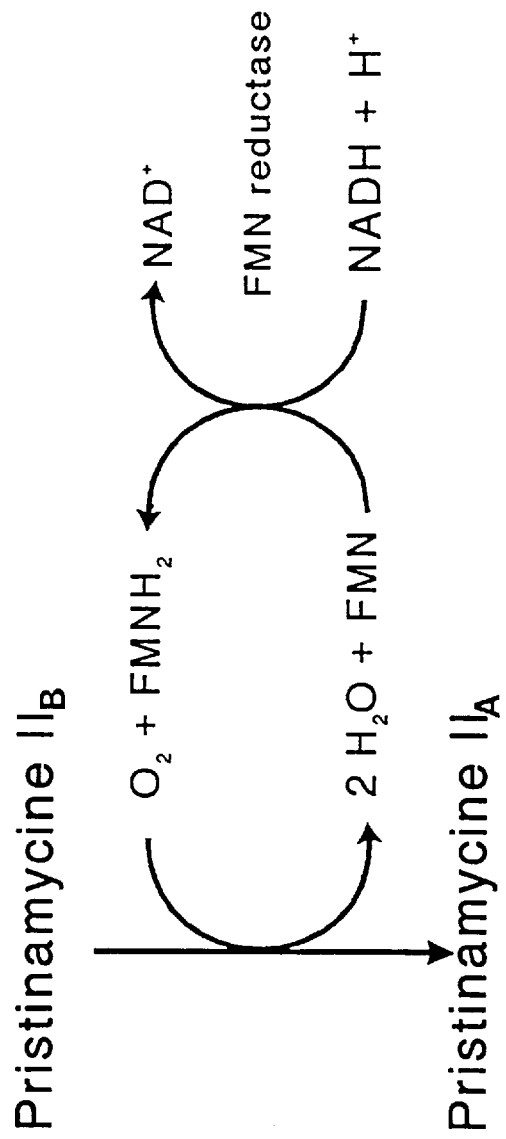
FIG. 13: Reaction catalysed by SnaC.

This example illustrates the assay of an activity of the biosynthesis pathway of pristinamycin IIA which has never before been described and which possesses the noteworthy property of being expressed only during the period of production of pristinamycins. The enzyme in question is FMN reductase, also referred to as NADH:FMN oxidoreductase, which catalyses the reduction of FMN to FMNH$_2$ (FIG. 13) in the presence of NADH. FMN reductases catalysing the same reaction which are specific or otherwise for NADH or NADPH and associated with other biosynthesis pathways have been described elsewhere (Duane et al., 1975, Jablonski et al., 1977, Watanabe et al., 1982).

Two assays are used to detect this activity:

The first is based on a coupling with the pristinamycin IIA synthase described in Example 5.1.1., and is used for the first steps of the purification. The enzyme fractions to be assayed (0.002 to 0.005 units) are incubated for 1 hour at 27° C. in a total volume of 500 $\mu$l of 50 mM bis-tris propane buffer pH 6.8 containing NADH (500 $\mu$M), FMN (2 $\mu$M), pristinamycin IIB (20 $\mu$M) and 0.01 units of pristinamycin IIA synthase described in Example 5.1.1. The pristinamycin IIA formed is assayed by HPLC as described in Example 5.1.1.A.

The unit of enzymatic activity is defined as the amount of enzyme needed to synthesize 1 $\mu$mol of pristinamycin IIA per minute under the conditions described above.

The second assay is a spectrophotometric assay, and can be employed only with at least partially purified fractions. The enzyme fractions to be assayed (0.006 to 0.030 units) are incubated for 13 min at 27° C. in a total volume of 3 ml of 50 mM bis-tris propane buffer pH 6.8 containing NADH (500 $\mu$M) and FMN (2 $\mu$M). After 7 min of incubation, 6 readings of the optical density at 340 nm taken at 1-min intervals are performed against a reference curve without enzyme. The activity in $\mu$mol/min is calculated by dividing the slope of decrease per min in the optical density by a factor of 6.2 (optical density of 1 mol of NADH at 340 nm).

The unit of enzymatic activity is defined as the amount of enzyme needed to consume 1 $\mu$mol of NADH per minute under the conditions described above.

5.6.1.B. Purification of S. pristinaespiralis SP92 FMN Reductase

This experiment illustrates how an enzyme of S. pristinaespiralis SP92 participating in the biosynthesis pathway of pristinamycin IIA may be purified.

Using the assays described above in Example 5.6.1.A., the purification of FMN reductase is carried out as described below, taking care to freeze and store the active fractions at −30° C. between successive steps if necessary.

500 g of a centrifugation pellet, washed with 0.1M phosphate buffer pH 7.2 containing 10% v/v of glycerol, of an S. pristinaespiralis SP92 culture harvested at the beginning of the pristinamycin production phase are taken up with 1500 ml of 50 mM bis-tris propane buffer pH 6.8 containing 5 mM DTT, 10% v/v of glycerol and 0.2 mg/ml of lysozyme. The suspension thereby obtained is incubated for 45 min at 27° C. and then centrifuged at 50,000 g for 1 hour. The crude extract thereby collected is fractionated by ammonium sulphate precipitation. The protein fraction precipitating at between 40 and 75% saturation is desalted on a column of Sephadex G-25 Fine and then injected in pH 6.8 50 mM bis-tris propane buffer, 5 mM DTT, 10% v/v glycerol onto a column (300 ml) of Q Sepharose Fast Flow. The active proteins are not retained on the column, and they are desalted on a column of Sephadex G-25 Fine and then reinjected in pH 8.2 50 mM Tris-HCl buffer, 5 mM DTT, 10% v/v glycerol onto a column (35 ml) of Q Sepharose Fast Flow and eluted with a linear KCl gradient (0 to 0.5M). The fractions containing the enzymatic activity (detected by means of the first test described in Example 5.6.1.A) are pooled, desalted on a column of Sephadex G-25 Fine and then injected in pH 8.2 50 mM Tris-HCl buffer, 5 mM DTT, 10% v/v glycerol onto a MonoQ HR 10/10 column. The proteins retained are eluted directly by the same buffer to which 0.2M KCl has been added. They are collected in a volume of 1 ml, which is immediately reinjected onto a column of Superdex 75 HR 10/30 eluted with pH 6.8 50 mM bis-tris propane buffer, 1 mM DTT, 10% v/v glycerol. The fractions containing the desired activity (detected from this step onwards by means of the spectrophotometric test as described in Example 5.6.1.A) are pooled and the total volume of the pool is made to 7 ml; these 7 ml are injected onto a column packed with 8 ml of FMN-agarose; the column is washed with pH 6.8 50 mM bis-tris propane buffer, 1 mM DTT, 10% v/v glycerol, and then eluted with the same buffer containing 10 μM FMN. The active fractions are pooled, desalted on PD-10 columns, injected in pH 8.2 50 mM Tris-HCl buffer, 5 mM DTT, 10% v/v glycerol onto a MonoQ HR 5/5 column and eluted with a linear KCl gradient (0 to 0.25M).

After this step, the enzyme is pure. In SDS-PAGE electrophoresis, a single fairly broad band is seen, centred at a molecular weight estimated at 28,000, while, in Bio-Sil SEC 125 gel permeation chromatography, this protein forms a symmetrical peak centred around a molecular weight of approximately 30,000.

For sequencing, the protein is desalted on a 25-cm Vydac C4 column eluted with a linear gradient of from 30 to 70% of acetonitrile in water containing 0.07% of trifluoroacetic acid.

TABLE 7

Purification of FMN reductase

| Purification Step | Vol. (ml) | Protein (mg) | Sp.Act.$^{a,b}$ (units/mg) | Yield (%) | Purification factor |
|---|---|---|---|---|---|
| Crude extract | 1620 | 5100 | 0.004$^a$ | 100 | 1 |
| 40–75% A.S. | 155 | 2930 | 0.005$^a$ | 69 | 1.2 |
| Q Seph. pH 6.8 | 357 | 180 | 0.058$^a$ | 49 | 14 |
| Q Seph. pH 9.2 | 153 | 15 | 0.36$^a$ | 25 | 85 |
| MonoQ HR 10/10 | 1.0 | 8.8 | 0.50$^a$ 4.4$^b$ | 19 | 120 |
| Superdex 75 | 1.5 | 3.1 | 7.4$^b$ | 12 | 200 |
| FMN-agarose | 7.5 | 0.28 | 96$^b$ | 14 | 2600 |
| MonoQ HR 5/5 | 3.0 | 0.29 | 68$^b$ | 11 | 1900 |
| Bio-Sil 125 | 7.5 | 0.18 | 106$^b$ | 10 | 2900 |

$^a$: assay coupled to pristinamycin IIA synthase
$^b$: spectrophotometric assay The purification factor is calculated from the increase in specific activity of the fractions during the purification.

5.6.2. Production of Oligonucleotides from the Protein Sequence

This example describes how, starting from NH$_2$-terminal and internal sequences of the protein FMN reductase, it is possible to synthesize oligonucleotides The NH$_2$-terminal sequence of FMN reductase was deduced by microsequencing as described in Example 5.1.2. About 30 residues were identified in this way.

(NH$_2$-Terminal sequences beginning at the 4th and at the 11th residue were also found in the sample sequenced.)

Two sequences internal to FMN reductase, of 13 and 21 amino acids, were also identified after trypsin hydrolysis and purification of fragments obtained on a Vydac C18 column.

NH$_2$-Terminal Sequence of the Protein FMN Reductase (See residues 2 to 25 on SEQ ID NO: 22)
1      5      10      15      20      25
T G A D D P A R P A V G P Q S F R D A M A Q L A S P V Internal Sequences of the Protein FMN Reductase (See residues 102 to 122 on SEQ ID NO: 22)
1      5      10      15      20
F A G G E F A A W D G T G V P Y L P D A K (See residues 149 to 161 on SEQ ID NO: 22)
1      5      10
T G D P A K P P L L W Y R From the underlined regions in each of the sequences, and in accordance with the degeneracy of the genetic code specific to Streptomyces (see Example 8), the following mixtures of oligonucleotides were synthesized:

Mixture Corresponding to the NH$_2$-terminal Sequence of the Protein FMN Reductase

```
5'                                               3'
 TTC CGC GAC GCC ATG GCC CAG CTC GC
      G       G       G       G
(SEQ ID NO: 41)
```

Mixtures Corresponding to the Internal Sequences of the Protein FMN Reductase

```
5'                                                          3'
TTC GCC GGC GGC GAG TTC GCC GCC TGG GAC GGC ACC GG
     G   G   G           G   G               G
(SEQ ID NO: 42)
```

```
5'                                          3'
GAC CCC GCC AAG CCC CCC CTG CTG TGG TAC CG
     G           G   G   C   C
(SEQ ID NO: 43)
```

5.6.3. Labelling of the Mixtures of Synthetic Oligonucleotides and Hybridization of the Genomic DNA Libraries of S. pristinaespiralis SP92

This example describes how oligonucleotides specific for a gene for the biosynthesis of pristinamycins may be radioactively labelled and then hybridized with membranes onto which DNA of genomic libraries of S. pristinaespiralis has been transferred.

Labelling the oligonucleotides is carried out by transfer at the 5'-terminal position of the [$\gamma$-$^{32}$P]phosphate group of ATP with T4 polynucleotide kinase, as described in Example 5.1.3.

Approximately 2×500 ng of each mixture of oligonucleotides were labelled in this way with $^{32}$P and were used to hybridize each of the two libraries.

Hybridization of the membranes of each library was carried out as described in Example 5.1.3.

5.6.4. Isolation of Cosmid pIBV4 and Determination of the Region Containing the Structural Gene for FMN Reductase (snaC)

Cosmid pIBV4 was isolated from a clone of the library produced in E. coli strain HB101 which hybridized with all three mixtures of oligonucleotides simultaneously.

Figure 7:
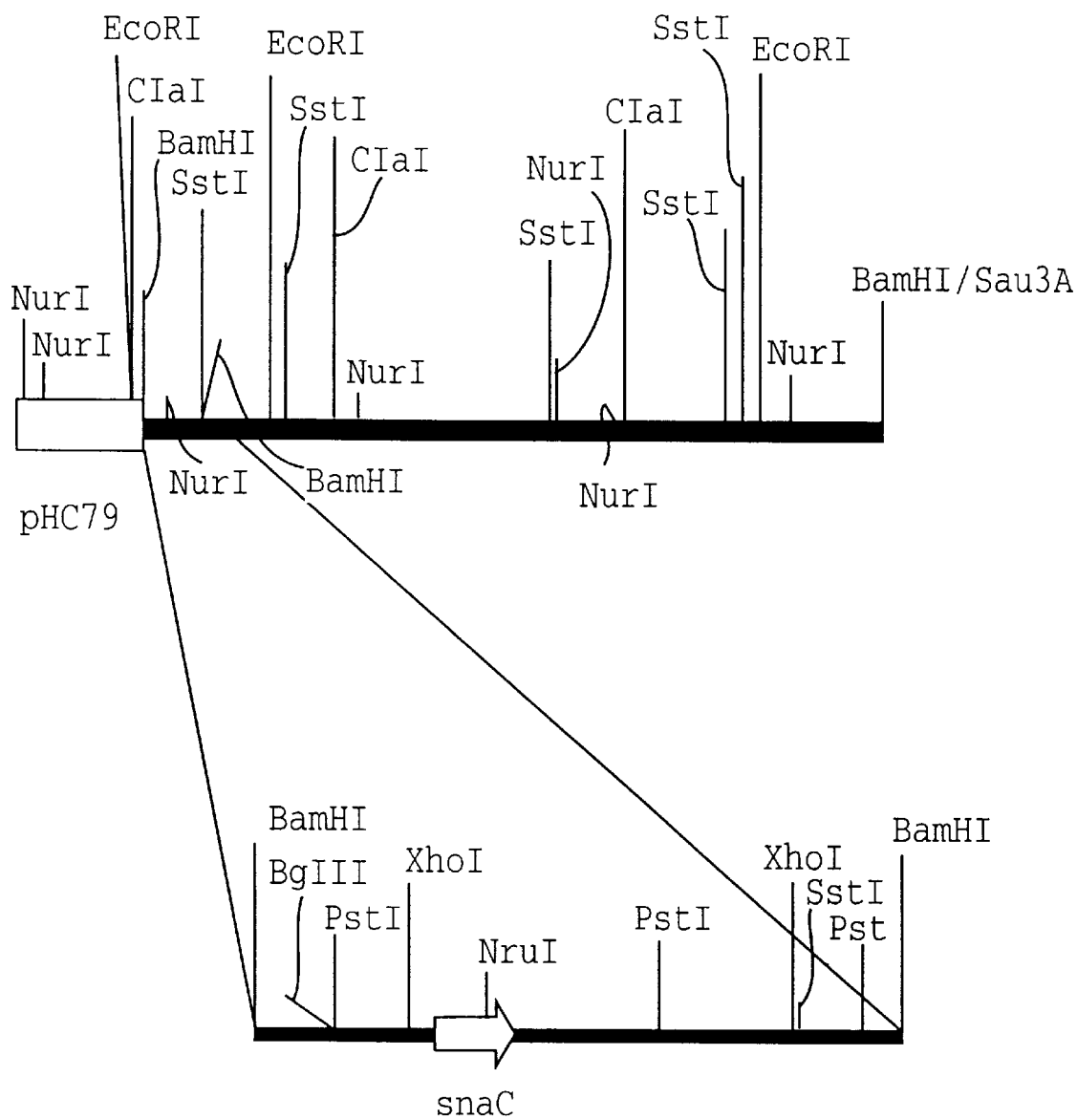
FIG. 7: Diagram of cosmid pIBV4.

This cosmid was purified as described in Example 2. It contains a genomic DNA insert of S. pristinaespiralis SP92 whose size was estimated at 48 kb. A map (FIG. 7) was established from digestions with different restriction enzymes, as described in 5.1.4.

Southern hybridizations of pIBV4 DNA, digested by means of different enzymes, with the mixtures of oligonucleotides enabled the region containing snaC, the structural gene for FMN reductase, to be identified. Southern blotting and hybridizations were carried out as described in Example 5.1.4.

The hybridization results enabled it to be shown that cosmid pIBV4 possessed a 4-kb BamHI-BamHI fragment containing the sequences homologous to the probes synthesized in Example 5.6.3.

5.7 Demonstration of the Presence of the Structural Gene for p-aminophenylalanine (phenyl-N)-methyltransferase on Cosmid pIBV2

This example illustrates how it is possible, starting from a purified protein, to identify the corresponding structural gene from among the genes which have already been analysed and sequenced as described in Examples 6.7 and 7.8 and which have also been expressed in E. coli as described in Example 11.

5.7.1. Identification and Purification of the Protein Involved in the Methylation of p-aminophenylalanine to p-dimethylaminophenylalanine This example illustrates how the protein responsible for the methylation of p-aminophenylalanine to p-dimethylaminophenylalanine [p-aminophenylalanine (phenyl-N)-methyltransferase] may be purified to homogeneity from S. pristinaespiralis strain SP92, and how it may also be obtained pure from a recombinant strain of E. coli.

Figure 14:
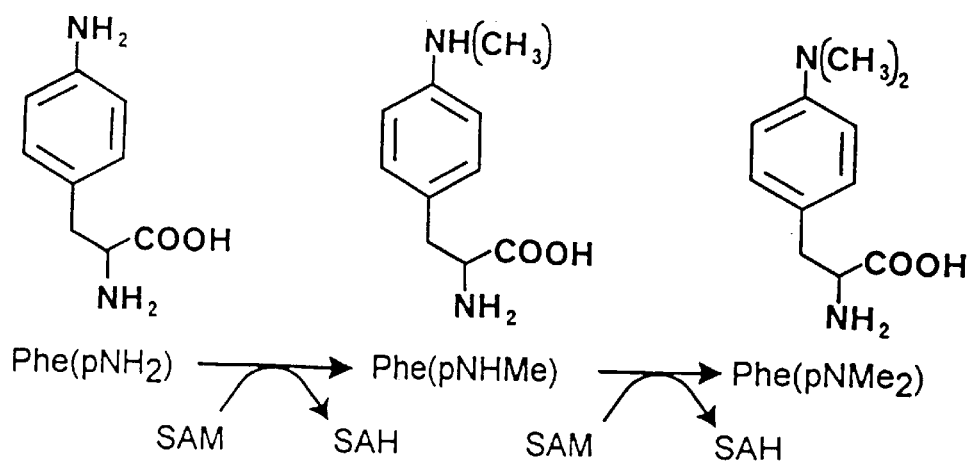
FIG. 14: Reaction catalysed by PapM.

5.7.1.A. Assay of the Activity of Methylation of p-aminophenylalanine to p-methylaminophenylalanine and of the Activity of Methylation of p-methylaminophenylalanine to p-dimethylaminophenylalanine This example illustrates the assay of two terminal activities of the biosynthesis of p-dimethylaminophenylalanine, a component of pristinamycin IA. These activities have never before been described, and possess the noteworthy property of being expressed only during the period of production of pristinamycins. They are the methylation of p-aminophenylalanine to p-methylaminophenylalanine (methylation 1) on the one hand, and the methylation of p-methylaminophenylalanine to p-dimethylaminophenylalanine (methylation 2), both of these activities utilizing SAM as a methyl group donor (FIG. 14).

The enzyme fractions to be assayed (1 to 20 units) are incubated for 30 min at 27° C. in a total volume of 200 $\mu$l of pH 6.8 50 mM bis-tris propane buffer containing SAM (200 $\mu$M) in which the methyl group is radioactively labelled with isotope 14 of the carbon atom (2 Ci/mol), in the presence of p-amino-L-phenylalanine (1 mM) for the assay of methylation 1 or of p-methylamino-L-phenylalanine (2.5 mM) for the assay of methylation 2.

The reaction is stopped by adding 16 $\mu$l of 37% hydrochloric acid and then 20 $\mu$l of sodium heptane sulphonate as a concentration of 240 g/l. After centrifugation, 150 $\mu$l of supernatant are injected into the HPLC system in the following gradient mode:

| | |
|---|---|
| mobile phase: | eluent A = 1.2 g of sodium heptanesulphonate + 2.5 ml of glacial acetic acid + water (qs 1000 ml) |
| | eluent B = 1.2 g of sodium heptanesulphonate + 2.5 ml of glacial acetic acid + 300 ml of acetonitrile + water (qs 1000 ml) |
| | gradient: t(min)  % B |
| | 0          30 |
| | 16         30 |
| | 17         100 |
| | 20         100 |
| | 21         30 |
| | 25         30 |
| stationary phase: | 150 × 4.6 mm Nucleosil 5 $\mu$m C18 column (Macherey-Nagel) |

At outflow from the column, the substrates and products of the enzymatic reaction are quantified by absorption at 254 nm. This detection is coupled to an in-line radiochemical detection by means of a Berthold LB506 detector equipped with a type GT400-U4 solid scintillation cell. This enables the incorporation of radioactive methyl groups into the reaction products to be monitored specifically.

The unit of enzymatic activity for methylation 1 (for methylation 2) is defined as the amount of enzyme needed to incorporate 1 nmol of methyl groups into p-aminophenylalanine (into p-methylaminophenylalanine).

5.7.1.B. Purification from S. pristinaespiralis SP92 of the SAM-dependent N-methyltransferase Catalysing the Methylation of p-aminophenylalanine to p-dimethylaminophenylalanine [p-aminophenylalanine (phenyl-N)-methyltransferase]

This experiment illustrates how an enzyme of S. pristinaespiralis SP92 participating in the biosynthesis pathway of pristinamycin IA may be purified.

Using the assay described above in Example 5.7.1.A, the purification of the SAM-dependent N-methyltransferase is carried out as described below, taking care to freeze and store the active fractions at −70° C. between successive steps if necessary.

240 g of a centrifugation pellet, washed with pH 7.2 100 mM phosphate buffer, 1 mM PMSF, 5 mM EDTA, 5 mM EGTA, 0.5M KCl, 10% v/v glycerol, of an *S. pristinaespiralis* SP92 culture harvested at the beginning of the pristinamycin production phase are taken up in 480 ml of pH 8.0 0.1M Tris-HCl buffer containing 4 mM DTE, 5 mM benzamidine, 0.2 mM Pefabloc, 100 μg/l E-64, 2 mg/l leupeptin, 1 mM EDTA, 1 mM EGTA, 2 mg/l STI, 2 mg/l aprotinin, 20% v/v glycerol and 2 mg/ml lysozyme, this buffer being maintained at +4° C. The suspension thereby obtained is stirred vigorously at 4° C. After 30 min of stirring, 0.2 mg/ml deoxyribonuclease I and 5 mM MgCl$_2$ are added. After 90 min of stirring, the extract is centrifuged for 1 hour at 50,000 g. The supernatant is divided into 3 fractions of approximately 180 ml. Each one is desalted by gel permeation on a 500 ml column of Sephadex G-25 Fine equilibrated at the natural flow rate in pH 6.8 20 mM bis-tris buffer containing 4 mM DTE, 5 mM benzamidine, 0.2 mM Pefabloc, 100 μg/l E-64, 2 mg/l leupeptin, 1 mM EDTA, 1 mM EGTA, 2 mg/l STI, 2 mg/l aprotinin, 20% v/v glycerol. The protein eluate is then chromatographed (400 mg of protein at each cycle) on a MonoQ HR 16/10 column at a flow rate of 6 ml/min with an increasing linear gradient of sodium chloride (0 to 0.3M) in pH 6.8 20 mM bis-tris buffer containing 4 mM DTE, 2 mM benzamidine, 100 μg/l E-64, 2 mg/l leupeptin, 20% v/v glycerol. At outflow from the column, the fractions are supplemented with 10% v/v of pH 6.8 20 mM bis-tris buffer containing 4 mM DTE, 30 mM benzamidine, 2 mM Pefabloc, 100 μg/l E-64, 2 mg/l leupeptin, 5 mM EDTA, 5 mM EGTA, 10 mg/l STI, 10 mg/l aprotinin, 20% v/v glycerol. Under these conditions, both methylation activities (1 and 2) are detected identically in the exclusion fractions and the first elution fractions. These fractions are pooled and concentrated by ultrafiltration on CentriPrep 10. This concentrate is made to 0.85M ammonium sulphate and then chromatographed (20 to 80 mg at each cycle) on a Phenyl Superose HR 10/10 column at a flow rate of 1 ml/min with a decreasing linear gradient of ammonium sulphate (0.85 to 0M) in pH 6.8 50 mM bis-tris buffer containing 4 mM DTE, 2 mM benzamidine, 100 μg/l E-64, 2 mg/l leupeptin, 1 mM EDTA, 1 mM EGTA, 10% v/v glycerol. At outflow from the column, the fractions are supplemented with 10% v/v of pH 6.8 50 mM bis-tris buffer containing 4 mM DTE, 30 mM benzamidine, 2 mM Pefabloc, 100 μg/l E-64, 2 mg/l leupeptin, 1 mM EDTA, 1 mM EGTA, 10 mg/l STI, 10 mg/l aprotinin, 10% v/v glycerol. Under these conditions, both methylation activities (1 and 2) are detected identically in the elution fractions corresponding to approximately 0.15M ammonium sulphate. These fractions are pooled, concentrated by ultrafiltration on Centricon 10, desalted on PD-10 columns equilibrated in pH 8.2 (at 5° C.) 50 mM Tris buffer containing 4 mM DTE, 2 mM benzamidine, 100 μg/l E-64, 2 mg/l leupeptin, 20% v/v glycerol, and then chromatographed (approximately 10 mg at each cycle) on a MonoQ HR 5/5 column equilibrated in the same buffer at a flow rate of 1 ml/min. Under these conditions, the two activities are not retained on the column. At outflow from the column, the exclusion fractions hence containing these two activities are supplemented with 10% v/v of pH 8.2 50 mM Tris buffer containing 4 mM DTE, 30 mM benzamidine, 2 mM Pefabloc, 100 μg/l E-64, 2 mg/l leupeptin, 1 mM EDTA, 1 mM EGTA, 20% v/v glycerol. These fractions are then concentrated by ultrafiltration on Centricon 10 and thereafter chromatographed on a 300×7.5 mm 10 μm TSK G2000 SW column equilibrated at a flow rate of 0.5 ml/min in pH 7.0 50 mM Hepes buffer containing 4 mM DTE, 0.2 mM Pefabloc, 1 mM EDTA, 1 mM EGTA, 10% v/v glycerol, 0.15M sodium chloride. The two activities co-elute in this technique at a retention time corresponding to a molecular weight close to 30,000. After this step, a preponderant protein is visible in SDS-PAGE. It is located at around 32,000.

TABLE 8

Purification of the enzyme methylating p-aminophenylalanine to p-dimethylaminophenylalanine

| Purification Step | Vol. (ml) | Protein (mg) | Sp.Act. (units/mg) | Yield (%) | Purification factor |
|---|---|---|---|---|---|
| Crude extract | 510 | 1800 | 29 | — | — |
| G-25 Fine | 560 | 1560 | 34 | 102 | 1.17 |
| MonoQ HR 16/10 | 670 | 82 | 430 | 67 | 14.8 |
| Phenyl Superose | 10 | 3.48 | 6300 | 42 | 217 |
| MonoQ HR 5/5 | 7 | 0.88 | 17200 | 29 | 593 |
| TSK G2000 | 0.8 | 0.113 | 40300 | 8.7 | 1390 |

[a]This refers to units of enzymatic activity for methylation 1. At each step, the value of the units of enzymatic activity for methylation 2 was equal to 120% of that of the units for methylation 1.

The purification factor is calculated from the increase in specific activity of the fractions during the purification.

5.7.1.C. Purification from *E. coli* pVRC706 of the Recombinant Protein of *S. pristinaespiralis* SP92 Displaying the SAM-dependent N-methyltransferase Activity Catalysing the Methylation of p-aminophenylalanine to p-dimethylaminophenylalanine This experiment illustrates how an enzyme of *S. prisinaespiralis* SP92 participating in the biosynthesis pathway of pristinamycin IA and expressed in *E. coli* by cloning of the papM gene may be purified.

Using the assay described above in Example 5.7.1.A., we showed that crude extracts of the recombinant strain *E. coli*::pVRC706 display a strong activity for methylation 1 and for methylation 2, whereas in the control *E. coli* strain (pMTL23) neither of these two activities was detected. The purification of the SAM-dependent p-aminophenylalanine (phenyl-N)-methyltransferase catalysing the methylation of p-aminophenylalanine to p-dimethylaminophenylalanine was then carried out.

Under the same conditions as those described in Example 5.7.1.B., except for a chromatography step which was eliminated (step of purification on MonoQ HR 5/5), we purified to homogeneity a protein which possesses a molecular weight in chromatography on a TSK G2000 column and in SDS-PAGE identical to those possessed by the protein purified in Example 5.7.1.B.

TABLE 9

Purification of the enzyme methylating p-aminophenylalanine to p-dimethylaminophenylalaine from *E. coli* strain pVRC706

| Purification Step | Vol. (ml) | Protein (mg) | Sp.Act. μmol/h/mg | Yield (%) | Purification factor |
|---|---|---|---|---|---|
| Crude extract | 15 | 190 | 235 | — | — |
| G-25 Fine | 22 | 175 | 231 | 91 | 1 |
| MonoQ HR 16/10 | 24 | 13.4 | 2100 | 63 | 8.9 |
| Phenyl Superose | 3.0 | 0.39 | 35500 | 31 | 145 |
| TSK G2000 | 0.6 | 0.092 | 45200 | 9.3 | 192 |

TABLE 9-continued

Purification of the enzyme methylating
p-aminophenylalanine to p-dimethylaminophenylalaine
from *E. coli* strain pVRC706

| Purification Step | Vol. (ml) | Protein (mg) | Sp.Act. μmol/h/mg | Yield (%) | Purification factor |
|---|---|---|---|---|---|

ªThis refers to units of enzymatic activity for methylation 1. At each step, the value of the units of enzymatic activity for methylation 2 was equal to 120% of that of the units for methylation 1.

The purification factor is calculated from the increase in specific activity of the fractions during the purification.

5.7.2. Identification of the Structural Gene for p-aminophenylalanine (phenyl-N)-methyltransferase The NH$_2$-terminal sequence of the 32,000 protein purified in Example 5.7.1.B was determined by microsequencing as described in Example 5.1.2. Ten residues were determined in this way:

TAAAPTLAQA

The NH$_2$-terminal sequence of the 32,000 protein purified in Example 5.7.1.C was determined by microsequencing as described in Example 5.1.2. Ten residues were determined in this way:

TAAAPTLAQA

In both cases the same residues are found, and this sequence corresponds exactly to the beginning of the protein sequence which is deduced from the sequence of the papM gene (see residues 2 to 11 on SEQ ID NO:25). The purified p-aminophenylalanine (phenyl-N)-methyltransferase is hence the protein PapM.

Example 6

Subcloning of DNA Fragments Cloned into Cosmids as Prepared in Example 3 and Containing the Genes of Interest This example illustrates how, starting from cosmids constructed as described in Example 3 and containing genes for the biosynthesis of pristinamycins II or pristinamycins I, it is possible to subclone DNA fragments containing these genes.

These subclonings were performed in order to be able to deduce subsequently the nucleic acid sequence of the genes identified, as well as to carry out the different construction presented in the examples which follow.

6.1. Isolation of the 5.5-kb EcoRI-BglII Fragment Containing the Structural Gene for 3-hydroxypicolinic acid:AMP Ligase This example describes how, starting from cosmid pIBV2 containing the structural gene for 3-hydroxypicolinic acid:AMP ligase, it is possible to subclone a DNA fragment of smaller size containing this gene.

Approxmiately 10 μg of cosmid pIBV2 were cut successively with the restriction enzymes BglII and EcoRI (New England Biolabs) under the conditions recommended by the supplier. The restriction fragments thereby obtained were separated by electrophoresis on 0.8% agarose gel, and the 5.5-kb BglII-EcoRI fragment was isolated by electroelution as described in Maniatis et al. (1989).

Approximately 100 ng of pUC19 (Viera and Messing 1982) cut with BamHI and EcoRI were ligated with 200 ng of the 5.5-kb BglII-EcoRI fragment under the conditions described in Example 3.3.

After transformation of the strain TG1 and selection of the transformants on solid LB medium containing 150 μg/ml of ampicillin and 20 μg/ml of X-gal according to the technique described by Maniatis et al. (1989), a clone carrying the desired fragment was isolated. The recombinant plasmid was designated pVRC402. Its restriction map is presented in FIG. 15(A). It was shown by hybridization, in Example 5.2., that the 5.5-kb EcoRI-BglII fragment contains the structural gene for *S. pristinaespiralis* SP92 3-hydroxypicolinic acid:AMP ligase. Plasmid pVRC402 hence contains the structural gene for *S. pristinaespiralis* SP92 3-hydroxypicolinic acid:AMP ligase.

6.2. Isolation of a 4.6-kb BglII-BglII Fragment from Cosmid pIBV2

This example describes how, starting from cosmid pIBV2, it is possible to subclone a DNA fragment of smaller size for the purpose of identifying, in the regions adjacent to the structural gene for 3-hydroxypicolinic acid:AMP ligase, the presence of other genes involved in the biosynthesis of pristinamycins I.

The different cloning steps were carried out as described above.

Approximately 10 μg of cosmid pIBV2 were cut with BglII. The restriction fragments thereby obtained were separated by electrophoresis on 0.8% agarose gel, and the 4.6-kb BglII-BglII fragment was isolated by electroelution.

Approximately 100 ng of pUC19 cut with BamHI were ligated with 200 ng of the BglII-BglII fragment.

A clone carrying the desired fragment was isolated after transformation of the strain TG1 as described in Example 6.1. The recombinant plasmid was designated pVRC501. Its restriction map is presented in FIG. 15(B).

6.3. Isolation of the 6-kb BamHI-BamHI Fragment Containing the Structural Genes for the Two Subunits of Pristinamycin IIA Synthase This example describes how, starting from cosmid pIBV1, it is possible to subclone a DNA fragment of smaller size containing the structural genes for the two subunits of pristinamycin IIA synthase.

The different cloning steps were carried out as described above.

Approximately 10 μg of cosmid pIBV1 were cut with BamHI. The restriction fragments thereby obtained were separated by electrophoresis on 0.8% agarose gel, and the 6-kb BamHI fragment was isolated by electroelution.

Approximately 100 ng of pBKS⁻ (Stratagene Cloning Systems, La Jolla Calif.) cut with BamHI were ligated with 200 ng of the 6-kb BamHI fragment.

A clone carrying the desired fragment was isolated after transformation of the strain TG1. The recombinant plasmid was designated pXL2045. Its restriction map is presented in FIG. 16. It was shown by hybridization, in Example 5.1, that the 6-kb BamHI fragment contains the snaA and snaB genes coding for the two subunits of *S. pristinaespiralis* SP92 pristinamycin IIA synthase. Plasmid pXL2045 hence contains the snaA and snaB genes coding for the two subunits of *S. pristinaespiralis* SP92 pristinamycin IIA synthase.

6.4. Isolation of the 6.2-kb SphI Fragment Containing a Portion of the Structural Gene for Pristinamycin I Synthase II This example describes how, starting from cosmid pIBV3, it is possible to subclone a DNA fragment of smaller size containing a portion of the structural gene for pristinamycin I synthase II.

The different cloning steps were carried out as described above.

Approximately 10 µg of cosmid pIBV3 were cut with SphI. The restriction fragments thereby obtained were separated on 0.8% agarose gel, and the 6.2-kb SphI fragment was isolated by the technique of the "Geneclean" kit marketed by the company Bio101-Ozyme.

Approximately 100 ng of pUC19 cut with SphI were ligated with 200 ng of the 6.2-kb SphI fragment.

A clone carrying the desired fragment was isolated after transformation of the strain TG1. The recombinant plasmid was designated pVRC1105. Its restriction map is presented in FIG. 17.

6.5. Isolation of the 8.4-kb SphI Fragment Containing a Portion of the Structural Gene for Pristinamycin I Synthase III This example describes how, starting from cosmid pIBV3, it is possible to subclone a DNA fragment of smaller size containing a portion of the structural gene for pristinamycin I synthase III.

The different cloning steps were carried out as described above.

Approximately 10 µg of cosmid pIBV3 were cut with SphI. The restriction fragments thereby obtained were separated on 0.8% agarose gel, and the 8.4-kb SphI fragment was isolated by the technique of the "Geneclean" kit marketed by the company Bio101-Ozyme.

Approximately 100 ng of pUC19 cut with SphI were ligated with 200 ng of the 8.4-kb SphI fragment.

Figure 18:
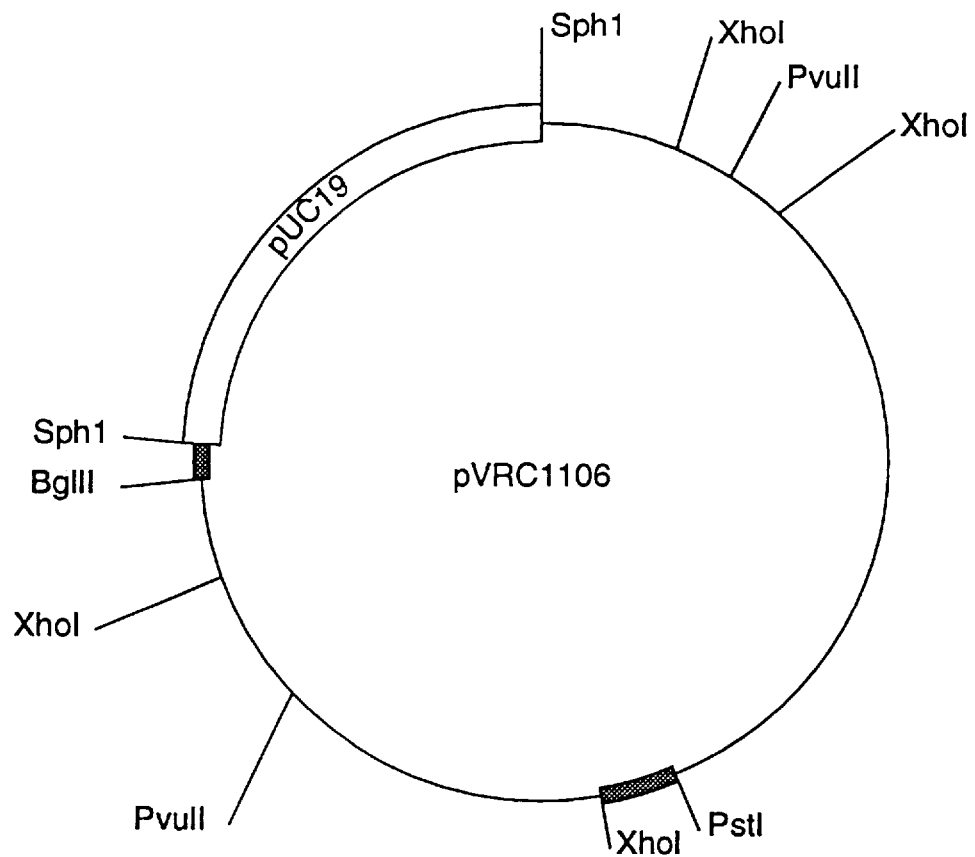
FIG. 18: Diagram of plasmid pVRC1106.

A clone carrying the desired fragment was isolated after transformation of the strain TG1. The recombinant plasmid was designated pVRC1106. Its restriction map is represented in FIG. 18.

6.6. Isolation of a 6.6-kb SphI Fragment Containing a Portion of the Structural Gene for Pristinamycin I Synthase IV This example describes how, starting from cosmid pIBV3, it is possible to subclone a DNA fragment of smaller size containing a portion of the structural gene for pristinamycin I synthase IV.

The different cloning steps were carried out as described above.

Approximately 10 µg of cosmid pIBV3 were cut with SphI. The restriction fragments thereby obtained were separated on 0.8% agarose gel, and the 6.6-kb SphI fragment was isolated by the technique of the "Geneclean" kit marketed by the company Bio101-Ozyme.

Approximately 100 ng of pUC19 cut with SphI were ligated with 200 ng of the 6.6-kb SphI fragment.

A clone carrying the desired fragment was isolated after transformation of the strain TG1. The recombinant plasmid was designated pVRC1104. Its restriction map is presented in FIG. 19.

6.7 Isolation of the 17-kb HindIII-HindIII Fragment Containing Cosmid pHC79 and Carrying the Genes Located Upstream of 3-hydroxypicolinic acid:AMP Ligase (Pristinamycin I Synthase I)

This example describes how, starting from cosmid pIBV2 containing the structural gene for 3-hydroxypicolinic acid:AMP ligase, it is possible to delete a large portion of this cosmid and retain only the portion located upstream of 3-hydroxypicolinic acid:AMP ligase.

Approximately 200 ng of cosmid pIBV2 were cut with the restriction enzyme HindIII. The enzyme was denatured for 30 min at 85° C. as recommended by the supplier. Cosmid pIBV2 digested in this way was precipitated with ethanol as described in Maniatis et al. (1989) and religated with itself in a volume of 50 µl.

Figure 20:
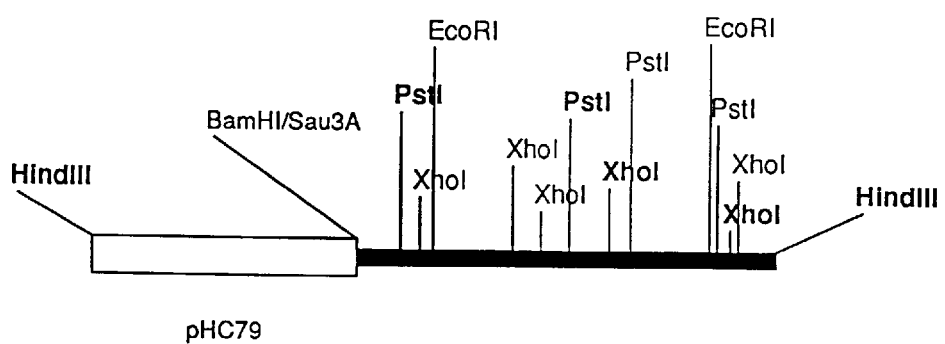
FIG. 20: Diagram of plasmid pVRC900.

After transformation of the strain TG1 and selection of the transformants on solid LB+150 µg/ml of ampicillin according to the technique described by Maniatis et al. (1989), a clone containing cosmid pHC79 and the portion located upstream of 3-hydroxypicolinic acid:AMP ligase (the whole corresponding to a size of approximately 17 kb) was isolated. The recombinant plasmid was designated pVRC900. Its restriction map is presented in FIG. 20.

6.8. Isolation of the 1.4-kb BamHI-SstI Fragment Originating from Cosmid pIBV3

This example describes how, starting from cosmid pIBV3 containing the snaA gene coding for the large subunit of PIIA synthase, it is possible to subclone a DNA fragment located upstream in order to study and sequence it.

Approximately 10 µg of cosmid pIBV3 were cut successively with the restriction enzymes SstI and BamHI. The restriction fragments thereby obtained were separated on 0.8% agarose gel, and the 1.4-kb BamHI-SstI fragment was isolated by the technique of the "Geneclean" kit marketed by the company Bio101-Ozyme.

Approximately 100 ng of pDH5 (Hilleman et al. 1991) cut with BamHI and SstI were ligated with 200 ng of the BamHI-SstI fragment under the conditions described in Example 3.3.

Figure 21:
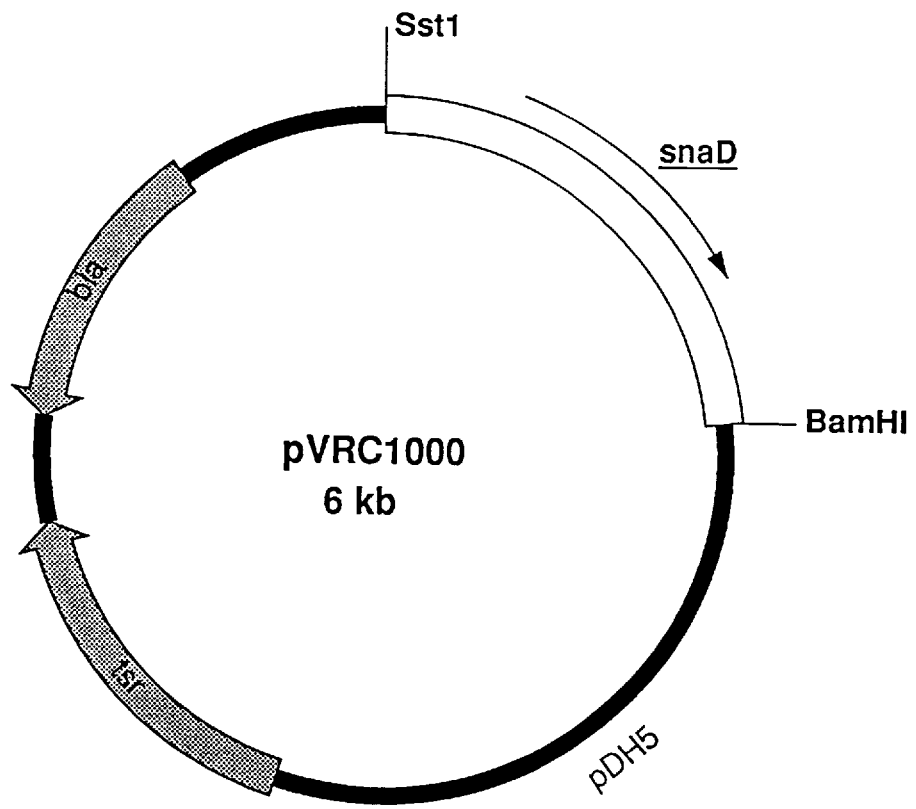
FIG. 21: Diagram of plasmid pVRC1000.

After transformation of the strain TG1 and selection of the transformants of solid LB+150 µg/ml of ampicillin+X-gal according to the technique described by Maniatis et al. (1989), a clone carrying the desired fragment was isolated. The recombinant plasmid was designated pVRC1000. Its restriction map is represented in FIG. 21.

6.9. Isolation of the 4-kb BamHI-BamHI Fragment Containing the Structural Gene for FMN Reductase This example describes how, starting from cosmid pIBV4 containing the structural gene for FMN reductase (snaC), it is possible to subclone a DNA fragment of smaller size containing this gene.

The different cloning steps were carried out as described above.

Approximately 10 µg of cosmid pIBV4 were cut with the restriction enzyme BamHI. The restriction fragments thereby obtained were separated on 0.8% agarose gel, and the 4-kb BamHI-BamHI fragment was isolated by electroelution.

Approximately 100 ng of pUC19 cut with BamHI were ligated with 200 ng of the 4-kb BamHI-BamHI fragment.

After transformation of *E. coli* strain DH5α (supE44 DlacU169 (f80lacZDM15) hsdR17 recA1 endA1 gyrA96 thi-1 relA1) (Hanahan, 1983) and selection of the transformants on solid LB+150 µg/ml of ampicillin+X-gal according to the technique described by Maniatis et al. (1989), a clone carrying the desired fragment was isolated. The recombinant plasmid was designated pVRC509. Its restriction map is presented in FIG. 22.

Example 7

Sequence of the Isolated DNA Fragments Containing the Genes for the Biosynthesis of Pristinamycins of *S. pristinaespiralis* SP92

This example illustrates the sequencing of DNA fragments carrying, on the one hand genes involved in the biosynthesis of pristinamycins of the pristinamycin I family, and on the other hand genes involved in the biosynthesis of pristinamycins of the pristinamycin II family, of the *S. pristinaespiralis* strain.

7.1. Sequencing of a 5-kb BamHI-XhoI Fragment

This example illustrates how the nucleotide sequence of a fragment containing the snaA and snaB genes of *S. pristinaespiralis* SP92 may be obtained.

Figure 16:
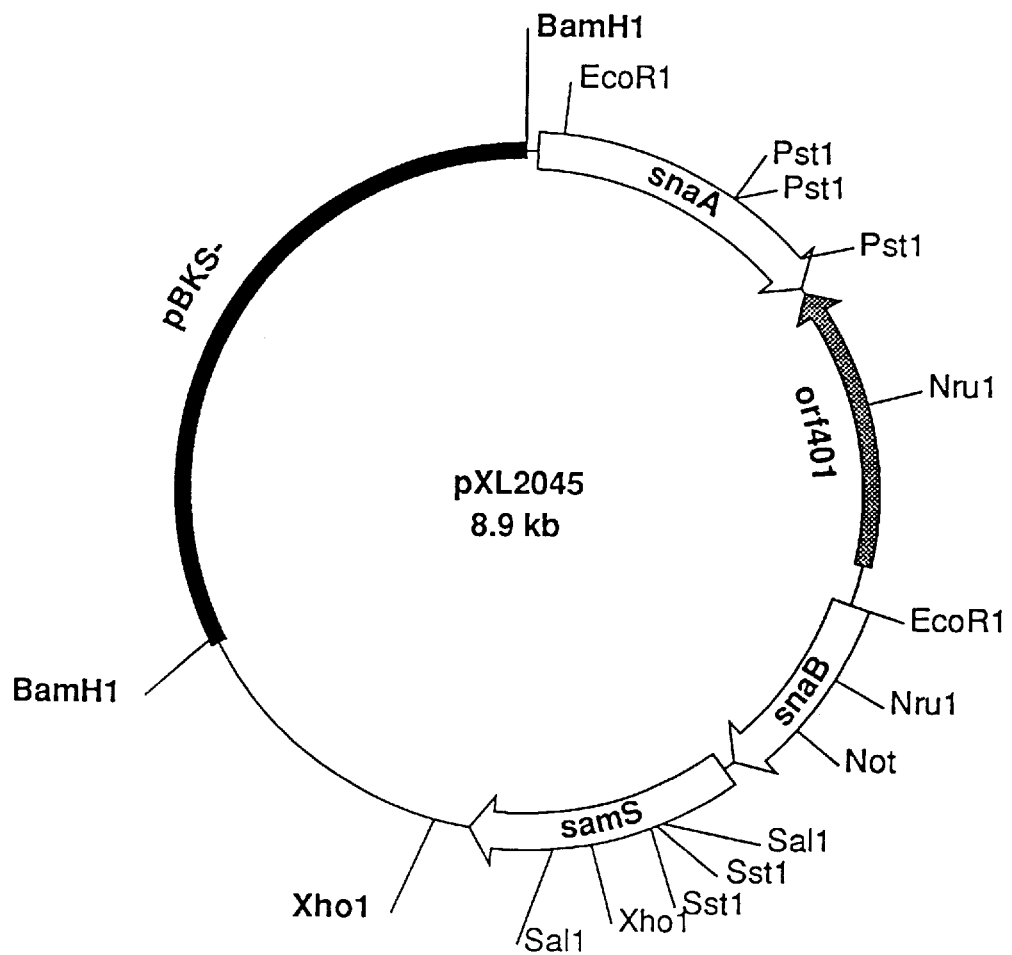
FIG. 16: Diagram of plasmid pXL2045.

The BamHI-XhoI fragment is part of the 6-kb BamHI-BamHI fragment which was cloned into phasmid pBKS⁻ to give plasmid pXL2045 described in Example 6.3. Subfragments of this 5-kb BamHI-XhoI insert were then obtained by enzymatic digestion and thereafter subcloned into phages M13mp18 or M13mp19 (Messing et al, 1981) in both orientations. The subcloning sites used are the following: EcoRI, PstI, PstI, NruI, EcoRI, NruI, NotI, SalI, SstI, XhoI, SalI and XhoI, and are shown in FIG. 16.

These different inserts were sequenced by the chain-termination reaction method, using as a synthetic primer the universal primer (Maniatis et al, 1989) or oligonucleotides which are synthesized (as is described in Example 5) and are complementary to a sequence of 20 nucleotides of the insert to be sequenced.

The overlap between these different inserts enabled the total nucleotide sequence to be established on both strands of the BamHI-XhoI fragment which comprises 5392 bp (SEQ ID no. 1).

7.2. Sequencing of a Region of 1870 bp of the 5.5-kb EcoRI-BglII Fragment

This example illustrates how the nucleotide sequence of a fragment containing the snbA gene of *S. pristinaespiralis* SP92 may be obtained.

Figure 15:
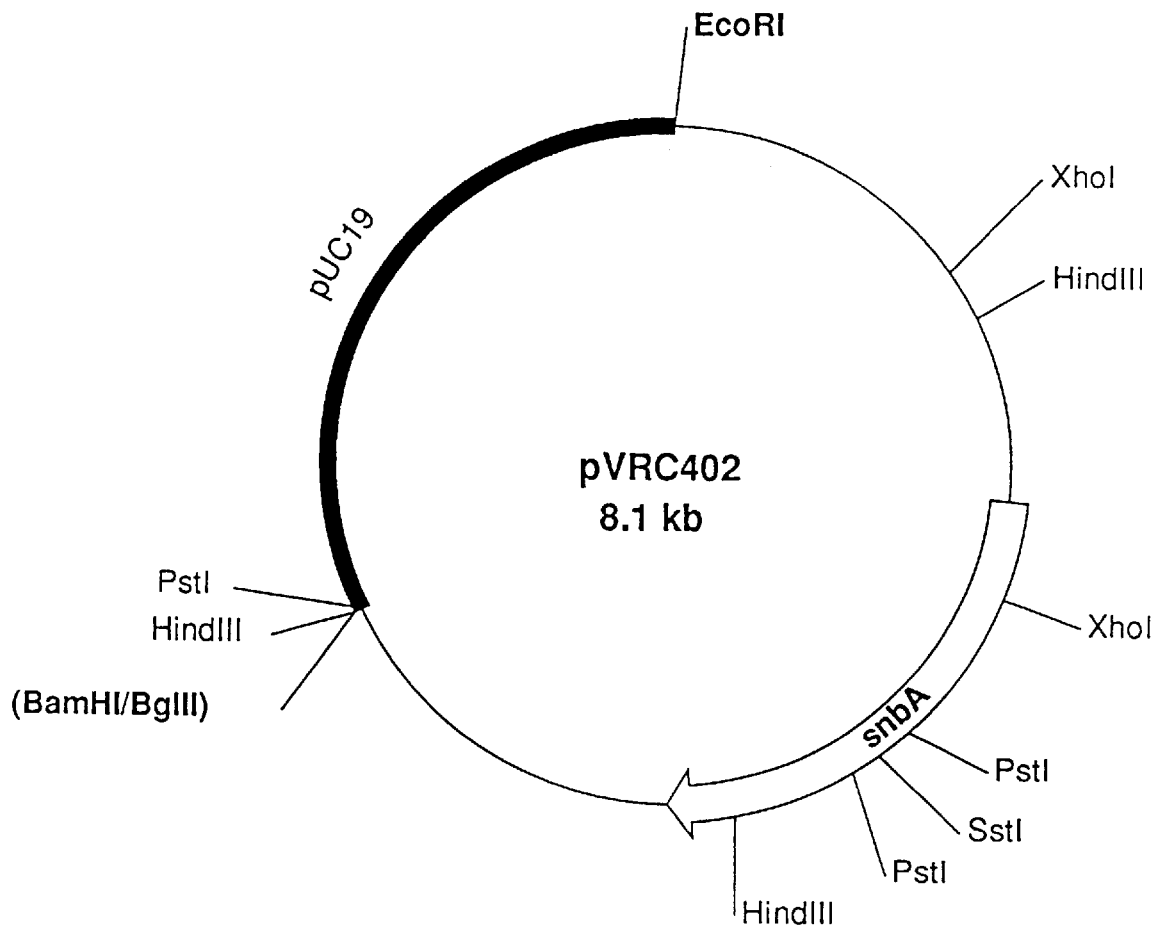
FIG. 15: Diagram of plasmids pVRC402 (A) and pVRC501 (B).
Figure 15:
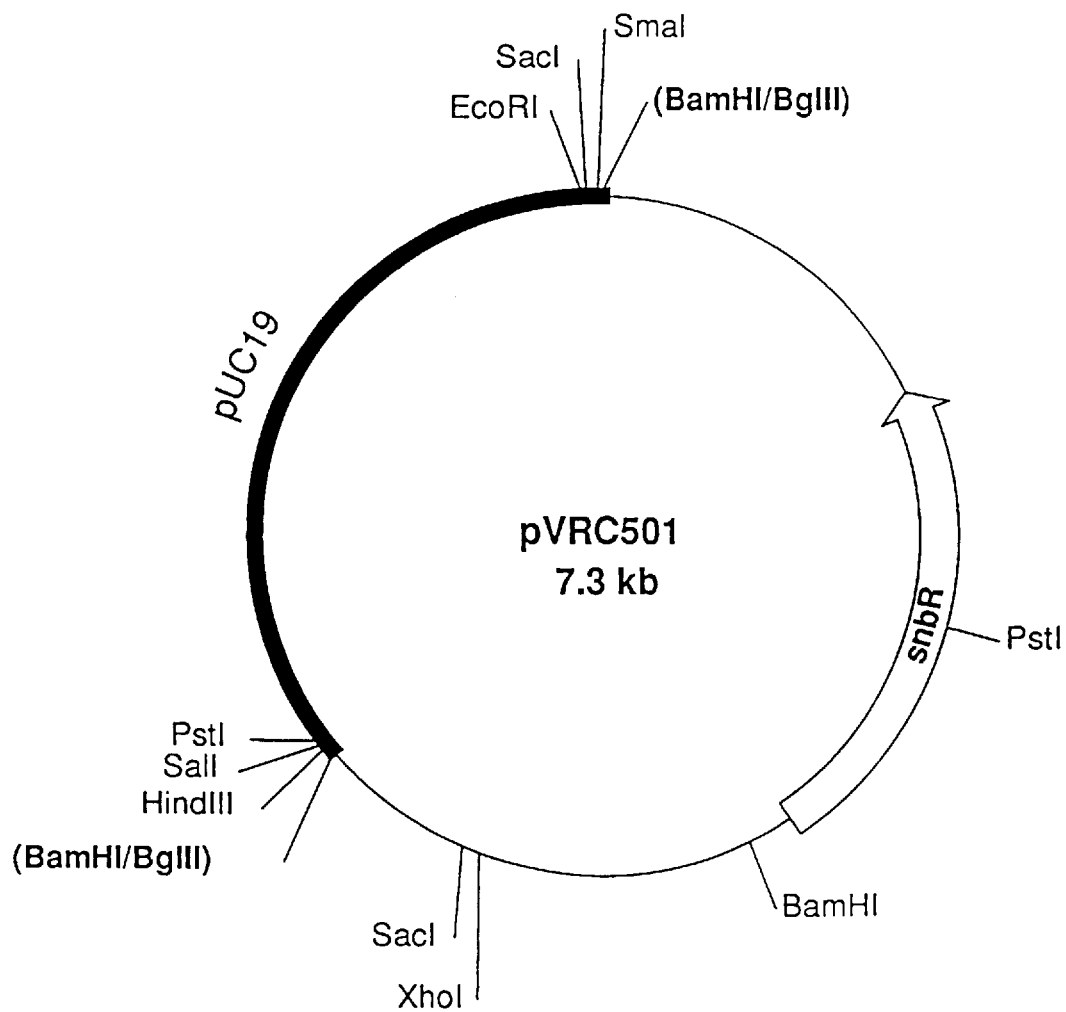

The region of 1870 bp sequenced is part of the 5.5-kb EcoRI-BglII fragment which was cloned into plasmid pUC19 to give plasmid pVRC402 described in Example 6 (FIG. 15(A). Subfragments of the 5.5-kb EcoRI-BglII insert were obtained by enzymatic cleavage and then subcloned into phages M13mp18 or M13mp19 in both orientations. The subcloning sites are HindIII, PstI and HindIII, and are shown in FIG. 15(A).

The overlap between these fragments enabled the total sequence of the Sau3A-Sau3A region, which comprises 1870 bp (SEQ ID no. 5), to be established.

7.3. Sequence of a Region of 1830 bp in the 4.6-kb BglII-BglII Fragment

This example illustrates how the nucleotide sequence of a fragment adjacent to that which contains the snbA gene of *S. pristinaespiralis* SP92 may be obtained.

This sequence was deduced by subcloning the 1-kb BamHI-PstI and 2.1-kb PstI-EcoRI fragments (FIG. 15(B)) from pVRC501 (Example 6) into the vectors M13mp18 and M13mp19. The PstI site was traversed by subcloning a 423-bp Sau3A-Sau3A fragment overlapping this site, followed by sequencing. The sequence of 1830 bp thereby obtained is shown in (SEQ ID no. 6).

7.4. Sequencing of Two Regions of 227 bp and 247 bp of the 6.2-kb SphI Fragment This example illustrates how the nucleotide sequence of fragments containing a portion of the structural gene for pristinamycin I synthase II (snbC) of *S. pristinaespiralis* may be obtained.

Figure 17:
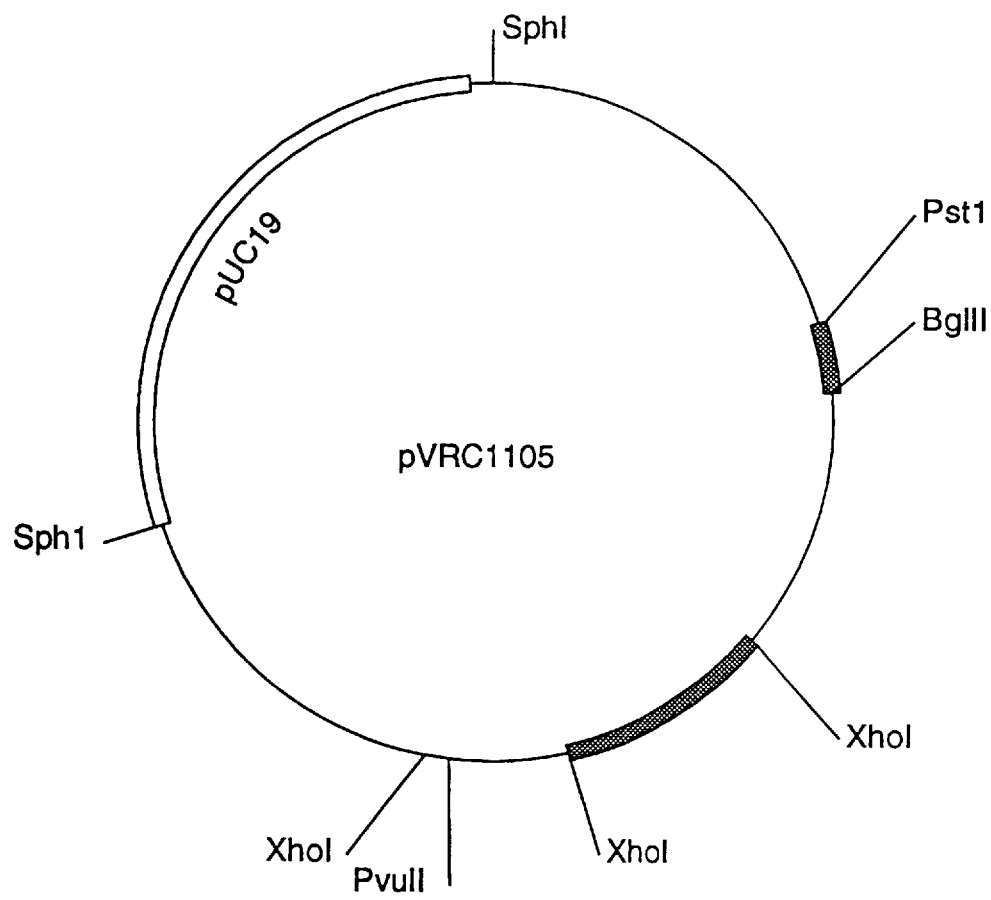
FIG. 17: Diagram of plasmid pVRC1105.

The regions of 227 and 247 bp sequenced are parts of the 6.2-kb SphI fragment which was cloned into plasmid pUC19 to give plasmid pVRC1105 described in Example 6.4 (FIG. 17). Subfragments of the 6.2-kb SphI insert were obtained by enzymatic cleavage and then subcloned into phages M13mp18 or M13mp19 in both orientations. The subcloning sites are XhoI, PstI and BglII, and are shown in FIG. 17. The 227-bp PstI-BglII fragment was sequenced completely, and 247 bp were sequenced from the 900-bp XhoI fragment: these sequences are presented in SEQ ID nos. 11 and 12.

7.5. Sequencing of Two Regions of 192 bp and 474 bp of the 8.4-kb SphI Fragment This example illustrates how the nucleotide sequence of fragments containing portions of the structural gene for pristinamycin I synthase III (snbD) of *S. pristinaespiralis* may be obtained.

The regions of 192 and 474 bp sequenced are parts of the 8.4-kb SphI fragment which was cloned into plasmid pUC19 to give plasmid pVRC1106 described in Example 6.5 (FIG. 18). Subfragments of the 8.4-kb SphI insert were obtained by enzymatic cleavage and then subcloned into phages M13mp18 or M13mp19 in both orientations. The subcloning sites are XhoI, PstI, SphI and BglII, and are shown in FIG. 18.

The 192-bp BglII-SphI and 474-bp PstI-XhoI fragments were sequenced completely: these sequences are presented in SEQ ID nos. 13 and 14.

7.6 Sequencing of Two Regions of 485 bp and 291 bp of the 6.6-kb SphI Fragment This example illustrates how the nucleotide sequence of fragments containing portions of the structural gene for pristinamycin I synthase IV (snbE) of *S. pristinaespiralis* may be obtained.

Figure 19:
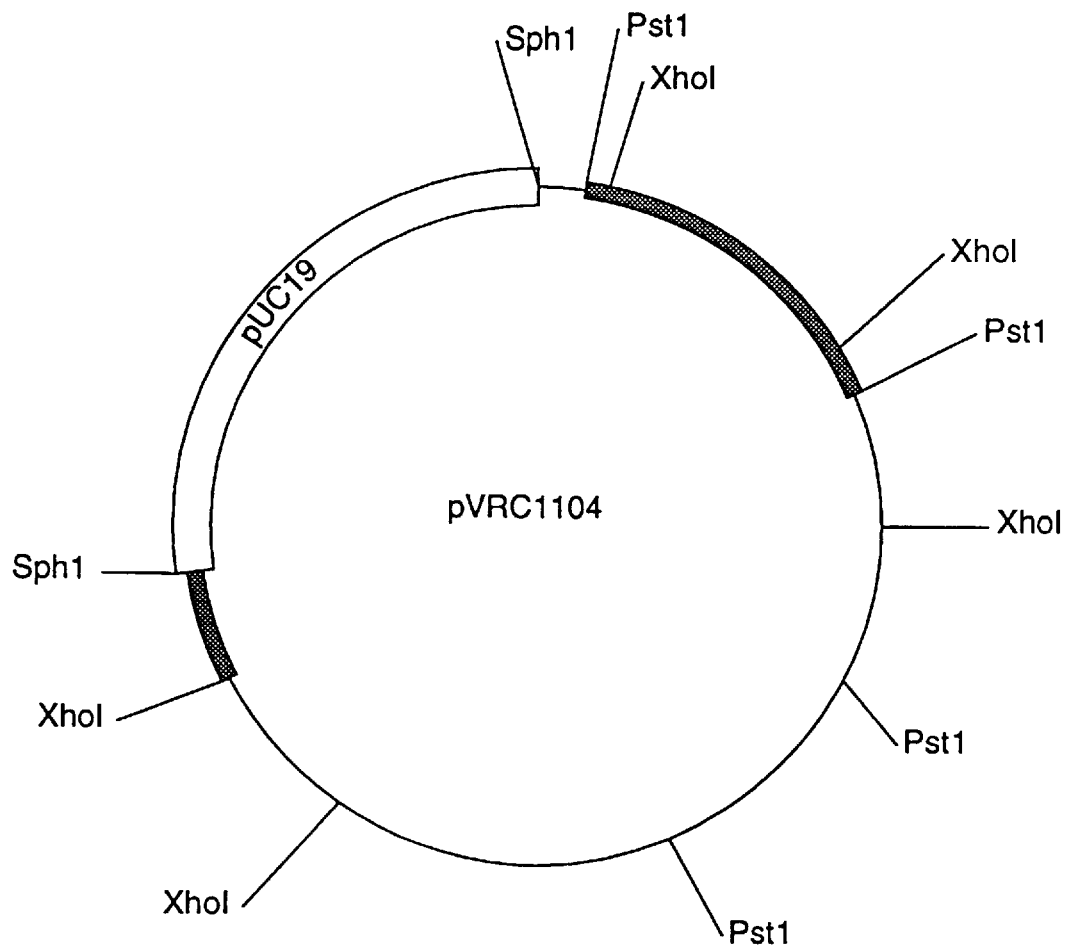
FIG. 19: Diagram of plasmid pVRC1104.

The regions of 291 and 485 bp sequenced are parts of the 6.6-kb SphI fragment which was cloned into plasmid pUC19 to give plasmid pVRC1104 described in Example 6.6 (FIG. 19). Subfragments of the 6.6-kb SphI insert were obtained by enzymatic cleavage and then subcloned into phages M13mp18 or M13mp19 in both orientations. The subcloning sites are XhoI, PstI and SphI, and are shown in FIG. 19. The 485-bp XhoI-SphI fragment was sequenced completely, and 291 bp were sequenced from the 1500-bp PstI fragment: these sequences are presented in SEQ ID nos. 15 and 16.

7.7. Sequence of a Region of 645 bp in a 3.4-kb XhoI-XhoI Fragment isolated from pVRC900

This example illustrates how the nucleotide sequence of a fragment located upstream of that which contains the snbA gene of *S. pristinaespiralis* may be obtained.

To deduce this sequence, the 3.4-kb XhoI-XhoI fragment was subcloned beforehand into the vector pUC18 from the vector pVRC900 described in 6.7. The different cloning steps were carried out as described in 6.1: plasmid pVRC900 was digested with the restriction enzyme XhoI, and the fragments thereby obtained were separated on 0.8% agarose gel. The 3.4-kb XhoI-XhoI fragment was purified by electroelution and was ligated with pUC18 cut with the restriction enzyme SalI. After transformation into TG1, a clone carrying the 3.4-kb XhoI-XhoI fragment was isolated. The recombinant plasmid was referred to as pVRC903. Its restriction map is presented in FIG. 23.

The 645-bp sequence was then deduced by subcloning the 1.4-kb PvuII-EcoRI and 0.9-kb PvuII-EcoRI fragments (FIG. 23) from pVRC903 described above into the vectors M13mp18 and M13mp19. To carry out these clonings, the vectors M13mp18 and M13mp19 were first digested with the restriction enzyme BamHI; the cohesive ends thereby liberated were filled in with the large fragment of DNA polymerase I (Klenow: New England Biolabs) according to the technique described by Maniatis et al. (1989) so as to generate blunt ends compatible with the ends liberated by PuvII digestion; the vectors were then digested with the restriction enzyme EcoRI. The PvuII site was traversed by subcloning a 2.2-kb PstI-PstI fragment, isolated from pVRC903, overlapping this site. The sequence of 645 bp thereby obtained is shown in SEQ ID no. 9.

7.8. Sequence of a Region of 1050 bp in a 4.1-kb PstI-PstI Fragment Isolated from pVRC900

This example illustrates how the nucleotide sequence of a fragment located upstream of that which contains the snbA gene of S. pristinaespiralis may be obtained.

Figure 24:
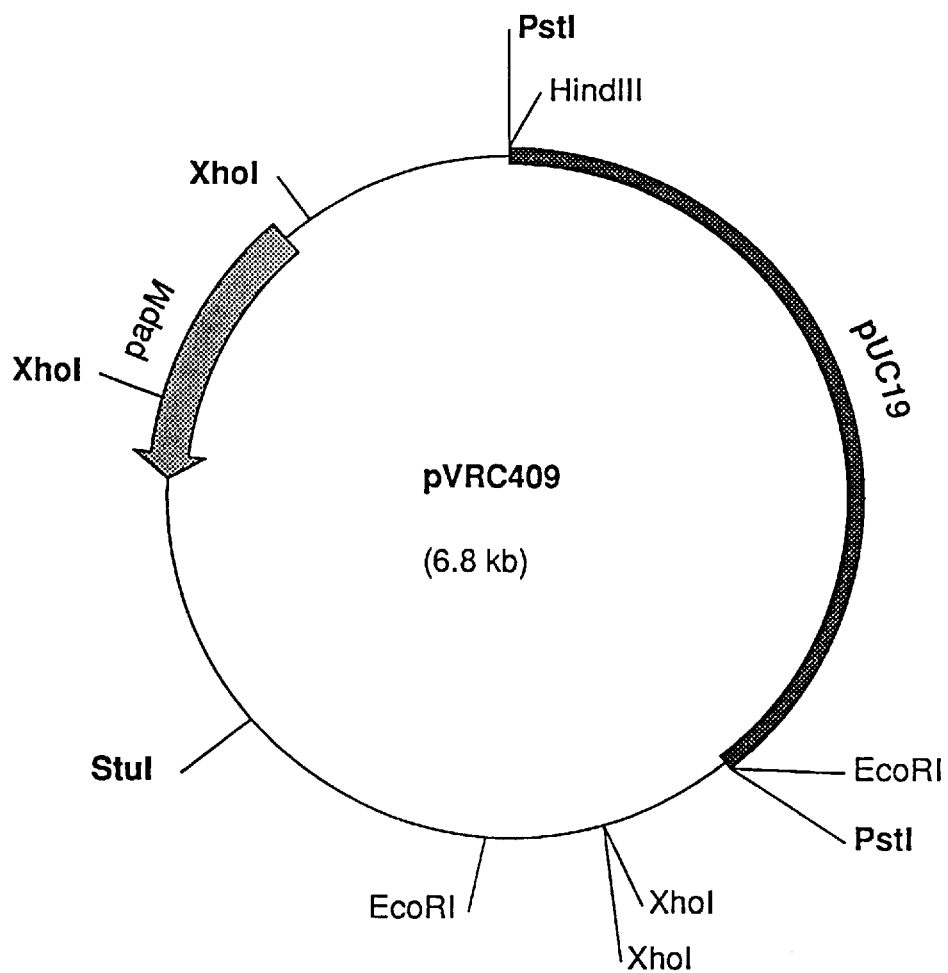
FIG. 24: Diagram of plasmid pVRC409.

To deduce this sequence, a 4.1-kb PstI-PstI fragment was subcloned beforehand into the vector pUC19 from the vector pVRC900 described in 6.7. The different cloning steps were carried out as described in 6.1. Plasmid pVRC900 was digested with restriction enzyme PstI, and the fragments thereby obtained were separated on 0.8% agarose gel. The 4.1-kb PstI-PstI fragment was purified by electroelution and was ligated with pUC19 cut with the restriction enzyme PstI. After transformation into TG1, a clone carrying the 4.1-kb PstI-PstI fragment was isolated. The recombinant plasmid was referred to as pVRC409. Its restriction map is presented in FIG. 24.

This sequence was then deduced by subcloning the 0.7-kb XhoI-XhoI and 1-kb XhoI-StuI fragments (FIG. 24) from pVRC409 described above into the vectors M13mp18 and M13mp19. The XhoI site internal to the sequence was traversed by double-strand sequencing from plasmid pVRC409. The sequence of 1050 bp thereby obtained is shown in SEQ ID no. 10.

7.9. Sequence of a Region of 640 bp in the 1.4-kb BamHI-SstI Fragment

This example illustrates how the nucleotide sequence of a fragment adjacent to that which contains the snaA and snaB genes of S. pristinaespiralis coding for the two subunits of PIIA synthase may be obtained.

This sequence was deduced by subcloning the 1.4-kb BamHI-SstI fragment (FIG. 21) from pVRC1000 (Example 6.8) into the vectors M13mp18 and M13mp19 (see Example 7.1). The sequence of 640 bp obtained is shown in SEQ ID no. 8.

7.10. Sequencing of the XhoI-KpnI Region of 694 bp Present in the 4-kb BamHI-BamHI Fragment This example illustrates how the nucleotide sequence of a fragment containing the snaC gene of S. pristinaespiralis may be obtained.

Figure 22:
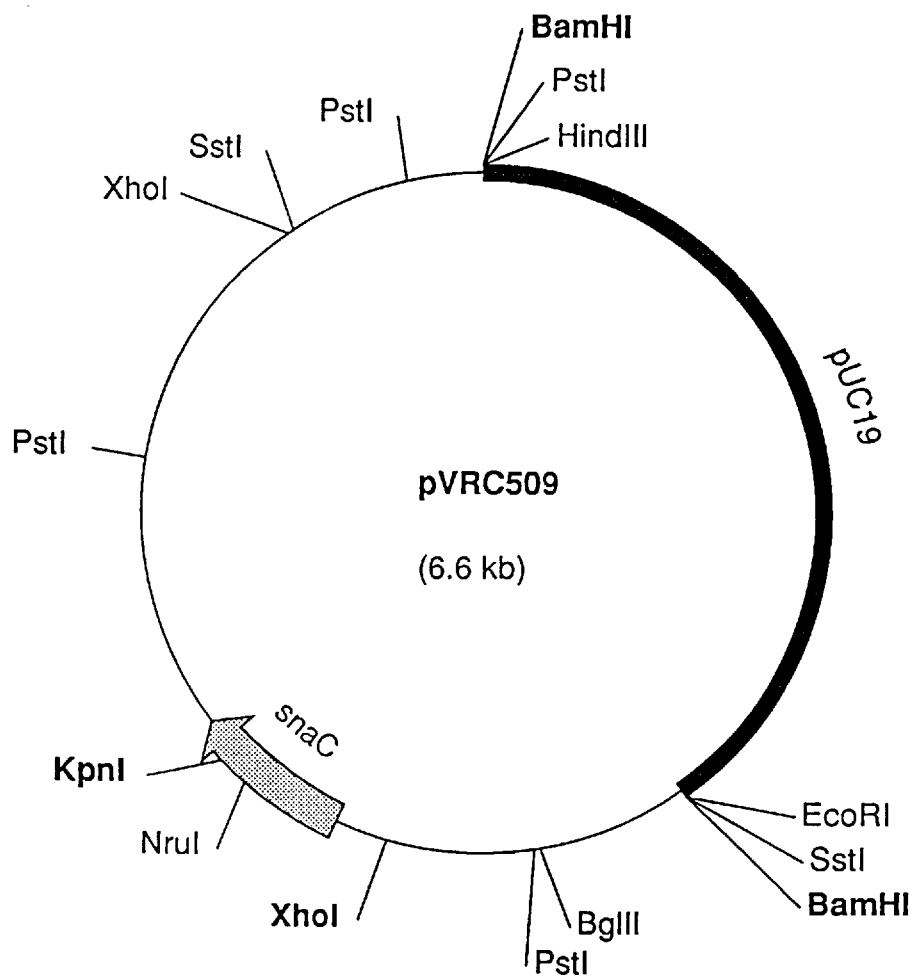
FIG. 22: Diagram of plasmid pVRC509.

The region of 694 bp sequenced is part of the 4-kb BamHI-BamHI fragment which was cloned into plasmid pUC19 to give plasmid pVRC509 described in Example 6.9. A 694-bp XhoI-KpnI fragment, obtained by double digestion of plasmid pVRC509 with the restriction enzymes XhoI and KpnI and which hybridizes with the 3 oligonucleotide probes described in 5.6, was cloned into phages M13mp18 and M13mp19. The XhoI and KpnI subcloning sites are shown in FIG. 22.

The sequence of the 694-bp fragment thereby obtained is presented in SEQ ID no. 7.

Example 8

Anaysis of the Nucleotide Sequences by Determination of the Open Reading Frames This example illustrates how it is possible to determine the open reading frames present in the nucleotide sequences defined in Example 7, and to identify the genes involved in the biosynthesis of pristinamycins I and pristinamycin II of S. pristinaespiralis SP92 as well as the polypeptides encoded by these genes.

8.1. 5-kb BamHI-XhoI Fragment (pXL2045)

This example illustrates how it is possible to determine the open reading frames present within the 5-kb BamHI-XhoI fragment isolated above and sequenced as described in Examples 6 and 7.

We looked for the presence of open reading frames within the 5-kb BamHI-XhoI fragment utilizing the fact that Streptomyces DNA has a high percentage of G and C bases as well as a strong bias in the use of the codons of which the coding frames are composed (Bibb et al. 1984). The Staden and McLachlan (1982) method enables the probability of the coding frames to be calculated on the basis of the use of the codons of Streptomyces genes which are already sequenced and collated in a file containing 19673 codons obtained from the BISANCE data-processing server (Dessen et al. 1900).

This method enabled four highly probable open reading frames, which are shown in the following table 10, to be characterized within the 5-kb BamHI-XhoI fragment. They are designated frames 1 to 4 according to their position starting from the BamHI site. For each one, their length in bases, their position within the fragment (the BamHI site being located at position 1) and also the molecular weight in kDa of the corresponding protein are given. Frames 1, 3 and 4 are coded by the same strand and frame 2 by the complementary strand (FIG. 16).

TABLE 10

| Frame number and gene name | Position | number of nucleotides | number of amino acids | MW in kDa of the protein encoded |
|---|---|---|---|---|
| 1 (snaA) | 48-1313 | 1266 | 422 | 46.5 |
| 2 | 2530-1328 | 1203 | 401 | — |
| 3 (snaB) | (inv) 2692-3522 | 831 | 277 | 29 |
| 4 (samS) | 3558-4763 | 1206 | 402 | 43 |

Frames 1 and 3 correspond respectively to the proteins SnaA (SEQ ID NO:17) and SnaB (SEQ ID NO:18) isolated above as described in Example 5 and for which the cloning of the genes is detailed in Example 6. In effect, the $NH_2$-terminal sequences of the products of ORFs 1 and 3 are identical to the $NH_2$-terminal sequences found for the proteins SnaA and SnaB, respectively, in Example 5.1.2, apart from the amino-terminal methionine which has been excized. Moreover, the molecular masses calculated from the sequences are comparable to the apparent molecular masses of the proteins SnaA and SnaB, estimated, respectively, in SDS-PAGE as described in Example 5.

Comparison of the product of open reading frame no. 4 with the protein sequences contained in the NBRF bank reveals a homology with various S-adenosylmethionine (or SAM) synthases, in particular of *E. coli* (Markham et al., (1984), of rat (Horikawa et al., 1989) and of *S. cerevisiae* (Thomas et al., 1988). The percentage homology values calculated over the whole of the sequence using Kanehisa's (1984) algorithm vary from 51.8 to 55.4%.

These sequence comparisons hence enable it to be demonstrated that the product of open reading frame no. 4 is an SAM synthase involved in the biosynthesis of pristinamycins I or II. This gene was designated samS (SEQ ID no. 4).

The demonstration of the involvement of the samS gene in the biosynthesis of pristinamycins is confirmed by the construction of the SP92 mutant disrupted in this gene, as described in Example 9.2.

Comparison of the sequence of the product of open reading frame no. 2 with the protein sequences contained in the Genpro bank reveals that an internal portion of this protein is 36% homologous with an internal portion of the first open reading frame of the insertion sequence (IS891) of Anabaena (Bancroft and Wolk, 1989). This result suggests that open reading frame no. 2, designated ORF 401, belongs to an insertion sequence, and that there is hence an insertion sequence located between the snaA and snaB genes.

8.2. 1870-bp Sau3A-Sau3A fragment (pVRC4021)

This example illustrates how it is possible to determine open reading frames present within the 1870-bp Sau3A-Sau3A fragment isolated above and sequenced as described in Examples 6 and 7.

The search for open reading frames for the Sau3A-Sau3A fragment was performed as above. A single complete open reading frame could be demonstrated in this way. Its characteristics are as follows: this frame extends from position 109 to position 1858 of the Sau3A-Sau3A fragment, which corresponds to a frame of 1749 bases coding for a protein of 582 amino acids having a molecular mass of 61400 Da. This protein corresponds to the protein SnbA purified above as described in Example 5 and for which the cloning of the gene is detailed in Example 6. In effect, the $NH_2$-terminal sequence of the product of the ORF present on the Sau3A-Sau3A fragment is identical to the $NH_2$-terminal sequence found for the protein SnbA in Example 5.2. The molecular mass of 61400 Da calculated from the sequence is comparable to the apparent molecular mass of the protein SnbA, estimated at 67000 Da in SDS-PAGE and at 60000 Da by gel permeation as described in Example 5.2.1.B.

The snbA gene hence codes for the enzyme which catalyses the formation of the acyladenylate 3-hydroxypicolinyl-AMP from one molecule of 3-hydroxypicolinic acid and one molecule of ATP: 3-hydroxypicolinic acid:AMP ligase (SEQ ID no. 5).

8.3. 1830-bp fragment (pVRC501)

This example illustrates how it is possible to determine the open reading frames present within the 1830-bp fragment sequenced from the 3.1-kb BamHI-EcoRI fragment isolated above.

The search for open reading frames for the 1830-bp fragment was performed as above. A single complete open reading frame could be demonstrated in this way. Its characteristics are as follows: the probable beginning of this frame is located at position 103 and the end at position 1686 of the region of 1830 bp sequenced from the BamHI-EcoRI fragment, which corresponds to a protein of 528 amino acids having an approximate molecular weight of 54000.

Comparison of the sequence of this protein with the sequences contained in the Genepro bank reveals that it is homologous to proteins having a transport function for various metabolites, in particular for tetracycline in various microorganisms (Khan and Novick, 1983; Hoshino et al., 1985), actinorhodine (Fernandez-Moreno et al., 1991) and methylenomycin (Neal and Chater, 1987b) in *S. coelicolor*.

These data indicate that the product of the open reading frame contained in the 3.1-kb BamHI-EcoRI fragment is a transport protein enabling pristinamycins I (and possibly pristinamycins II) to be exported out of the cell. This protein was designated SnbR (SEQ ID NO:21) and the corresponding gene snbR (SEQ ID no. 6).

Analysis of the hydrophobicity profile of the protein SnbR by the method of Kyte and Doolittle (1982) corroborates its membrane localization and hence its transport function.

8.4. 1050-bp Fragment (pVRC409)

This example illustrates how it is possible to determine the open reading frames present within the 1050-bp fragment sequenced above from pVRC409 as described in Example 7.8.

The search for open reading frames for the 1050-bp fragment was performed as above. A single complete open reading frame could be demonstrated in this way. Its characteristics are as follows: this phase extends from position 84 to position 962 of the sequenced portion, which corresponds to a frame of 878 bases coding for a protein of 292 amino acids having a molecular mass of 32000 Da. This protein was referred to as protein PapM. It was, moreover, purified from *S. pristinaespiralis* strain SP92 as described in Example 5. The molecular mass of 32000 Da calculated from the sequence is identical to the apparent molecular mass of 32000 Da estimated on SDS-PAGE as described in Example 5. Moreover, the $NH_2$-terminal sequence of this protein, deduced as described in Example 5, corresponds well to the $NH_2$-terminal sequence of the protein PapM (SEQ ID NO:25) identified by analysis of the open reading frames of the sequence of 1050 bp (SEQ ID no. 10).

8.5. 220-bp and 247-bp Fragments (pVRC1105)

This example illustrates how it is possible to determine the open reading frames present within the 227-bp and 247-bp fragments sequenced from pVRC1105 as described in Examples 6 and 7.

The search for open reading frames for these two fragments was performed as above. An incomplete reading frame could be demonstrated in both cases over the whole length of the fragment.

The sequence obtained from the open reading frame identified on the 247-bp fragment isolated from the 900-bp XhoI fragment contains one of the internal sequences of the protein SnbC purified as described in Example 5.

Comparison of the product of the open reading frames identified on the 227-bp and 247-bp fragments isolated from pVRC1105 with sequences of the Genpro bank reveals that they are homologous to peptide synthases. The one deduced from the 227-bp fragment displays 24.5% homology with *Acremonium chrysogenum* (α-aminoadipyl)cysteinylvaline synthetase (Gutierrez et al. 1991). The one deduced from the 247-bp fragment displays 34.9% homology with Bacillus gramicidin S synthase II (Hori et al. 1991) and 28% homology with *Acremonium chrysogenum* (α-aminoadipyl) cysteinylvaline synthetase (Gutierrez et al. 1991).

This confirms that cosmid pIBV3 isolated in Example 5.1 does indeed contain a portion of the structural gene for pristinamycin I synthase II described in Example 5.3, designated SnbC (SEQ ID NO:26 and SEQ ID NO:27).

8.6. 192-bp and 474-bp Fragments (pVRC1106)

This example illustrates how it is possible to determine the open reading frames present within the 192-bp and 474-bp fragments sequenced from pVRC1106 as described in Examples 6 and 7.

To search for open reading frames for these two fragments was performed as above. An incomplete reading frame could also be demonstrated on the 192-bp fragment isolated from pVRC1106. Its characteristics are as follows: this frame begins at position 29 of the portion sequenced in the direction of BglII. No stop codon was identified, indicating that this open frame is not terminated.

The sequence obtained from the open reading frame identified on the 192-bp BglII-SphI fragment contains the internal sequence of the protein SnbD purified as described in Example 5, which proves, in fact, to be the $NH_2$-terminal sequence of the protein.

An incomplete reading frame could be demonstrated over the whole length of the 474-bp XhoI-PstI fragment.

Comparison of the product of the open reading frame identified on the 474-bp fragment isolated from pVRC1106 with the sequences of the Genpro bank reveals that this protein fragment displays from 30 to 40% homology with peptide syntheses, for example 39.4% with Bacillus gramicidin S synthase II (Hori et al. 1991) and and 34% with *Acremonium chrysogenum* (α-aminoadipyl)cysteinylvaline synthetase (Gutierrez et al. 1991).

This confirms that cosmid pIBV3 isolated in Example 5.1 does indeed contain a portion of the structural gene for pristinamycin I synthase III described in Example 5.4, designated SnbD (SEQ ID NO:28 and SEQ ID NO:29).

8.7. 291-pb and 485-bp Fragments (pVRC1104)

This example illustrates how it is possible to determine the open reading frames present within the 291-bp and 485-bp fragments sequenced from pVRC1104 as described in Examples 6 and 7.

The search for open frames for these two fragments was performed as above. An incomplete reading frame could be demonstrated in both cases over the whole length of the fragment.

The sequence obtained from the open frame identified on the 291 fragment isolated from the 1450-bp PstI fragment contains the internal sequence of the protein SnbE purified as described in Example 5.

Comparison of the product of the open frame identified on the 485-bp XhoI-SphI fragment isolated from pVRC1104 with the sequences of the Genpro bank reveals that it is homologous to peptide syntheses, for example 34.7% homologous with Bacillus gramicidin S synthase II (Hori et al. 1991) and and 36.2% with *Acremonium chrysogenum* (α-aminoadipyl)cysteinylvaline synthetase (Gutierrez et al. 1991).

This confirms that cosmid pIBV3 isolated in Example 5.1 does indeed contain a portion of the structural gene for pristinamycin I synthase IV described in Example 5.5, designated SnbE (SEQ ID NO:30 and SEQ ID NO:31).

8.8. 645-bp Fragment (pVRC903)

This example illustrates how it is possible to determine the open reading frames present within the 645-bp fragment sequenced above from plasmid pVRC903 as described in Example 6.7.

The search for open reading frames for the 645-bp fragment was performed as above. An incomplete open reading frame could be demonstrated in this way. Its characteristics are as follows: this frame affords two possibilities for initiation of translation, a GTG at position 61 and a GTG at position 70 of the sequenced portion (the ATG located at position 124 was not taken into account owing to the sequence homologies described later). Analysis of the probabilities of the presence of Shine-Dalgarno regions does not make it possible to distinguish which of these codons corresponds to the initiation. No stop codon was identified, which indicates that this open reading frame is not terminated. The gene identified in this way was referred to as papA, and the corresponding protein was referred to as protein PapA (SEQ ID no. 9 and SEQ ID NO:24).

Comparison of the product of the open reading frame identified in the 3.4-kb XhoI-XhoI fragment isolated from pVRC900 with sequences contained in the Genpro bank reveals that it is homologous to the II components of proteins of the p-aminobenzoate synthase and anthranilate synthase type, involved, respectively, in the synthesis of p-aminobenzoic acid (folic acid precursor) and in the synthesis of anthranilic acid (tryptophan precursor) of various microorganisms. It displays, in particular, a 48% homology with the protein TrpG of Azospirillum (Zimmer W., Aparicio C., and Elmerich c. Mol. Gen. Genet. (1991) 229:41–51) and a 47% homology with the protein PabA of *Klebsiella pneumoniae* (Kaplan J. B., Merkel W. K. and Nichols B. P. J. Mol. Biol. (1985) 183:327–340). The proteins TrpG and PabA carry the glutaminase activity involved in the transamination of chorismic acid. The homologies demonstrated tend to show that the protein PapA might be involved as well in the activity of transamination of chorismic acid. Chorismic acid is proposed as a precursor of p-dimethylaminophenylalanine, a component of pristinamycins I, by analogy with the synthesis of chloramphenicol, an antibiotic deduced by Streptomyces (Sharka B., Westlake D. W. S. and Vining L. C. (1970) Chem. Zvesti 24, 66–72).

The role of the protein PapA will be shown subsequently (Example 9.3.) by analysis of mutants of the strain SP92 in the papA gene.

8.9. 1.5-kb BamHI-SstI Fragment (PVRC1000)

This example illustrates how it is possible to determine the open reading frames present within the 1.5-kb BamHI-SstI fragment isolated above and sequenced as described in Examples 6.8 and 7.9.

The search for open reading frames for the sequenced region of 640 bp present in the 1.5-kb BamHI-SstI fragment was performed as described in Example 8.1. A single complete open reading frame could be demonstrated in this way. No initiation and no termination of translation could be demonstrated, which indicates that the sequenced region of 640 bp is probably internal to a much larger reading frame, designated snaD (SEQ ID no. 8).

Comparison of the protein sequence encoded by the region of 640 bp with the protein sequences contained in the Genpro and NBRF banks reveals that this protein is 20–25% homologous to an internal portion of peptide synthases such as *B. brevis* gramicidin synthase I (Hori et al. 1989), *B. brevis* tyrocidin synthase I (Weckermann et al. 1988) and *Acremonium chrysogenum* ACV synthase (Gutierrez et al. (1991).

These data indicate that the protein partially encoded by the region of 640 bp is probably a peptide synthase involved in the biosynthesis of the peptide portion of pristinamycins II: in effect, all the peptide synthases involved in the biosynthesis of pristinamycins I have already been identified in other regions of the *S. pristinaespiralis* chromosome, as is described in Examples 5.2, 5.3, 5.4 and 5.5.

8.10. 694-bp Fragment (pVRC509)

This example illustrates how it is possible to determine the open reading frames present within the 694-bp fragment sequenced above from pVRC509 as described in Examples 6 and 7.

The search for open reading frames for the 694-bp fragment was performed as above. An incomplete open reading frame could be demonstrated in this way. Its characteristics are as follows: this frame begins at position 210 of the sequenced portion. No stop codon was identified, which indicates that this open frame is not terminated. Hence the molecular mass of the corresponding protein cannot be calculated and compared to the apparent molecular mass of 28,000 Da of the FMN reductase, estimated on SDS-PAGE as described in Example 5.6. On the other hand, the $NH_2$-terminal sequence of the protein identified in this way by analysis of the open reading frames of the sequence of 694-bp is identical to that $NH_2$-terminal sequence of the proteins SnaC purified as described in Example 5. Similarly, the two internal protein sequences of the FMN reductase described in 5.6 occur in the protein deduced from the sequenced portion. This confirms that the gene isolated from cosmid pIBV4 does indeed correspond to the protein FMN reductase described in Example 5.6, designated SnaC (SEQ ID no. 7).

A study of the DNA fragments of *S. pristinaespiralis* strain SP92 carried by cosmids pIBV1 to pIBV2 demonstrated the presence of several genes involved in the biosynthesis of pristinamycins II and pristinamycins I. The snaA, snaB and samS genes code for enzymes participating in the biosynthesis of pristinamycins II, pristinamycin IIA synthase and probable SAM synthase, and are grouped together physically on a large DNA fragment cloned into plasmid pIBV1. Similarly, the snbA, snbR, papA and papM genes—which code for proteins participating in the biosynthesis of pristinamycins I, 3-hydroxypicolinic acid:AMP ligase (SnbA), the protein SnbR probably responsible for the transport of pristinamycins I, the protein Papa involved in the biosynthesis of p-aminophenylalanine from chorisimic acid, and p-aminophenylalanine (phenyl-N)-methyltransferase (PapM)—are grouped together on a large DNA fragment cloned into cosmid pIBV2. Similarly, the snaA and snaD genes on the one hand—which code for proteins participating in the biosynthesis of pristinamycins II, the protein SnaD probably being a peptide synthase—and the snbC, snbD and snbE genes on the other hand—which code for the 3 peptide synthases SnbC, SnbD and SnbE involved in the formation of the peptide chain of pristinamycin I from its 6 separate amino acids—are grouped together on a large DNA fragment cloned into cosmid pIVB3. These results confirm the hypothesis of the grouping together of the genes for the biosynthesis of pristinamycins II, and also of the genes for the biosynthesis of pristinamycins I, and afford the possibility of cloning the other genes involved in these biosyntheses, by chromosome walking, upstream and downstream of the regions studied.

Furthermore, it is possible by hybridization of the total DNA of the different strains producing streptogramins (see Table 1) with the snaA, snaB, snaC, snaD, samS, snbA, snbR, snbC, snbD, snbE, papA and papM genes, or with the genes identified by chromosome walking, or with fragments of these genes, to isolate the genes corresponding to the same functions in the other microorganisms producing streptogramins. This makes it possible, by the same approach as that envisaged for the pristinamycins, to isolate all the genes involved in the biosynthesis of the different streptogramins.

Example 9

Genetic Study of DNA Fragments by Gene Disruption

This example illustrates how it is possible to demonstrate the involvement of genes in the biosynthesis of streptogramins by constructing strains derived from a producing strain and mutated in these genes by disruption, and by analysing the phenotype of such mutants. This example shows, furthermore, how to obtain strains that are left producing only one or other of the A and B components of streptogramins, or producing A and B components with ratios different from those observed with the strain SP92.

9.1. Construction of a Mutant of *S. pritinaespiralis* SP92 Disrupted in the snaA Gene This example illustrates how it is possible, by disruption of the snaA gene, to construct a strain of *S. pristinaespiralis* SP92 which no longer produces pristinamycin IIA and which produces, in contrast, pristinamycin IIB.

This mutant was constructed for the purpose of confirming the functionality of the protein SnaA and of providing an intermediate of pristinamycin II production capable of being modified subsequently.

Its construction was carried out using a suicide vector capable of replicating in *E. coli* only but carrying a resistance marker which is expressed in Streptomyces. This vector, pDH5, was developed by Hillemann et al. (1991).

9.1.1. Construction of Plasmid pVRC505

This example illustrates how it is possible to construct a plasmid which does not replicate in *S. pristinaespiralis* SP92 and which may be used to disrupt the snaA gene by single homologous recombination.

Plasmid pVRC505 was constructed to produce the SP92 chromosomal mutant disrupted in the snaA gene from plasmid pXL2045 described in Example 6.3.

The 6-kb BamHI fragment, cloned into pXL2045 (FIG. 16), was cut with the restriction enzymes EcoRI and PstI. After separation of the fragments thereby generated by electrophoresis on 1% agarose gel, a 0.7-kb fragment containing the 5' end of the snaA gene was isolated and purified by Geneclean (Bio101, La Jolla, Calif.).

Figure 25:
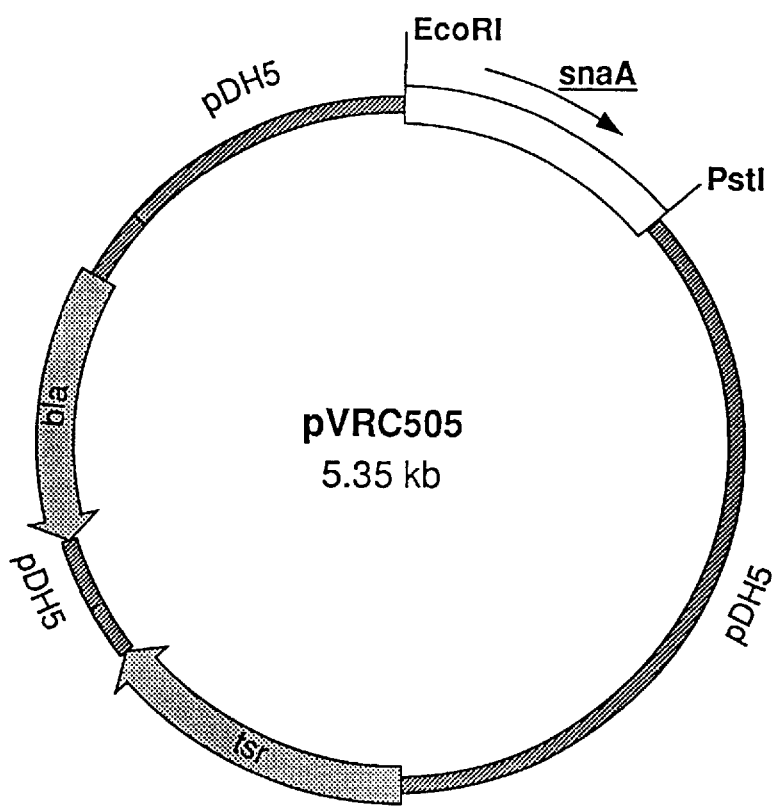
FIG. 25: Diagram of plasmid pVRC505.

100 ng of vector pDH5 linearized by an EcoRI/PstI double digestion were ligated with 100 ng of the 0.7-kb fragment, as described in Example 3.3. A clone carrying the desired fragment was isolated after transformation of the strain TG1. The recombinant plasmid was designated pVRC505. Plasmid pVRC505 was prepared as described in Example 2.1. Its restriction map is presented in FIG. 25.

9.1.2. Isolation of the SP92 Mutant Disrupted in the snaA Gene by Homologous Recombination This example illustrates how the mutant of *S. pristinaespiralis* SP92 disrupted in the snaA gene was constructed.

This mutant was isolated by transformation of the strain SP92 with the suicide plasmid pVRC505.

The preparation of the protoplasts and their transformation were carried out as described in D. Hopwood et al. (1985).

The strain SP92 was cultured in YEME medium, 34% sucrose, 5 mM $MgCl_2$, 0.25% glycine for 40 hours at 30° C. The mycelium was converted to protoplasts in the presence of lysozyme, and 5×1 µg of pVRC505 were used for the transformation (by the method employing PEG) of the protoplasts. After overnight regeneration of the protoplasts on R2YE medium (D. Hopwood et al. 1985), the recombinants were selected by overlaying 3 ml of SNA medium (D. Hopwood et al. 1985) containing 2.6 µg/ml of thiostrepton.

Of the 5 transformations carried out, 3 thiostrepton-resistant clones were isolated. This gives a recombinant efficiency of less than 1 per µg of DNA. These recombinants result from integration by single homologous recombination between the snaA gene carried by the chromosome of the strain SP92 and the 0.7-kb fragment of the suicide plasmid pVRC505. The small size of the fragment inserted into pVRC505, 0.7-kb, explains the low recombination efficiency.

The spores of the recombinants were isolated by plating out and growth on R2YE medium supplemented with 400 µg/ml of thiostrepton, and plated out again on the same medium to obtain isolated colonies.

In order to verify the position of integration of plasmid pVRC505, various Southern blots of the total DNA of several recombinant clones, which was digested with the appropriate restriction enzymes, were produced and hybridized with the vector pDH5 and the 0.7-kb fragment, used successively as probes after labelling by random priming (Random Primed DNA labeling kit, Boehringer Mannheim, France) with $[\alpha-^{32}P]$-dCTP, as described in Maniatis et al. (1989). The hybridization results show the appearance in the genome of the recombinant clones of an additional EcoRI-PstI band, of the size of the vector pDH5 and which hybridizes with the latter, as well as of an additional EcoRI-EcoRI band which hybridizes with both the 2 probes. One of these mutants was designated SP92::pVRC505. This mutant corresponds well to the integration of plasmid pVRC505 in the snaA gene by single homologous recombination.

9.1.3. Production of Pristinamycins by the Mutant SP92::pVRC505

This example illustrates how it is determined that the mutant of S. pristinaespiralis SP92 disrupted in the snaA gene by integration of plasmid pVRC505 no longer produces pristinamycin IIA while continuing to produce pristinamycin IIB.

The mutant SP92::pVRC505, as well as the strain SP92 as control strain, were culture in liquid production medium. Fermentation was carried out as follows: 0.5 ml of a suspension of spores of the strains mentioned are added under sterile conditions to 40 ml of inoculum medium in a 300-ml Erlenmeyer. The inoculum medium consists of 10 g/l of corn steep, 15 g/l of sucrose, 10 g/l of $(NH_4)_2SO_4$, 1 g/l of $K_2HPO_4$, 3 g/l of NaCl, 0.2 g/l of $MgSO_4.7H_2O$ and 1.25 g/l of $CaCO_3$. The pH is adjusted to 6.9 with sodium hydroxide before the introduction of calcium carbonate. The Erlenmeyers are stirred for 44 hours at 27° C. on a rotary stirrer at a speed of 325 rpm. 2.5 ml of the above culture when 44 hours old are added under sterile conditions to 30 ml of production medium in a 300-ml Erlenmeyer. The production medium consists of 25 g/l of soya flour, 7.5 g/l of starch, 22.5 g/l of glucose, 3.5 g/l of feeding yeast, 0.5 g/l of zinc sulphate and 6 g/l of calcium carbonate. The pH is adjusted to 6.0 with hydrochloric acid before the introduction of calcium carbonate. The Erlenmeyers are stirred for 24, 28 and 32 hours at 27° C. At each time, 10 g of must are weighed into a smooth Erlenmeyer, and 20 ml of mobile phase composed of 62.5% of acetonitrile and 37.5% of 0.1M $KH_2PO_4$ solution (adjusted to pH 3.0 with $H_3PO_4$), and which enables the pristinamycins to be extracted, are added to this. After stirring on a stirrer (325 rpm) for 20 min at room temperature, the whole is filtered through filter paper and the pristinamycins are assayed by HPLC as described in Example 5.1.1.A.

The results showed that, under the fermentation conditions implemented, the mutant SP92::pVRC505 produced an amount of pristinamycin I equivalent to that of the SP92 control, this being the case for all 3 times tested. In contrast, whereas the control produced approximately 70% of pristinamycin IIA and 30% of pristinamycin IIB at 24, 28 and 32 hours of fermentation, the mutant SP92::pVRC505 produced 100% of pristinamycin IIB for these same times, in amounts equivalent to the sum of pristinamycin IIA+ pristinamycin IIB produced by the strain SP92. Hence the mutant is indeed blocked in a step of biosynthesis of pristinamycin II which corresponds to the oxidation of the 2,3 bond of the D-proline of the intermediate pristinamycin IIB. This mutant hence accumulates pristinamycin IIB. This shows well the functional involvement of SnaA in the conversion of pristinamycin IIB to pristinamycin IIA.

This example shows that is possible, starting from cloned genes for biosynthesis, to construct strains that are mutated in the steps of biosynthesis of pristinamycin. This was shown for pristinamycin II, but the same results may be obtained for pristinamycins I and, by extension, for the different components of streptogramins. Strains producing different intermediates may thus be obtained. These strains may be used to produce novel molecules by chemical, biochemical, enzymatic, and the like, modification(s) of the said intermediates. A block in an early step of the biosynthesis pathway of one or other of the components of streptogramins may also lead to mutated strains that are left producing only one or other of the coponents.

Figure 2:
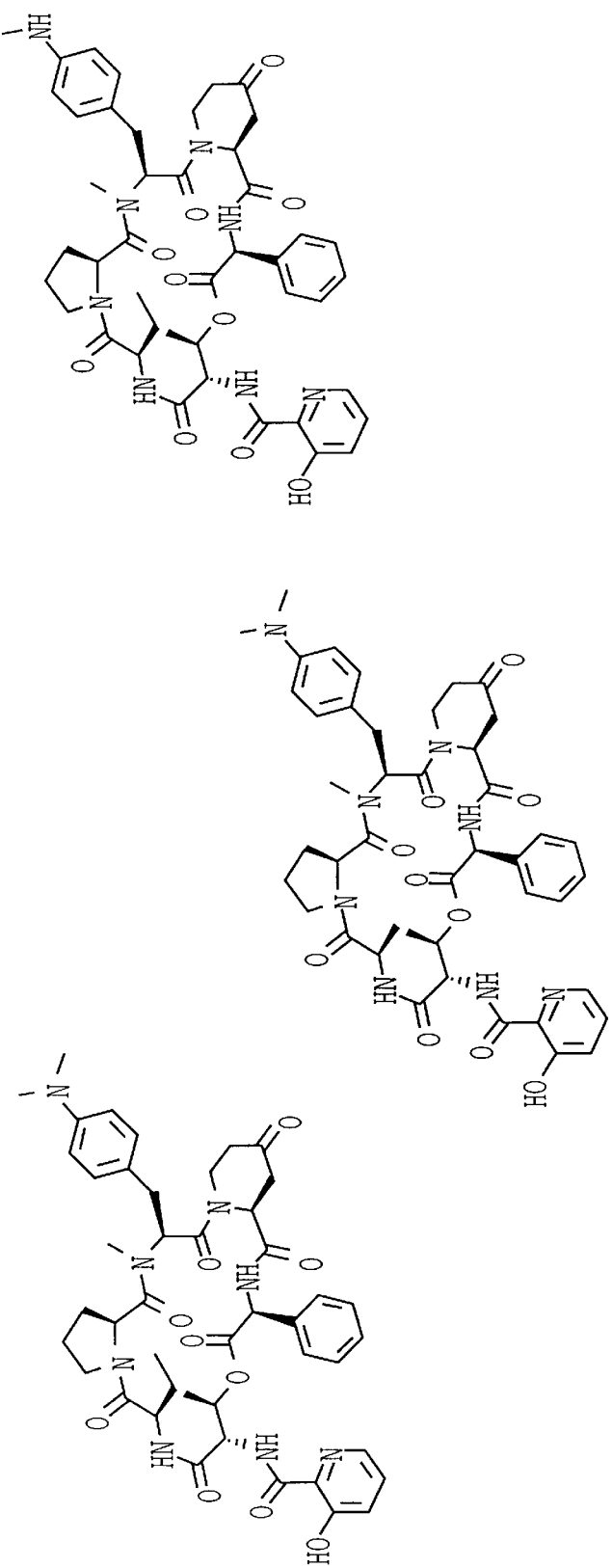
FIG. 2: Example of structure of the B components of streptogramins.
Figure 3:
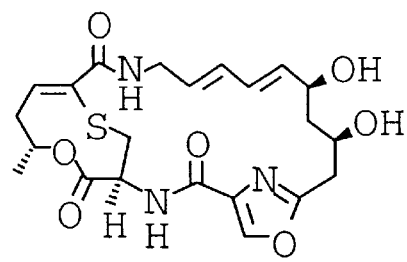
FIGS. 3A and B: Other examples of structures of streptogramins.
Figure 3:
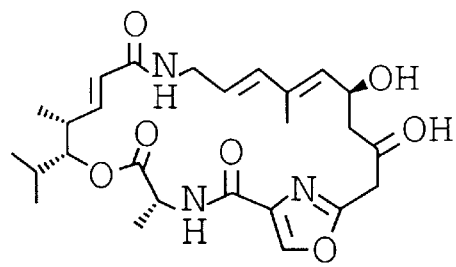
Figure 3:
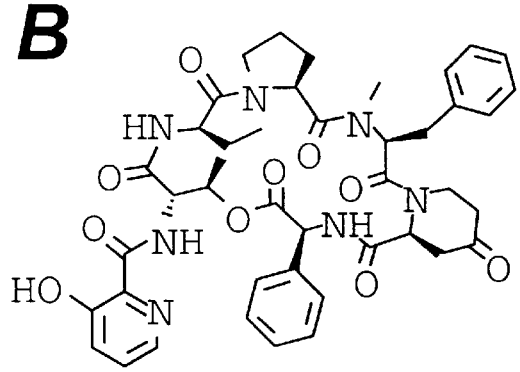
Figure 3:
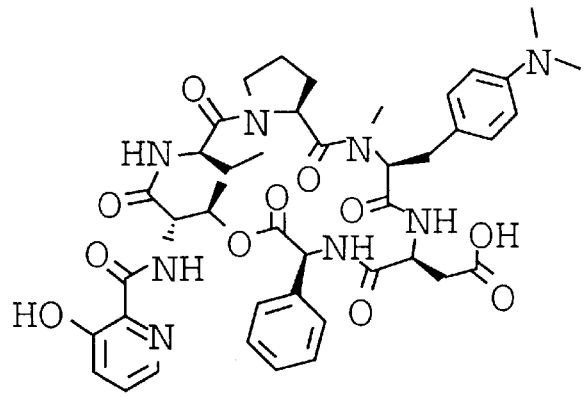
Figure 3:
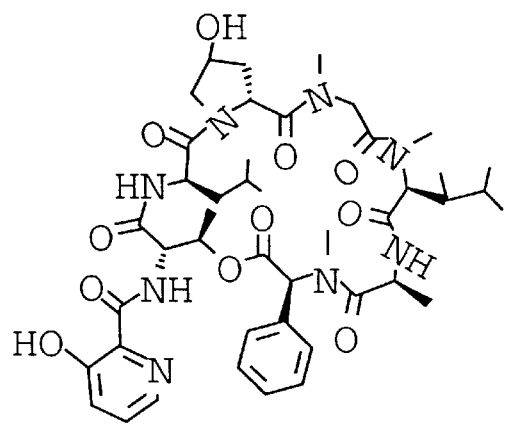

9.2. Construction of a Mutant of S. pristinaespiralis SP92 Disrupted in the samS Gene This example illustrates how it is possible, by disruption of the samS gene, to construct a strain of S. pristinaespiralis SP92 which produces 35% less PIA and 10 times as much PIB (the chemical structures are shown in FIG. 2) relative to the wild-type SP92 strain. This mutant was constructed for the purpose of confirming the presumed SAM synthase function for the protein encoded by the samS gene, and for obtaining a strain that synthesizes more PIB than the wild-type SP92 strain.

9.2.1. Construction of Plasmid pVRC702

Figure 26:
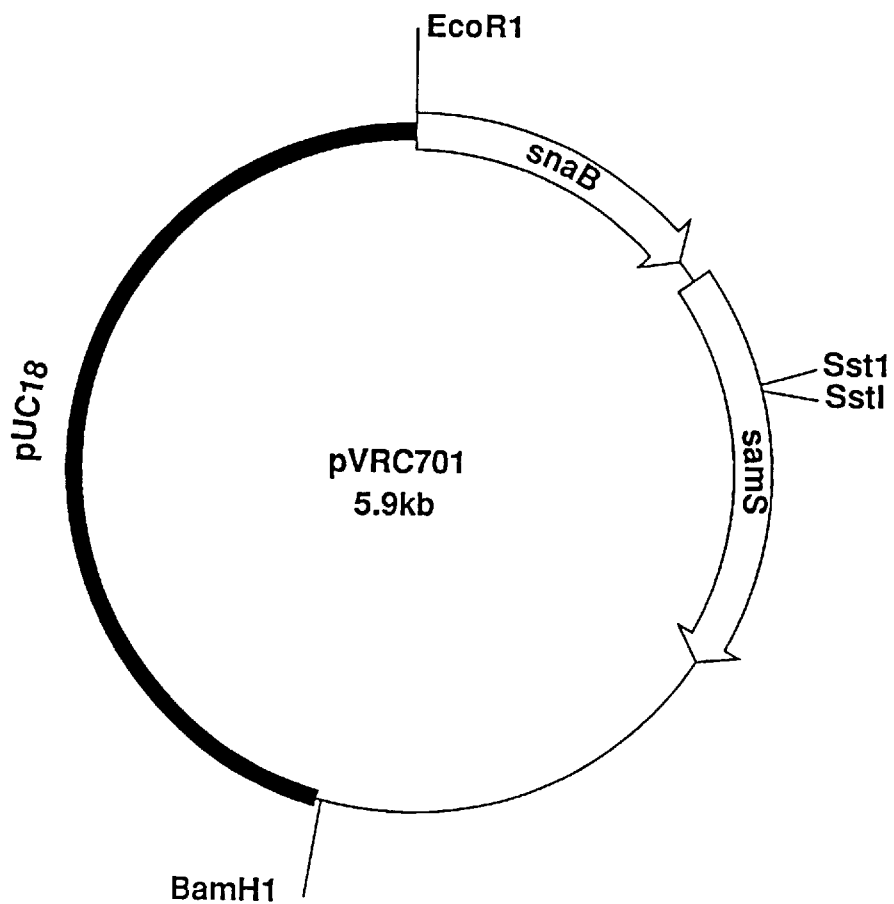
FIG. 26: Diagram of plasmid pVRC701.

From plasmid pXL2045 (described in Example 6.3), the 3.2-kb BamH1-EcoR1 fragment was isolated by enzymatic cleavage and purified after electrophoresis on 1% agarose gel by the Geneclean kit method (see Example 6.8). This fragment carries snaB gene as well as the samS gene (FIG. 16). This fragment is then cloned into a plasmid pUC18 in the following manner: 50 ng of pUC18 were linearized by double digestion using the enzymes EcoR1 and BamH1, and then ligated in the presence of T$ DNA ligase (Biolabs) with 300 ng of the 3.2-kb BamH1-EcoR1 fragment. After transformation of competent cells of E. coli strain TG1 with this ligation mixture, a recombinant clone possessing plasmid pUC18 with the 3.2-kb insert could be isolated, and this was designated pVRC701 (FIG. 26).

Figure 27:
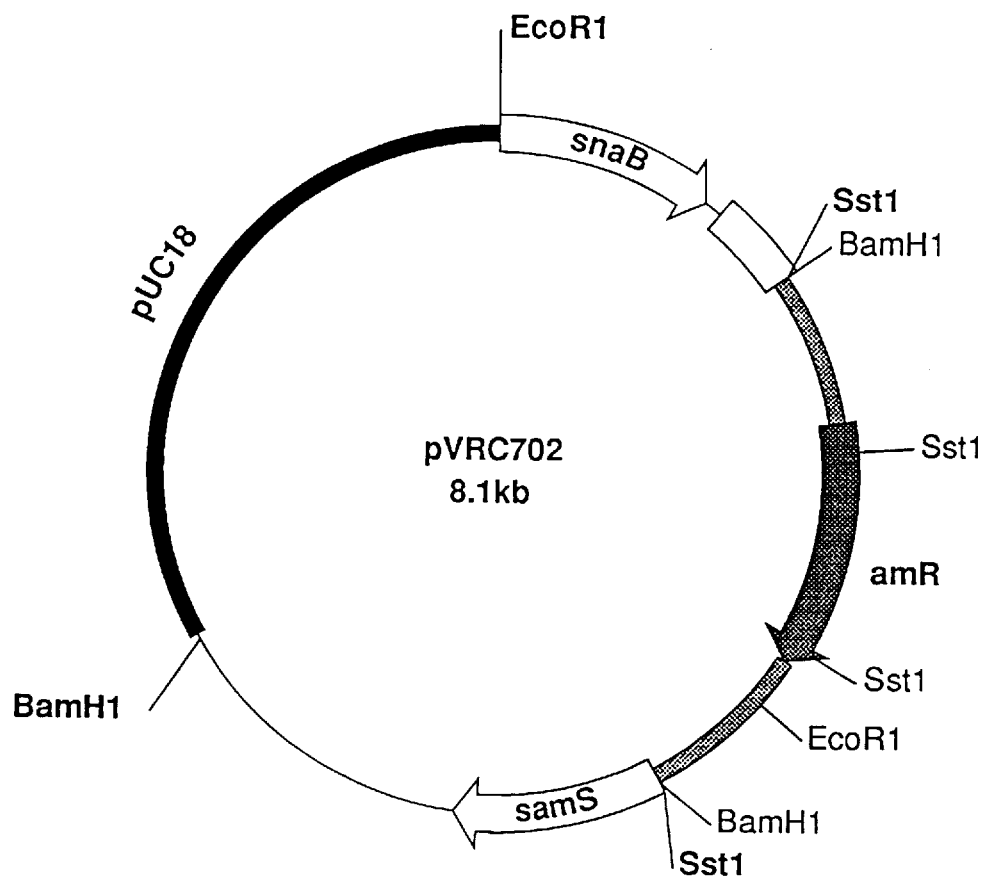
FIG. 27: Diagram of plasmid pVRC702.

Plasmid pVRC702 is derived from plasmid pVRC701 by the introduction between the two Sst1 sites located in the middle of the samS gene (FIG. 27) of a cassette carrying the amR gene coding for resistance to amramycin and geniticin. To this end, a 2.2-kb BamH1-BamH1 fragment carrying the ΩamR cassette was first isolated by BamH1 digestion of plasmid pHP45ΩamR (given by J. L. Pernodet, Laboratoire de Génétique d'Orsay) using the same technique as above. 200 ng of this fragment were then ligated with 50 ng of plasmid pUC1318 (Kay and McPherson, 1987) linearized with the enzyme BamH1, and this ligation mixture was introduced into competent E. coli TG1 cells. From the recombinant zone possessing plasmid pUC1318 containing the ΩamR cassette, 50 ng of a 2.2-kb Sst1-Sst1 fragment containing the ΩamR cassette could be reisolated by partial cleavage using the enzyme Sst1, and this fragment was ligated with 30 ng of plasmid PVRC701 cut with Sst1 (FIG. 26) to give, after transformation of competent E. coli TG1 cells, plasmid PVRC702, the structure odf which is detailed in FIG. 27.

Plasmid pVRC702 thereby obtained was prepared in large amounts according to the method described above in Example 2.1.

9.2.2. Construction of the Strain Having the samS::ΩamR Chromosomal Gene

This strain was obtained by transformation of S. pristinaespiralis protoplasts with 1 μg of the suicide plasmid pVRC702 which is incapable of replicating in a Streptomyces cell. The protocols for preparation of the protoplasts and for transformation are the same as above (Example 9.1). The only modifications made with respect to Example 10.1 relate to the selection antibiotic. In the present case, the recombinant protoplasts after regeneration for 18 hours at 30° C. on R2YE medium are selected in the presence of 50 μg/ml final of geniticin (Sigma Chemical Co.). Thus, an overlayer composed of 3 ml of SNA containing 383 μg/ml of geniticin is added to each dish of R2YE.

In this way, it was possible to isolate 500 geniticin-resistant recombinant clones, which may result either from an integration of plasmid pVRC702 into the chromosome following a single homologous recombination between chromosomal and plasmid samS genes (in the case of single crossing-over), or from an exchange between the chromosomal samS gene and the plasmid samS::ΩamR plasmid gene following a double homologous recombination event (in the case of double crossing-over). In these two cases in point, the ΩamR cassette becomes transferred onto the chromosome of the strain, and endows it with an amR resistance which is stable over generations.

The recombinant clones were isolated by plating out and growth on HT7 medium containing 50 μg/ml final of geniticin, and then analyzed by the colony hybridization technique. Hybridization of the clones with a first probe obtained as described in Example 9.1 from the 2.7-kb BamH1-EcoRI fragment originating from pVRC702 and corresponding to pUC18, as well as with a second probe corresponding to the 2.2-kb BamH1 fragment carrying the ΩamR cassette, enable the cases of single crossing-over (hybridizing with both probes) to be distinguished from the cases of double crossing-over (hybridizing only with the second probe). The 3 clones resulting from a double crossing-over thereby selected were purified by plating out and growth on YVD medium containing 50 mg/ml final of geniticin, and stocks of spores were obtained.

In order to verify the genomic structure of the 3 double recombinants, various Southern blots of the chromosomal DNA of these clones digested with the enzymes EcoRI and BamHI were produced and hybridized with the following three probes: the probe corresponding to the ΩamR cassette obtained from the 2.2-kb BamHI fragment of pVRC702, the probe corresponding to pUC18 obtained from the 2.7-kb BamHI-EcoRI fragment of pVRC701, and lastly a probe obtained from the 1.3-kb EcoRI-SstI fragment of pVRC701 carrying the snaB gene and the beginning of samS. These hybridizations enabled it to be verified that the three clones tested did indeed result from a double homologous recombination event permitting replacement of the intact chromosomal samS gene by the mutated samS gene interrupted by the ΩamR cassette.

One of these three mutant clones was designated SP92 samS::ΩamR.

9.2.3. Production of Pristinamycins by the Mutant Strain samS::ΩamR

This example illustrates how it is determined that the mutant SP92 samS::ΩamR having the disrupted samS gene produces 35% less pristinamycin IA and 10-fold more pristinamycin IB than the wild-type SP92 strain.

The mutant SP92 samS::ΩamR as well as the control SP92 strain were cultured in liquid production medium, and their productions of pristinamycin II and pristinamycin I were assayed as described in Example 9.1.

The results showed that, under the fermentation conditions implemented, the mutant SP92 samS::ΩamR produces an amount of pristinamycins II equivalent to that of the SP92 control for all three times tested. In contrast, the mutant SP92 samS::ΩamR produces approximately 35% less pristinamycin IA and 10-fold more pristinamycin IB than the control strain at all three times tested. The IB form of pristinamycins thus represents 20% of the collective total type I pristinamycins produced by the mutant SP92 samS::ΩamR, whereas the control strain synthesizes only of the order of 1% of PIB. The IB form of pristinamycins differs from the IA form in that the fifth residue is p-methylaminophenylalanine, instead of p-dimethylaminophenylalanine for pristinamycin IA. The fact that the mutant SP92 samS::ΩamR produces more pristinamycin IB and less pristinamycin IA shows that disruption of the samS gene causes a decrease in the degree of methylation of the fifth residue of pristinamycins I, and hence that the samS gene is probably involved in the biosynthesis of the methyl donor, SAM, that is to say that it codes for a SAM synthase.

9.3 Construction of a Mutant of S. pristinaespiralis SP92 Disrupted in the papA Gene This example illustrates how it is possible, by disruption of the papA gene, to construct a strain of S. pristinaespiralis SP92 which no longer produces PI. This mutant is constructed for the purpose of confirming the functionality of the PapA protein. Its construction was carried out using the suicide vector pDH5 described in Example 9.1.

9.3.1. Construction of Plasmid pVRC508

This example illustrates how it is possible to construct a plasmid which does not replicate in S. pristinaespiralis SP92 and which may be used to disrupt the papA gene by single homologous recombination.

Plasmid pVRC508 was constructed to produce the SP92 chromosomal mutant disrupted in the papA gene from plasmid pVRC903 described in Example 7.7.

Figure 23:
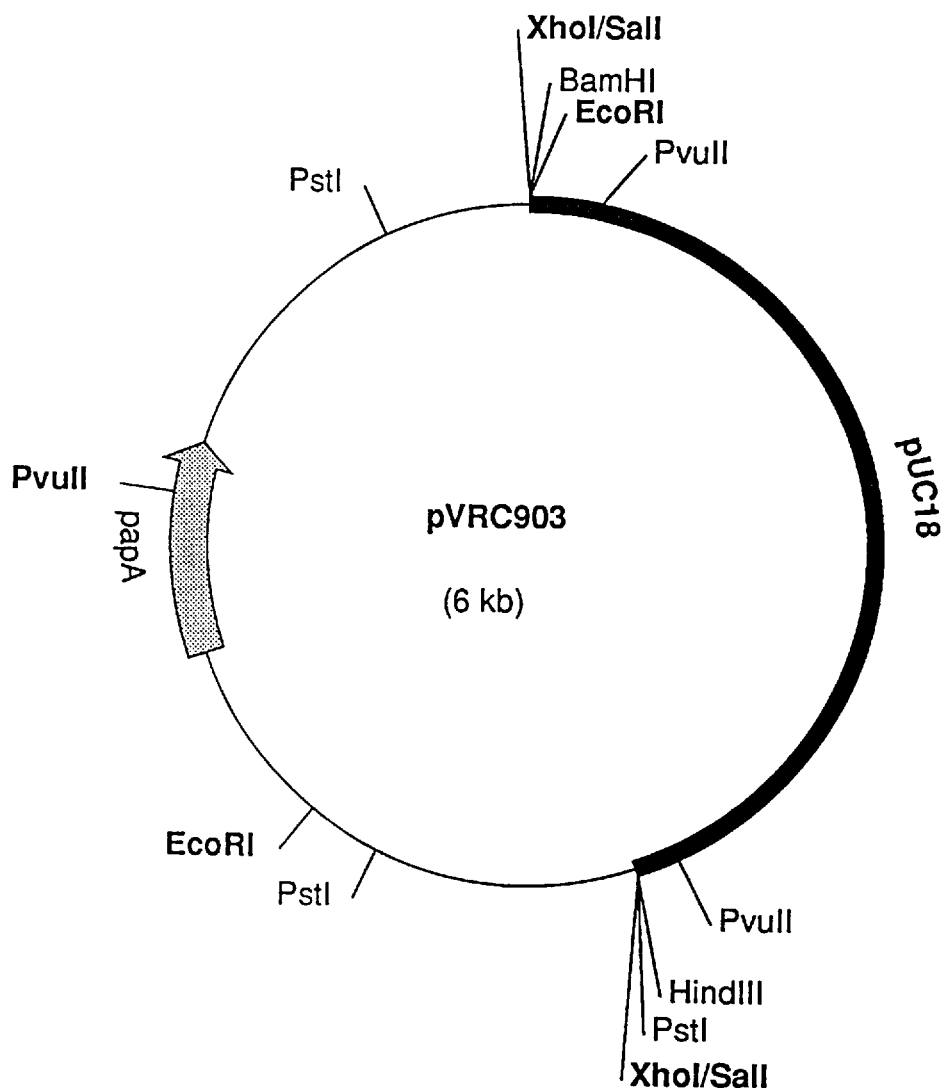
FIG. 23: Diagram of plasmid pVRC903.

In Example 7.7, the cloning of the 1.4-kb PvuII-EcoRI fragment into M13mp18 from plasmid pVRC903 for the purpose of sequencing the papA gene was described (this fragment corresponds to the 1.4-kb PvuII-XhoI fragment present in the vector pVRC900, FIG. 23).

This construction in M13mp18 was digested with the restriction enzyme HindIII and EcoRI. After separation of the vector M13mp18 and the 1.4-kb fragment containing a portion of the papA gene on 0.8% agarose gel, the latter fragment was isolated and purified by Geneclean (Bio101, La Jolla, Calif.). The localization of the fragment in the papA gene is presented in FIG. 23.

Figure 28:
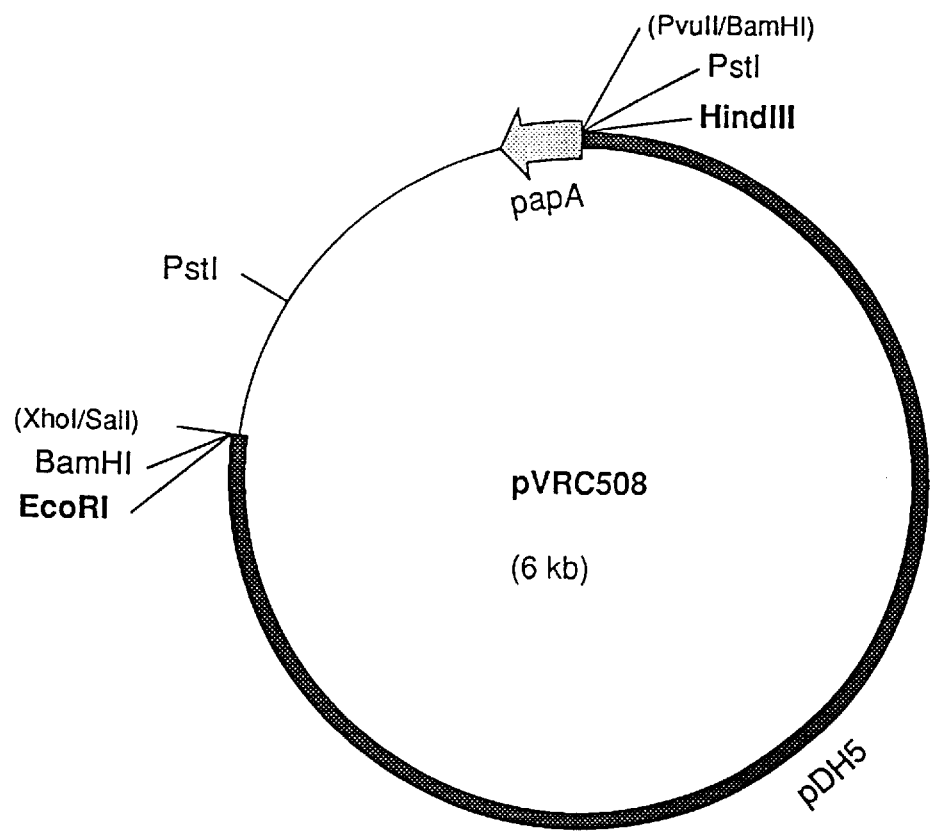
FIG. 28: Diagram of plasmid pVRC508.

100 ng of vector pDH5 linearized by a double digestion with the restriction enzymes HindIII and EcoRI were ligated with 200 ng of the 1.4-kb fragment as described in Example 3.3. A clone carrying the desired fragment was isolated after transformation of the strain TG1. The recombinant plasmid was designated pVRC508. Plasmid pVRC508 was prepared as described in Example 2.1. Its restriction map is presented in FIG. 28.

9.3.2. Isolation of the SP92 Mutant Disrupted in the papA Gene by Homologous Recombination This example illustrates how the mutant of *S. pristinaespiralis* SP92 disrupted in the papA gene was constructed. This mutant was isolated by transformation of the strain SP92 with the suicide plasmid pVRC508. The preparation of the protoplasts and their transformation were carried out as described in Example 9.1. After transformation of protoplasts of the strain SP92, the recombinants were selected by overlaying 3 ml of SNA medium containing 2.6 mg/ml of thiostrepton. Of the 5 transformations carried out with 5 times 1 µg of plasmid pVRC508, ten thiostrepton-resistant clones were isolated. This gives a recombinant efficiency of approximately 2 per µg of DNA. These recombinants result from integration by single homologous recombination between the papA gene carried by the chromosome of the strain SP92 and the 1.4-kb fragment of the suicide plasmid pVRC508.

The spores of the recombinants were isolated by plating out and growth on R2YE medium containing 400 µg/ml of thiostrepton, and plated out again on the same medium to obtain isolated colonies.

In order to verify the position of integration of plasmid pVRC508, various Southern blots of the total DNA of several recombinant clones, purified as described above, were produced and hybridized with the vector pDH5 and the 1.4-kb fragment, used successively as probes after labelling by random priming with [α-$^{32}$P]dCTP as described in Maniatis et al. (1989). The hybridization results show the disappearance from the genome of the recombinant clones digested with the restriction enzyme EcoRI (site flanking the 1.4-kb fragment) of the 6.8-kb EcoRI band, and the appearance of two additional bands relative to the control SP92 strain, one of 2.4 kb hybridizing with the 1.4-kb fragment, and the other of 10.5 kb hybridizing both with pDH5 and with the 1.4-kb fragment. Digestion of the recombinant clones with the restriction enzyme PstI shows the appearance of two additional bands relative to the control SP92 strain, one of 1.0 kb hybridizing with the 1.4-kb fragment, and the other of 5.1 kb hybridizing both with pDH5 and with the 1.4-kb fragment. One of these mutants was designated SP92::pVRC508.

9.3.3. Production of Pristinamycins by the Mutant SP92::pVRC508

This example illustrates how it is determined that the mutant of *S. pristinaespiralis* SP92 disrupted in the papA gene by integration of plasmid pVRC508 no longer produces PI.

The mutant SP92::pVRC508, as well as the strain SP92 as control strain, were cultured in liquid production medium. The fermentation and also the assay of pristinamycins I and II were carried out as described in Example 9.1.

The results showed that, under the fermentation conditions implemented, whereas the control SP92 strain produced a standard amount of pristinamycins I, no trace of type I pristinamycins was detected in the fermentation must of the mutant SP92::pVRC508. Moreover, the production of pristinamycins II by the mutant SP92::pVRC508 is equivalent to that of the SP92 control. The mutant SP92::pVRC508 is left producing only pristinamycins II. These results show clearly that the papA gene codes for a protein involved in the biosynthesis of pristinamycins I.

To check the absence of polarity of the disruption carried out in the mutant SP92::pVRC508, the latter was fermented in the presence p-dimethylaminophenylalanine. The mutant SP92::pVRC508 was fermented as described above, with the addition, at 17 hours of fermentation, of 100 mg/l of p-dimethylaminophenylalanine. Under these conditions of complementation, the mutant SP92::pVRC508 produces an amount of pristinamycins I equivalent to that produced by the strain SP92. The production of pristinamycins II is equivalent in both strains. This enables us to conclude that the mutant SP92::pVRC508 does not produce pristinamycins I because it is indeed disrupted in a gene that participates in the biosynthesis of p-dimethylaminophenylalanine (the papA gene). Complementation of this mutant with p-dimethylaminophenylalanine restores its capacity to produce pristinamycins I, proving that the mutation has no polar effect on the synthesis of other pristinamycin I precursors or on the condensation of these precursors.

This example shows that it is possible, starting from cloned genes for biosynthesis, to construct strains that are mutated in the steps of biosynthesis of pristinamycins, and especially pristinamycins I. This example also shows that it is possible, by this approach, to construct strains of *S. pristinaespiralis* specifically producing pristinamycins II and, by extension, strains specifically producing pristinamycins I. This same approach could also be used for other strains of actinomycetes producing streptogramins.

9.4. Construction of Mutant of *S. pristinaespiralis* SP92 Distrusted in the snbA Gene This example illustrates how it is possible, by disruption of the snbA gene, to construct a strain of *S. pristinaespiralis* SP92 which no longer produces pristinamycins I. This mutant was constructed for the purpose of confirming the functionality of the SnbA protein. Its construction was carried out using the suicide vector pDH5 described in Example 9.1.

9.4.1. Construction of Plasmid pVRC404

This example illustrates how it is possible to construct a plasmid which no longer replicates in *S. pristinaespiralis* SP92 and which may be used to disrupt the snbA gene by single homologous recombination.

Plasmid pVRC404 was constructed from plasmid pVRC402 described in Example 6.2, to produce the SP92 chromosomal mutant disrupted in the snbA gene. Plasmid pVRC402 was digested with the restriction enzyme XhoI and HindIII. After separation of the fragments thereby generated by electrophroesis on 0.8% agarose gel, a 1170-bp fragment containing an internal portion of the snbA gene was isolated and purified by Geneclean (Bio101, La Jolla, Calif.). The localization of the fragment in the snbA gene is presented in FIG. 15A.

Figure 29:
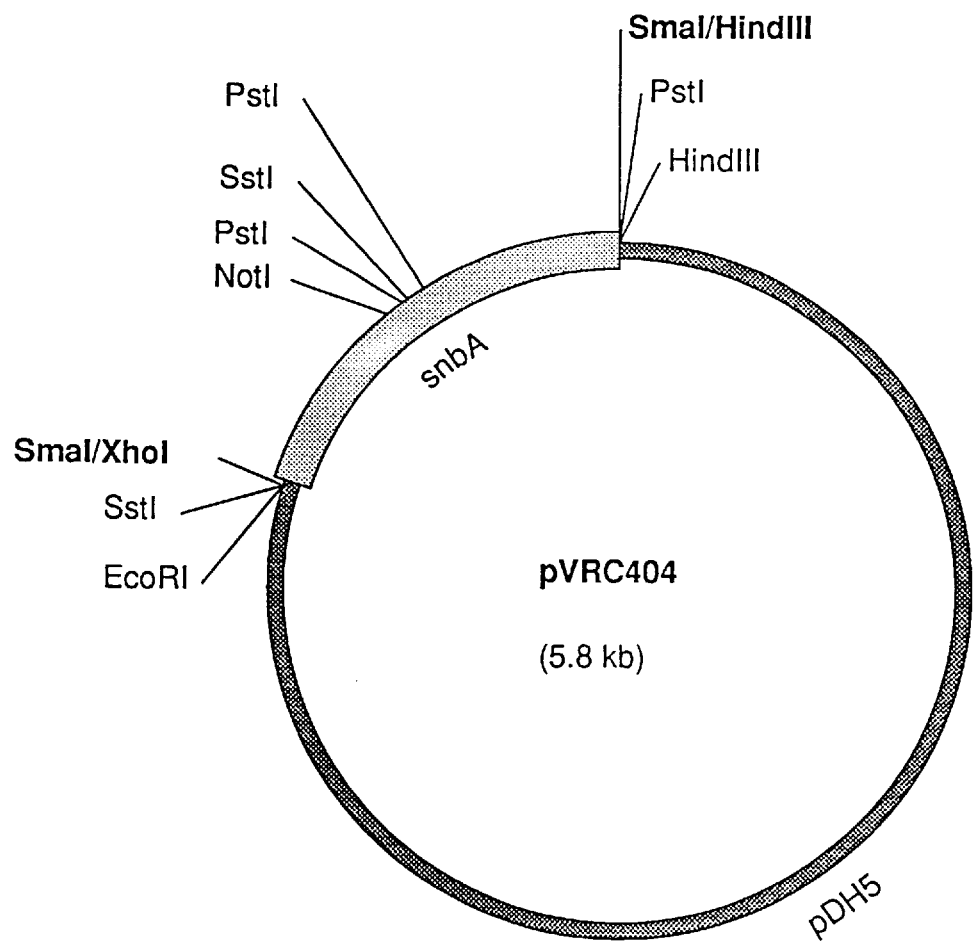
FIG. 29: Diagram of plasmid pVRC404.

100 ng of vector pDH5 linearized by an SmaI digestion were ligated with 200 ng of the 1173-bp fragment as described in Example 3.3. A clone carrying the desired fragment was isolated after transformation of the strain TG1. The recombinant plasmid was designated pVRC404. Plasmid pVRC404 was prepared as described in Example 2.1. Its restriction map is presented in FIG. 29.

9.4.2. Isolation of the SP92 Mutant Disrupted in the snbA Gene by Homologous Recombination This example illustrates how the mutant of *S. pristinaespiralis* SP92 disrupted in the snbA gene was constructed.

This mutant was isolated by transformation of the strain SP92 with the suicide plasmid pVRC404. The preparation of the protoplasts and their transformation were carried out as described in Example 9.1. After transformation of protoplasts of the strain SP92, the recombinants were selected by overlaying 3 ml of SNA medium containing 2.6 mg/ml of thiostrepton. Of the 5 transformations carried out with 5 times 1 µg of plasmid pVRC404, about thirty thiostrepton-resistant clones were isolated. This gives a recombinant efficiency of approximately 5 per µg DNA. These recombinants result from integration by single homologous recombination between the snbA gene carried by the chromosome of strain SP92 and the 1170-bp fragment of the suicide plasmid pVRC404. The spores of the recombinants were isolated by plating out and growth on R2YE medium+400 mg/ml of thiostrepton, and plated out again on the same medium to obtain isolated colonies. In order to verify the position of integration of plasmid pVRC404, various Southern blots of the total DNA of several recombinant clones, purified as described above, were produced and hybridized with the vector pDH5 and the 1170-kb fragment, used successively as probes after labelling by random priming with [α-$^{32}$P]dCTP as described in Maniatis et al. (1989). The hybridization results show the appearance in the genome of the recombinant clones digested with the restriction enzymes XhoI and HindIII of an additional 4.7-kb XhoI-HindIII band relative to the control SP92 strain (vector pDH5+1.17 kb), hybridizing both with pDH5 and with the 1170-bp fragment. Digestion of the recombinant clones with the restriction enzyme PflMI (sites flanking tbhe 1170-bp XhoI-HindIII fragment) shows the disappearance of the 3.1-kb PflMI-PflMI band and the appearance of a band at 8.8 kb hybridizing with both probes. These results indicate that the genomic structure of the clones analysed is indeed that expected after a homologous recombination event between pVRC404 and the chromosomal snbA gene. One of these mutants was designated SP92::pVRC404.

9.4.3. Production of Pristinamycins by the Mutant SP92::VRC404

This example illustrates how it is determined that the mutant of *S. pristinaespiralis* SP92 disrupted in the snbA gene by integration of plasmid pVRC404 no longer produces PI.

The mutant SP92::pVRC404, as well as the strains SP92 as control strain, were cultured in liquid production medium. The fermentation and also the assay of pristinamycins I and II were carried out as described in Example 9.1. The results showed that, under the fermentation conditions implemented, whereas the control SP92 strain produces a standard amount of pristinamycins I, no trace of pristinamycins I was detected in the fermentation must of the mutant SP92::pVRC404. Moreover, the production of pristinamycins II by the mutant SP92::pVRC404 is equivalent to that of the SP92 control. The mutant SP92::pVRC404 is left producing only pristinamycins II. This shows clearly that the snbA gene codes for a protein SnbA involved in the biosynthesis of pristinamycins I, as had been shown during the purification in Example 5.2.

This example shows, as in the preceding example, that it is possible, starting from cloned genes for biosynthesis, to construct strains that are mutated in the steps of biosynthesis of pristinamycins, and especially pristinamycins I. This example also shows that is possible, by this approach, to produce strains of *S. pristinaespiralis* specifically producing pristinamycins II and, by extension, strains specifically producing pristinamycins I, as described in the following example: 9.5. This same approach could also be used for other strains of actinomycetes producing streptogramins.

9.5. Construction of a Mutant of *S. pristinaespiralis* SP92 Disrupted in the snaD Gene Probably Coding for a Peptide Synthase Involved in the Biosynthesis of Pristinamycins II This example illustrates how it is possible, by disruption of the snaD gene probably coding for a peptide synthase involved in the biosynthesis of pristinamycins II, to construct a strain of *S. pristinaespiralis* SP92 which no longer produces pristinamycins II.

This mutant was constructed for the purpose of confirming the functionality of the snaD gene, and of obtaining a strain derived from SP92 left synthesizing only pristinamycins I.

Its construction was carried out using plasmid PVRC1000 described in Example 6.8, derived from the suicide vector pDH5, capable of replicating in *E. coli* only and carrying a resistance marker which is expressed in Streptomyces (see Example 9.1).

9.5.1 Construction of Plasmid pVRC1000

This example illustrates how it is possible to construct a plasmid which does not replicate in *S. pristinaespiralis* SP92 and which may be used to disrupt the snaD gene by single homologous recombination. The construction of plasmid pVRC1000 carrying a portion of the snaD gene is described in Example 6.8.

9.5.2. Isolation of the SP92 Mutant Disrupted in the snaD Gene by Homologous Recombination This example illustrates how the mutant of *S. pristinaespiralis* SP92 disrupted in the snaD gene was constructed. This mutant was isolated by transformation of the strain SP92 with the suicide plasmid pVRC1000. The preparation of the protoplasts and their transformation were carried out as described in Example 9.1. Of the 5 transformations carried out with 1 mg of pVRC1000, approximately 1500 thiostrepton-resistant clones were isolated. This gives a recombinant efficiency of approximately 375 per µg of DNA. These recombinants result from integration by single homologous recombination between then snaD gene carried by the chromosome of the strain SP92 and the 1.5-kb BamHI-SstI fragment of the suicide plasmid pVRC1000. About twenty recombinants were subcultured on R2YE medium containing 400 µg/ml of thiostrepton, and the spores of these recombinants were isolated by plating out again and growth on R2YE medium containing 400 µg/ml of thiostrepton.

In order to verify the position of integration of plasmid pVRC1000, various Southern blots of the total DNA of 7 recombinant clones, purified as described above, were produced and hybridized with the vector pDH5 and the 1.5-kb BamHI-SstI fragment contained in PVRC1000, used successively as probes after labelling with [α-$^{32}$P]dCTP as described in Example 9.1. The hybridization results show the appearance in the genome of the 7 recombinant clones of a 13.8-kb EcoRI band and an approximately 17-kb BglII band hybridizing with both probes, as well as a 3.7-kb EcoRI band hybridizing with the 1.2-kb BamHI-StsI probe. One of these mutants was designated SP92::pVRC1000 and corresponds well to the integration of plasmid pVRC1000 in the snaD gene by single homologous recombination.

9.5.3. Production of Pristinamycins by the Mutant SP92::pVRC1000

This example illustrates how it is determined that the mutant of *S. pristinaespiralis* SP922 disrupted in the snaD gene by integration of plasmid pVRC1000 no longer produces pristinamycins II, but only pristinamycins I. The mutant SP92::pVRC1000, as well as the control SP92 strain, were cultured in liquid production medium, and their productions of pristinamycins II and I were assayed as described in Example 9.1.

The results showed that, under the fermentation conditions implemented and for all three times tested, the mutant SP92::pVRC1000 produces 0 mg/l of pristinamycins II and an amount of pristinamycins I equivalent to that of the SP92 control. Hence this mutant is indeed blocked in a step of biosynthesis of pristinamycins II, which shows that the snaD gene codes for an enzyme involved in the biosynthesis of pristinamycins II, and very probably for a peptide synthase.

This example shows, as in the preceding example, that it is possible, starting from cloned genes for biosynthesis, to construct strains that are mutated in the steps of biosynthesis of pristinamycins, and especially pristinamycins II. This example also shows that it is possible, by this approach, to produce strains of *S. pristinaespiralis* specifically producing pristinamycins I and, by extension, strains specifically producing pristinamycins II. This same approach could also be used for other strains of actinomycetes producing streptogramins.

Example 10

Complementation of a Non-producing Mutant of the Strain SP92

This example shows how it is possible to express genes for the biosynthesis of pristinamycins. This expression was implemented more especially for the snaA and snaB genes carried by cosmid pIBV1 in a mutant strain derived from SP92:SP120. This mutant does not produce pristinamycin IIA. It accumulates the last intermediate of the biosynthesis pathway of pristinamycin II: pristinamycin IIB.

10.1 Cloning of the snaA and snaB Genes into the Shuttle Vector pIJ903

This example illustrates how a subfragment of cosmid pIVB1 containing the snaA and snaB genes was cloned into a vector capable of replicating both in *E. coli* and in Streptomyces.

The vector pIJ903 (Lydiate D. J. et al., 1985) is a low copy number (1 to 3 per cell) shuttle vector capable of replicating both in *E. coli* as a result of its origin of replication of pBR322, and in Streptomyces as a result of its origin of replication of SCP2*. The ampicillin resistance gene permits selection in *E. coli*, and the thiostrepton resistance gene permits selection in Streptomyces.

Cosmid pIBV1 was digested with the restriction enzyme SstI. A large 7.6-kb DNA fragment carrying the snaA and snaB genes was isolated by electrophoresis on 0.8% agarose gel and electroeluted. 500 ng of this fragment were ligated with 100 ng of the vector pUC1813 (Kay and McPherson, 1987) linearized with SstI. After transformation of *E. coli* strain DH5α (supE44 ΔlacU169 (f80lacZΔM15) hsdR17 recA1 endA1 gyrA96 thi-1 relA1), and selection of the transformants on solid LB containing 150 μg/ml of ampicillin and 20 μg/ml of X-gal, a clone carrying the 7.6-kb fragment was isolated. The plasmid was designated pVRC506. A preparation of this recombinant plasmid was carried out as described in Example 2.1.

Figure 30:
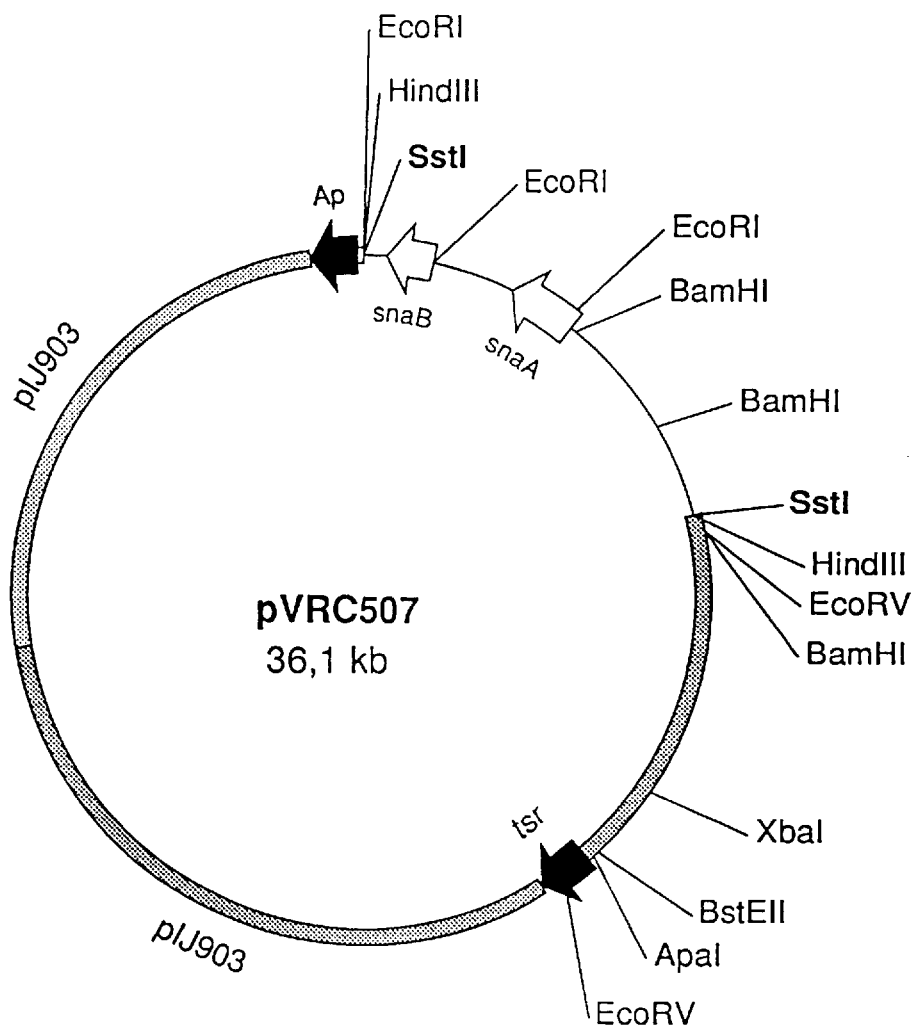
FIG. 30: Diagram of plasmid pVRC507.

Cloning into the vector pIJ903 was carried out at the HindIII site. Plasmid pVRC506 was cut with HindIII, and 7.6-kb fragment carrying the snaA and snaB genes was isolated by electrophoresis on 0.8% agarose gel and electroeluted. 500 ng of this fragment were ligated with 500 ng of the vector pIJ903 linearized with HindIII. After transformation of *E. coli* strain DH5α and selection of the transformants on solid LB containing 150 μg/ml of ampicillin, a clone carrying the 7.6-kb fragment was isolated. The plasmid was designated pVRC507. A preparation of this recombinant plasmid was carried out as described in Example 2.1. Its map is presented in FIG. 30.

10.2. Expression of the snaA and snaB Genes in the Mutant SP120

This example illustrates how it is possible to produce the proteins SnaA and SnaB in *S. pristinaespiralis* SP92 by introducing a plasmid carrying the corresponding structural genes into this strain. Expression of the snaA and snaB genes was carried out after transformation of the mutant strain SP120 with 500 ng of plasmid pVRC507. Transformation of the protoplasts of SP120 and selection of the transformants with thiostrepton were carried out as described in Example 9.1.2.

Many transformants were obtained in this way, and 3 of them were chosen for the tests of production in a liquid medium. The strain SP120 carrying plasmid pIJ903 was chosen as control. The fermentations and also the extraction of the biosynthesis products were carried out as described in Example 9.1.3.

The results showed that, under the fermentation conditions implemented, whereas the control (SP120 carrying plasmid pIJ903) produced 100% of P IIB and 0% of P IIA at 24, 28 and 32 hours of fermentation, the 3 clones of the strain SP120 transformed with plasmid pVRC507 produced, for these same times, approximately 85 to 80% of pristinamycin IIB and 15 to 20% of pristinamycin IIA, the sum of which is equivalent in amount to the pristinamycin IIB production of the control strain (SP120 carrying plasmid pIJ903). The clones carrying pVRC507 were indeed partially complemented for the step of biosynthesis of pristinamycins II corresponding to the oxidation of the 2,3 bond of the D-proline of the intermediate pristinamycin IIB. This was confirmed by enzymatic assay of pristinamycin IIA synthase activity, as described in Example 5.1.1.A, for the strains SP120 carrying pVRC507 and SP120 carrying pIJ903. Whereas the control strain SP120 carrying pIJ903 displays no pristinamycin IIA synthase activity, the strain SP120 carrying pVRC507 displays PIIA synthase activity.

This example shows that it is possible to express genes for the biosynthesis of streptogramins. This expression was studied more especially for the genes coding for pristinamycin IIA synthase, but the other genes for the biosynthesis of pristinamycins II and pristinamycins I, as well as those involved in the biosynthesis of the components of the different streptogramins, may be expressed in this way. This expression may be carried out in mutant strains as is the case in Example 10, but also in producing strains in order to increase the levels of streptogramin production. The expression may be modified by cloning the genes into a vector having a different copy number (low or high) or into an integrative vector, by deregulation of these genes, by cloning these genes under a homologous or heterologous promoter (strong or specifically regulated promoter). Expression of the different genes for the biosynthesis of streptogramins may also be carried out in heterologous strains using appropriate expression vectors in order to produce hybrid antibiotics.

Example 11

Expression of the papM Gene of S. pristinaespiralis in E. coli

This example illustrates how it is possible to express an S. pristinaespiralis gene in E. coli so as to be able to identify, purify and study the protein encoded by this gene.

11.1. Construction of Plasmid pVRC706

Figure 31:
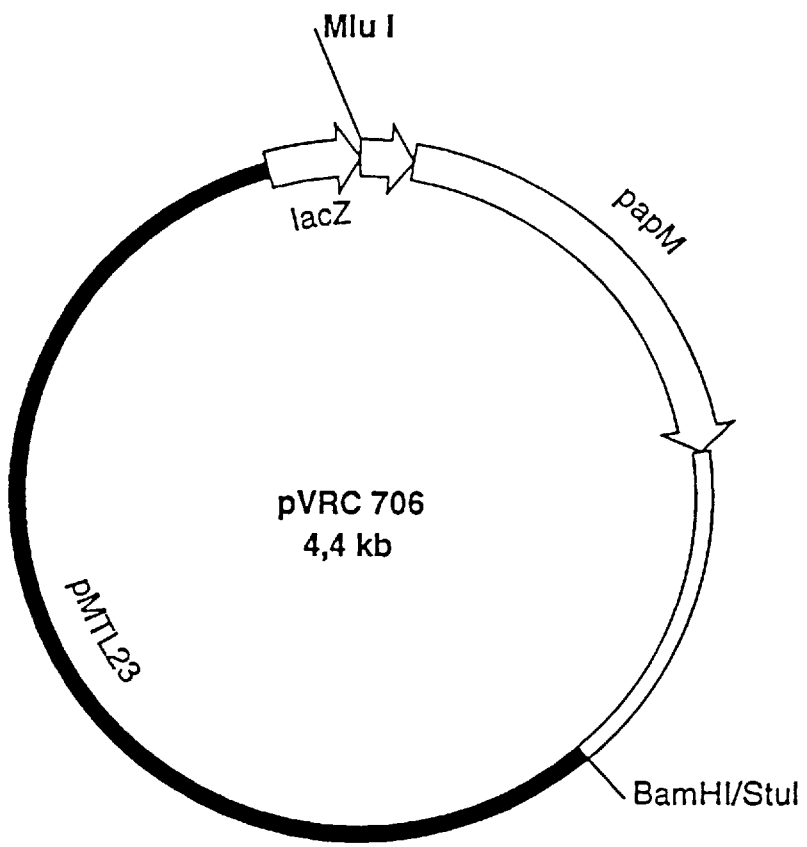
FIG. 31: Diagram of plasmid pVRC706.

Expression of the papM gene in E. coli is obtained by placing this gene downstream of the promoter and ribosomes binding site of the lacZ gene of E. coli. The 1.7-kb MluI-StuI fragment was isolated from plasmid pVRC409 described in Example 7.8, and then cloned into plasmid pMT123 (Chambers et al. 1988) cut at the BamHI site subsequently filled in using the Klenow enzyme (Maniatis et al. 1989) and at the MluI site, to give plasmid pVRC706 shown in FIG. 31. Cloning at the MluI site enables an in-frame fusion to be obtained between the first 32 amino acids of β-galactosidase encoded by the lacZ gene of plasmid pMTL23 and the last eleven amino acids of the gene located immediately upstream of papM, thereby making it possible to preserve the translational coupling which appears to exist between the papM gene and this upstream gene in the light of the nucleotide sequence given in Example 7.8. Thus, the expression of the hybrid gene between lacZ and the gene upstream of papM and that of the papM gene is under the control of the expression signals of the lacZ gene.

11.2 Expression in E. coli Strain DH5a of the Product of the papM Gene

Plasmids pVRC706 and pMTL23 were introduced by transformation into E. coli strain DH5α, and the expression of their genes was studied under conditions where the promoter of lacZ gene is induced as already described (Maniatis et al. 1989). The E. coli strains carrying plasmid pVRC706 or the control plasmid pMTL23 were cultured in 500 ml of LB rich medium containing 100 mg/ml of ampicillin and 1 mM IPTG, permitting induction of the promoter of the lacZ gene. These cultures are sampled when they have reached an optical density at 600 nm in the region of 1, and the protein extracts are prepared as described below.

11.3. Assay of the Activity of the Product of the pamM Gene Expressed in E. coli The activity corresponding to the protein encoded by the papM gene is assayed on the two extracts prepared from E. coli cultures carrying plasmid pVRC706 or plasmid pMTL23 Example 5.7). It was shown that the extract prepared from the strain E. coli::pVRC706 catalyses the methylation of p-aminophenylalanine to p-dimethylaminophenylalanine with an activity of 235 unit/mg, whereas this activity is absent in the extracts of the control strain E. coli::pMTL23 (see Example 5.7.1.C). These results indicate that it is possible to express the papM gene of S. pristinae-spiralis in E. coli, and that the corresponding protein is indeed the enzyme catalysing the methylation of p-aminophenylalanine to p-dimethylaminophenylalanine. This example shows that it is possible to express genes for the biosynthesis of streptogramins in heterologous strains (such as E. coli, but also in other microorganisms) using appropriate expression vectors in order to produce precursors of antibiotics or even natural or hybrid antibiotics.

Example 12

Demonstration of the Homology of Genes Involved in the Biosynthesis of Streptogramins in Different Streptomyces This example illustrates how it is possible to demonstrate, by hybridization with total DNAs, the homology existing between different genes involved in the biosynthesis of streptogramins in different strains of Streptomyces producing streptogramins.

12.1. Extraction of Total DNA of Different Streptomyces Producing Streptogramins This example illustrates how the DNA of different strains producing streptogramins was purified. These strains of Streptomyces were chosen from those described in Table 1:

Streptomyces loidensis

Streptomyces olivaceus

Streptomyces ostreogriseus

Streptomyces virginiae

A strain not producing streptogramins: Streptomyces hygroscopicus, was chosen as negative control.

The extractions of the different total DNAs were carried out from cultures in YEME medium, as described in Example 1.

12.2. Hybridization of Total DNAs of Strains Producing Streptogramins with DNA Fragments Containing Genes Involved in the Biosynthesis of Pristinamycins and Isolated from S. pristinaespiralis Strain SP92

This example illustrates how it is possible, starting from genes involved in the biosynthesis of pristinamycins and isolated from the strain SP92 as described in the preceding examples, to demonstrate homologous genes by hybridization of the total DNAs of strains producing streptogramins.

The DNA fragments used as a probe were:

The 3.9-kb XhoI-XhoI fragment isolated from pVRC1106 described in Example 6.5, the restriction map of which is presented in FIG. 18. This fragment contains a portion of the gene coding for pristinamycin I synthase II.

The 6-kb BamHI-BamHI fragment isolated from plasmid pXL2045 described in Example 6.3, the map of which is presented in FIG. 16. This fragment contains the structural genes for the two subunits of PIIA synthase.

The total DNAs of the four strains producing streptogramins, the strain S. hygroscopicus and also the strain SP92, were digested with the restriction enzymes BamHI and XhoI. The DNA fragments thereby obtained were separated on 0.7% agarose gel and the DNA was transferred onto a nylon membrane as described by Maniatis et al. (1989). Labelling of the 3.6-kb XhoI-XhoI and 6-kb BamHI-BamHI fragments was carried out by labelling by random priming as described in Example 9.1.2. Hybridization of the membranes was carried out in the presence of formamide at 42° C. as described in Maniatis et al. (1989). Washing of the membranes after hybridization was carried out at 50° and 60° C. in a solution containing SSC (Maniatis et al. (1989) diluted 10-fold and 0.1% SDS.

The following results are demonstrated by these hybridizations:

The strain S. hygroscopicus does not display and hybridization with the two probes used.

The total DNAs (digested with XhoI and BamHI) of the strains S. ostreogirseus, S. olivaceus, S. loidensis and S. virginiae all display hybridization signals of intensity comparable to those observed on the total DNA of the strain SP92 with both probes used.

The total DNA (digested with XhoI and BamHI) of the strain S. virginiae displays signals with both probes used, but their intensity is weaker than that observed in SP92.

This example shows that different strains of Streptomyces producing streptogramins contain genes that hybridize with genes isolated in S. pristinaespiralis SP92 and which are involved in the biosynthesis of streptogramins, as presented in the preceding examples. These hybridizations thus demonstrate the homology existing between the genes involved in the biosynthesis of streptogramins of the strains SP92 and those involved in the biosynthesis of streptogramins of other strains producing streptogramins.

This example hence shows that it is possible, starting from genes isolated from SP92 and involved in the biosynthesis of streptogramins, to isolate by hybridization and cloning the homologous genes present in other strains producing streptogramins.

Example 13

Study of the Physical Binding of the Different S. pristinaespiralis SP 92 Genes Involved in the Biosynthesis of Pristinamycins I and Pristinamycins II This example illustrates how it is possible to study the physical binding of the S. pristinaespiralis SP 92 genes involved in the biosynthesis of pristinamycins I and II. This study was carried out for the purpose of showing that all these genes are grouped together on the chromosome in a cluster, and that it is hence possible by chromosome walking from the genes already identified to isolate other genes involved in the biosynthesis of pristinamycins I and II. Such an approach mahy be envisaged for the genes involved in the biosynthesis of other streptogramins.

13.1 Restriction Enzymes Used for Pulsed-Field Electrophoresis

The S. pristinaespiralis SP92 genome is composed of 70% to 75% of nucleotides containing the basis G and C. To cut its genome into a small number of large fragments, we used enzymes which recognize a sequence rich in AT, such as AseI (AT/TAAT) and SspI (AAT/ATT) but also HindIII (A/AGCTT), EcoRI (G/AATTC), NdeI (CA/TATG) and ClaI (AT/CGAT).

13.2. S. pristinaespiralis Strains Used for Pulsed-Field Electrophoresis

We used the chromosomal DNA of several strains to study by pulsed-field electrophrosis the physical binding of the genes involved in the biosynthesis of pristinamycins I and pristinamycins II. We prepared inserts as described ibn Example 4.1 of the chromosomal DNA of S. pristinaespiralis strain SP92, and also of the chromosomal DNA of the strains derived from SP92 whose construction is described in Examples 9.1 and 9.4. These are the strain SP92::pVRC505 in which the snaA gene has been disrupted by integration of plasmid pVRC505 (Example 9.1), and the strain SP92::pVRC404 in which the snbA gene has been disrupted by integration of plasmid pVRC404 (Example 9.4). The latter two strains were included in this study since they enabled the snaA and snbB genes to be positioned accurately on the chromosome map by exploiting the presence of sites which rarely cut chromosomal DNA, AseI, SspI, HindIII, EcoRI, NdeI and ClaI, in plasmids pVRC505 and pVRC404.

13.3. DNA Probes Used for Hybridization of the Fragments Isolated by Pulsed-Field Electrophoresis We used different DNA fragments to obtain radioactively labelled probes as is described in Example 9.1, which we hybridized with the fragments separated by pulsed-field electrophoresis after enzymatic cleavage of the chromosomal DNA inserts of the three strains presented above. The probes are as follows: the 3,2-kb EcoRI-BamHI fragment isolated from plasmid pVRC701 carrying the snaB and samS genes (see Example 9.2), the 1.5-kb BamH1-Sst1 fragment isolated from plasmid pVRC1000 carrying a portion of the snaD gene (see Example 6.8), the 1.1-kb XhoI-HindIII fragment isolated from plasmid pVRC402 carrying the snbA gene (see Example 6.1), the 2.4-kb Pst1-Pst1 fragment isolated from plasmid pVRC900 carrying papA gene (see Example 6.7) and the 1.5-kb XhoI-PstI fragment isolated from plasmid pVRC509 carrying the snaC gene (see Example 6.9).

Figure 32:
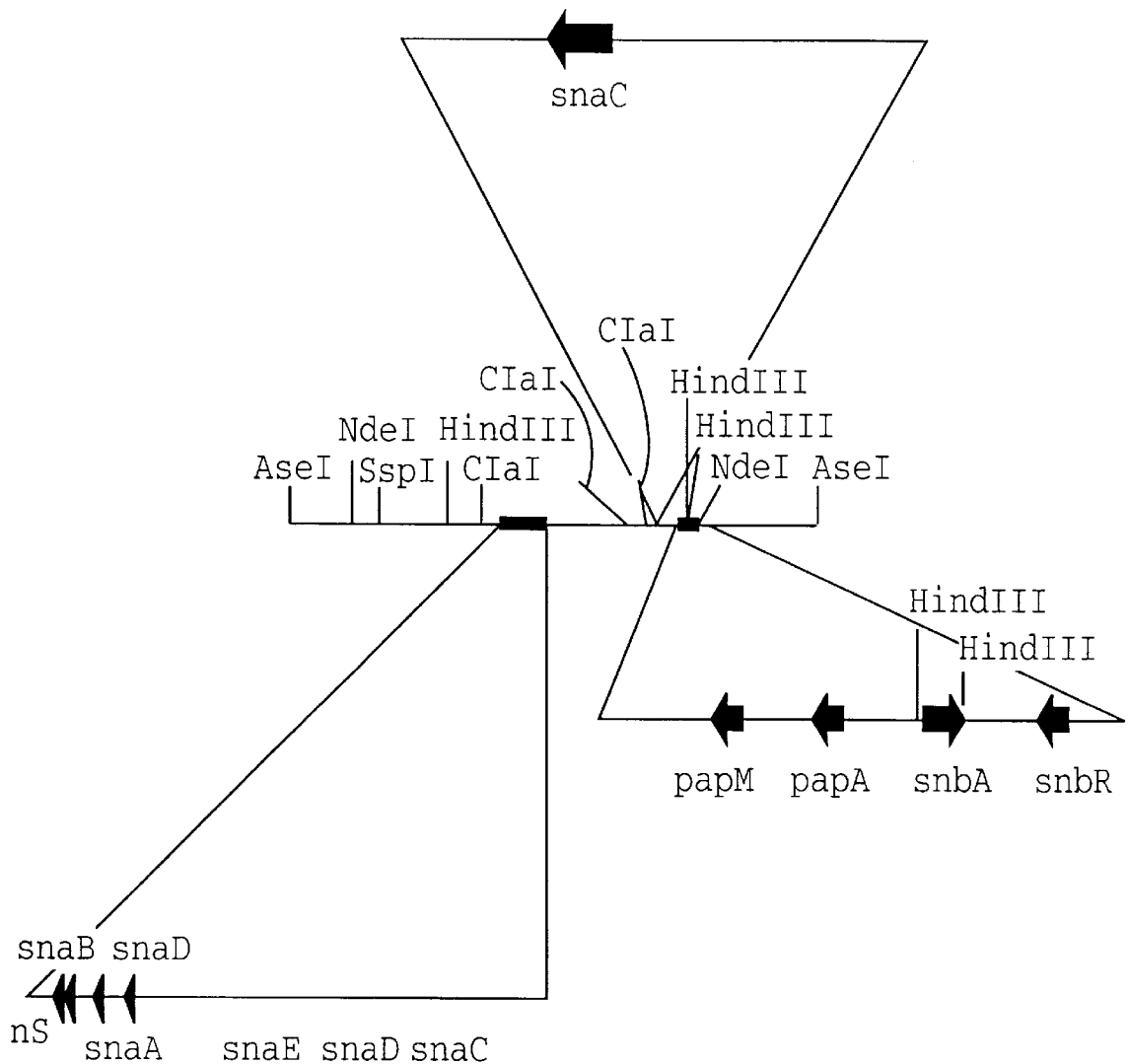
FIG. 32: General map.

13.4. Localization on the Chromosome of the Different Genes Involved in the Biosynthesis of Pristinamycins I and II and Study of their Physical Binding Hybridization of the chromosomal DNAs of S. pristinaespiralis strains SP92, SP92::pVRC404 and SP92::pVRC505, cut by single digestions and double digestions using the six enzymes mentioned above, with the different probes described above lead to the general map shown in FIG. 32: the position of major sites has been indicated, together with the position and direction of transcription of the genes involved in the biosynthesis of pristinamycins PI and PII. Thus, it is possible to calculate the distance separating the 3 chromosomal regions containing the genes identified, namely that of the snbA, snbR, papA and papM genes (cosmid pIBV2, Example 5.2), that of the snaA, snaB, samS, snaD, snbC, snbD and snbE genes (cosmids pIBV1 and 3, Example 5.1) and lastly that of the snaC gene (cosmid pIBV4, Example 5.6). For example, the distance between the snaA and snbA genes has been evaluated at approximately 160–170 kb. This shows that the genes already identified are all contained in a region covering only 200 kb of the chromosome of the S. pristinaespiralis strain, equivalent to less than 3% of the total length of the genome, which we have been able to estimate at 7500 kb by the pulsed-field electrophoresis technique.

These results show that the genes involved in the biosynthesis of pristinamycins I and II are grouped together on the chromosome in a cluster, and that it is hence possible by chromosome walking from the genes already identified to isolate other genes involved in the biosynthesis of pristinamycins I and pristinamycins II. More generally, it is possible, by chromosome walking from any gene involved in the biosynthesis of streptogramins, to identify the other genes involved in this biosynthesis.

TABLE 1

| MICROORGANISMS | ANTIBIOTICS |
|---|---|
| FUNGI | |
| *Micromonospora sp.* | Vernamycins |
| STREPTOMYCES | |
| *S. albiorectus* | Virginiamycins |
| *S. conganesis* (ATCC13528) | F1370 A, B |
| *S. diastaticus* | Plauracins, Streptogramins |
| *S. graminofasciens* | Streptogramins |
| *S. griseus* (NRRL2426) | Viridogrisein (Etamycin) |
| *S. griseoviridus* | Griseoviridin |
| *S. griseoviridus* (FERMP3562) | Neoviridogriseins |
| *S. lavendulae* | Etamycins |
| *S. loidensis* (ATCC11415) | Vernamycins |
| *S. mitakaensis* (ATCC15297) | Mikamycins |
| *S. olivaceus* (ATCC12019) | Synergistins (PA114 A, B) |
| *S. ostreogriseus* (ATCC27455) | Ostreogrycins |
| *S. pristinaespiralis* (ATCC25486) | Pristinamycins |
| *S. virginiae* (ATCC13161) | Virgiuniamycins (Staphylomycins) |
| ACTINOMYCETES | |
| *A. auranticolor* (ATCC31011) | Plauracins |
| *A. azureus* (ATCC31157) | Plauracins |
| *A. daghestanicus* | Etamycin |
| *A. philippinensis* | A-2315 A, B, C |
| *Actinioplanes sp.* (ATCC33002) | A15104 |
| *Actinoplanes sp.* | A17002 A, B, C, F |
| *Actinomadura flava* | Madumycins |

Abbreviations used:
DNA: deoxyribonucleic acid
AMP: adenosine 5'-monophosphate
ATP: adenosine 5'-triphosphate
ETB: ethidium bromide
bis-tris: (bis[2-hydroxyethyl]iminotris[hydroxymethyl] methane)
bis-tris propane: (1,3-bis[tris(hydroxymethyl) methylamino]propane)
BSA: bovine serum albumin
HPLC: high performance liquid chromatography
OD: optical density
DTE: dithioerythritol
DTT: dithiothreitol
E64: trans-epoxysuccinyl-L-leucylamido-(4-guanidino) butane
EDTA: ethylenediaminetetraacetic acid
EGTA: ethylene glycol bis(β-aminoethyl)tetraacetic acid
FMN: flavin mononucleotide
$FMNH_2$: reduced flavin mononucleotide
Hepes: (N-[2-hydroxyethyl]piperazine-N'-[2-ethanesulphonic acid])
IPTG: isopropyl β-D-thiogalactopyranoside
kDa: kilodalton
kb: kilobase
LB: Luria broth (rich growth medium for *E. coli*)
NAD: nicotinamide dinucleotide
NADH: reduced nicotinamide dinucleotide
PAGE: polyacrylamide gel electrophoresis
bp: base pair
PMSF: phenylmethylsulphonyl fluoride
PPi: pyrophosphate
rpm: revolutions per min
A.S.: ammonium sulphate
SAM: S-adenosylmethionine
SDS: sodium dodecyl sulphate
STI: soybean trypsin inhibitor
TE: buffer comprising 10 mM Tris-HCl, 1 mM EDTA, pH 7.5
Tris: 2-amino-2-hydroxymethyl-1,3-propanediol
UV: ultraviolet rays
Xgal: 5-bromo-4-chloro-3-indoyl b-D-galactoside
YEME: yeast extract-malt extract medium (rich growth medium for Streptomyces)
PEG: Polyethylene glycol
LMP: Low melting point
MW: Molecular weight Bibliography:

Anzai H., Murakami T., Imai A., Satoh A., Nagaoka K. and Thompson C. J. (1987) *J. Bacteriol.*, 169: 3482–3488.
Bancroft I. and WolK C. P. (1989) *J. Bacteriol.*, 171: 5949–5954.
Bibb M. J., Findlay P. R. and Johnson M. W. (1984) *Gene*, 30: 157–166.
Birnboim H. C. and Doly J. (1979) *Nucleic Acids Res.*, 7: 1513–1523.
Blattner F. R., Williams B. G., Blechl A. E., Denniston-Thompson K., Faber H. E., Furlong L. A., Grunwald D. J., Kiefer D. O., Moore D. D., Schumm J. W., Sheldon E. L. and Smithies O. (1977) *Science*, 196: 161–169.
Bolivar F., Rodriguez R. L., Greene P. J., Betlach M. C., Heynecker H. L., Boyer H. W., Crosa J. H. and Falkow S. (1977) *Gene*, 2: 95–113.
Boyer H. W. and Roulland-Dussoix D. (1969) *J. Mol. Biol.*, 41: 459.
Chater K. F. (1990) *Bio/Technology*, 8: 115–121.
Cocito C. G. (1979) *Microbiol. Rev.*, 43: 145–198.
Cocito C. G. (1983) In *Antibiotics*, 6: (Ed. F. E. Hahn), 296–332.
Dessen P. C., Fondrat C., Valencien C. et Mugnier C. (1990) *Comp. Appl. in Biosciences*, 6: 355–356.
Di Giambattista M., Chinali G. and Cocito C. G. (1989) *J. Antim. Chemother.*, 24: 485–507.
Fernandez-Moreno M. A., Caballero J. L., Hopwood D. A. and Malpartida F. (1991) *Cell*, 66: 769–780.
Gibson T. J. (1984) *Ph.D. thesis*, Cambridge University, England.
Hallam S. E., Malpartida F. and Hopwood D. A. (1988) *Gene*, 74: 305–320.
Hames B. D. and Higgins S. J. (1985) IRL Press Ltd., Oxford, U.K.,
Hanahan D. (1983) *J. Mol. Biol.*, 166: 557
Hillemann D., Pülher A. and Wohlleben W. (1991) *Nucl. Acids Res.*, 19: 727–731.
Hohn B. and Collins J. F. (1980) *Gene*, 11: 291–298.
Hook J. D. and Vining L. C. (1973) *J.C.S. Chem. Comm.*, 185–186.
Hopwood D. A., Bibb M. J., Chater K. F., Kieser T., Bruton C. J., Kieser H. M., Lydiate D. J., Smith C. P., Ward J. M.

and Scrempf H. (1985) *A laboratory manual.*, The John Innes Fondation, Norwich, England.

Hopwood D. A., Bibb M. J., Chater K. F., Janssen G. R., Malpartida F. and Smith C. (1986b) *In Regulation of gene expression—25 years on* (ed. I; A. Booth C; F. Higgins), 251–276.

Hopwood D. A., Malpartida F., Kieser H. M., Ikeda H., Duncan J., Fujii I., Rudd A. M., Floss H. G. and Omura S. (1985a) *Nature*, 314: 642–644.

Hopwood D. A., Malpartida F., Kieser H. M., Ikeda H. and Omura S. (1985b) *In Microbiology* (ed S. Silver). *American Society for Microbiology*, Washington D.C., 409–413.

Hopwood D. A., Malpartida F. and Chater K. F. (1986a) *In Regulation of secondary metabolite formation.* (eds. H. Kleinkauf, H. von Hohren, H. Dornauer G. Nesemann), 22–33.

Hoshino T., Ikeda T., Tomizuka N. and Furukawa K. (1985) *Gene*, 37: 131–138.

Hutchinson C. R., Borell C. W., Otten S. L., Stutzman-Engwall K. J. and Wang Y. (1989) *J. Med. Chem.*, 32: 929–937.

Ish-Horowitz D. and Burk J. F. (1981) *Nucleic Acids Res.*, 9: 2989–298.

Kanehisa M. I. (1984) *Nucleic Acids Res.*, 12: 203–215.

Kay R. and McPherson J. (1987) *Nucleic Acids Res.*, 15 (6): 2778.

Khan S. A. and Novick R. (1983) *Plasmid*, 10: 251–259.

Kingston D. G. I., Kolpak M. X, Lefevre W. and Borup-Grochtmann I. B. (1983) *J. Am. Chem. Soc.*, 105: 5106–5110.

Kyte J. and Doolittle R. (1982) *J. Biol. Mol.*, 157: 105–135.

Low B. (1968) *Proc. Nalt. Acad. Sci.*, 60: 160.

Lydiate D. J., Malpartida F. and Hopwood D. A. (1985) *Gene*, 35: 223–235.

Maniatis T., Fritsh E. F. and Sambrook J (1989) Molecular cloning: a laboratory manual. Cold Spring Harbor, N.Y., Meinkoth J. and Wahl G. (1984) *Anal. Biochem.*, 138: 267–284.

Messing J., Crea R. and Seeburg P. H. (1981) *Nucleic Acids Res.*, 9: 309.

Neal R. J. and Chater K. F. (1987) *Gene*, 58: 229–241.

Ohnuki T., Imanaka T. and Aiba S. (1985) *J. Bacteriol.*, 164: 85–94.

Sawadogo M. and Van Dyke M. W. (1991) *Nucl. Acids Res.*, 19: 674.

Staad J. F., Elkins M. F. and Earhart C. F. (1989) *FEMS Microbial. Lett.*, 59: 15.

Staden R. and McLachlan A. D. (1982) *Nucleic Acids Res.*, 10: 141–156.

Videau D. (1982) *Path. Biol.*, 30: 529–534.

Chambers S. P., Prior S. E., Barstow D. A. and Minton N. P. (1988) *Gene*, 68:139

Gutierrez S., Diez B., Montenegro E. and Martin J. F. (1991) Journal of bacteriology, 173:2354–2365.

Hori K., Yamamoto Y., Minetoki T., Kurotsu T., Kanda M., Miura S., Okamura K., Kuruyama J. and Saito Y. (1989) J. Biochem., 106: 639–645.

Horikawa S., Ishikawa M., Ozaka H. and Tsukada K. (1989) Eur. J. Biochem., 184: 497–501.

Kaplan J., Merkel W. and Nichols B. (1985) J. Mol. Biol., 183: 327–340.

Markham G. D., DeParasis J. and Gatmaitan J. (1984) J. Biol Chem., 259: 14505–14507.

Sharka B., Westlake D. W. S. and Vining L. C. (1970) Chem. Zvesti, 24:66–72.

Thomas D., Rothstein R., Rosenberg N. and Surdin-Kerjan Y. (1988) Mol. Cell. Biol., 8:5132–5139.

Turgay K. et al (1992) Molecular Microbiology, 6(4):546.

Weckermann R., FŸrbab R. and Marahiel M. A. (1988) Nucl. Acids Res., 16:11841

Yanisch-Perron C., Vieira J. and Messing J. (1985) Gene, 33: 103–119.

Zimmer W., Aparicio C. and Elmerich C. (1991) Mol. Gen. Genet., 229:41–51.

Reed et al. J. Nat. Prod 49 (1986) 626

Molinero et al., J. Nat. Peod 52 (1989) 99

Reed et al. J. Org. Chem. 54 (1989) 1161

Watanabe et al., Mol. Cell. Biochem. 44(1982) 181

Jablonski et al., Biochemistry 16 (1977) 2832

Duane et al., Mol. Cell. Biochem. 6 (1975) 53.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

SEQUENCE LISTING ( 1 ) GENERAL INFORMATION:

( i i i ) NUMBER OF SEQUENCES: 43

( 2 ) INFORMATION FOR SEQ ID NO: 1:

( i ) SEQUENCE CHARACTERISTICS:
        ( A ) LENGTH: 5392 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:

(A) ORGANISM: S.pristinaespiralis (xi) SEQUENCE DESCRIPTION: SEQ ID NO: 1:

```
GGATCCTGGC GTCCGCCGTC AAGAACTGAA CCGAGGAGAC ACCCACCATG ACCGCACCCC      60
GCCGGCGCAT CACCCTCGCC GGCATCATCG ACGGCCCCGG CGGCCATGTG GCCGCCTGGC     120
GCCACCCGGC GACCAAGGCG GACGCCCAGC TCGACTTCGA ATTCCACCGC GACAACGCCC     180
GCACCCTCGA ACGCGGCCTG TTCGACGCCG TGTTCATCGC GGACATCGTC GCCGTGTGGG     240
GCACCCGCCT GGACTCCCTG TGCCGCACCT CGCGCACCGA GCACTTCGAA CCGCTCACCC     300
TGCTCGCCGC CTACGCCGCG GTCACCGAGC ACATCGGCCT GTGCGCCACC GCCACCACCA     360
CGTACAACGA ACCGGCGCAC ATCGCCGCCC GCTTCGCCTC CCTCGACCAC CTCAGCGGCG     420
GCCGGGCCGG CTGGAACGTC GTCACCTCCG CCGCACCGTG GGAGTCCGCC AACTTCGGCT     480
TCCCCGAGCA CCTGGAGCAC GGCAAACGCT ACGAGCGGGC CGAGGAGTTC ATCGACGTCG     540
TCAAAAAACT GTGGGACAGC GACGGCCGCC CCGTCGACCA CCGCGGCACC CACTTCGAGG     600
CCCCCGGCCC GCTCGGGATC GCCCGCCCCC CGCAGGGCCG CCCCGTCATC ATCCAGGCCG     660
GCTCCTCGCC GGTGGGACGC GAGTTCGCCG CCCGGCACGC CGAGGTCATC TTCACCCGGC     720
ACAACCGGCT CTCCGACGCC CAGGACTTCT ACGGCGACCT CAAGGCACGC GTCGCCCGGC     780
ACGGCCGCGA CCCCGAGAAG GTCCTCGTGT GGCCGACCCT CGCGCCGATC GTCGCCGCCA     840
CCGACACCGA GGCGAAGCAG CGCCTGCAGG AACTGCAGGA CCTCACCCAC GACCATGTCG     900
CCCTGCGCAC CCTTCAGGAC CACCTCGGCG ACGTCGACCT GAGCGCGTAC CCGATCGACG     960
GGCCCGTCCC CGACATCCCG TACACCAACC AGTCCCAGTC GACGACCGAG CGGCTGATCG    1020
GCCTGGCCAG GCGCGAGAAC CTCAGCATCC GCGAGCTGGC CCTGCGGCTG ATGGGCGACA    1080
TCGTCGTCGG CACACCGGAG CAGCTCGCCG ACCACATGGA GAGCTGGTTC ACCGGCCGCG    1140
GCGCCGACGG CTTCAACATC GACTTCCCGT ACCTGCCGGG CTCCGCCGAC GACTTCGTCG    1200
ACCACGTGGT GCCCGAACTG CAGCGCCGCG GCCTGTACCG CTCGGGCTAC GAGGGCACCA    1260
CCCTGCGGGC CAACCTCGGC ATCGACGCCC CCGGAAGGC AGGTGCAGCG GCTTGACTTC    1320
CGTCCTAAAG GCGGGGGATT CCAGCGGTCG CCCGCTGGGG TTCCTGCTTC ACCGACGACC    1380
GCCCCGTCCG GGAGGACTCC CGTTGAGGTC TTATACCGTC TCCACAGGCC GACGCCGCCA    1440
GCCCGGCGGC CAGGATGTTG CGTGCCGCAT TCACGTCGCG GTCATGCACA GCGCCGCAGT    1500
CGCACGTCCA CTCCCGGACG TTCAGCGGCA GCTTCCCGCG GACCGTGCCG CAGGTTCCGC    1560
ACAGCTTGGA GCTGGGGAAC CAGCGGTCGA TCACGACGAG TTCGCGCCCA TACCAGGCGC    1620
ACTTGTACTC CAGCATGGAG CGCAGTTCCG TCCAGGCCGC GTCGGAGATG GCGCGCGCGA    1680
GCTTGCCGTT CTTCAGCAGG TTGCGGACGG TGAGGTCCTC GATCACGACC GTTTGGTTCT    1740
CACGGACGAG TCGAGTCGAC AGCTTGTGGA GGAAGTCGCA GCGCCGGTCG GTGATCCGGG    1800
CGTGGACGCG GGCGACCTTG CGGCGGGCTT TCTTCCGGTT CGCCGACCCC TTCGCCTTGC    1860
GCGACACGTC CCGCTGAGCC TTCGCGAGGC GGGCGCGGTC ACGGCGCTCG TGCTTGGGGT    1920
TGGTGATCTT CTCCCCGGTG GACAGGGTCA CCAGGGAGGT GATCCCGGCG TCGATGCCGA    1980
CGGCCGCCGT GGTGGCGGGC GCGGGGGTGA TGGTGTCCTC GCACAGCAGG GACACGAACC    2040
AGCGGCCCGC ACGGTCGCGG GACACGGTCA CCGTCGTCGG CTCCGCCCCT TCGGGAAGGG    2100
GACGGGACCA GCGGATGTCC AGGGGCTCCG CGGTCTTCGC CAGCGTGAGC TGTCCGTTAC    2160
GCCACGTGAA GGCGCTGCGG GTGTACTCGG CCGACGCCCT GGACTTTTTC CGCGACTTGT    2220
ACCGCGGGTA CTTCGACCGC TTGGCGAAGA AGTTGGCGAA CGCCGTCTGC AAGTGCCGCA    2280
```

```
GCGCCTGCTG GAGCGGGACG GAGGACACCT CCGAGAGGAA GGCGAGTTCT TCGGTCTTCT    2340
TCCACTCCGT CAGCGCGGCG GACGACTGCA CGTAGGAGAC CCGGCGCTGC TCGCCGTACC    2400
AGGCTCGCGT GCGCCCCTCA AGCGCTTGT  TGTACACGAG GCGGACACAG CCGAACGTGC    2460
GGGACAGCTC AGCCGCCTGC TCGTCCGTGG GATAAAGCG  GTACTTGAAA GCCCGCTTGA    2520
CCTGCTGCAT CACGCCTCAC ACGCTATCAG TTCCCGTGTG AGCGGCGGGT GTCTGCCGGT    2580
GGTTGCAGAC GCCGAACCGC CTGGCGGCG  ATTCGCCCAT CCCTGCCCTG CTCCGCAAGA    2640
GCTTCGTCTC CTCCCCGGTC TGAAGGCCGG GGTATCCACG AAGGAATTCT GATGACCGCG    2700
CCCATCCTCG TCGCCACCCT CGACACCCGC GGCCCCGCCG CCACCCTCGG CACGATCACC    2760
CGCGCCGTGC GGGCCGCGGA GGCCGCCGGA TTCGACGCCG TCCTGATCGA CGACCGGGCC    2820
GCCGCCGGCG TCCAGGGCCG GTTCGAGACG ACGACGCTGA CCGCCGCGCT GGCCGCCGTC    2880
ACCGAGCACA TCGGCCTGAT CACCGCCCCG CTCCCGGCCG ACCAGGCCCC CTACCACGTG    2940
TCCCGGATCA CCGCCTCGCT CGACCACCTC GCCCACGGCC GCACCGGCTG GCTCGCGAGC    3000
ACGGACACCA CCGACCCCGA GGGCCGCACC GGCGAACTCA TCGACGTCGT CCGCGGCCTG    3060
TGGGACAGCT TCGACGACGA CGCCTTCGTC CACGACCGCG CCGACGGCCT GTACTGGCGG    3120
CTGCCCGCCG TCCACCAACT CGACCACCAG GGCAGGCACT TCGACGTGGC CGGCCCCCTC    3180
AACGTCGCCC GCCCGCCGCA GGGCCACCCC GTCGTCGCCG TCACCGGCCC CGCCCTCGCC    3240
GCGGCCGCCG ACCTCGTCCT GCTCGACGAG GCGGCCGACG CCGCCTCGGT GAAGCAGCAG    3300
GCACCGCACG CCAAGATCCT CCTGCCGCTG CCCGGCCCGG CCGCCGAACT GCCCGCCGAC    3360
AGCCCCGCGG ACGGCTTCAC GGTGGCGCTC ACCGGCTCCG ACGACCCGGT CCTGGCCGCG    3420
CTCGCCGCCC GGCCCGGCCG CCCGGACCGC ACCGCGGCCA CCACCCTGCG CGAACGCCTG    3480
GGCCTGGCCC GCCCCGAGAG CCGCCACGCC CTCACCACCG CCTGACGACC CGTCCGCCCG    3540
CTGCTTCCTG GAGAGTCATG TCCCGTCGCC TGTTCACCTC GGAGTCCGTG ACCGAGGGCC    3600
ACCCCGACAA GATCGCCGAC CAGATCAGTG ACACCGTCCT CGACGCCCTG CTGCGCGAGG    3660
ACCCCGCCTC ACGCGTCGCG GTCGAGACCC TGATCACCAC CGGCCAGGTC CACATCGCCG    3720
GCGAGGTCAC CACCAAGGCG TACGCGCCCA TCGCCCAACT GGTCCGCGAC ACGATCCTGG    3780
CCATCGGCTA CGACTCGTCC GCCAAGGGCT TCGACGGCGC CTCCTGCGGC GTCTCCGTCT    3840
CCATCGGCGC GCAGTCCCCG GACATCGCCC AGGGCGTCGA CAGCGCCTAC GAGACCCGCG    3900
TCGAGGGCGA GGACGACGAG CTCGACCAGC AGGGCGCCGG CGACCAGGGC CTGATGTTCG    3960
GCTACGCCAC CGACGAGACC CCCTCGCTGA TGCCGCTGCC CATCGAGCTC GCCCACCGCC    4020
TCTCGCGCCG GCTCACCGAG GTCCGCAAGG ACGGCACCGT CCCCTACCTG CGCCCCGACG    4080
GCAAGACCCA GGTCACCATC GAGTACCAGG GCAGCCGCCC GGTGCGCCTG GACACCGTCG    4140
TCGTCTCCTC CCAGCACGCC GCCGACATCG ACCTCGGCTC CCTGCTCACC CCCGACATCC    4200
GCGAGCACGT CGTCGAGCAC GTCCTCGCCG CACTCGCCGA GGACGGCATC AAGCTCGAGA    4260
CGGACAACTA CCGCCTGCTG GTCAACCCGA CCGGCCGTTT CGAGATCGGC GGCCCGATGG    4320
GCGACGCCGG CCTGACCGGC CGCAAGATCA TCATCGACAC GTACGGCGGC ATGGCCCGCC    4380
ACGGCGGTGG CGCGTTCTCC GGCAAGGACC CGTCCAAGGT CGACCGTTCC GCCGCGTACG    4440
CGATGCGCTG GGTCGCCAAG AACGTCGTCG CCGCGGGCCT CGCCTCCCGC TGCGAGGTCC    4500
AGGTCGCCTA CGCCATCGGC AAGGCCGAGC CGGTCGGCCT GTTCGTCGAG ACGTTCGGCA    4560
CCGGCACCGT CGCCCAGGAG CGCATCGAGA AGGCCATCAC CGAGGTCTTC GACCTGCGCC    4620
CCGCGGCCAT CATCCGCGAC CTCGACCTGC TGCGGCCCAT CTACGCCGCC ACCGCCGCCT    4680
```

| | | | | | |
|---|---|---|---|---|---|
| ACGGCCACTT | CGGCCGCGAA | CTGCCCGACT | TCACCTGGGA | GCGGACCGAC | CGCGCCCACC | 4740
| GGCTCAAGGC | CGCGGCCGGT | CTCTGAGCCG | GCCGGACCTG | TGAGGAGACC | TGACGTGCGC | 4800
| ATCGCTGTCA | CCGGTTCCAT | CGCCACCGAC | CATCTGATGG | TCTTCCCCGG | CCGGTTCGCG | 4860
| GATCAGCTGA | TCCCCGACCA | GCTCGCTCAT | GTCTCGCTCT | CCTTCCTGGT | CGACGCACTC | 4920
| GAGGTGCGCC | GGGGCGGAGT | GGCGGACAAC | GTCGCCTTCG | GCCTCGGCGG | CCTCGGCCTC | 4980
| ACCCCCCAGC | TGGTCGGCGC | CGTGGGCAGC | GACTTCGCCG | AGTACGAGGT | CTGGCTCAAG | 5040
| GAACACGGCG | TCGACACCGG | CCCCGTCCTG | GTCTCCACCG | AGCGGCAGAC | CGCCCGGTTC | 5100
| ATGTGCATCA | CCGACCAGGA | CTCCAACCAG | ATCGCCTCCT | TCTACGCGGG | CGCCATGCAA | 5160
| GAGGCCCGCG | ACATCGACCT | GTGGCACCTG | ACCACCGGCA | GCGTCCGCCC | CGACCTCGTC | 5220
| CTGGTCTGCC | CGAACGACCC | GGCGGCGATG | CTGCGCCACA | CGGGGAGTGC | CGCGAAACTG | 5280
| GGCCTGCCGT | TCGCCGCCGA | CCCCTCCCAG | CAGCTCGCCC | GCCTGGAGGG | AGGGAGGTAC | 5340
| GCGAACTCGG | TCGACGGGGC | CCGTTGGTTT | TTCACCAACG | AAGTACGAGG | CC | 5392

( 2 ) INFORMATION FOR SEQ ID NO: 2:

( i ) SEQUENCE CHARACTERISTICS:
        ( A ) LENGTH: 1268 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 1..1268

( x i ) SEQUENCE DESCRIPTION: SEQ ID NO: 2:

```
ATG  ACC  GCA  CCC  CGC  CGG  CGC  ATC  ACC  CTC  GCC  GGC  ATC  ATC  GAC  GGC        48
Met  Thr  Ala  Pro  Arg  Arg  Arg  Ile  Thr  Leu  Ala  Gly  Ile  Ile  Asp  Gly
 1                   5                        10                       15

CCC  GGC  GGC  CAT  GTG  GCC  GCC  TGG  CGC  CAC  CCG  GCG  ACC  AAG  GCG  GAC        96
Pro  Gly  Gly  His  Val  Ala  Ala  Trp  Arg  His  Pro  Ala  Thr  Lys  Ala  Asp
                20                       25                       30

GCC  CAG  CTC  GAC  TTC  GAA  TTC  CAC  CGC  GAC  AAC  GCC  CGC  ACC  CTC  GAA       144
Ala  Gln  Leu  Asp  Phe  Glu  Phe  His  Arg  Asp  Asn  Ala  Arg  Thr  Leu  Glu
          35                       40                       45

CGC  GGC  CTG  TTC  GAC  GCC  GTG  TTC  ATC  GCG  GAC  ATC  GTC  GCC  GTG  TGG       192
Arg  Gly  Leu  Phe  Asp  Ala  Val  Phe  Ile  Ala  Asp  Ile  Val  Ala  Val  Trp
     50                       55                       60

GGC  ACC  CGC  CTG  GAC  TCC  CTG  TGC  CGC  ACC  TCG  CGC  ACC  GAG  CAC  TTC       240
Gly  Thr  Arg  Leu  Asp  Ser  Leu  Cys  Arg  Thr  Ser  Arg  Thr  Glu  His  Phe
65                       70                       75                       80

GAA  CCG  CTC  ACC  CTG  CTC  GCC  GCC  TAC  GCC  GCG  GTC  ACC  GAG  CAC  ATC       288
Glu  Pro  Leu  Thr  Leu  Leu  Ala  Ala  Tyr  Ala  Ala  Val  Thr  Glu  His  Ile
                    85                       90                       95

GGC  CTG  TGC  GCC  ACC  GCC  ACC  ACC  ACG  TAC  AAC  GAA  CCG  GCG  CAC  ATC       336
Gly  Leu  Cys  Ala  Thr  Ala  Thr  Thr  Thr  Tyr  Asn  Glu  Pro  Ala  His  Ile
               100                      105                      110

GCC  GCC  CGC  TTC  GCC  TCC  CTC  GAC  CAC  CTC  AGC  GGC  GGC  CGG  GCC  GGC       384
Ala  Ala  Arg  Phe  Ala  Ser  Leu  Asp  His  Leu  Ser  Gly  Gly  Arg  Ala  Gly
          115                      120                      125
```

|   |   |   |   |   |   |   |   |   |   |   |   |   |   |   |   |   |
|---|---|---|---|---|---|---|---|---|---|---|---|---|---|---|---|---|
| TGG | AAC | GTC | GTC | ACC | TCC | GCC | GCA | CCG | TGG | GAG | TCC | GCC | AAC | TTC | GGC | 432 |
| Trp | Asn | Val | Val | Thr | Ser | Ala | Ala | Pro | Trp | Glu | Ser | Ala | Asn | Phe | Gly | |
| | 130 | | | | 135 | | | | | 140 | | | | | | |
| TTC | CCC | GAG | CAC | CTG | GAG | CAC | GGC | AAA | CGC | TAC | GAG | CGG | GCC | GAG | GAG | 480 |
| Phe | Pro | Glu | His | Leu | Glu | His | Gly | Lys | Arg | Tyr | Glu | Arg | Ala | Glu | Glu | |
| 145 | | | | 150 | | | | | 155 | | | | | | 160 | |
| TTC | ATC | GAC | GTC | GTC | AAA | AAA | CTG | TGG | GAC | AGC | GAC | GGC | CGC | CCC | GTC | 528 |
| Phe | Ile | Asp | Val | Val | Lys | Lys | Leu | Trp | Asp | Ser | Asp | Gly | Arg | Pro | Val | |
| | | | | 165 | | | | | 170 | | | | | 175 | | |
| GAC | CAC | CGC | GGC | ACC | CAC | TTC | GAG | GCC | CCC | GGC | CCG | CTC | GGG | ATC | GCC | 576 |
| Asp | His | Arg | Gly | Thr | His | Phe | Glu | Ala | Pro | Gly | Pro | Leu | Gly | Ile | Ala | |
| | | | 180 | | | | | 185 | | | | | 190 | | | |
| CGC | CCC | CCG | CAG | GGC | CGC | CCC | GTC | ATC | ATC | CAG | GCC | GGC | TCC | TCG | CCG | 624 |
| Arg | Pro | Pro | Gln | Gly | Arg | Pro | Val | Ile | Ile | Gln | Ala | Gly | Ser | Ser | Pro | |
| | | 195 | | | | | | 200 | | | | | 205 | | | |
| GTG | GGA | CGC | GAG | TTC | GCC | GCC | CGG | CAC | GCC | GAG | GTC | ATC | TTC | ACC | CGG | 672 |
| Val | Gly | Arg | Glu | Phe | Ala | Ala | Arg | His | Ala | Glu | Val | Ile | Phe | Thr | Arg | |
| | | 210 | | | | | 215 | | | | | 220 | | | | |
| CAC | AAC | CGG | CTC | TCC | GAC | GCC | CAG | GAC | TTC | TAC | GGC | GAC | CTC | AAG | GCA | 720 |
| His | Asn | Arg | Leu | Ser | Asp | Ala | Gln | Asp | Phe | Tyr | Gly | Asp | Leu | Lys | Ala | |
| 225 | | | | | 230 | | | | | 235 | | | | | 240 | |
| CGC | GTC | GCC | CGG | CAC | GGC | CGC | GAC | CCC | GAG | AAG | GTC | CTC | GTG | TGG | CCG | 768 |
| Arg | Val | Ala | Arg | His | Gly | Arg | Asp | Pro | Glu | Lys | Val | Leu | Val | Trp | Pro | |
| | | | | 245 | | | | | 250 | | | | | 255 | | |
| ACC | CTC | GCG | CCG | ATC | GTC | GCC | GCC | ACC | GAC | ACC | GAG | GCG | AAG | CAG | CGC | 816 |
| Thr | Leu | Ala | Pro | Ile | Val | Ala | Ala | Thr | Asp | Thr | Glu | Ala | Lys | Gln | Arg | |
| | | | 260 | | | | | 265 | | | | | 270 | | | |
| CTG | CAG | GAA | CTG | CAG | GAC | CTC | ACC | CAC | GAC | CAT | GTC | GCC | CTG | CGC | ACC | 864 |
| Leu | Gln | Glu | Leu | Gln | Asp | Leu | Thr | His | Asp | His | Val | Ala | Leu | Arg | Thr | |
| | | 275 | | | | | 280 | | | | | 285 | | | | |
| CTT | CAG | GAC | CAC | CTC | GGC | GAC | GTC | GAC | CTG | AGC | GCG | TAC | CCG | ATC | GAC | 912 |
| Leu | Gln | Asp | His | Leu | Gly | Asp | Val | Asp | Leu | Ser | Ala | Tyr | Pro | Ile | Asp | |
| | 290 | | | | | 295 | | | | | 300 | | | | | |
| GGG | CCC | GTC | CCC | GAC | ATC | CCG | TAC | ACC | AAC | CAG | TCC | CAG | TCG | ACG | ACC | 960 |
| Gly | Pro | Val | Pro | Asp | Ile | Pro | Tyr | Thr | Asn | Gln | Ser | Gln | Ser | Thr | Thr | |
| 305 | | | | | 310 | | | | | 315 | | | | | 320 | |
| GAG | CGG | CTG | ATC | GGC | CTG | GCC | AGG | CGC | GAG | AAC | CTC | AGC | ATC | CGC | GAG | 1008 |
| Glu | Arg | Leu | Ile | Gly | Leu | Ala | Arg | Arg | Glu | Asn | Leu | Ser | Ile | Arg | Glu | |
| | | | | 325 | | | | | 330 | | | | | 335 | | |
| CTG | GCC | CTG | CGG | CTG | ATG | GGC | GAC | ATC | GTC | GTC | GGC | ACA | CCG | GAG | CAG | 1056 |
| Leu | Ala | Leu | Arg | Leu | Met | Gly | Asp | Ile | Val | Val | Gly | Thr | Pro | Glu | Gln | |
| | | | 340 | | | | | 345 | | | | | 350 | | | |
| CTC | GCC | GAC | CAC | ATG | GAG | AGC | TGG | TTC | ACC | GGC | CGC | GGC | GCC | GAC | GGC | 1104 |
| Leu | Ala | Asp | His | Met | Glu | Ser | Trp | Phe | Thr | Gly | Arg | Gly | Ala | Asp | Gly | |
| | | 355 | | | | | 360 | | | | | 365 | | | | |
| TTC | AAC | ATC | GAC | TTC | CCG | TAC | CTG | CCG | GGC | TCC | GCC | GAC | GAC | TTC | GTC | 1152 |
| Phe | Asn | Ile | Asp | Phe | Pro | Tyr | Leu | Pro | Gly | Ser | Ala | Asp | Asp | Phe | Val | |
| | 370 | | | | | 375 | | | | | 380 | | | | | |
| GAC | CAC | GTG | GTG | CCC | GAA | CTG | CAG | CGC | CGC | GGC | CTG | TAC | CGC | TCG | GGC | 1200 |
| Asp | His | Val | Val | Pro | Glu | Leu | Gln | Arg | Arg | Gly | Leu | Tyr | Arg | Ser | Gly | |
| 385 | | | | | 390 | | | | | 395 | | | | | 400 | |
| TAC | GAG | GGC | ACC | ACC | CTG | CGG | GCC | AAC | CTC | GGC | ATC | GAC | GCC | CCC | CGG | 1248 |
| Tyr | Glu | Gly | Thr | Thr | Leu | Arg | Ala | Asn | Leu | Gly | Ile | Asp | Ala | Pro | Arg | |
| | | | | 405 | | | | | 410 | | | | | 415 | | |
| AAG | GCA | GGT | GCA | GCG | GCT | TG | | | | | | | | | | 1268 |
| Lys | Ala | Gly | Ala | Ala | Ala | | | | | | | | | | | |
| | | 420 | | | | | | | | | | | | | | |

( 2 ) INFORMATION FOR SEQ ID NO: 3:

( i ) SEQUENCE CHARACTERISTICS:

(A) LENGTH: 833 base pairs
(B) TYPE: nucleic acid
(C) STRANDEDNESS: double
(D) TOPOLOGY: linear (ii) MOLECULE TYPE: cDNA (iii) HYPOTHETICAL: NO (iii) ANTI-SENSE: NO (vi) ORIGINAL SOURCE:
(A) ORGANISM: S.pristinaespiralis (ix) FEATURE:
(A) NAME/KEY: CDS
(B) LOCATION: 1..833

(xi) SEQUENCE DESCRIPTION: SEQ ID NO: 3:

| ATG | ACC | GCG | CCC | ATC | CTC | GTC | GCC | ACC | CTC | GAC | ACC | CGC | GGC | CCC | GCC | 48 |
| Met | Thr | Ala | Pro | Ile | Leu | Val | Ala | Thr | Leu | Asp | Thr | Arg | Gly | Pro | Ala | |
| 1 | | | | 5 | | | | | 10 | | | | | 15 | | |

| GCC | ACC | CTC | GGC | ACG | ATC | ACC | CGC | GCC | GTG | CGG | GCC | GCG | GAG | GCC | GCC | 96 |
| Ala | Thr | Leu | Gly | Thr | Ile | Thr | Arg | Ala | Val | Arg | Ala | Ala | Glu | Ala | Ala | |
| | | | 20 | | | | 25 | | | | | 30 | | | | |

| GGA | TTC | GAC | GCC | GTC | CTG | ATC | GAC | GAC | CGG | GCC | GCC | GCC | GGC | GTC | CAG | 144 |
| Gly | Phe | Asp | Ala | Val | Leu | Ile | Asp | Asp | Arg | Ala | Ala | Ala | Gly | Val | Gln | |
| | | 35 | | | | | 40 | | | | | 45 | | | | |

| GGC | CGG | TTC | GAG | ACG | ACG | ACG | CTG | ACC | GCC | GCG | CTG | GCC | GCC | GTC | ACC | 192 |
| Gly | Arg | Phe | Glu | Thr | Thr | Thr | Leu | Thr | Ala | Ala | Leu | Ala | Ala | Val | Thr | |
| | 50 | | | | | 55 | | | | | 60 | | | | | |

| GAG | CAC | ATC | GGC | CTG | ATC | ACC | GCC | CCG | CTC | CCG | GCC | GAC | CAG | GCC | CCC | 240 |
| Glu | His | Ile | Gly | Leu | Ile | Thr | Ala | Pro | Leu | Pro | Ala | Asp | Gln | Ala | Pro | |
| 65 | | | | | 70 | | | | 75 | | | | | | 80 | |

| TAC | CAC | GTG | TCC | CGG | ATC | ACC | GCC | TCG | CTC | GAC | CAC | CTC | GCC | CAC | GGC | 288 |
| Tyr | His | Val | Ser | Arg | Ile | Thr | Ala | Ser | Leu | Asp | His | Leu | Ala | His | Gly | |
| | | | | 85 | | | | | 90 | | | | | 95 | | |

| CGC | ACC | GGC | TGG | CTC | GCG | AGC | ACG | GAC | ACC | ACC | GAC | CCC | GAG | GGC | CGC | 336 |
| Arg | Thr | Gly | Trp | Leu | Ala | Ser | Thr | Asp | Thr | Thr | Asp | Pro | Glu | Gly | Arg | |
| | | | 100 | | | | | 105 | | | | | 110 | | | |

| ACC | GGC | GAA | CTC | ATC | GAC | GTC | GTC | CGC | GGC | CTG | TGG | GAC | AGC | TTC | GAC | 384 |
| Thr | Gly | Glu | Leu | Ile | Asp | Val | Val | Arg | Gly | Leu | Trp | Asp | Ser | Phe | Asp | |
| | | 115 | | | | | 120 | | | | | 125 | | | | |

| GAC | GAC | GCC | TTC | GTC | CAC | GAC | CGC | GCC | GAC | GGC | CTG | TAC | TGG | CGG | CTG | 432 |
| Asp | Asp | Ala | Phe | Val | His | Asp | Arg | Ala | Asp | Gly | Leu | Tyr | Trp | Arg | Leu | |
| | 130 | | | | | 135 | | | | | 140 | | | | | |

| CCC | GCC | GTC | CAC | CAA | CTC | GAC | CAC | CAG | GGC | AGG | CAC | TTC | GAC | GTG | GCC | 480 |
| Pro | Ala | Val | His | Gln | Leu | Asp | His | Gln | Gly | Arg | His | Phe | Asp | Val | Ala | |
| 145 | | | | | 150 | | | | 155 | | | | | | 160 | |

| GGC | CCC | CTC | AAC | GTC | GCC | CGC | CCG | CCG | CAG | GGC | CAC | CCC | GTC | GTC | GCC | 528 |
| Gly | Pro | Leu | Asn | Val | Ala | Arg | Pro | Pro | Gln | Gly | His | Pro | Val | Val | Ala | |
| | | | | 165 | | | | | 170 | | | | | 175 | | |

| GTC | ACC | GGC | CCC | GCC | CTC | GCC | GCG | GCC | GCC | GAC | CTC | GTC | CTG | CTC | GAC | 576 |
| Val | Thr | Gly | Pro | Ala | Leu | Ala | Ala | Ala | Ala | Asp | Leu | Val | Leu | Leu | Asp | |
| | | | 180 | | | | | 185 | | | | | 190 | | | |

| GAG | GCG | GCC | GAC | GCC | GCC | TCG | GTG | AAG | CAG | CAG | GCA | CCG | CAC | GCC | AAG | 624 |
| Glu | Ala | Ala | Asp | Ala | Ala | Ser | Val | Lys | Gln | Gln | Ala | Pro | His | Ala | Lys | |
| | | 195 | | | | | 200 | | | | | 205 | | | | |

| ATC | CTC | CTG | CCG | CTG | CCC | GGC | CCG | GCC | GCC | GAA | CTG | CCC | GCC | GAC | AGC | 672 |
| Ile | Leu | Leu | Pro | Leu | Pro | Gly | Pro | Ala | Ala | Glu | Leu | Pro | Ala | Asp | Ser | |
| | 210 | | | | | 215 | | | | | 220 | | | | | |

| CCC | GCG | GAC | GGC | TTC | ACG | GTG | GCG | CTC | ACC | GGC | TCC | GAC | GAC | CCG | GTC | 720 |
| Pro | Ala | Asp | Gly | Phe | Thr | Val | Ala | Leu | Thr | Gly | Ser | Asp | Asp | Pro | Val | |
| 225 | | | | 230 | | | | | 235 | | | | | | 240 | |

| | | | | | | | | | | | | | | | | |
|---|---|---|---|---|---|---|---|---|---|---|---|---|---|---|---|---|
| CTG | GCC | GCG | CTC | GCC | GCC | CGG | CCC | GGC | CGC | CCG | GAC | CGC | ACC | GCG | GCC | 768 |
| Leu | Ala | Ala | Leu | Ala | Ala | Arg | Pro | Gly | Arg | Pro | Asp | Arg | Thr | Ala | Ala | |
| | | | | 245 | | | | | 250 | | | | | 255 | | |
| ACC | ACC | CTG | CGC | GAA | CGC | CTG | GGC | CTG | GCC | CGC | CCC | GAG | AGC | CGC | CAC | 816 |
| Thr | Thr | Leu | Arg | Glu | Arg | Leu | Gly | Leu | Ala | Arg | Pro | Glu | Ser | Arg | His | |
| | | | 260 | | | | | 265 | | | | | 270 | | | |
| GCC | CTC | ACC | ACC | GCC | TG | | | | | | | | | | | 833 |
| Ala | Leu | Thr | Thr | Ala | | | | | | | | | | | | |
| | | 275 | | | | | | | | | | | | | | |

( 2 ) INFORMATION FOR SEQ ID NO: 4:

( i ) SEQUENCE CHARACTERISTICS:
        ( A ) LENGTH: 1208 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 1..1208

( x i ) SEQUENCE DESCRIPTION: SEQ ID NO: 4:

| | | | | | | | | | | | | | | | | |
|---|---|---|---|---|---|---|---|---|---|---|---|---|---|---|---|---|
| ATG | TCC | CGT | CGC | CTG | TTC | ACC | TCG | GAG | TCC | GTG | ACC | GAG | GGC | CAC | CCC | 48 |
| Met | Ser | Arg | Arg | Leu | Phe | Thr | Ser | Glu | Ser | Val | Thr | Glu | Gly | His | Pro | |
| 1 | | | | 5 | | | | | 10 | | | | | 15 | | |
| GAC | AAG | ATC | GCC | GAC | CAG | ATC | AGT | GAC | ACC | GTC | CTC | GAC | GCC | CTG | CTG | 96 |
| Asp | Lys | Ile | Ala | Asp | Gln | Ile | Ser | Asp | Thr | Val | Leu | Asp | Ala | Leu | Leu | |
| | | | 20 | | | | | 25 | | | | | 30 | | | |
| CGC | GAG | GAC | CCC | GCC | TCA | CGC | GTC | GCG | GTC | GAG | ACC | CTG | ATC | ACC | ACC | 144 |
| Arg | Glu | Asp | Pro | Ala | Ser | Arg | Val | Ala | Val | Glu | Thr | Leu | Ile | Thr | Thr | |
| | | | 35 | | | | 40 | | | | | 45 | | | | |
| GGC | CAG | GTC | CAC | ATC | GCC | GGC | GAG | GTC | ACC | ACC | AAG | GCG | TAC | GCG | CCC | 192 |
| Gly | Gln | Val | His | Ile | Ala | Gly | Glu | Val | Thr | Thr | Lys | Ala | Tyr | Ala | Pro | |
| | 50 | | | | | 55 | | | | | 60 | | | | | |
| ATC | GCC | CAA | CTG | GTC | CGC | GAC | ACG | ATC | CTG | GCC | ATC | GGC | TAC | GAC | TCG | 240 |
| Ile | Ala | Gln | Leu | Val | Arg | Asp | Thr | Ile | Leu | Ala | Ile | Gly | Tyr | Asp | Ser | |
| 65 | | | | | 70 | | | | | 75 | | | | | 80 | |
| TCC | GCC | AAG | GGC | TTC | GAC | GGC | GCC | TCC | TGC | GGC | GTC | TCC | GTC | TCC | ATC | 288 |
| Ser | Ala | Lys | Gly | Phe | Asp | Gly | Ala | Ser | Cys | Gly | Val | Ser | Val | Ser | Ile | |
| | | | | 85 | | | | | 90 | | | | | 95 | | |
| GGC | GCG | CAG | TCC | CCG | GAC | ATC | GCC | CAG | GGC | GTC | GAC | AGC | GCC | TAC | GAG | 336 |
| Gly | Ala | Gln | Ser | Pro | Asp | Ile | Ala | Gln | Gly | Val | Asp | Ser | Ala | Tyr | Glu | |
| | | | 100 | | | | | 105 | | | | | 110 | | | |
| ACC | CGC | GTC | GAG | GGC | GAG | GAC | GAC | GAG | CTC | GAC | CAG | CAG | GGC | GCC | GGC | 384 |
| Thr | Arg | Val | Glu | Gly | Glu | Asp | Asp | Glu | Leu | Asp | Gln | Gln | Gly | Ala | Gly | |
| | | | 115 | | | | 120 | | | | | 125 | | | | |
| GAC | CAG | GGC | CTG | ATG | TTC | GGC | TAC | GCC | ACC | GAC | GAG | ACC | CCC | TCG | CTG | 432 |
| Asp | Gln | Gly | Leu | Met | Phe | Gly | Tyr | Ala | Thr | Asp | Glu | Thr | Pro | Ser | Leu | |
| | | 130 | | | | | 135 | | | | | 140 | | | | |
| ATG | CCG | CTG | CCC | ATC | GAG | CTC | GCC | CAC | CGC | CTC | TCG | CGC | CGG | CTC | ACC | 480 |
| Met | Pro | Leu | Pro | Ile | Glu | Leu | Ala | His | Arg | Leu | Ser | Arg | Arg | Leu | Thr | |
| 145 | | | | | 150 | | | | | 155 | | | | | 160 | |
| GAG | GTC | CGC | AAG | GAC | GGC | ACC | GTC | CCC | TAC | CTG | CGC | CCC | GAC | GGC | AAG | 528 |
| Glu | Val | Arg | Lys | Asp | Gly | Thr | Val | Pro | Tyr | Leu | Arg | Pro | Asp | Gly | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| ACC | CAG | GTC | ACC | ATC | GAG | TAC | CAG | GGC | AGC | CGC | CCG | GTG | CGC | CTG | GAC | 576 |
| Thr | Gln | Val | Thr | Ile | Glu | Tyr | Gln | Gly | Ser | Arg | Pro | Val | Arg | Leu | Asp | |
| | | | 180 | | | | 185 | | | | | 190 | | | | |
| ACC | GTC | GTC | GTC | TCC | TCC | CAG | CAC | GCC | GCC | GAC | ATC | GAC | CTC | GGC | TCC | 624 |
| Thr | Val | Val | Val | Ser | Ser | Gln | His | Ala | Ala | Asp | Ile | Asp | Leu | Gly | Ser | |
| | | 195 | | | | | 200 | | | | 205 | | | | | |
| CTG | CTC | ACC | CCC | GAC | ATC | CGC | GAG | CAC | GTC | GTC | GAG | CAC | GTC | CTC | GCC | 672 |
| Leu | Leu | Thr | Pro | Asp | Ile | Arg | Glu | His | Val | Val | Glu | His | Val | Leu | Ala | |
| | 210 | | | | | 215 | | | | | 220 | | | | | |
| GCA | CTC | GCC | GAG | GAC | GGC | ATC | AAG | CTC | GAG | ACG | GAC | AAC | TAC | CGC | CTG | 720 |
| Ala | Leu | Ala | Glu | Asp | Gly | Ile | Lys | Leu | Glu | Thr | Asp | Asn | Tyr | Arg | Leu | |
| 225 | | | | | 230 | | | | | 235 | | | | | 240 | |
| CTG | GTC | AAC | CCG | ACC | GGC | CGT | TTC | GAG | ATC | GGC | GGC | CCG | ATG | GGC | GAC | 768 |
| Leu | Val | Asn | Pro | Thr | Gly | Arg | Phe | Glu | Ile | Gly | Gly | Pro | Met | Gly | Asp | |
| | | | | 245 | | | | | 250 | | | | | 255 | | |
| GCC | GGC | CTG | ACC | GGC | CGC | AAG | ATC | ATC | ATC | GAC | ACG | TAC | GGC | GGC | ATG | 816 |
| Ala | Gly | Leu | Thr | Gly | Arg | Lys | Ile | Ile | Ile | Asp | Thr | Tyr | Gly | Gly | Met | |
| | | | 260 | | | | | 265 | | | | | 270 | | | |
| GCC | CGC | CAC | GGC | GGT | GGC | GCG | TTC | TCC | GGC | AAG | GAC | CCG | TCC | AAG | GTC | 864 |
| Ala | Arg | His | Gly | Gly | Gly | Ala | Phe | Ser | Gly | Lys | Asp | Pro | Ser | Lys | Val | |
| | | 275 | | | | | 280 | | | | | 285 | | | | |
| GAC | CGT | TCC | GCC | GCG | TAC | GCG | ATG | CGC | TGG | GTC | GCC | AAG | AAC | GTC | GTC | 912 |
| Asp | Arg | Ser | Ala | Ala | Tyr | Ala | Met | Arg | Trp | Val | Ala | Lys | Asn | Val | Val | |
| | 290 | | | | | 295 | | | | | 300 | | | | | |
| GCC | GCG | GGC | CTC | GCC | TCC | CGC | TGC | GAG | GTC | CAG | GTC | GCC | TAC | GCC | ATC | 960 |
| Ala | Ala | Gly | Leu | Ala | Ser | Arg | Cys | Glu | Val | Gln | Val | Ala | Tyr | Ala | Ile | |
| 305 | | | | | 310 | | | | | 315 | | | | | 320 | |
| GGC | AAG | GCC | GAG | CCG | GTC | GGC | CTG | TTC | GTC | GAG | ACG | TTC | GGC | ACC | GGC | 1008 |
| Gly | Lys | Ala | Glu | Pro | Val | Gly | Leu | Phe | Val | Glu | Thr | Phe | Gly | Thr | Gly | |
| | | | | 325 | | | | | 330 | | | | | 335 | | |
| ACC | GTC | GCC | CAG | GAG | CGC | ATC | GAG | AAG | GCC | ATC | ACC | GAG | GTC | TTC | GAC | 1056 |
| Thr | Val | Ala | Gln | Glu | Arg | Ile | Glu | Lys | Ala | Ile | Thr | Glu | Val | Phe | Asp | |
| | | | 340 | | | | | 345 | | | | | 350 | | | |
| CTG | CGC | CCC | GCG | GCC | ATC | ATC | CGC | GAC | CTC | GAC | CTG | CTG | CGG | CCC | ATC | 1104 |
| Leu | Arg | Pro | Ala | Ala | Ile | Ile | Arg | Asp | Leu | Asp | Leu | Leu | Arg | Pro | Ile | |
| | | 355 | | | | | 360 | | | | | 365 | | | | |
| TAC | GCC | GCC | ACC | GCC | GCC | TAC | GGC | CAC | TTC | GGC | CGC | GAA | CTG | CCC | GAC | 1152 |
| Tyr | Ala | Ala | Thr | Ala | Ala | Tyr | Gly | His | Phe | Gly | Arg | Glu | Leu | Pro | Asp | |
| | 370 | | | | | 375 | | | | | 380 | | | | | |
| TTC | ACC | TGG | GAG | CGG | ACC | GAC | CGC | GCC | CAC | CGG | CTC | AAG | GCC | GCG | GCC | 1200 |
| Phe | Thr | Trp | Glu | Arg | Thr | Asp | Arg | Ala | His | Arg | Leu | Lys | Ala | Ala | Ala | |
| 385 | | | | | 390 | | | | | 395 | | | | | 400 | |
| GGT | CTC | TG | | | | | | | | | | | | | | 1208 |
| Gly | Leu | | | | | | | | | | | | | | | |

( 2 ) INFORMATION FOR SEQ ID NO: 5:

( i ) SEQUENCE CHARACTERISTICS:
        ( A ) LENGTH: 1879 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 110..1858

( x i ) SEQUENCE DESCRIPTION: SEQ ID NO: 5:

```
GATCGGCTCC TGACGGAGCG GCGGCGCGCG GGCGCGGCGC ATCAGCGGCG TGTCAACGGC         60

GCTGCCGACA CTGGGCGCGA CGCGAGGACG AAGCCGGAAA GGACCAACG ATG CTG          115
                                                        Met Leu
                                                         1

GAC GGA TGC GTT CCC TGG CCC GAG GAT GTG GCC GCG AAG TAC CGG GCG         163
Asp Gly Cys Val Pro Trp Pro Glu Asp Val Ala Ala Lys Tyr Arg Ala
         5               10                  15

GCC GGC TAC TGG CGG GGC GAG CCG CTG GGC ATG CTG CTG GGC CGC TGG         211
Ala Gly Tyr Trp Arg Gly Glu Pro Leu Gly Met Leu Leu Gly Arg Trp
         20              25                  30

GCG GAG CAG TAC GGC GAG CGG GAG GCG CTG GTC GGC GCG GAC GGG TGC         259
Ala Glu Gln Tyr Gly Glu Arg Glu Ala Leu Val Gly Ala Asp Gly Cys
35                  40                  45                  50

TCC CGT GTC ACC TAC CGT GCC CTG GAC CGC TGG TGC GAC CGG CTG GCG         307
Ser Arg Val Thr Tyr Arg Ala Leu Asp Arg Trp Cys Asp Arg Leu Ala
                     55                  60                  65

GCG GGG TTC GCG GCG CGC GGG ATC GGC GCC GGC GAG CGG GTG CTG GTG         355
Ala Gly Phe Ala Ala Arg Gly Ile Gly Ala Gly Glu Arg Val Leu Val
             70                  75                  80

CAG CTG CCG AAC ACG CCC GAG TTC GTC GCG GTG TGC TTC GCG CTG TTC         403
Gln Leu Pro Asn Thr Pro Glu Phe Val Ala Val Cys Phe Ala Leu Phe
             85                  90                  95

CGT CTG GGC GCG CTG CCG GTG TTC GCG CTG CCC GCG CAC CGT GCC GCC         451
Arg Leu Gly Ala Leu Pro Val Phe Ala Leu Pro Ala His Arg Ala Ala
100                 105                 110

GAG GTG GGG CAC CTG CTC GAG CTG TCC GGC GCC GTC GCC CAC ATC CTG         499
Glu Val Gly His Leu Leu Glu Leu Ser Gly Ala Val Ala His Ile Leu
115                 120                 125                 130

CCG GGC ACC GGC ACC GGC TAC GAC CAT GTC GCG GCG GCC GTG GAG GCC         547
Pro Gly Thr Gly Thr Gly Tyr Asp His Val Ala Ala Ala Val Glu Ala
                     135                 140                 145

CGT GCC CGC CGT GCC CGC CCG GTG CAG GTG TTC GTG GCG GGC GAG GCG         595
Arg Ala Arg Arg Ala Arg Pro Val Gln Val Phe Val Ala Gly Glu Ala
                150                 155                 160

CCC GCG GTG CTG CCC GAG GGG TTC ACC GCG CTG GCC GAC GTG GAC GGC         643
Pro Ala Val Leu Pro Glu Gly Phe Thr Ala Leu Ala Asp Val Asp Gly
             165                 170                 175

GAC CCG GTG GCG CCG GCG GAC GTG GAC GCC TTC CGA CGT GGC GTC TTC         691
Asp Pro Val Ala Pro Ala Asp Val Asp Ala Phe Arg Arg Gly Val Phe
     180                 185                 190

CTG CTG TCC GGG GGG ACG ACC GCG CTG CCG AAG CTG ATC CCG CGC ACC         739
Leu Leu Ser Gly Gly Thr Thr Ala Leu Pro Lys Leu Ile Pro Arg Thr
195                 200                 205                 210

CAC GAC GAC TAC GCC TAC CAG TGC CGG GTC ACG GCC GGT ATC TGC GGC         787
His Asp Asp Tyr Ala Tyr Gln Cys Arg Val Thr Ala Gly Ile Cys Gly
                     215                 220                 225

CTG GAC GCG GAC AGT GTC TAT CTG GCG GTG CTG CCG GCC GAG TTC AAC         835
Leu Asp Ala Asp Ser Val Tyr Leu Ala Val Leu Pro Ala Glu Phe Asn
                 230                 235                 240

TTC CCC TTC GGC TGC CCG GGC ATC CTG GGC ACC CTG CAC GCC GGC GGG         883
Phe Pro Phe Gly Cys Pro Gly Ile Leu Gly Thr Leu His Ala Gly Gly
             245                 250                 255

CGG GTG GTG TTC GCG CTG TCA CCG CAG CCC GAG GAG TGC TTC GCG CTG         931
Arg Val Val Phe Ala Leu Ser Pro Gln Pro Glu Glu Cys Phe Ala Leu
260                 265                 270

ATC GAA CGC GAA CAC GTC ACC TTC ACC TCC GTC ATC CCC ACG ATC GTG         979
Ile Glu Arg Glu His Val Thr Phe Thr Ser Val Ile Pro Thr Ile Val
275                 280                 285                 290
```

| | | | | | | | | | | | | | | | | |
|---|---|---|---|---|---|---|---|---|---|---|---|---|---|---|---|---|
| CAC | CTG | TGG | CTG | GCG | GCC | GCC | GCA | CAA | GGC | CAC | GGC | CGC | GAC | CTG | GGC | 1027 |
| His | Leu | Trp | Leu | Ala | Ala | Ala | Ala | Gln | Gly | His | Gly | Arg | Asp | Leu | Gly | |
| | | | | 295 | | | | | 300 | | | | | 305 | | |
| AGC | CTT | CAG | CTG | CTG | CAG | GTC | GGC | AGC | GCC | AAA | CTC | CAC | GAG | GAG | CTC | 1075 |
| Ser | Leu | Gln | Leu | Leu | Gln | Val | Gly | Ser | Ala | Lys | Leu | His | Glu | Glu | Leu | |
| | | | 310 | | | | | 315 | | | | | 320 | | | |
| GCC | GCC | CGG | ATC | GGC | CCC | GAA | CTG | GGG | GTG | CGG | CTG | CAG | CAG | GTG | TTC | 1123 |
| Ala | Ala | Arg | Ile | Gly | Pro | Glu | Leu | Gly | Val | Arg | Leu | Gln | Gln | Val | Phe | |
| | | 325 | | | | | 330 | | | | | 335 | | | | |
| GGC | ATG | GCC | GAG | GGA | CTG | CTG | ACC | TTC | ACC | CGC | GAC | GAC | GAC | CCG | GCG | 1171 |
| Gly | Met | Ala | Glu | Gly | Leu | Leu | Thr | Phe | Thr | Arg | Asp | Asp | Asp | Pro | Ala | |
| | 340 | | | | | 345 | | | | | 350 | | | | | |
| GAC | GTG | GTG | CTG | CGC | ACC | CAG | GGC | CGG | CCG | GTG | TCC | GAG | GCC | GAC | GAG | 1219 |
| Asp | Val | Val | Leu | Arg | Thr | Gln | Gly | Arg | Pro | Val | Ser | Glu | Ala | Asp | Glu | |
| 355 | | | | | 360 | | | | | 365 | | | | | 370 | |
| ATA | CGC | GTC | GCC | GAC | CCC | GAC | GGC | CGG | CCC | GTG | CCC | CGC | GGT | GAG | ACC | 1267 |
| Ile | Arg | Val | Ala | Asp | Pro | Asp | Gly | Arg | Pro | Val | Pro | Arg | Gly | Glu | Thr | |
| | | | | 375 | | | | | 380 | | | | | 385 | | |
| GGT | GAA | CTG | CTC | ACC | CGC | GGC | CCC | TAC | ACG | CTG | CGC | GGC | TAC | TAC | CGG | 1315 |
| Gly | Glu | Leu | Leu | Thr | Arg | Gly | Pro | Tyr | Thr | Leu | Arg | Gly | Tyr | Tyr | Arg | |
| | | | 390 | | | | | 395 | | | | | 400 | | | |
| GCC | CCC | GAG | CAC | AAC | GCC | CGC | GCG | TTC | ACC | GAG | GAC | GGC | TTC | TAC | CGC | 1363 |
| Ala | Pro | Glu | His | Asn | Ala | Arg | Ala | Phe | Thr | Glu | Asp | Gly | Phe | Tyr | Arg | |
| | | 405 | | | | | 410 | | | | | 415 | | | | |
| AGC | GGC | GAT | CTG | GTG | CGG | CTC | ACC | GCC | GAC | GGG | CAG | TTG | GTG | GTG | GAG | 1411 |
| Ser | Gly | Asp | Leu | Val | Arg | Leu | Thr | Ala | Asp | Gly | Gln | Leu | Val | Val | Glu | |
| | 420 | | | | | 425 | | | | | 430 | | | | | |
| GGC | AGG | ATC | AAG | GAC | GTC | GTC | ATC | CGC | GGC | GGC | GAC | AAG | GTC | TCC | GCG | 1459 |
| Gly | Arg | Ile | Lys | Asp | Val | Val | Ile | Arg | Gly | Gly | Asp | Lys | Val | Ser | Ala | |
| 435 | | | | | 440 | | | | | 445 | | | | | 450 | |
| ACC | GAG | GTC | GAG | GGC | CAC | CTG | GGC | GCC | CAC | CCC | GAC | GTC | CAG | CAG | GCC | 1507 |
| Thr | Glu | Val | Glu | Gly | His | Leu | Gly | Ala | His | Pro | Asp | Val | Gln | Gln | Ala | |
| | | | | 455 | | | | | 460 | | | | | 465 | | |
| GCC | GTC | GTC | GCC | ATG | CCC | GAC | CCG | GTG | TGG | GGC | GAG | AAG | GTC | TGC | GCC | 1555 |
| Ala | Val | Val | Ala | Met | Pro | Asp | Pro | Val | Trp | Gly | Glu | Lys | Val | Cys | Ala | |
| | | | 470 | | | | | 475 | | | | | 480 | | | |
| TAC | ATC | GTG | CCC | GCA | CCC | GGC | CGT | CCC | GCA | CCG | CCG | ATG | GCG | GCG | CTG | 1603 |
| Tyr | Ile | Val | Pro | Ala | Pro | Gly | Arg | Pro | Ala | Pro | Pro | Met | Ala | Ala | Leu | |
| | | 485 | | | | | 490 | | | | | 495 | | | | |
| CGC | CGG | CTG | CTG | CGC | GCG | CGG | GGA | CTG | GCC | GAC | TAC | AAG | CTT | CCC | GAC | 1651 |
| Arg | Arg | Leu | Leu | Arg | Ala | Arg | Gly | Leu | Ala | Asp | Tyr | Lys | Leu | Pro | Asp | |
| | 500 | | | | | 505 | | | | | 510 | | | | | |
| CGG | GTG | GAG | GTC | GTC | GAC | GCG | TTC | CCG | CTG | ACC | GGC | CTC | AAC | AAG | GTC | 1699 |
| Arg | Val | Glu | Val | Val | Asp | Ala | Phe | Pro | Leu | Thr | Gly | Leu | Asn | Lys | Val | |
| 515 | | | | | 520 | | | | | 525 | | | | | 530 | |
| GAC | AAG | AAG | GCC | CTG | GCG | GCC | GAC | ATC | GCC | GCC | AAG | ACC | GCC | CCC | ACC | 1747 |
| Asp | Lys | Lys | Ala | Leu | Ala | Ala | Asp | Ile | Ala | Ala | Lys | Thr | Ala | Pro | Thr | |
| | | | | 535 | | | | | 540 | | | | | 545 | | |
| CGC | CCC | ACC | ACC | GCC | GGC | CAC | GGC | CCG | ACC | ACG | GAC | GGC | GAT | ACG | GCC | 1795 |
| Arg | Pro | Thr | Thr | Ala | Gly | His | Gly | Pro | Thr | Thr | Asp | Gly | Asp | Thr | Ala | |
| | | | 550 | | | | | 555 | | | | | 560 | | | |
| GGT | GGG | GGT | GGG | TCC | GCG | GGC | GGG | GTG | ACG | GCC | GCC | GGT | GGC | GGG | CGG | 1843 |
| Gly | Gly | Gly | Gly | Ser | Ala | Gly | Gly | Val | Thr | Ala | Ala | Gly | Gly | Gly | Arg | |
| | | 565 | | | | | 570 | | | | | 575 | | | | |
| GAG | GAG | GCG | GCG | TGAGCGGGCC | | CGGGCCCGAG | | GGCG | | | | | | | | 1879 |
| Glu | Glu | Ala | Ala | | | | | | | | | | | | | |
| | 580 | | | | | | | | | | | | | | | |

( 2 ) INFORMATION FOR SEQ ID NO: 6:

( i ) SEQUENCE CHARACTERISTICS:
  ( A ) LENGTH: 1833 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: S.pristinaespiralis ( i x ) FEATURE:
  ( A ) NAME/KEY: CDS
  ( B ) LOCATION: 103..1689

( x i ) SEQUENCE DESCRIPTION: SEQ ID NO: 6:

| | | | | | |
|---|---|---|---|---|---|
| GGATCCCCTC | GCCCAGGGCC | CTGGCGGGCC | CGCCGGGCCG | TGGGGGAGGT | GCGGGGGCCG | 60 |

| | | | | | | | | |
|---|---|---|---|---|---|---|---|---|
| CGGGCCCCGG | CACCGCACGA | ACAGAACAAC | CGCTCCGGGC | CC | ATG | CGG | ACT | TCA | 114 |
| | | | | | Met | Arg | Thr | Ser |
| | | | | | 1 | | | |

| CGG | TCC | CAC | GAC | CAG | CGG | GCC | CCT | ACC | CCC | TGG | AGA | CAT | CCC | TTG | CAC | 162 |
|---|---|---|---|---|---|---|---|---|---|---|---|---|---|---|---|---|
| Arg | Ser | His | Asp | Gln | Arg | Ala | Pro | Thr | Pro | Trp | Arg | His | Pro | Leu | His | |
| 5 | | | | 10 | | | | | 15 | | | | | | 20 | |

| AGC | ACC | CGG | CCC | GCG | CCC | GCG | GCC | GAC | CGT | GAC | CCC | AGG | CGC | TGG | GTC | 210 |
|---|---|---|---|---|---|---|---|---|---|---|---|---|---|---|---|---|
| Ser | Thr | Arg | Pro | Ala | Pro | Ala | Ala | Asp | Arg | Asp | Pro | Arg | Arg | Trp | Val | |
| | | | | 25 | | | | | 30 | | | | | 35 | | |

| ATC | CTC | GGC | GTG | ATC | TGC | CTG | GCC | CAA | CTC | GTC | GTC | CTG | CTC | GAC | AAC | 258 |
|---|---|---|---|---|---|---|---|---|---|---|---|---|---|---|---|---|
| Ile | Leu | Gly | Val | Ile | Cys | Leu | Ala | Gln | Leu | Val | Val | Leu | Leu | Asp | Asn | |
| | | | 40 | | | | | 45 | | | | | 50 | | | |

| ACC | GTC | CTC | AAC | GTC | GCC | ATC | CCG | GTG | CTC | ACC | ACC | GAC | CTG | GGC | GCC | 306 |
|---|---|---|---|---|---|---|---|---|---|---|---|---|---|---|---|---|
| Thr | Val | Leu | Asn | Val | Ala | Ile | Pro | Val | Leu | Thr | Thr | Asp | Leu | Gly | Ala | |
| | | 55 | | | | | 60 | | | | | 65 | | | | |

| AGC | ACC | GCC | GAC | ATC | CAG | TGG | ATG | ATC | AAC | GCC | TAC | GCG | CTC | GTG | CAG | 354 |
|---|---|---|---|---|---|---|---|---|---|---|---|---|---|---|---|---|
| Ser | Thr | Ala | Asp | Ile | Gln | Trp | Met | Ile | Asn | Ala | Tyr | Ala | Leu | Val | Gln | |
| | 70 | | | | | 75 | | | | | 80 | | | | | |

| TCC | GGG | CTG | CTG | CTC | ACC | GCG | GGC | AGC | CTC | GCG | GAC | CGC | TAC | GGC | CGC | 402 |
|---|---|---|---|---|---|---|---|---|---|---|---|---|---|---|---|---|
| Ser | Gly | Leu | Leu | Leu | Thr | Ala | Gly | Ser | Leu | Ala | Asp | Arg | Tyr | Gly | Arg | |
| 85 | | | | | 90 | | | | | 95 | | | | | 100 | |

| AAA | CGG | CTG | CTG | ATG | CTC | GGA | CTG | GTG | CTC | TTC | GGC | GCC | GGG | TCC | GCC | 450 |
|---|---|---|---|---|---|---|---|---|---|---|---|---|---|---|---|---|
| Lys | Arg | Leu | Leu | Met | Leu | Gly | Leu | Val | Leu | Phe | Gly | Ala | Gly | Ser | Ala | |
| | | | | 105 | | | | | 110 | | | | | 115 | | |

| TGG | GCG | GCC | TTC | GCC | CAG | GAC | TCC | GCC | CAA | CTC | ATC | GCC | GCC | CGG | GCC | 498 |
|---|---|---|---|---|---|---|---|---|---|---|---|---|---|---|---|---|
| Trp | Ala | Ala | Phe | Ala | Gln | Asp | Ser | Ala | Gln | Leu | Ile | Ala | Ala | Arg | Ala | |
| | | | 120 | | | | | 125 | | | | | 130 | | | |

| GGC | ATG | GGC | GTG | GGC | GGG | GCG | CTG | CTG | GCG | ACC | ACC | ACC | CTC | GCC | GTC | 546 |
|---|---|---|---|---|---|---|---|---|---|---|---|---|---|---|---|---|
| Gly | Met | Gly | Val | Gly | Gly | Ala | Leu | Leu | Ala | Thr | Thr | Thr | Leu | Ala | Val | |
| | | 135 | | | | | 140 | | | | | 145 | | | | |

| ATC | ATG | CAG | GTC | TTC | GAC | GAC | GAC | GAA | CGC | CCC | CGG | GCG | ATC | GGC | CTG | 594 |
|---|---|---|---|---|---|---|---|---|---|---|---|---|---|---|---|---|
| Ile | Met | Gln | Val | Phe | Asp | Asp | Asp | Glu | Arg | Pro | Arg | Ala | Ile | Gly | Leu | |
| | 150 | | | | | 155 | | | | | 160 | | | | | |

| TGG | GGA | GCG | GCC | AGC | TCA | CTG | GGC | TTC | GCG | GCC | GGC | CCG | CTG | CTC | GGC | 642 |
|---|---|---|---|---|---|---|---|---|---|---|---|---|---|---|---|---|
| Trp | Gly | Ala | Ala | Ser | Ser | Leu | Gly | Phe | Ala | Ala | Gly | Pro | Leu | Leu | Gly | |
| 165 | | | | | 170 | | | | | 175 | | | | | 180 | |

| GGC | GCC | CTC | CTC | GAC | CAC | TTC | TGG | TGG | GGC | TCC | ATC | TTC | CTG | ATC | AAC | 690 |
|---|---|---|---|---|---|---|---|---|---|---|---|---|---|---|---|---|
| Gly | Ala | Leu | Leu | Asp | His | Phe | Trp | Trp | Gly | Ser | Ile | Phe | Leu | Ile | Asn | |
| | | | | 185 | | | | | 190 | | | | | 195 | | |

| CTG | CCC | GTC | GCG | CTG | CTG | GGC | CTG | CTG | GCC | GTC | GCC | CGC | CTG | GTG | CCC | 738 |
|---|---|---|---|---|---|---|---|---|---|---|---|---|---|---|---|---|
| Leu | Pro | Val | Ala | Leu | Leu | Gly | Leu | Leu | Ala | Val | Ala | Arg | Leu | Val | Pro | |
| | | | 200 | | | | | 205 | | | | | 210 | | | |

| GAG | ACG | AAG | AAC | CCC | GAA | GGC | CGG | CGC | CCC | GAC | CTG | CTC | GGC | GCC | GTG | 786 |
|---|---|---|---|---|---|---|---|---|---|---|---|---|---|---|---|---|

```
Glu  Thr  Lys  Asn  Pro  Glu  Gly  Arg  Arg  Pro  Asp  Leu  Leu  Gly  Ala  Val
          215                      220                      225

CTC  TCC  ACC  CTC  GGC  ATG  GTC  GGC  GTC  GTC  TAC  GCC  ATC  ATC  TCC  GGC     834
Leu  Ser  Thr  Leu  Gly  Met  Val  Gly  Val  Val  Tyr  Ala  Ile  Ile  Ser  Gly
     230                      235                      240

CCC  GAA  CAC  GGC  TGG  ACG  GCC  CCG  CAG  GTC  CTC  CTG  CCG  GCC  GCC  GTC     882
Pro  Glu  His  Gly  Trp  Thr  Ala  Pro  Gln  Val  Leu  Leu  Pro  Ala  Ala  Val
245                      250                      255                      260

GCG  GCC  GCC  GCG  CTC  ACC  GCG  TTC  GTC  CGC  TGG  GAA  CTG  CAC  ACC  CCC     930
Ala  Ala  Ala  Ala  Leu  Thr  Ala  Phe  Val  Arg  Trp  Glu  Leu  His  Thr  Pro
               265                      270                      275

CAC  CCC  ATG  CTC  GAC  ATG  GGC  TTC  TTC  ACC  GAC  CGG  CGC  TTC  AAC  GGG     978
His  Pro  Met  Leu  Asp  Met  Gly  Phe  Phe  Thr  Asp  Arg  Arg  Phe  Asn  Gly
               280                      285                      290

CCG  TCG  CCG  GCG  GAG  TGC  TCG  TCG  TTC  GGC  ATG  GCC  GGC  TCG  CTC  TTC    1026
Pro  Ser  Pro  Ala  Glu  Cys  Ser  Ser  Phe  Gly  Met  Ala  Gly  Ser  Leu  Phe
          295                      300                      305

CTG  CTC  ACC  CAG  CAC  CTC  CAA  CTC  GTC  CTC  GGC  TAC  GAC  GCC  CTG  CAG    1074
Leu  Leu  Thr  Gln  His  Leu  Gln  Leu  Val  Leu  Gly  Tyr  Asp  Ala  Leu  Gln
          310                      315                      320

GCC  GGC  CTG  CGC  ACC  GCG  CCA  CTG  GCT  TTG  ACG  ATC  GTC  GCC  CTC  AAC    1122
Ala  Gly  Leu  Arg  Thr  Ala  Pro  Leu  Ala  Leu  Thr  Ile  Val  Ala  Leu  Asn
325                      330                      335                      340

CTG  GCC  GGC  CTC  GGC  GCG  AAA  CTC  CTC  GCC  GCG  CTC  GGC  ACC  GCC  CGC    1170
Leu  Ala  Gly  Leu  Gly  Ala  Lys  Leu  Leu  Ala  Ala  Leu  Gly  Thr  Ala  Arg
               345                      350                      355

AGC  ATC  GCC  CTG  GGC  ATG  ACA  CTG  CTG  GCC  GCC  GGC  CTC  AGC  GCG  GTG    1218
Ser  Ile  Ala  Leu  Gly  Met  Thr  Leu  Leu  Ala  Ala  Gly  Leu  Ser  Ala  Val
               360                      365                      370

GCC  GTC  GGC  GGA  TCG  GGC  CCC  GAC  GCC  GGC  TAC  GGC  GGC  ATG  CTC  GCC    1266
Ala  Val  Gly  Gly  Ser  Gly  Pro  Asp  Ala  Gly  Tyr  Gly  Gly  Met  Leu  Ala
          375                      380                      385

GGC  CTG  CTC  CTC  ATG  GGC  GCG  GGC  ATC  GCA  CTG  GCC  ATG  CCC  GCC  ATG    1314
Gly  Leu  Leu  Leu  Met  Gly  Ala  Gly  Ile  Ala  Leu  Ala  Met  Pro  Ala  Met
     390                      395                      400

GCC  ACC  GCC  GTG  ATG  TCC  TCC  ATC  CCG  CCC  GCC  AAG  GCC  GGG  GCC  GGA    1362
Ala  Thr  Ala  Val  Met  Ser  Ser  Ile  Pro  Pro  Ala  Lys  Ala  Gly  Ala  Gly
405                      410                      415                      420

GCG  GGC  GTG  CAG  GGC  ACC  CTG  ACC  GAG  TTC  GGC  GGC  GGA  CTG  GGA  GTG    1410
Ala  Gly  Val  Gln  Gly  Thr  Leu  Thr  Glu  Phe  Gly  Gly  Gly  Leu  Gly  Val
               425                      430                      435

GCG  ATC  CTC  GGC  GCC  GTC  CTC  GGC  TCC  CGC  TTC  GCC  TCC  CAA  CTG  CCC    1458
Ala  Ile  Leu  Gly  Ala  Val  Leu  Gly  Ser  Arg  Phe  Ala  Ser  Gln  Leu  Pro
               440                      445                      450

GCC  GCC  ATC  ACC  GGC  ACC  GGC  TCC  CTC  GAC  GAG  GCA  CTG  CGC  GAC  GCC    1506
Ala  Ala  Ile  Thr  Gly  Thr  Gly  Ser  Leu  Asp  Glu  Ala  Leu  Arg  Asp  Ala
          455                      460                      465

ACA  CCC  CAA  CAG  GCC  GGG  CAG  GTC  CAC  GAC  GCG  TTC  GCC  GAC  GCG  GTG    1554
Thr  Pro  Gln  Gln  Ala  Gly  Gln  Val  His  Asp  Ala  Phe  Ala  Asp  Ala  Val
          470                      475                      480

AAC  ACC  AGC  CAA  CTC  ATC  GGC  GCC  GCC  GCC  GTG  TTC  ACC  GGC  GGC  CTG    1602
Asn  Thr  Ser  Gln  Leu  Ile  Gly  Ala  Ala  Ala  Val  Phe  Thr  Gly  Gly  Leu
485                      490                      495                      500

CTC  GCC  GCG  CTG  CTG  CTG  CAC  CGC  GCC  GAC  CGC  AAG  GCC  GCC  CCC  CAG    1650
Leu  Ala  Ala  Leu  Leu  Leu  His  Arg  Ala  Asp  Arg  Lys  Ala  Ala  Pro  Gln
               505                      510                      515

CCC  ACC  GCC  CCC  ACC  CCC  GAA  CCC  ACC  ACC  ACC  GCC  TGACCCCCGG            1696
Pro  Thr  Ala  Pro  Thr  Pro  Glu  Pro  Thr  Thr  Thr  Ala
          520                      525

CCCGCCGGGC  ACCACACAAC  CCACGGCCCC  ACCCCTGCGG  CTCCCCACCG  GGACCCACAG             1756
```

```
GGGCGGGGCC  GTGCCGCTGC  CCTGCCCACA  CACACAGCCC  CCACACACAC  AGCCCCCGCA      1816

CGGCCGACAG  CGCCGGG                                                         1833
```

( 2 ) INFORMATION FOR SEQ ID NO: 7:

( i ) SEQUENCE CHARACTERISTICS:
    ( A ) LENGTH: 695 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: S.pristinaespiralis ( i x ) FEATURE:
    ( A ) NAME/KEY: CDS
    ( B ) LOCATION: 212..695
    ( D ) OTHER INFORMATION: /product= "Gene SnaC"

( x i ) SEQUENCE DESCRIPTION: SEQ ID NO: 7:

```
CTCGAGCCGC  GCCCCCAGGT  GCTGGTGTCG  CTCGCCGTGG  AGAAGGGCGC  CGACGGCACC       60

GCGCCGCCGG  ACCGGCTGCT  GATCCACGAC  GGCTTCCCCT  GGGGCCGCGC  CGCCCCGCGC      120

GAAGCGGAGC  TGCCCACCGG  GCACCGCGCC  CTGCCGGCCC  TGGCCGGCGC  CGCCCGCTGA      180

GGCGCGGCAA  CCACCAACAG  AAGGAGCCCC  C  GTG  ACA  GGA  GCC  GAC  GAC  CCG    232
                                      Val  Thr  Gly  Ala  Asp  Asp  Pro
                                        1              5

GCA  AGG  CCC  GCG  GTC  GGC  CCG  CAG  AGT  TTC  CGA  GAC  GCG  ATG  GCG  CAG    280
Ala  Arg  Pro  Ala  Val  Gly  Pro  Gln  Ser  Phe  Arg  Asp  Ala  Met  Ala  Gln
          10                       15                      20

CTG  GCG  TCG  CCC  GTC  ACC  GTC  GTA  ACC  GTC  CTC  GAC  GCG  GCC  GGA  CGC    328
Leu  Ala  Ser  Pro  Val  Thr  Val  Val  Thr  Val  Leu  Asp  Ala  Ala  Gly  Arg
          25                       30                      35

CGC  CAC  GGC  TTC  ACG  GCC  GGC  TCG  GTG  GTC  TCT  GTG  TCG  CTG  GAC  CCG    376
Arg  His  Gly  Phe  Thr  Ala  Gly  Ser  Val  Val  Ser  Val  Ser  Leu  Asp  Pro
40                            45                      50                      55

CCG  CTG  GTG  ATG  GTC  GGC  ATC  GCG  CTC  ACC  TCC  AGC  TGC  CAC  ACG  GCG    424
Pro  Leu  Val  Met  Val  Gly  Ile  Ala  Leu  Thr  Ser  Ser  Cys  His  Thr  Ala
                         60                       65                      70

ATG  GCC  GCC  GCC  GCC  GAG  TTC  TGC  GTC  AGC  ATC  CTC  GGC  GAG  GAC  CAG    472
Met  Ala  Ala  Ala  Ala  Glu  Phe  Cys  Val  Ser  Ile  Leu  Gly  Glu  Asp  Gln
               75                       80                      85

CGC  GCC  GTC  GCG  AAG  CGG  TGC  GCG  ACG  CAC  GGC  GCC  GAC  CGG  TTC  GCG    520
Arg  Ala  Val  Ala  Lys  Arg  Cys  Ala  Thr  His  Gly  Ala  Asp  Arg  Phe  Ala
               90                       95                     100

GGC  GGC  GAG  TTC  GCC  GCC  TGG  GAC  GGT  ACG  GGG  GTG  CCC  TAC  CTG  CCG    568
Gly  Gly  Glu  Phe  Ala  Ala  Trp  Asp  Gly  Thr  Gly  Val  Pro  Tyr  Leu  Pro
     105                      110                     115

GAC  GCC  AAG  GTC  GTC  CTG  CGC  TGC  CGC  ACC  ACG  GAC  GTG  GTG  CGC  GCC    616
Asp  Ala  Lys  Val  Val  Leu  Arg  Cys  Arg  Thr  Thr  Asp  Val  Val  Arg  Ala
120                      125                     130                     135

GGC  GAC  CAC  GAC  CTG  GTG  CTC  GGC  ACG  CCC  GTG  GAG  ATC  CGC  ACG  GGC    664
Gly  Asp  His  Asp  Leu  Val  Leu  Gly  Thr  Pro  Val  Glu  Ile  Arg  Thr  Gly
                         140                     145                     150

GAC  CCG  GCG  AAG  CCA  CCC  CTG  CTG  TGG  TAC  C                             695
Asp  Pro  Ala  Lys  Pro  Pro  Leu  Leu  Trp  Tyr
               155                     160
```

( 2 ) INFORMATION FOR SEQ ID NO: 8:

( i ) SEQUENCE CHARACTERISTICS:
        ( A ) LENGTH: 640 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 1..640
        ( D ) OTHER INFORMATION: /product= "gene SnaD"

( x i ) SEQUENCE DESCRIPTION: SEQ ID NO: 8:

```
GCG  ACC  GCC  CGG  CTC  ATC  GGC  CCG  CTG  CCG  CGC  CGG  CTG  GGC  CTC  CAG     48
Ala  Thr  Ala  Arg  Leu  Ile  Gly  Pro  Leu  Pro  Arg  Arg  Leu  Gly  Leu  Gln
 1                   5                   10                  15

GTG  CAC  CAG  GTG  ATG  ACG  GGC  GCG  TTC  GCG  CAG  GCC  CTC  GCC  CGC  TGG     96
Val  His  Gln  Val  Met  Thr  Gly  Ala  Phe  Ala  Gln  Ala  Leu  Ala  Arg  Trp
                     20                  25                  30

CGG  GGC  AGC  CGC  GCC  GTC  ACC  TTC  GAC  GTG  GAG  ACC  CAC  GGA  CGG  CAC    144
Arg  Gly  Ser  Arg  Ala  Val  Thr  Phe  Asp  Val  Glu  Thr  His  Gly  Arg  His
              35                  40                  45

GGC  CGC  GAC  GAA  CTG  TTC  CGT  ACC  GTC  GGC  TGG  TTC  ACC  TCC  ATC  CAC    192
Gly  Arg  Asp  Glu  Leu  Phe  Arg  Thr  Val  Gly  Trp  Phe  Thr  Ser  Ile  His
      50                  55                  60

CCC  GTC  GTC  CTG  GGC  GCG  GAC  CGC  TCC  GTG  CAC  CCC  GAG  CAG  TAC  CTC    240
Pro  Val  Val  Leu  Gly  Ala  Asp  Arg  Ser  Val  His  Pro  Glu  Gln  Tyr  Leu
 65                  70                  75                  80

GCC  CAG  ATC  GGC  GCG  GCG  CTG  ACC  GCC  GTA  CCG  GAC  GGC  GGC  GTC  GGC    288
Ala  Gln  Ile  Gly  Ala  Ala  Leu  Thr  Ala  Ala  Pro  Asp  Gly  Gly  Val  Gly
                     85                  90                  95

TTC  GGC  GCC  TGC  CGC  GAG  TTC  TCC  CCG  GAC  GCC  GGG  CTG  CGC  ACT  CTG    336
Phe  Gly  Ala  Cys  Arg  Glu  Phe  Ser  Pro  Asp  Ala  Gly  Leu  Arg  Thr  Leu
              100                 105                 110

CTG  CGT  GAC  CTG  CCG  CCC  GCC  CTG  GTG  TGC  TTC  AAC  TAC  TAC  GGT  CAG    384
Leu  Arg  Asp  Leu  Pro  Pro  Ala  Leu  Val  Cys  Phe  Asn  Tyr  Tyr  Gly  Gln
      115                 120                 125

GCC  GAC  CAG  TTG  AGC  CCG  AAC  GGC  GGT  TTC  CGT  ATG  TCG  GGC  CGT  CCC    432
Ala  Asp  Gln  Leu  Ser  Pro  Asn  Gly  Gly  Phe  Arg  Met  Ser  Gly  Arg  Pro
     130                 135                 140

ATC  CCG  CGC  GAG  CAC  TCC  GCC  CGC  TGC  GAG  CGC  GTC  TAC  GGC  ATC  GAG    480
Ile  Pro  Arg  Glu  His  Ser  Ala  Arg  Cys  Glu  Arg  Val  Tyr  Gly  Ile  Glu
145                  150                 155                 160

GTG  TAC  GGC  ATC  GTC  CAC  GGC  GGC  CGC  CTG  CGC  ATG  GGC  CTG  ACC  TGG    528
Val  Tyr  Gly  Ile  Val  His  Gly  Gly  Arg  Leu  Arg  Met  Gly  Leu  Thr  Trp
                     165                 170                 175

GTG  CCG  AGC  CCG  GCG  GAC  GGT  GTG  GAC  GAG  GCC  GGC  GTC  GAC  GCG  CTC    576
Val  Pro  Ser  Pro  Ala  Asp  Gly  Val  Asp  Glu  Ala  Gly  Val  Asp  Ala  Leu
              180                 185                 190

GTG  GAG  CAG  ATG  AGC  TGG  GTG  CTG  GCC  ACG  CTC  GCG  GGC  GCC  GAC  CCG    624
Val  Glu  Gln  Met  Ser  Trp  Val  Leu  Ala  Thr  Leu  Ala  Gly  Ala  Asp  Pro
     195                 200                 205

CAC  GCC  GTG  ACC  CCG  G                                                        640
His  Ala  Val  Thr  Pro
     210
```

(2) INFORMATION FOR SEQ ID NO: 9:

(i) SEQUENCE CHARACTERISTICS:
        (A) LENGTH: 645 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: S.pristinaespiralis (ix) FEATURE:
        (A) NAME/KEY: CDS
        (B) LOCATION: 61..645
        (D) OTHER INFORMATION: /product= "gene papA"

(xi) SEQUENCE DESCRIPTION: SEQ ID NO: 9:

```
GGCGTCAAGA  ACCTGCCGCT  GACCGTACGG  CGCGGCTGAC  ACAGACAAGG  GGGCCACCTG         60

GTG  CGC  ACC  GTG  CGA  ACC  CTG  CTG  ATC  GAC  AAC  TAC  GAC  TCG  TTC  ACC    108
Val  Arg  Thr  Val  Arg  Thr  Leu  Leu  Ile  Asp  Asn  Tyr  Asp  Ser  Phe  Thr
 1              5                        10                      15

TAC  AAC  CTC  TTC  CAG  ATG  CTG  GCC  GAG  GTG  AAC  GGC  GCC  GCT  CCG  CTC    156
Tyr  Asn  Leu  Phe  Gln  Met  Leu  Ala  Glu  Val  Asn  Gly  Ala  Ala  Pro  Leu
              20                        25                      30

GTC  GTC  CGC  AAC  GAC  GAC  ACC  CGC  ACC  TGG  CAG  GCC  CTG  GCG  CCG  GGC    204
Val  Val  Arg  Asn  Asp  Asp  Thr  Arg  Thr  Trp  Gln  Ala  Leu  Ala  Pro  Gly
         35                       40                       45

GAC  TTC  GAC  AAC  GTC  GTC  GTC  TCA  CCC  GGC  CCC  GGC  CAC  CCC  GCC  ACC    252
Asp  Phe  Asp  Asn  Val  Val  Val  Ser  Pro  Gly  Pro  Gly  His  Pro  Ala  Thr
         50                       55                       60

GAC  ACC  GAC  CTG  GGC  CTC  AGC  CGC  CGG  GTG  ATC  ACC  GAA  TGG  GAC  CTG    300
Asp  Thr  Asp  Leu  Gly  Leu  Ser  Arg  Arg  Val  Ile  Thr  Glu  Trp  Asp  Leu
 65                      70                       75                      80

CCG  CTG  CTC  GGG  GTG  TGC  CTG  GGC  CAC  CAG  GCC  CTG  TGC  CTG  CTC  GCC    348
Pro  Leu  Leu  Gly  Val  Cys  Leu  Gly  His  Gln  Ala  Leu  Cys  Leu  Leu  Ala
                    85                       90                      95

GGC  GCC  GCC  GTC  GTC  CAC  GCA  CCC  GAA  CCC  TTT  CAC  GGC  CGC  ACC  AGC    396
Gly  Ala  Ala  Val  Val  His  Ala  Pro  Glu  Pro  Phe  His  Gly  Arg  Thr  Ser
                   100                      105                     110

GAC  ATC  CGC  CAC  GAC  GGG  CAG  GGC  CTG  TTC  GCG  AAC  ATC  CCC  TCC  CCG    444
Asp  Ile  Arg  His  Asp  Gly  Gln  Gly  Leu  Phe  Ala  Asn  Ile  Pro  Ser  Pro
         115                      120                     125

CTG  ACC  GTG  GTC  CGC  TAC  CAC  TCG  CTG  ACC  GTC  CGG  CAA  CTG  CCC  GCC    492
Leu  Thr  Val  Val  Arg  Tyr  His  Ser  Leu  Thr  Val  Arg  Gln  Leu  Pro  Ala
     130                      135                      140

GAC  CTG  CGC  GCC  ACC  GCC  CAC  ACC  GCC  GAC  GGG  CAG  CTG  ATG  GCC  GTC    540
Asp  Leu  Arg  Ala  Thr  Ala  His  Thr  Ala  Asp  Gly  Gln  Leu  Met  Ala  Val
145                      150                      155                     160

GCC  CAC  CGC  CAC  CTG  CCC  CGC  TTC  GGC  GTG  CAG  TTC  CAC  CCC  GAA  TCG    588
Ala  His  Arg  His  Leu  Pro  Arg  Phe  Gly  Val  Gln  Phe  His  Pro  Glu  Ser
                         165                      170                     175

ATC  AGC  AGC  GAA  CAC  GGC  CAC  CGG  ATG  CTC  GCC  AAC  TTC  CGC  GAC  CTG    636
Ile  Ser  Ser  Glu  His  Gly  His  Arg  Met  Leu  Ala  Asn  Phe  Arg  Asp  Leu
                    180                      185                     190

TCC  CTG  CGC                                                                      645
Ser  Leu  Arg
    195
```

( 2 ) INFORMATION FOR SEQ ID NO: 10:

( i ) SEQUENCE CHARACTERISTICS:
        ( A ) LENGTH: 1052 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 84..962
        ( D ) OTHER INFORMATION: /product= "Gene PapM"

( x i ) SEQUENCE DESCRIPTION: SEQ ID NO: 10:

```
CTCGAGGACG AGTGGATCGC CTCCGGCGGC GCCCCGTCC  CCACGCCCGT GCACGCGTCC            60

GCGTCCGCGC GGGGGGCCGT GTC GTG ACC GCC GCC GCA CCC ACC CTC GCC             110
                         Val Thr Ala Ala Ala Pro Thr Leu Ala
                          1                   5

CAG GCG CTG GAC GAG GCC ACC GGG CAG CTG ACC GGC GCC GGG ATC ACC           158
Gln Ala Leu Asp Glu Ala Thr Gly Gln Leu Thr Gly Ala Gly Ile Thr
 10              15                  20                  25

GCC GAC GCC GCC CGG GCC GAC ACC CGG CTG CTG GCC GCC CAC GCC TGC           206
Ala Asp Ala Ala Arg Ala Asp Thr Arg Leu Leu Ala Ala His Ala Cys
                 30                  35                  40

CAG GTC GCC CCG GGG GAC CTC GAC ACC TGC CTG GCC GGC CCG GTG CCG           254
Gln Val Ala Pro Gly Asp Leu Asp Thr Cys Leu Ala Gly Pro Val Pro
             45                  50                  55

CCC CGG TTC TGG CAC TAC GTC CGG CGC CGT CTG ACC CGC GAA CCC GCC           302
Pro Arg Phe Trp His Tyr Val Arg Arg Arg Leu Thr Arg Glu Pro Ala
         60                  65                  70

GAA CGC ATC GTC GGC CAC GCC TAC TTC ATG GGC CAC CGC TTC GAC CTG           350
Glu Arg Ile Val Gly His Ala Tyr Phe Met Gly His Arg Phe Asp Leu
     75                  80                  85

GCC CCC GGC GTC TTC GTC CCC AAA CCC GAG ACC GAG GAG ATC ACC CGG           398
Ala Pro Gly Val Phe Val Pro Lys Pro Glu Thr Glu Glu Ile Thr Arg
 90                  95                 100                 105

GAC GCC ATC GCC CGC CTG GAG GCC CTC GTC CGC CGC GGC ACC ACC GCA           446
Asp Ala Ile Ala Arg Leu Glu Ala Leu Val Arg Arg Gly Thr Thr Ala
                 110                 115                 120

CCC CTG GTC GTC GAC CTG TGC GCC GGA CCG GGC ACC ATG GCC GTC ACC           494
Pro Leu Val Val Asp Leu Cys Ala Gly Pro Gly Thr Met Ala Val Thr
             125                 130                 135

CTG GCC CGC CAC GTA CCG GCC GCC CGC GTC CTG GGC ATC GAA CTC TCC           542
Leu Ala Arg His Val Pro Ala Ala Arg Val Leu Gly Ile Glu Leu Ser
         140                 145                 150

CAG GCC GCC GCC CGC GCC GCC CGG CGC AAC GCC CGC GGC ACC GGC GCC           590
Gln Ala Ala Ala Arg Ala Ala Arg Arg Asn Ala Arg Gly Thr Gly Ala
 155                 160                 165

CGC ATC GTG CAG GGC GAC GCC CGC GAC GCC TTC CCC GAA CTG AGC GGC           638
Arg Ile Val Gln Gly Asp Ala Arg Asp Ala Phe Pro Glu Leu Ser Gly
170                 175                 180                 185

ACC GTC GAC CTC GTC GTC ACC AAC CCG CCC TAC ATC CCC ATC GGA CTG           686
Thr Val Asp Leu Val Val Thr Asn Pro Pro Tyr Ile Pro Ile Gly Leu
                 190                 195                 200

CGC ACC TCC GCA CCC GAA GTG CTC GAG CAC GAC CCG CCG CTG GCC CTG           734
```

```
Arg  Thr  Ser  Ala  Pro  Glu  Val  Leu  Glu  His  Asp  Pro  Pro  Leu  Ala  Leu
               205                      210                      215

TGG  GCC  GGG  GAG  GAG  GGC  CTC  GGC  ATG  ATC  CGC  GCC  ATG  GAA  CGC  ACC        782
Trp  Ala  Gly  Glu  Glu  Gly  Leu  Gly  Met  Ile  Arg  Ala  Met  Glu  Arg  Thr
               220                      225                      230

GCG  GCC  CGG  CTG  CTG  GCC  CCC  GGC  GGC  GTC  CTG  CTC  CTC  GAA  CAC  GGC        830
Ala  Ala  Arg  Leu  Leu  Ala  Pro  Gly  Gly  Val  Leu  Leu  Leu  Glu  His  Gly
               235                      240                      245

TCC  TAC  CAA  CTC  GCC  TCC  GTG  CCC  GCC  CTG  TTC  CGC  GCA  ACC  GGC  CGC        878
Ser  Tyr  Gln  Leu  Ala  Ser  Val  Pro  Ala  Leu  Phe  Arg  Ala  Thr  Gly  Arg
250                      255                      260                      265

TGG  AGC  CAC  GCC  TCG  TCC  CGT  CCC  ACC  TGC  AAC  GAC  GGC  TGC  CTG  ACC        926
Trp  Ser  His  Ala  Ser  Ser  Arg  Pro  Thr  Cys  Asn  Asp  Gly  Cys  Leu  Thr
               270                      275                      280

GCC  GTA  CGC  AAC  CAC  ACC  TGC  GCA  CCG  CCC  GCC  TGACACGGCG  TCACGGCACG         979
Ala  Val  Arg  Asn  His  Thr  Cys  Ala  Pro  Pro  Ala
               285                      290

GCCGGCCTGT  CGGCAACGAC  CCTACGCCAT  TGACAAACCG  ACCGTGCCGT  TTTTTAATG                1039

TCGGGGTGGC  GGA                                                                      1052
```

( 2 ) INFORMATION FOR SEQ ID NO: 11:

( i ) SEQUENCE CHARACTERISTICS:
        ( A ) LENGTH: 227 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 3..227
        ( D ) OTHER INFORMATION: /product= "Partie du gene SnbC"

( x i ) SEQUENCE DESCRIPTION: SEQ ID NO: 11:

```
AG  ATC  TTC  GAG  CAC  AAG  ACC  GTC  GCC  CAG  CTC  GCA  CCC  GTC  GCC  GAG         47
    Ile  Phe  Glu  His  Lys  Thr  Val  Ala  Gln  Leu  Ala  Pro  Val  Ala  Glu
    1                   5                        10                       15

ACG  CTC  GCC  GAC  ACC  ACC  CGC  GAG  GAA  CCC  GCC  GCC  GTC  GCC  GCG  ACC         95
Thr  Leu  Ala  Asp  Thr  Thr  Arg  Glu  Glu  Pro  Ala  Ala  Val  Ala  Ala  Thr
               20                       25                       30

GGC  GAC  GTA  CCG  CTC  ACC  CCG  ATC  ATG  CAC  TGG  CTG  CGC  GAA  CGC  GGC        143
Gly  Asp  Val  Pro  Leu  Thr  Pro  Ile  Met  His  Trp  Leu  Arg  Glu  Arg  Gly
               35                       40                       45

GGC  CCC  GTC  GAC  GCG  TTC  AGC  CAG  ACG  ATG  GCC  GTC  ACC  GTC  CCC  GCC        191
Gly  Pro  Val  Asp  Ala  Phe  Ser  Gln  Thr  Met  Ala  Val  Thr  Val  Pro  Ala
               50                       55                       60

GGC  CTG  GAC  CGG  GAA  CGG  CTC  GTG  GCC  GCC  CTG  CAG                           227
Gly  Leu  Asp  Arg  Glu  Arg  Leu  Val  Ala  Ala  Leu  Gln
65                        70                       75
```

( 2 ) INFORMATION FOR SEQ ID NO: 12:

( i ) SEQUENCE CHARACTERISTICS:
        ( A ) LENGTH: 247 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: S.pristinaespiralis ( i x ) FEATURE:
    ( A ) NAME/KEY: CDS
    ( B ) LOCATION: 1..247
    ( D ) OTHER INFORMATION: /product= "Partie du gene SnbC"

( x i ) SEQUENCE DESCRIPTION: SEQ ID NO: 12:

```
CTC  GAG  TAC  GAC  ACC  GCC  CTG  TAC  GAG  CGG  GCC  ACC  GCC  GAA  GCC  CTC        48
Leu  Glu  Tyr  Asp  Thr  Ala  Leu  Tyr  Glu  Arg  Ala  Thr  Ala  Glu  Ala  Leu
 1                    5                        10                       15

ACC  GGC  CGG  CTG  CTG  CGG  CTC  CTC  GAC  GCC  GTC  GTC  ACC  GAC  CCG  CAG        96
Thr  Gly  Arg  Leu  Leu  Arg  Leu  Leu  Asp  Ala  Val  Val  Thr  Asp  Pro  Gln
                    20                       25                       30

GCG  CCG  GTC  GGC  TCC  CAC  GAC  CTC  CTC  GAA  GAG  GCC  GAA  CAC  GCC  CGC       144
Ala  Pro  Val  Gly  Ser  His  Asp  Leu  Leu  Glu  Glu  Ala  Glu  His  Ala  Arg
               35                       40                       45

CTG  GCA  GCC  TTC  AAC  GAC  ACC  GCC  CGG  CCC  GTG  CCG  CGA  GCC  GGC  CTC       192
Leu  Ala  Ala  Phe  Asn  Asp  Thr  Ala  Arg  Pro  Val  Pro  Arg  Ala  Gly  Leu
      50                       55                       60

GCC  GAA  CTC  TTC  ACC  GCC  CAG  GCC  CGC  CGC  ACC  GCC  GAT  GCG  GTC  GCC       240
Ala  Glu  Leu  Phe  Thr  Ala  Gln  Ala  Arg  Arg  Thr  Ala  Asp  Ala  Val  Ala
 65                        70                       75                       80

GTC  GTC  G                                                                          247
Val  Val
```

( 2 ) INFORMATION FOR SEQ ID NO: 13:

( i ) SEQUENCE CHARACTERISTICS:
        ( A ) LENGTH: 192 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 3..192
        ( D ) OTHER INFORMATION: /product= "Partie du gene SnbD"

( x i ) SEQUENCE DESCRIPTION: SEQ ID NO: 13:

```
GC  ATG  CCC  CCC  GTC  ACC  CCC  TAC  CGC  GCC  TAC  CTG  GCC  CAC  CTC  GCC        47
    Met  Pro  Pro  Val  Thr  Pro  Tyr  Arg  Ala  Tyr  Leu  Ala  His  Leu  Ala
     1                    5                       10                       15

GGC  CGT  GAC  GAC  GAC  GCC  GCC  CGC  GCC  GCG  TGG  CGG  ACC  GCC  CTC  GCG        95
Gly  Arg  Asp  Asp  Asp  Ala  Ala  Arg  Ala  Ala  Trp  Arg  Thr  Ala  Leu  Ala
                    20                       25                       30

GAC  CTG  GAG  GAG  CCG  AGC  CTC  GTC  GCG  GGC  GCC  GGA  GCA  GGC  CGC  GGC       143
Asp  Leu  Glu  Glu  Pro  Ser  Leu  Val  Ala  Gly  Ala  Gly  Ala  Gly  Arg  Gly
               35                       40                       45

GCC  GCC  GAC  GGC  TCC  GCC  CTG  CCC  GGC  CAG  ATC  CCC  GGT  TAC  CGA  GCT  C    192
Ala  Ala  Asp  Gly  Ser  Ala  Leu  Pro  Gly  Gln  Ile  Pro  Gly  Tyr  Arg  Ala
      50                       55                       60
```

( 2 ) INFORMATION FOR SEQ ID NO: 14:

( i ) SEQUENCE CHARACTERISTICS:
        ( A ) LENGTH: 474 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: S.pristinaespiralis ( i x ) FEATURE:
        ( A ) NAME/KEY: CDS
        ( B ) LOCATION: 1..474
        ( D ) OTHER INFORMATION: /product= "Partie du gene SnbD"

( x i ) SEQUENCE DESCRIPTION: SEQ ID NO: 14:

```
CTG   CAG   GTC   GAG   GGC   CGG   CCC   GCG   CAC   CTG   GAA   CTG   CCC   TGC   GAC   CAC        48
Leu   Gln   Val   Glu   Gly   Arg   Pro   Ala   His   Leu   Glu   Leu   Pro   Cys   Asp   His
 1                             5                            10                           15

CCC   CGG   CCC   GCC   GTC   GCC   ACC   CAC   CGC   GGC   GCC   ACC   GTG   CCC   TTC   CAC        96
Pro   Arg   Pro   Ala   Val   Ala   Thr   His   Arg   Gly   Ala   Thr   Val   Pro   Phe   His
                   20                            25                            30

ATC   GAC   GCC   GGC   CTC   CAC   GAG   AAG   CTG   ACC   GCG   CTC   TCC   AAG   GCC   TGC       144
Ile   Asp   Ala   Gly   Leu   His   Glu   Lys   Leu   Thr   Ala   Leu   Ser   Lys   Ala   Cys
             35                            40                            45

GAC   AGC   AGC   CTG   TTC   ATG   GTG   CTC   CAG   GCC   GCG   GTC   GCC   GCC   CTG   CTC       192
Asp   Ser   Ser   Leu   Phe   Met   Val   Leu   Gln   Ala   Ala   Val   Ala   Ala   Leu   Leu
       50                            55                            60

ACC   CGG   CAC   GGC   GCC   GGC   ACC   GAC   ATC   CCC   GTC   GGC   AGC   CCC   GTC   GCC       240
Thr   Arg   His   Gly   Ala   Gly   Thr   Asp   Ile   Pro   Val   Gly   Ser   Pro   Val   Ala
 65                            70                            75                           80

GGC   CGC   ACC   GAC   GAC   GCC   CTC   GAC   GAC   CTG   GTG   GGC   TTC   TTC   GTC   AAC       288
Gly   Arg   Thr   Asp   Asp   Ala   Leu   Asp   Asp   Leu   Val   Gly   Phe   Phe   Val   Asn
                         85                            90                           95

ACC   CTC   GTC   CTG   CGC   ACC   GAC   ACC   TCC   GGC   GAC   CCC   ACC   TTC   CGC   GAA       336
Thr   Leu   Val   Leu   Arg   Thr   Asp   Thr   Ser   Gly   Asp   Pro   Thr   Phe   Arg   Glu
                  100                           105                           110

CTC   GTC   GCA   CGC   GTG   CGG   CAG   TTC   GAC   CTC   GCC   GCC   TAC   ACG   CAC   CAG       384
Leu   Val   Ala   Arg   Val   Arg   Gln   Phe   Asp   Leu   Ala   Ala   Tyr   Thr   His   Gln
            115                           120                           125

GAC   ATG   CCG   TTC   GAA   AAG   CTC   GTC   GAA   GAG   GTC   AAC   CCC   GAG   CGC   TCC       432
Asp   Met   Pro   Phe   Glu   Lys   Leu   Val   Glu   Glu   Val   Asn   Pro   Glu   Arg   Ser
      130                           135                           140

CTG   GCC   CGC   AAC   CCG   CTC   TTC   CAG   GTC   GTC   CTG   GCG   CTG   CAG                    474
Leu   Ala   Arg   Asn   Pro   Leu   Phe   Gln   Val   Val   Leu   Ala   Leu   Gln
145                           150                           155
```

( 2 ) INFORMATION FOR SEQ ID NO: 15:

( i ) SEQUENCE CHARACTERISTICS:
        ( A ) LENGTH: 485 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO (v i) ORIGINAL SOURCE:
(A) ORGANISM: S.pristinaespiralis (i x) FEATURE:
(A) NAME/KEY: CDS
(B) LOCATION: 3..485
(D) OTHER INFORMATION: /product= "Partie du gene SnbE"

(x i) SEQUENCE DESCRIPTION: SEQ ID NO: 15:

| GC | ATG | CCG | CGC | TCC | CTC | GAC | CTG | TAC | GTC | GCA | CTG | CTC | GCC | GTC | CTC | 47 |
|---|---|---|---|---|---|---|---|---|---|---|---|---|---|---|---|---|
| | Met | Pro | Arg | Ser | Leu | Asp | Leu | Tyr | Val | Ala | Leu | Leu | Ala | Val | Leu | |
| | 1 | | | | 5 | | | | | 10 | | | | | 15 | |

| AAG | ACC | GGC | GCC | GCC | TAC | CTG | CCC | GTC | GAC | ATC | TCC | TAC | CCG | GCC | GAA | 95 |
|---|---|---|---|---|---|---|---|---|---|---|---|---|---|---|---|---|
| Lys | Thr | Gly | Ala | Ala | Tyr | Leu | Pro | Val | Asp | Ile | Ser | Tyr | Pro | Ala | Glu | |
| | | | | 20 | | | | | 25 | | | | | 30 | | |

| CGC | ATC | GCG | TTC | ATG | ATC | GAG | GAC | GCC | CGC | CCG | GTG | ACC | GTC | CTC | GAC | 143 |
|---|---|---|---|---|---|---|---|---|---|---|---|---|---|---|---|---|
| Arg | Ile | Ala | Phe | Met | Ile | Glu | Asp | Ala | Arg | Pro | Val | Thr | Val | Leu | Asp | |
| | | | 35 | | | | | 40 | | | | | 45 | | | |

| CGC | CTG | CCC | GAC | GAC | CTG | GGC | GCC | TAC | CGG | GAC | ACC | GAC | CTC | ACC | GAC | 191 |
|---|---|---|---|---|---|---|---|---|---|---|---|---|---|---|---|---|
| Arg | Leu | Pro | Asp | Asp | Leu | Gly | Ala | Tyr | Arg | Asp | Thr | Asp | Leu | Thr | Asp | |
| | | 50 | | | | | 55 | | | | | 60 | | | | |

| GCC | GAC | CGC | ACG | GCG | CCG | CTA | CGG | CCC | GAA | CAC | CCG | GCG | TAC | GTC | ATC | 239 |
|---|---|---|---|---|---|---|---|---|---|---|---|---|---|---|---|---|
| Ala | Asp | Arg | Thr | Ala | Pro | Leu | Arg | Pro | Glu | His | Pro | Ala | Tyr | Val | Ile | |
| | 65 | | | | | 70 | | | | | 75 | | | | | |

| CAC | ACC | TCC | GGC | TCC | ACC | GGC | ACC | CCC | AAG | GCC | GTC | GTC | ATG | CCC | CAC | 287 |
|---|---|---|---|---|---|---|---|---|---|---|---|---|---|---|---|---|
| His | Thr | Ser | Gly | Ser | Thr | Gly | Thr | Pro | Lys | Ala | Val | Val | Met | Pro | His | |
| 80 | | | | | 85 | | | | | 90 | | | | | 95 | |

| GCC | GGC | CTG | GTC | AAC | CTG | CTG | ACC | TGG | CAC | GCC | CGC | CGC | TTC | CCC | GGC | 335 |
|---|---|---|---|---|---|---|---|---|---|---|---|---|---|---|---|---|
| Ala | Gly | Leu | Val | Asn | Leu | Leu | Thr | Trp | His | Ala | Arg | Arg | Phe | Pro | Gly | |
| | | | | 100 | | | | | 105 | | | | | 110 | | |

| GGC | ACC | GGG | GTG | CGC | ACC | GCC | CAG | TTC | ACC | GCC | ATC | GGC | TTC | GAC | TTC | 383 |
|---|---|---|---|---|---|---|---|---|---|---|---|---|---|---|---|---|
| Gly | Thr | Gly | Val | Arg | Thr | Ala | Gln | Phe | Thr | Ala | Ile | Gly | Phe | Asp | Phe | |
| | | | 115 | | | | | 120 | | | | | 125 | | | |

| TCG | GTG | CAG | GAG | ATC | CTC | TCC | CCG | CTC | GTC | ATG | GGC | AAG | ACC | CTC | GCC | 431 |
|---|---|---|---|---|---|---|---|---|---|---|---|---|---|---|---|---|
| Ser | Val | Gln | Glu | Ile | Leu | Ser | Pro | Leu | Val | Met | Gly | Lys | Thr | Leu | Ala | |
| | | 130 | | | | | 135 | | | | | 140 | | | | |

| GTG | CCC | TCG | GAA | GAG | GTC | CGC | CAC | AGC | GCC | GAA | CTG | CTG | GCC | GGC | TGG | 479 |
|---|---|---|---|---|---|---|---|---|---|---|---|---|---|---|---|---|
| Val | Pro | Ser | Glu | Glu | Val | Arg | His | Ser | Ala | Glu | Leu | Leu | Ala | Gly | Trp | |
| | 145 | | | | | 150 | | | | | 155 | | | | | |

| CTC | GAG | | | | | | | | | | | | | | | 485 |
|---|---|---|---|---|---|---|---|---|---|---|---|---|---|---|---|---|
| Leu | Glu | | | | | | | | | | | | | | | |
| 160 | | | | | | | | | | | | | | | | |

(2) INFORMATION FOR SEQ ID NO: 16:

(i) SEQUENCE CHARACTERISTICS:
(A) LENGTH: 291 base pairs
(B) TYPE: nucleic acid
(C) STRANDEDNESS: double
(D) TOPOLOGY: linear (i i) MOLECULE TYPE: cDNA (i i i) HYPOTHETICAL: NO (i i i) ANTI-SENSE: NO (v i) ORIGINAL SOURCE:
(A) ORGANISM: S.pristinaespiralis (i x) FEATURE:
(A) NAME/KEY: CDS
(B) LOCATION: 1..291
(D) OTHER INFORMATION: /product= "Partie du gene SnbE"

(x i) SEQUENCE DESCRIPTION: SEQ ID NO: 16:

| | | | | | | | | | | | | | | | | |
|---|---|---|---|---|---|---|---|---|---|---|---|---|---|---|---|---|
| CTG | CAG | GCC | GAG | GGC | GCC | GAA | GTG | AGC | CTG | CTG | GCC | GTC | CTC | GAC | GGC | 48 |
| Leu | Gln | Ala | Glu | Gly | Ala | Glu | Val | Ser | Leu | Leu | Ala | Val | Leu | Asp | Gly | |
| 1 | | | | 5 | | | | | 10 | | | | | 15 | | |
| TAC | CCC | GAC | GCC | TAC | GAC | GGC | ACC | GAG | CAC | GAG | GTC | GGC | GAG | GAA | CAG | 96 |
| Tyr | Pro | Asp | Ala | Tyr | Asp | Gly | Thr | Glu | His | Glu | Val | Gly | Glu | Glu | Gln | |
| | | | 20 | | | | 25 | | | | | 30 | | | | |
| GTC | CTG | GCG | ATC | CTC | CTC | AAC | GCC | GCC | GGC | GTC | GAC | CGG | GCC | CAG | GCC | 144 |
| Val | Leu | Ala | Ile | Leu | Leu | Asn | Ala | Ala | Gly | Val | Asp | Arg | Ala | Gln | Ala | |
| | | 35 | | | | | 40 | | | | | 45 | | | | |
| TTC | GGC | GAC | GCC | CCC | CTC | CAA | CGG | GCC | GCC | GTG | CTC | GAG | AAG | CTG | CGC | 192 |
| Phe | Gly | Asp | Ala | Pro | Leu | Gln | Arg | Ala | Ala | Val | Leu | Glu | Lys | Leu | Arg | |
| | 50 | | | | | 55 | | | | | 60 | | | | | |
| GAC | AGC | GGC | AGC | GCC | CTG | GGC | AAC | CTC | GAC | GAC | GAC | GCG | GTC | GGC | CGC | 240 |
| Asp | Ser | Gly | Ser | Ala | Leu | Gly | Asn | Leu | Asp | Asp | Asp | Ala | Val | Gly | Arg | |
| 65 | | | | | 70 | | | | | 75 | | | | | 80 | |
| ATG | GTC | ACC | GTC | TTC | CTC | AAC | AAC | ACG | CGC | CTC | ATC | CAG | AAC | TTC | CGG | 288 |
| Met | Val | Thr | Val | Phe | Leu | Asn | Asn | Thr | Arg | Leu | Ile | Gln | Asn | Phe | Arg | |
| | | | | 85 | | | | | 90 | | | | | 95 | | |
| CCC | | | | | | | | | | | | | | | | 291 |
| Pro | | | | | | | | | | | | | | | | |

( 2 ) INFORMATION FOR SEQ ID NO: 17:

( i ) SEQUENCE CHARACTERISTICS:
        ( A ) LENGTH: 422 amino acids
        ( B ) TYPE: amino acid
        ( C ) STRANDEDNESS: single
        ( D ) TOPOLOGY: linear ( x i ) SEQUENCE DESCRIPTION: SEQ ID NO: 17:

| | | | | | | | | | | | | | | | |
|---|---|---|---|---|---|---|---|---|---|---|---|---|---|---|---|
| Met | Thr | Ala | Pro | Arg | Arg | Arg | Ile | Thr | Leu | Ala | Gly | Ile | Ile | Asp | Gly |
| 1 | | | | 5 | | | | | 10 | | | | | 15 | |
| Pro | Gly | Gly | His | Val | Ala | Ala | Trp | Arg | His | Pro | Ala | Thr | Lys | Ala | Asp |
| | | | 20 | | | | 25 | | | | | 30 | | | |
| Ala | Gln | Leu | Asp | Phe | Glu | Phe | His | Arg | Asp | Asn | Ala | Arg | Thr | Leu | Glu |
| | | 35 | | | | | 40 | | | | | 45 | | | |
| Arg | Gly | Leu | Phe | Asp | Ala | Val | Phe | Ile | Ala | Asp | Ile | Val | Ala | Val | Trp |
| | 50 | | | | | 55 | | | | | 60 | | | | |
| Gly | Thr | Arg | Leu | Asp | Ser | Leu | Cys | Arg | Thr | Ser | Arg | Thr | Glu | His | Phe |
| 65 | | | | | 70 | | | | | 75 | | | | | 80 |
| Glu | Pro | Leu | Thr | Leu | Leu | Ala | Ala | Tyr | Ala | Ala | Val | Thr | Glu | His | Ile |
| | | | | 85 | | | | | 90 | | | | | 95 | |
| Gly | Leu | Cys | Ala | Thr | Ala | Thr | Thr | Tyr | Asn | Glu | Pro | Ala | His | Ile | |
| | | | 100 | | | | | 105 | | | | | 110 | | |
| Ala | Ala | Arg | Phe | Ala | Ser | Leu | Asp | His | Leu | Ser | Gly | Gly | Arg | Ala | Gly |
| | | 115 | | | | | 120 | | | | | 125 | | | |
| Trp | Asn | Val | Val | Thr | Ser | Ala | Ala | Pro | Trp | Glu | Ser | Ala | Asn | Phe | Gly |
| | 130 | | | | | 135 | | | | | 140 | | | | |
| Phe | Pro | Glu | His | Leu | Glu | His | Gly | Lys | Arg | Tyr | Glu | Arg | Ala | Glu | Glu |
| 145 | | | | | 150 | | | | | 155 | | | | | 160 |
| Phe | Ile | Asp | Val | Val | Lys | Lys | Leu | Trp | Asp | Ser | Asp | Gly | Arg | Pro | Val |
| | | | | 165 | | | | | 170 | | | | | 175 | |
| Asp | His | Arg | Gly | Thr | His | Phe | Glu | Ala | Pro | Gly | Pro | Leu | Gly | Ile | Ala |
| | | | 180 | | | | | 185 | | | | | 190 | | |
| Arg | Pro | Pro | Gln | Gly | Arg | Pro | Val | Ile | Ile | Gln | Ala | Gly | Ser | Ser | Pro |
| | | 195 | | | | | 200 | | | | | 205 | | | |
| Val | Gly | Arg | Glu | Phe | Ala | Ala | Arg | His | Ala | Glu | Val | Ile | Phe | Thr | Arg |
| | 210 | | | | | 215 | | | | | 220 | | | | |

| His | Asn | Arg | Leu | Ser | Asp | Ala | Gln | Asp | Phe | Tyr | Gly | Asp | Leu | Lys | Ala |
| 225 | | | | | 230 | | | | 235 | | | | | | 240 |

| Arg | Val | Ala | Arg | His | Gly | Arg | Asp | Pro | Glu | Lys | Val | Leu | Val | Trp | Pro |
| | | | | 245 | | | | | 250 | | | | | 255 | |

| Thr | Leu | Ala | Pro | Ile | Val | Ala | Ala | Asp | Thr | Glu | Ala | Lys | Gln | Arg |
| | | | 260 | | | | | 265 | | | | 270 | | |

| Leu | Gln | Glu | Leu | Gln | Asp | Leu | Thr | His | Asp | His | Val | Ala | Leu | Arg | Thr |
| | | 275 | | | | | 280 | | | | | 285 | | | |

| Leu | Gln | Asp | His | Leu | Gly | Asp | Val | Asp | Leu | Ser | Ala | Tyr | Pro | Ile | Asp |
| | 290 | | | | | 295 | | | | | 300 | | | | |

| Gly | Pro | Val | Pro | Asp | Ile | Pro | Tyr | Thr | Asn | Gln | Ser | Gln | Ser | Thr | Thr |
| 305 | | | | | 310 | | | | 315 | | | | | 320 | |

| Glu | Arg | Leu | Ile | Gly | Leu | Ala | Arg | Arg | Glu | Asn | Leu | Ser | Ile | Arg | Glu |
| | | | | 325 | | | | | 330 | | | | | 335 | |

| Leu | Ala | Leu | Arg | Leu | Met | Gly | Asp | Ile | Val | Val | Gly | Thr | Pro | Glu | Gln |
| | | | 340 | | | | | 345 | | | | | 350 | | |

| Leu | Ala | Asp | His | Met | Glu | Ser | Trp | Phe | Thr | Gly | Arg | Gly | Ala | Asp | Gly |
| | | 355 | | | | | 360 | | | | | 365 | | | |

| Phe | Asn | Ile | Asp | Phe | Pro | Tyr | Leu | Pro | Gly | Ser | Ala | Asp | Asp | Phe | Val |
| | 370 | | | | | 375 | | | | | 380 | | | | |

| Asp | His | Val | Val | Pro | Glu | Leu | Gln | Arg | Arg | Gly | Leu | Tyr | Arg | Ser | Gly |
| 385 | | | | | 390 | | | | | 395 | | | | | 400 |

| Tyr | Glu | Gly | Thr | Thr | Leu | Arg | Ala | Asn | Leu | Gly | Ile | Asp | Ala | Pro | Arg |
| | | | | 405 | | | | | 410 | | | | | 415 | |

| Lys | Ala | Gly | Ala | Ala | Ala |
| | | | 420 | | |

( 2 ) INFORMATION FOR SEQ ID NO: 18:

( i ) SEQUENCE CHARACTERISTICS:
        ( A ) LENGTH: 277 amino acids
        ( B ) TYPE: amino acid
        ( C ) STRANDEDNESS: single
        ( D ) TOPOLOGY: linear ( x i ) SEQUENCE DESCRIPTION: SEQ ID NO: 18:

| Met | Thr | Ala | Pro | Ile | Leu | Val | Ala | Thr | Leu | Asp | Thr | Arg | Gly | Pro | Ala |
| 1 | | | | 5 | | | | | 10 | | | | | 15 | |

| Ala | Thr | Leu | Gly | Thr | Ile | Thr | Arg | Ala | Val | Arg | Ala | Ala | Glu | Ala | Ala |
| | | | 20 | | | | | 25 | | | | | 30 | | |

| Gly | Phe | Asp | Ala | Val | Leu | Ile | Asp | Asp | Arg | Ala | Ala | Ala | Gly | Val | Gln |
| | | 35 | | | | | 40 | | | | | 45 | | | |

| Gly | Arg | Phe | Glu | Thr | Thr | Thr | Leu | Thr | Ala | Ala | Leu | Ala | Ala | Val | Thr |
| | 50 | | | | | 55 | | | | | 60 | | | | |

| Glu | His | Ile | Gly | Leu | Ile | Thr | Ala | Pro | Leu | Pro | Ala | Asp | Gln | Ala | Pro |
| 65 | | | | | 70 | | | | | 75 | | | | | 80 |

| Tyr | His | Val | Ser | Arg | Ile | Thr | Ala | Ser | Leu | Asp | His | Leu | Ala | His | Gly |
| | | | | 85 | | | | | 90 | | | | | 95 | |

| Arg | Thr | Gly | Trp | Leu | Ala | Ser | Thr | Asp | Thr | Asp | Pro | Glu | Gly | Arg |
| | | | 100 | | | | | 105 | | | | | 110 | | |

| Thr | Gly | Glu | Leu | Ile | Asp | Val | Val | Arg | Gly | Leu | Trp | Asp | Ser | Phe | Asp |
| | | 115 | | | | | 120 | | | | | 125 | | | |

| Asp | Asp | Ala | Phe | Val | His | Asp | Arg | Ala | Asp | Gly | Leu | Tyr | Trp | Arg | Leu |
| | 130 | | | | | 135 | | | | | 140 | | | | |

| Pro | Ala | Val | His | Gln | Leu | Asp | His | Gln | Gly | Arg | His | Phe | Asp | Val | Ala |
| 145 | | | | | 150 | | | | | 155 | | | | | 160 |

| | | | | | | | | | | | | | |
|---|---|---|---|---|---|---|---|---|---|---|---|---|---|
| Gly | Pro | Leu | Asn | Val<br>165 | Ala | Arg | Pro | Pro<br>170 | Gln | Gly | His | Pro | Val<br>175 | Ala |
| Val | Thr | Gly | Pro<br>180 | Ala | Leu | Ala | Ala | Ala<br>185 | Ala | Asp | Leu | Val | Leu<br>190 | Leu | Asp |
| Glu | Ala | Ala<br>195 | Asp | Ala | Ala | Ser | Val<br>200 | Lys | Gln | Gln | Ala | Pro<br>205 | His | Ala | Lys |
| Ile | Leu<br>210 | Leu | Pro | Leu | Pro | Gly<br>215 | Pro | Ala | Ala | Glu | Leu<br>220 | Pro | Ala | Asp | Ser |
| Pro<br>225 | Ala | Asp | Gly | Phe | Thr<br>230 | Val | Ala | Leu | Thr | Gly<br>235 | Ser | Asp | Asp | Pro | Val<br>240 |
| Leu | Ala | Ala | Leu | Ala<br>245 | Ala | Arg | Pro | Gly | Arg<br>250 | Pro | Asp | Arg | Thr | Ala<br>255 | Ala |
| Thr | Thr | Leu | Arg<br>260 | Glu | Arg | Leu | Gly | Leu<br>265 | Ala | Arg | Pro | Glu | Ser<br>270 | Arg | His |
| Ala | Leu | Thr<br>275 | Thr | Ala | | | | | | | | | | | |

(2) INFORMATION FOR SEQ ID NO: 19:

(i) SEQUENCE CHARACTERISTICS:
        (A) LENGTH: 402 amino acids
        (B) TYPE: amino acid
        (C) STRANDEDNESS: single
        (D) TOPOLOGY: linear (xi) SEQUENCE DESCRIPTION: SEQ ID NO: 19:

| | | | | | | | | | | | | | | | |
|---|---|---|---|---|---|---|---|---|---|---|---|---|---|---|---|
| Met<br>1 | Ser | Arg | Arg | Leu<br>5 | Phe | Thr | Ser | Glu | Ser<br>10 | Val | Thr | Glu | Gly | His<br>15 | Pro |
| Asp | Lys | Ile | Ala<br>20 | Asp | Gln | Ile | Ser | Asp<br>25 | Thr | Val | Leu | Asp | Ala<br>30 | Leu | Leu |
| Arg | Glu | Asp<br>35 | Pro | Ala | Ser | Arg | Val<br>40 | Ala | Val | Glu | Thr | Leu<br>45 | Ile | Thr | Thr |
| Gly | Gln<br>50 | Val | His | Ile | Ala | Gly<br>55 | Glu | Val | Thr | Thr | Lys<br>60 | Ala | Tyr | Ala | Pro |
| Ile<br>65 | Ala | Gln | Leu | Val | Arg<br>70 | Asp | Thr | Ile | Leu | Ala<br>75 | Ile | Gly | Tyr | Asp | Ser<br>80 |
| Ser | Ala | Lys | Gly | Phe<br>85 | Asp | Gly | Ala | Ser | Cys<br>90 | Gly | Val | Ser | Val | Ser<br>95 | Ile |
| Gly | Ala | Gln | Ser<br>100 | Pro | Asp | Ile | Ala | Gln<br>105 | Gly | Val | Asp | Ser | Ala<br>110 | Tyr | Glu |
| Thr | Arg | Val<br>115 | Glu | Gly | Glu | Asp | Asp<br>120 | Glu | Leu | Asp | Gln | Gly<br>125 | Gly | Ala | Gly |
| Asp | Gln<br>130 | Gly | Leu | Met | Phe | Gly<br>135 | Tyr | Ala | Thr | Asp | Glu<br>140 | Thr | Pro | Ser | Leu |
| Met<br>145 | Pro | Leu | Pro | Ile | Glu<br>150 | Leu | Ala | His | Arg | Leu<br>155 | Ser | Arg | Arg | Leu | Thr<br>160 |
| Glu | Val | Arg | Lys | Asp<br>165 | Gly | Thr | Val | Pro | Tyr<br>170 | Leu | Arg | Pro | Asp | Gly<br>175 | Lys |
| Thr | Gln | Val | Thr<br>180 | Ile | Glu | Tyr | Gln | Gly<br>185 | Ser | Arg | Pro | Val | Arg<br>190 | Leu | Asp |
| Thr | Val | Val<br>195 | Val | Ser | Ser | Gln | His<br>200 | Ala | Ala | Asp | Ile | Asp<br>205 | Leu | Gly | Ser |
| Leu | Leu<br>210 | Thr | Pro | Asp | Ile | Arg<br>215 | Glu | His | Val | Val | Glu<br>220 | His | Val | Leu | Ala |
| Ala<br>225 | Leu | Ala | Glu | Asp | Gly<br>230 | Ile | Lys | Leu | Glu | Thr<br>235 | Asp | Asn | Tyr | Arg | Leu<br>240 |

-continued

| | | | | | | | | | | | | | | |
|---|---|---|---|---|---|---|---|---|---|---|---|---|---|---|
| Leu | Val | Asn | Pro | Thr 245 | Gly | Arg | Phe | Glu 250 | Ile | Gly | Gly | Pro | Met | Gly Asp 255 |
| Ala | Gly | Leu | Thr 260 | Gly | Arg | Lys | Ile | Ile 265 | Ile | Asp | Thr | Tyr | Gly 270 | Gly Met |
| Ala | Arg | His 275 | Gly | Gly | Gly | Ala | Phe 280 | Ser | Gly | Lys | Asp | Pro 285 | Ser | Lys Val |
| Asp | Arg 290 | Ser | Ala | Ala | Tyr | Ala 295 | Met | Arg | Trp | Val | Ala 300 | Lys | Asn | Val Val |
| Ala 305 | Ala | Gly | Leu | Ala | Ser 310 | Arg | Cys | Glu | Val | Gln 315 | Val | Ala | Tyr | Ala Ile 320 |
| Gly | Lys | Ala | Glu | Pro 325 | Val | Gly | Leu | Phe | Val 330 | Glu | Thr | Phe | Gly 335 | Thr Gly |
| Thr | Val | Ala | Gln 340 | Glu | Arg | Ile | Glu | Lys 345 | Ala | Ile | Thr | Glu 350 | Val | Phe Asp |
| Leu | Arg | Pro 355 | Ala | Ala | Ile | Ile | Arg 360 | Asp | Leu | Asp | Leu 365 | Leu | Arg | Pro Ile |
| Tyr | Ala 370 | Ala | Thr | Ala | Ala | Tyr 375 | Gly | His | Phe | Gly 380 | Arg | Glu | Leu | Pro Asp |
| Phe 385 | Thr | Trp | Glu | Arg | Thr 390 | Asp | Arg | Ala | His 395 | Arg | Leu | Lys | Ala | Ala Ala 400 |
| Gly | Leu | | | | | | | | | | | | | |

( 2 ) INFORMATION FOR SEQ ID NO: 20:

( i ) SEQUENCE CHARACTERISTICS:
      ( A ) LENGTH: 582 amino acids
      ( B ) TYPE: amino acid
      ( C ) STRANDEDNESS: single
      ( D ) TOPOLOGY: linear ( x i ) SEQUENCE DESCRIPTION: SEQ ID NO: 20:

| | | | | | | | | | | | | | | |
|---|---|---|---|---|---|---|---|---|---|---|---|---|---|---|
| | | | | | | | | | | | | | Met 1 | Leu |
| Asp | Gly | Cys 5 | Val | Pro | Trp | Pro | Glu 10 | Asp | Val | Ala | Ala | Lys 15 | Tyr | Arg Ala |
| Ala | Gly 20 | Tyr | Trp | Arg | Gly | Glu 25 | Pro | Leu | Gly | Met | Leu 30 | Leu | Gly | Arg Trp |
| Ala 35 | Glu | Gln | Tyr | Gly | Glu 40 | Arg | Glu | Ala | Leu | Val 45 | Gly | Ala | Asp | Gly Cys 50 |
| Ser | Arg | Val | Thr | Tyr 55 | Arg | Ala | Leu | Asp | Arg 60 | Trp | Cys | Asp | Arg | Leu Ala 65 |
| Ala | Gly | Phe | Ala 70 | Ala | Arg | Gly | Ile | Gly 75 | Ala | Gly | Glu | Arg | Val 80 | Leu Val |
| Gln | Leu | Pro 85 | Asn | Thr | Pro | Glu | Phe 90 | Val | Ala | Val | Cys | Phe 95 | Ala | Leu Phe |
| Arg | Leu 100 | Gly | Ala | Leu | Pro | Val 105 | Phe | Ala | Leu | Pro | Ala 110 | His | Arg | Ala Ala |
| Glu 115 | Val | Gly | His | Leu | Leu 120 | Glu | Leu | Ser | Gly | Ala 125 | Val | Ala | His | Ile Leu 130 |
| Pro | Gly | Thr | Gly | Thr 135 | Gly | Tyr | Asp | His | Val 140 | Ala | Ala | Ala | Val 145 | Glu Ala |
| Arg | Ala | Arg | Arg 150 | Ala | Arg | Pro | Val | Gln 155 | Val | Phe | Val | Ala | Gly 160 | Glu Ala |
| Pro | Ala | Val 165 | Leu | Pro | Glu | Gly | Phe 170 | Thr | Ala | Leu | Ala | Asp 175 | Val | Asp Gly |
| Asp | Pro | Val | Ala | Pro | Ala | Asp | Val | Asp | Ala | Phe | Arg | Arg | Gly | Val Phe |

```
                    180                          185                          190
Leu  Leu  Ser  Gly  Gly  Thr  Ala  Leu  Pro  Lys  Leu  Ile  Pro  Arg  Thr
195                      200                      205                      210

His  Asp  Asp  Tyr  Ala  Tyr  Gln  Cys  Arg  Val  Thr  Ala  Gly  Ile  Cys  Gly
                    215                      220                      225

Leu  Asp  Ala  Asp  Ser  Val  Tyr  Leu  Ala  Val  Leu  Pro  Ala  Glu  Phe  Asn
                    230                      235                      240

Phe  Pro  Phe  Gly  Cys  Pro  Gly  Ile  Leu  Gly  Thr  Leu  His  Ala  Gly  Gly
               245                      250                      255

Arg  Val  Val  Phe  Ala  Leu  Ser  Pro  Gln  Pro  Glu  Glu  Cys  Phe  Ala  Leu
          260                      265                      270

Ile  Glu  Arg  Glu  His  Val  Thr  Phe  Thr  Ser  Val  Ile  Pro  Thr  Ile  Val
275                      280                      285                      290

His  Leu  Trp  Leu  Ala  Ala  Ala  Gln  Gly  His  Gly  Arg  Asp  Leu  Gly
                    295                      300                      305

Ser  Leu  Gln  Leu  Leu  Gln  Val  Gly  Ser  Ala  Lys  Leu  His  Glu  Glu  Leu
                    310                      315                      320

Ala  Ala  Arg  Ile  Gly  Pro  Glu  Leu  Gly  Val  Arg  Leu  Gln  Gln  Val  Phe
               325                      330                      335

Gly  Met  Ala  Glu  Gly  Leu  Leu  Thr  Phe  Thr  Arg  Asp  Asp  Asp  Pro  Ala
     340                      345                      350

Asp  Val  Val  Leu  Arg  Thr  Gln  Gly  Arg  Pro  Val  Ser  Glu  Ala  Asp  Glu
355                      360                      365                      370

Ile  Arg  Val  Ala  Asp  Pro  Asp  Gly  Arg  Pro  Val  Pro  Arg  Gly  Glu  Thr
                    375                      380                      385

Gly  Glu  Leu  Leu  Thr  Arg  Gly  Pro  Tyr  Thr  Leu  Arg  Gly  Tyr  Tyr  Arg
               390                      395                      400

Ala  Pro  Glu  His  Asn  Ala  Arg  Ala  Phe  Thr  Glu  Asp  Gly  Phe  Tyr  Arg
          405                      410                      415

Ser  Gly  Asp  Leu  Val  Arg  Leu  Thr  Ala  Asp  Gly  Gln  Leu  Val  Val  Glu
     420                      425                      430

Gly  Arg  Ile  Lys  Asp  Val  Val  Ile  Arg  Gly  Gly  Asp  Lys  Val  Ser  Ala
435                      440                      445                      450

Thr  Glu  Val  Glu  Gly  His  Leu  Gly  Ala  His  Pro  Asp  Val  Gln  Gln  Ala
                    455                      460                      465

Ala  Val  Val  Ala  Met  Pro  Asp  Pro  Val  Trp  Gly  Glu  Lys  Val  Cys  Ala
               470                      475                      480

Tyr  Ile  Val  Pro  Ala  Pro  Gly  Arg  Pro  Ala  Pro  Met  Ala  Ala  Leu
          485                      490                      495

Arg  Arg  Leu  Leu  Arg  Ala  Arg  Gly  Leu  Ala  Asp  Tyr  Lys  Leu  Pro  Asp
     500                      505                      510

Arg  Val  Glu  Val  Val  Asp  Ala  Phe  Pro  Leu  Thr  Gly  Leu  Asn  Lys  Val
515                      520                      525                      530

Asp  Lys  Lys  Ala  Leu  Ala  Ala  Asp  Ile  Ala  Ala  Lys  Thr  Ala  Pro  Thr
                    535                      540                      545

Arg  Pro  Thr  Thr  Ala  Gly  His  Gly  Pro  Thr  Thr  Asp  Gly  Asp  Thr  Ala
               550                      555                      560

Gly  Gly  Gly  Gly  Ser  Ala  Gly  Gly  Val  Thr  Ala  Ala  Gly  Gly  Gly  Arg
               565                      570                      575

Glu  Glu  Ala  Ala
     580
```

( 2 ) INFORMATION FOR SEQ ID NO: 21:

( i ) SEQUENCE CHARACTERISTICS:
    ( A ) LENGTH: 528 amino acids
    ( B ) TYPE: amino acid
    ( C ) STRANDEDNESS: single
    ( D ) TOPOLOGY: linear ( x i ) SEQUENCE DESCRIPTION: SEQ ID NO: 21:

```
                                                                    Met  Arg  Thr  Ser
                                                                     1
Arg  Ser  His  Asp  Gln  Arg  Ala  Pro  Thr  Pro  Trp  Arg  His  Pro  Leu  His
 5                   10                       15                        20
Ser  Thr  Arg  Pro  Ala  Pro  Ala  Ala  Asp  Arg  Asp  Pro  Arg  Arg  Trp  Val
                     25                       30                        35
Ile  Leu  Gly  Val  Ile  Cys  Leu  Ala  Gln  Leu  Val  Val  Leu  Leu  Asp  Asn
                40                        45                       50
Thr  Val  Leu  Asn  Val  Ala  Ile  Pro  Val  Leu  Thr  Thr  Asp  Leu  Gly  Ala
                55                        60                       65
Ser  Thr  Ala  Asp  Ile  Gln  Trp  Met  Ile  Asn  Ala  Tyr  Ala  Leu  Val  Gln
           70                       75                       80
Ser  Gly  Leu  Leu  Leu  Thr  Ala  Gly  Ser  Leu  Ala  Asp  Arg  Tyr  Gly  Arg
 85                       90                       95                        100
Lys  Arg  Leu  Leu  Met  Leu  Gly  Leu  Val  Leu  Phe  Gly  Ala  Gly  Ser  Ala
                     105                      110                       115
Trp  Ala  Ala  Phe  Ala  Gln  Asp  Ser  Ala  Gln  Leu  Ile  Ala  Ala  Arg  Ala
                120                       125                      130
Gly  Met  Gly  Val  Gly  Gly  Ala  Leu  Leu  Ala  Thr  Thr  Thr  Leu  Ala  Val
           135                      140                      145
Ile  Met  Gln  Val  Phe  Asp  Asp  Glu  Arg  Pro  Arg  Ala  Ile  Gly  Leu
           150                      155                      160
Trp  Gly  Ala  Ala  Ser  Ser  Leu  Gly  Phe  Ala  Ala  Gly  Pro  Leu  Leu  Gly
165                       170                      175                       180
Gly  Ala  Leu  Leu  Asp  His  Phe  Trp  Trp  Gly  Ser  Ile  Phe  Leu  Ile  Asn
                     185                      190                       195
Leu  Pro  Val  Ala  Leu  Leu  Gly  Leu  Leu  Ala  Val  Ala  Arg  Leu  Val  Pro
                200                       205                      210
Glu  Thr  Lys  Asn  Pro  Glu  Gly  Arg  Arg  Pro  Asp  Leu  Leu  Gly  Ala  Val
           215                      220                      225
Leu  Ser  Thr  Leu  Gly  Met  Val  Gly  Val  Val  Tyr  Ala  Ile  Ile  Ser  Gly
     230                      235                      240
Pro  Glu  His  Gly  Trp  Thr  Ala  Pro  Gln  Val  Leu  Pro  Ala  Ala  Val
245                       250                      255                       260
Ala  Ala  Ala  Ala  Leu  Thr  Ala  Phe  Val  Arg  Trp  Glu  Leu  His  Thr  Pro
                265                       270                      275
His  Pro  Met  Leu  Asp  Met  Gly  Phe  Phe  Thr  Asp  Arg  Arg  Phe  Asn  Gly
                280                       285                      290
Pro  Ser  Pro  Ala  Glu  Cys  Ser  Ser  Phe  Gly  Met  Ala  Gly  Ser  Leu  Phe
                295                       300                      305
Leu  Leu  Thr  Gln  His  Leu  Gln  Leu  Val  Leu  Gly  Tyr  Asp  Ala  Leu  Gln
           310                      315                      320
Ala  Gly  Leu  Arg  Thr  Ala  Pro  Leu  Ala  Leu  Thr  Ile  Val  Ala  Leu  Asn
325                       330                      335                       340
Leu  Ala  Gly  Leu  Gly  Ala  Lys  Leu  Leu  Ala  Ala  Leu  Gly  Thr  Ala  Arg
                     345                      350                       355
Ser  Ile  Ala  Leu  Gly  Met  Thr  Leu  Leu  Ala  Ala  Gly  Leu  Ser  Ala  Val
                360                       365                      370
```

-continued

| | | | | | | | | | | | | | | |
|---|---|---|---|---|---|---|---|---|---|---|---|---|---|---|
| Ala | Val | Gly | Gly | Ser | Gly | Pro | Asp | Ala | Gly | Tyr | Gly | Gly | Met | Leu | Ala |
| | | 375 | | | | 380 | | | | | 385 | | | | |
| Gly | Leu | Leu | Leu | Met | Gly | Ala | Gly | Ile | Ala | Leu | Ala | Met | Pro | Ala | Met |
| | 390 | | | | | 395 | | | | | 400 | | | | |
| Ala | Thr | Ala | Val | Met | Ser | Ser | Ile | Pro | Pro | Ala | Lys | Ala | Gly | Ala | Gly |
| 405 | | | | | 410 | | | | | 415 | | | | | 420 |
| Ala | Gly | Val | Gln | Gly | Thr | Leu | Thr | Glu | Phe | Gly | Gly | Gly | Leu | Gly | Val |
| | | | | 425 | | | | | 430 | | | | | 435 | |
| Ala | Ile | Leu | Gly | Ala | Val | Leu | Gly | Ser | Arg | Phe | Ala | Ser | Gln | Leu | Pro |
| | | | 440 | | | | | 445 | | | | | 450 | | |
| Ala | Ala | Ile | Thr | Gly | Thr | Gly | Ser | Leu | Asp | Glu | Ala | Leu | Arg | Asp | Ala |
| | | | 455 | | | | | 460 | | | | | 465 | | |
| Thr | Pro | Gln | Gln | Ala | Gly | Gln | Val | His | Asp | Ala | Phe | Ala | Asp | Ala | Val |
| | 470 | | | | | 475 | | | | | 480 | | | | |
| Asn | Thr | Ser | Gln | Leu | Ile | Gly | Ala | Ala | Ala | Val | Phe | Thr | Gly | Gly | Leu |
| 485 | | | | | 490 | | | | | 495 | | | | | 500 |
| Leu | Ala | Ala | Leu | Leu | Leu | His | Arg | Ala | Asp | Arg | Lys | Ala | Ala | Pro | Gln |
| | | | | 505 | | | | | 510 | | | | | 515 | |
| Pro | Thr | Ala | Pro | Thr | Pro | Glu | Pro | Thr | Thr | Thr | Ala | | | | |
| | | | 520 | | | | | 525 | | | | | | | |

( 2 ) INFORMATION FOR SEQ ID NO: 22:

( i ) SEQUENCE CHARACTERISTICS:
        ( A ) LENGTH: 161 amino acids
        ( B ) TYPE: amino acid
        ( C ) STRANDEDNESS: single
        ( D ) TOPOLOGY: linear ( x i ) SEQUENCE DESCRIPTION: SEQ ID NO: 22:

| | | | | | | | | | | | | | | | |
|---|---|---|---|---|---|---|---|---|---|---|---|---|---|---|---|
| | | | | | | | | | Val | Thr | Gly | Ala | Asp | Asp | Pro |
| | | | | | | | | | 1 | | | | 5 | | |
| Ala | Arg | Pro | Ala | Val | Gly | Pro | Gln | Ser | Phe | Arg | Asp | Ala | Met | Ala | Gln |
| | | 10 | | | | | 15 | | | | | 20 | | | |
| Leu | Ala | Ser | Pro | Val | Thr | Val | Val | Thr | Val | Leu | Asp | Ala | Ala | Gly | Arg |
| | | 25 | | | | 30 | | | | | 35 | | | | |
| Arg | His | Gly | Phe | Thr | Ala | Gly | Ser | Val | Val | Ser | Val | Ser | Leu | Asp | Pro |
| 40 | | | | | 45 | | | | | 50 | | | | | 55 |
| Pro | Leu | Val | Met | Val | Gly | Ile | Ala | Leu | Thr | Ser | Ser | Cys | His | Thr | Ala |
| | | | | 60 | | | | | 65 | | | | | 70 | |
| Met | Ala | Ala | Ala | Ala | Glu | Phe | Cys | Val | Ser | Ile | Leu | Gly | Glu | Asp | Gln |
| | | | 75 | | | | | 80 | | | | | 85 | | |
| Arg | Ala | Val | Ala | Lys | Arg | Cys | Ala | Thr | His | Gly | Ala | Asp | Arg | Phe | Ala |
| | | 90 | | | | | 95 | | | | | 100 | | | |
| Gly | Gly | Glu | Phe | Ala | Ala | Trp | Asp | Gly | Thr | Gly | Val | Pro | Tyr | Leu | Pro |
| | 105 | | | | | 110 | | | | | 115 | | | | |
| Asp | Ala | Lys | Val | Val | Leu | Arg | Cys | Arg | Thr | Thr | Asp | Val | Val | Arg | Ala |
| 120 | | | | | 125 | | | | | 130 | | | | | 135 |
| Gly | Asp | His | Asp | Leu | Val | Leu | Gly | Thr | Pro | Val | Glu | Ile | Arg | Thr | Gly |
| | | | | 140 | | | | | 145 | | | | | 150 | |
| Asp | Pro | Ala | Lys | Pro | Pro | Leu | Leu | Trp | Tyr | | | | | | |
| | | | 155 | | | | | 160 | | | | | | | |

( 2 ) INFORMATION FOR SEQ ID NO: 23:

( i ) SEQUENCE CHARACTERISTICS:
        ( A ) LENGTH: 213 amino acids
        ( B ) TYPE: amino acid (C) STRANDEDNESS: single
(D) TOPOLOGY: linear (xi) SEQUENCE DESCRIPTION: SEQ ID NO: 23:

| Ala | Thr | Ala | Arg | Leu | Ile | Gly | Pro | Leu | Pro | Arg | Arg | Leu | Gly | Leu | Gln |
|---|---|---|---|---|---|---|---|---|---|---|---|---|---|---|---|
| 1 | | | | 5 | | | | | 10 | | | | | 15 | |

| Val | His | Gln | Val | Met | Thr | Gly | Ala | Phe | Ala | Gln | Ala | Leu | Ala | Arg | Trp |
|---|---|---|---|---|---|---|---|---|---|---|---|---|---|---|---|
| | | | 20 | | | | | 25 | | | | | 30 | | |

| Arg | Gly | Ser | Arg | Ala | Val | Thr | Phe | Asp | Val | Glu | Thr | His | Gly | Arg | His |
|---|---|---|---|---|---|---|---|---|---|---|---|---|---|---|---|
| | | 35 | | | | | 40 | | | | | 45 | | | |

| Gly | Arg | Asp | Glu | Leu | Phe | Arg | Thr | Val | Gly | Trp | Phe | Thr | Ser | Ile | His |
|---|---|---|---|---|---|---|---|---|---|---|---|---|---|---|---|
| | 50 | | | | | 55 | | | | | 60 | | | | |

| Pro | Val | Val | Leu | Gly | Ala | Asp | Arg | Ser | Val | His | Pro | Glu | Gln | Tyr | Leu |
|---|---|---|---|---|---|---|---|---|---|---|---|---|---|---|---|
| 65 | | | | | 70 | | | | | 75 | | | | | 80 |

| Ala | Gln | Ile | Gly | Ala | Ala | Leu | Thr | Ala | Ala | Pro | Asp | Gly | Gly | Val | Gly |
|---|---|---|---|---|---|---|---|---|---|---|---|---|---|---|---|
| | | | | 85 | | | | | 90 | | | | | 95 | |

| Phe | Gly | Ala | Cys | Arg | Glu | Phe | Ser | Pro | Asp | Ala | Gly | Leu | Arg | Thr | Leu |
|---|---|---|---|---|---|---|---|---|---|---|---|---|---|---|---|
| | | | 100 | | | | | 105 | | | | | 110 | | |

| Leu | Arg | Asp | Leu | Pro | Pro | Ala | Leu | Val | Cys | Phe | Asn | Tyr | Tyr | Gly | Gln |
|---|---|---|---|---|---|---|---|---|---|---|---|---|---|---|---|
| | | 115 | | | | | 120 | | | | | 125 | | | |

| Ala | Asp | Gln | Leu | Ser | Pro | Asn | Gly | Gly | Phe | Arg | Met | Ser | Gly | Arg | Pro |
|---|---|---|---|---|---|---|---|---|---|---|---|---|---|---|---|
| | 130 | | | | | 135 | | | | | 140 | | | | |

| Ile | Pro | Arg | Glu | His | Ser | Ala | Arg | Cys | Glu | Arg | Val | Tyr | Gly | Ile | Glu |
|---|---|---|---|---|---|---|---|---|---|---|---|---|---|---|---|
| 145 | | | | | 150 | | | | | 155 | | | | | 160 |

| Val | Tyr | Gly | Ile | Val | His | Gly | Gly | Arg | Leu | Arg | Met | Gly | Leu | Thr | Trp |
|---|---|---|---|---|---|---|---|---|---|---|---|---|---|---|---|
| | | | | 165 | | | | | 170 | | | | | 175 | |

| Val | Pro | Ser | Pro | Ala | Asp | Gly | Val | Asp | Glu | Ala | Gly | Val | Asp | Ala | Leu |
|---|---|---|---|---|---|---|---|---|---|---|---|---|---|---|---|
| | | | 180 | | | | | 185 | | | | | 190 | | |

| Val | Glu | Gln | Met | Ser | Trp | Val | Leu | Ala | Thr | Leu | Ala | Gly | Ala | Asp | Pro |
|---|---|---|---|---|---|---|---|---|---|---|---|---|---|---|---|
| | | 195 | | | | | 200 | | | | | 205 | | | |

| His | Ala | Val | Thr | Pro |
|---|---|---|---|---|
| | 210 | | | |

(2) INFORMATION FOR SEQ ID NO: 24:

(i) SEQUENCE CHARACTERISTICS:
(A) LENGTH: 195 amino acids
(B) TYPE: amino acid
(C) STRANDEDNESS: single
(D) TOPOLOGY: linear (xi) SEQUENCE DESCRIPTION: SEQ ID NO: 24:

| Val | Arg | Thr | Val | Arg | Thr | Leu | Leu | Ile | Asp | Asn | Tyr | Asp | Ser | Phe | Thr |
|---|---|---|---|---|---|---|---|---|---|---|---|---|---|---|---|
| 1 | | | | 5 | | | | | 10 | | | | | 15 | |

| Tyr | Asn | Leu | Phe | Gln | Met | Leu | Ala | Glu | Val | Asn | Gly | Ala | Ala | Pro | Leu |
|---|---|---|---|---|---|---|---|---|---|---|---|---|---|---|---|
| | | | 20 | | | | | 25 | | | | | 30 | | |

| Val | Val | Arg | Asn | Asp | Asp | Thr | Arg | Thr | Trp | Gln | Ala | Leu | Ala | Pro | Gly |
|---|---|---|---|---|---|---|---|---|---|---|---|---|---|---|---|
| | | 35 | | | | | 40 | | | | | 45 | | | |

| Asp | Phe | Asp | Asn | Val | Val | Val | Ser | Pro | Gly | Pro | Gly | His | Pro | Ala | Thr |
|---|---|---|---|---|---|---|---|---|---|---|---|---|---|---|---|
| | 50 | | | | | 55 | | | | | 60 | | | | |

| Asp | Thr | Asp | Leu | Gly | Leu | Ser | Arg | Arg | Val | Ile | Thr | Glu | Trp | Asp | Leu |
|---|---|---|---|---|---|---|---|---|---|---|---|---|---|---|---|
| 65 | | | | | 70 | | | | | 75 | | | | | 80 |

| Pro | Leu | Leu | Gly | Val | Cys | Leu | Gly | His | Gln | Ala | Leu | Cys | Leu | Leu | Ala |
|---|---|---|---|---|---|---|---|---|---|---|---|---|---|---|---|
| | | | | 85 | | | | | 90 | | | | | 95 | |

| Gly | Ala | Ala | Val | Val | His | Ala | Pro | Glu | Pro | Phe | His | Gly | Arg | Thr | Ser |
|---|---|---|---|---|---|---|---|---|---|---|---|---|---|---|---|
| | | | 100 | | | | | 105 | | | | | 110 | | |

| Asp | Ile | Arg | His | Asp | Gly | Gln | Gly | Leu | Phe | Ala | Asn | Ile | Pro | Ser | Pro |

|   |   |   | 115 |   |   |   |   | 120 |   |   |   |   | 125 |   |   |
|---|---|---|---|---|---|---|---|---|---|---|---|---|---|---|---|
| Leu | Thr 130 | Val | Val | Arg | Tyr | His 135 | Ser | Leu | Thr | Val | Arg 140 | Gln | Leu | Pro | Ala |
| Asp 145 | Leu | Arg | Ala | Thr 150 | Ala | His | Thr | Ala | Asp 155 | Gly | Gln | Leu | Met | Ala | Val 160 |
| Ala | His | Arg | His | Leu 165 | Pro | Arg | Phe | Gly | Val 170 | Gln | Phe | His | Pro | Glu 175 | Ser |
| Ile | Ser | Ser | Glu 180 | His | Gly | His | Arg | Met 185 | Leu | Ala | Asn | Phe | Arg 190 | Asp | Leu |
| Ser | Leu | Arg 195 |   |   |   |   |   |   |   |   |   |   |   |   |   |

( 2 ) INFORMATION FOR SEQ ID NO: 25:

( i ) SEQUENCE CHARACTERISTICS:
        ( A ) LENGTH: 292 amino acids
        ( B ) TYPE: amino acid
        ( C ) STRANDEDNESS: single
        ( D ) TOPOLOGY: linear ( x i ) SEQUENCE DESCRIPTION: SEQ ID NO: 25:

|   |   |   |   |   |   |   |   | Val 1 | Thr | Ala | Ala | Ala 5 | Pro | Thr | Leu | Ala |
|---|---|---|---|---|---|---|---|---|---|---|---|---|---|---|---|---|
| Gln 10 | Ala | Leu | Asp | Glu | Ala 15 | Thr | Gly | Gln | Leu | Thr 20 | Gly | Ala | Gly | Ile | Thr 25 |
| Ala | Asp | Ala | Ala | Arg 30 | Ala | Asp | Thr | Arg | Leu 35 | Leu | Ala | Ala | His | Ala 40 | Cys |
| Gln | Val | Ala | Pro 45 | Gly | Asp | Leu | Asp | Thr 50 | Cys | Leu | Ala | Gly | Pro 55 | Val | Pro |
| Pro | Arg | Phe 60 | Trp | His | Tyr | Val | Arg 65 | Arg | Leu | Thr | Arg 70 | Glu | Pro | Ala |
| Glu | Arg 75 | Ile | Val | Gly | His | Ala 80 | Tyr | Phe | Met | Gly | His 85 | Arg | Phe | Asp | Leu |
| Ala 90 | Pro | Gly | Val | Phe | Val 95 | Pro | Lys | Pro | Glu | Thr 100 | Glu | Glu | Ile | Thr | Arg 105 |
| Asp | Ala | Ile | Ala | Arg 110 | Leu | Glu | Ala | Leu | Val 115 | Arg | Arg | Gly | Thr | Thr 120 | Ala |
| Pro | Leu | Val | Val 125 | Asp | Leu | Cys | Ala | Gly 130 | Pro | Gly | Thr | Met | Ala 135 | Val | Thr |
| Leu | Ala | Arg 140 | His | Val | Pro | Ala | Ala 145 | Arg | Val | Leu | Gly | Ile 150 | Glu | Leu | Ser |
| Gln | Ala 155 | Ala | Ala | Arg | Ala | Ala 160 | Arg | Arg | Asn | Ala | Arg 165 | Gly | Thr | Gly | Ala |
| Arg 170 | Ile | Val | Gln | Gly | Asp 175 | Ala | Arg | Asp | Ala | Phe 180 | Pro | Glu | Leu | Ser | Gly 185 |
| Thr | Val | Asp | Leu | Val 190 | Val | Thr | Asn | Pro | Pro 195 | Tyr | Ile | Pro | Ile | Gly 200 | Leu |
| Arg | Thr | Ser | Ala 205 | Pro | Glu | Val | Leu | Glu 210 | His | Asp | Pro | Pro | Leu 215 | Ala | Leu |
| Trp | Ala | Gly 220 | Glu | Glu | Gly | Leu | Gly 225 | Met | Ile | Arg | Ala | Met 230 | Glu | Arg | Thr |
| Ala | Ala 235 | Arg | Leu | Leu | Ala | Pro 240 | Gly | Gly | Val | Leu | Leu 245 | Leu | Glu | His | Gly |
| Ser 250 | Tyr | Gln | Leu | Ala | Ser 255 | Val | Pro | Ala | Leu | Phe 260 | Arg | Ala | Thr | Gly | Arg 265 |
| Trp | Ser | His | Ala | Ser | Ser | Arg | Pro | Thr | Cys | Asn | Asp | Gly | Cys | Leu | Thr |

```
                              270                          275                          280
Ala  Val  Arg  Asn  His  Thr  Cys  Ala  Pro  Pro  Ala
                    285                      290
```

(2) INFORMATION FOR SEQ ID NO: 26:

(i) SEQUENCE CHARACTERISTICS:
    (A) LENGTH: 75 amino acids
    (B) TYPE: amino acid
    (C) STRANDEDNESS: single
    (D) TOPOLOGY: linear (xi) SEQUENCE DESCRIPTION: SEQ ID NO: 26:

```
     Ile  Phe  Glu  His  Lys  Thr  Val  Ala  Gln  Leu  Ala  Pro  Val  Ala  Glu
      1              5                        10                            15

Thr  Leu  Ala  Asp  Thr  Arg  Glu  Glu  Pro  Ala  Ala  Val  Ala  Ala  Thr
                    20                   25                        30

Gly  Asp  Val  Pro  Leu  Thr  Pro  Ile  Met  His  Trp  Leu  Arg  Glu  Arg  Gly
                    35                   40                        45

Gly  Pro  Val  Asp  Ala  Phe  Ser  Gln  Thr  Met  Ala  Val  Thr  Val  Pro  Ala
               50                   55                        60

Gly  Leu  Asp  Arg  Glu  Arg  Leu  Val  Ala  Ala  Leu  Gln
          65                   70                        75
```

(2) INFORMATION FOR SEQ ID NO: 27:

(i) SEQUENCE CHARACTERISTICS:
    (A) LENGTH: 82 amino acids
    (B) TYPE: amino acid
    (C) STRANDEDNESS: single
    (D) TOPOLOGY: linear (xi) SEQUENCE DESCRIPTION: SEQ ID NO: 27:

```
Leu  Glu  Tyr  Asp  Thr  Ala  Leu  Tyr  Glu  Arg  Ala  Thr  Ala  Glu  Ala  Leu
 1              5                        10                            15

Thr  Gly  Arg  Leu  Leu  Arg  Leu  Leu  Asp  Ala  Val  Val  Thr  Asp  Pro  Gln
               20                        25                        30

Ala  Pro  Val  Gly  Ser  His  Asp  Leu  Leu  Glu  Glu  Ala  Glu  His  Ala  Arg
               35                        40                        45

Leu  Ala  Ala  Phe  Asn  Asp  Thr  Ala  Arg  Pro  Val  Pro  Arg  Ala  Gly  Leu
     50                        55                        60

Ala  Glu  Leu  Phe  Thr  Ala  Gln  Ala  Arg  Arg  Thr  Ala  Asp  Ala  Val  Ala
 65                       70                        75                        80

Val  Val
```

(2) INFORMATION FOR SEQ ID NO: 28:

(i) SEQUENCE CHARACTERISTICS:
    (A) LENGTH: 63 amino acids
    (B) TYPE: amino acid
    (C) STRANDEDNESS: single
    (D) TOPOLOGY: linear (xi) SEQUENCE DESCRIPTION: SEQ ID NO: 28:

```
     Met  Pro  Pro  Val  Thr  Pro  Tyr  Arg  Ala  Tyr  Leu  Ala  His  Leu  Ala
      1              5                        10                            15

Gly  Arg  Asp  Asp  Asp  Ala  Ala  Arg  Ala  Ala  Trp  Arg  Thr  Ala  Leu  Ala
                    20                   25                        30

Asp  Leu  Glu  Glu  Pro  Ser  Leu  Val  Ala  Gly  Ala  Gly  Ala  Gly  Arg  Gly
                    35                   40                        45

Ala  Ala  Asp  Gly  Ser  Ala  Leu  Pro  Gly  Gln  Ile  Pro  Gly  Tyr  Arg  Ala
```

50                                  55                                  60

( 2 ) INFORMATION FOR SEQ ID NO: 29:

( i ) SEQUENCE CHARACTERISTICS:
        ( A ) LENGTH: 158 amino acids
        ( B ) TYPE: amino acid
        ( C ) STRANDEDNESS: single
        ( D ) TOPOLOGY: linear ( x i ) SEQUENCE DESCRIPTION: SEQ ID NO: 29:

```
Leu Gln Val Glu Gly Arg Pro Ala His Leu Glu Leu Pro Cys Asp His
 1               5                  10                 15

Pro Arg Pro Ala Val Ala Thr His Arg Gly Ala Thr Val Pro Phe His
            20                  25                 30

Ile Asp Ala Gly Leu His Glu Lys Leu Thr Ala Leu Ser Lys Ala Cys
        35                  40                 45

Asp Ser Ser Leu Phe Met Val Leu Gln Ala Ala Val Ala Ala Leu Leu
    50                  55                 60

Thr Arg His Gly Ala Gly Thr Asp Ile Pro Val Gly Ser Pro Val Ala
65                  70                 75                      80

Gly Arg Thr Asp Asp Ala Leu Asp Asp Leu Val Gly Phe Phe Val Asn
                85                 90                  95

Thr Leu Val Leu Arg Thr Asp Thr Ser Gly Asp Pro Thr Phe Arg Glu
            100                 105                110

Leu Val Ala Arg Val Arg Gln Phe Asp Leu Ala Ala Tyr Thr His Gln
        115                 120                125

Asp Met Pro Phe Glu Lys Leu Val Glu Val Asn Pro Glu Arg Ser
    130                 135                 140

Leu Ala Arg Asn Pro Leu Phe Gln Val Val Leu Ala Leu Gln
145                 150                 155
```

( 2 ) INFORMATION FOR SEQ ID NO: 30:

( i ) SEQUENCE CHARACTERISTICS:
        ( A ) LENGTH: 161 amino acids
        ( B ) TYPE: amino acid
        ( C ) STRANDEDNESS: single
        ( D ) TOPOLOGY: linear ( x i ) SEQUENCE DESCRIPTION: SEQ ID NO: 30:

```
    Met Pro Arg Ser Leu Asp Leu Tyr Val Ala Leu Leu Ala Val Leu
     1               5                  10                 15

Lys Thr Gly Ala Ala Tyr Leu Pro Val Asp Ile Ser Tyr Pro Ala Glu
                20                  25                 30

Arg Ile Ala Phe Met Ile Glu Asp Ala Arg Pro Val Thr Val Leu Asp
            35                  40                 45

Arg Leu Pro Asp Asp Leu Gly Ala Tyr Arg Asp Thr Asp Leu Thr Asp
        50                  55                 60

Ala Asp Arg Thr Ala Pro Leu Arg Pro Glu His Pro Ala Tyr Val Ile
65                  70                 75

His Thr Ser Gly Ser Thr Gly Thr Pro Lys Ala Val Val Met Pro His
80                  85                 90                  95

Ala Gly Leu Val Asn Leu Leu Thr Trp His Ala Arg Arg Phe Pro Gly
                100                 105                110

Gly Thr Gly Val Arg Thr Ala Gln Phe Thr Ala Ile Gly Phe Asp Phe
            115                 120                125

Ser Val Gln Glu Ile Leu Ser Pro Leu Val Met Gly Lys Thr Leu Ala
        130                 135                140
```

Val Pro Ser Glu Glu Val Arg His Ser Ala Glu Leu Leu Ala Gly Trp
    145                 150                 155

Leu Glu
160

( 2 ) INFORMATION FOR SEQ ID NO: 31:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( x i ) SEQUENCE DESCRIPTION: SEQ ID NO: 31:

Leu Gln Ala Glu Gly Ala Glu Val Ser Leu Leu Ala Val Leu Asp Gly
 1               5                  10                  15

Tyr Pro Asp Ala Tyr Asp Gly Thr Glu His Glu Val Gly Glu Glu Gln
            20                  25                  30

Val Leu Ala Ile Leu Leu Asn Ala Ala Gly Val Asp Arg Ala Gln Ala
            35                  40                  45

Phe Gly Asp Ala Pro Leu Gln Arg Ala Ala Val Leu Glu Lys Leu Arg
        50                  55                  60

Asp Ser Gly Ser Ala Leu Gly Asn Leu Asp Asp Ala Val Gly Arg
 65                 70                  75                  80

Met Val Thr Val Phe Leu Asn Asn Thr Arg Leu Ile Gln Asn Phe Arg
                85                  90                  95

Pro ( 2 ) INFORMATION FOR SEQ ID NO: 32:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 32:

ATC GAY TTY CCN TAY CTS CCS GG                                                                    23

( 2 ) INFORMATION FOR SEQ ID NO: 33:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 33:

TTC GAC GAY GAY GCN TTC GTS CAY GAC                                               27

( 2 ) INFORMATION FOR SEQ ID NO: 34:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 34:

GTS CCS TGG CCS GAG GAC GTS GCS GCS AAG TAC                             33

( 2 ) INFORMATION FOR SEQ ID NO: 35:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 35:

```
GAG  GTS  GAG  GGS  CAC  CTS  GGS  GCS  CAC  CCS  GAC  GTS  CAG  CAG  GC           44
```

( 2 ) INFORMATION FOR SEQ ID NO: 36:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO: 36:

```
Val  Pro  Ala  Ala  Phe  Val  Pro  Leu  Asp  Ala  Leu  Pro  Leu  Thr  Gly  Asn
 1                  5                  10                 15
Gly  Val  Leu  Asp
             20
```

( 2 ) INFORMATION FOR SEQ ID NO: 37:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 37:

```
GCS  GCS  TTC  AAC  GAC  ACS  GCS  CGS  CC                                         26
```

( 2 ) INFORMATION FOR SEQ ID NO: 38:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

```
TTC  GTS  CCS  CTS  GAC  GCS  CTS  CCS  CT                                         26
```

( 2 ) INFORMATION FOR SEQ ID NO: 39:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 39:

```
GTS  ACS  CCS  TAC  CGS  GCS  TAC                                                  21
```

( 2 ) INFORMATION FOR SEQ ID NO: 40:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 40:

```
ACS  CGB  CTS  ATC  CAG  AAC  TTC  CGB  CC                                         26
```

(2) INFORMATION FOR SEQ ID NO: 41:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO: 41:

TTC CGS GAC GCS ATG GCS CAG CTS GC    26

(2) INFORMATION FOR SEQ ID NO: 42:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 42:

TTC GCS GGS GGS GAG TTC GCS GCS TGG GAC GGC ACC GG    38

(2) INFORMATION FOR SEQ ID NO: 43:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO: 43:

GAC CCS GCS AAG CCS CCS CTS CTS TGG TAC CG    32

We claim:

1. A purified nucleotide sequence selected from the group consisting of the genes snaA, snaB, snaC, snaD, papA, papM, samS, snbA, snbC, snbD, snbE, and snbR of *Streptomyces pristinaespiralis*, and a nucleotide sequence which hybridizes to one of said genes in the presence of formamide at 42° C. with washes at 50° and 60° C., wherein said purified nucleotide sequence encodes a polypeptide selected from the group of polypeptides consisting of SnaA, SnaB, SnaC, SnaD, PapA, PapM, SamS, SnbA, SnbC, SnbD, SnbE, and SnbR.

2. A recombinant DNA sequence comprising a gene selected from the group consisting of the genes snaA, snaB, snaC, snaD, papA, papM, samS, snbA, snbC, snbD, snbE, and snbR of *S. pristinaespiralis*, and a nucleotide sequence which hybridizes to one of said genes in the presence of formamide at 42° C. with washes at 50° and 60° C., wherein said recombinant DNA encodes a polypeptide selected from the group of polypeptides consisting of SnaA, SnaB, SnaC, SnaD, PapA, PapM, SamS, SnbA, SnbC, SnbD, SnbE, and SnbR.

3. A recombinant DNA sequence selected from the group consisting of cosmids pIBV1, pIBV2, pIBV3 and pIBV4 as shown in FIGS. 4 to 7, and nucleotide sequence which hybridizes to one of said cosmids in the presence of formamide at 42° C. with washes at 50° and 60° C., wherein said recombinant DNA encodes a polypeptide selected from the group of polypeptides consisting of SnaA, SnaB, SnaC, SnaD, PapA, PapM, SamS, SnbA, SnbC, SnbD, SnbE, and SnbR.

4. A purified nucleotide sequence selected from the group consisting of:

(a) the snaA (SEQ ID NO: 2), snaB (SEQ ID NO: 3), snaC (SEQ ID NO: 7), snaD (SEQ ID NO: 8), papA (SEQ ID NO: 9), papM (SEQ ID NO: 10), samS (SEQ ID NO: 4), snbA (SEQ ID NO: 5), snbC (SEQ ID NOS: 11 and 12), snbD (SEQ ID NOS: 13 and 14), snbE (SEQ ID NOS: 15 and 16), and snbR (SEQ ID NO: 6) genes, (b) the sequences which hybridize in the presence of formamide at 42° C. with washes at 50° and 60° C. with the genes in (a) and wherein said sequences encode a polypeptide selected from the group of polypeptides consisting of SnaA, SnaB, SnaC, SnaD, PapA, PapM, SamS, SnbA, SnbC, SnbD, SnbE, and SnbR, and (c) sequences which encode the polypeptides encoded by (a) and (b), and which differ from the sequences (a) and (b) owing to the degeneracy of the genetic code.

5. The nucleotide sequence according to claim 4, wherein said nucleotide sequence is selected from the snaA, snaB, snaC, snaD, papA, papM, samS, snbA, snbC, snbD, snbE, and snbR genes.

6. A recombinant cell containing a nucleotide sequence, a recombinant DNA, or an expression vector according to any one of claims 1, 2, 3, or 4.

7. An autonomously replicating or integrative expression vector, wherein said vector comprises a nucleotide sequence or a recombinant DNA according to any one of claims 1, 2, 3, or 4.

8. A vector selected from the group consisting of cosmid pIBV1 (FIG. 4), cosmid pIBV2 (FIG. 5), cosmid pIBV3 (FIG. 6), cosmid pIBV4 (FIG. 7), plasmid pVRC402 (FIG. 15(A)), plasmid pVRC501 (FIG. 8(B)), plasmid pXL2045 (FIG. 9), and plasmids pVRC1105, pVRC1106, pVRC1104, pVRC900, pVRC1000, pVRC509, pVRC903, pVRC409, pVRC505, pVRC701, pVRC702, pVRC508, pVRC404, pVRC507, and pVRC706, shown in FIGS. 17 to 31, respectively.

9. A method for producing a polypeptide selected from the group of polypeptides consisting of SnaA, SnaB, SnaC, SnaD, PapA, PapM, SamS, SnbA, SnbC, SnbD, SnbE, and SnbR, comprising culturing a recombinant cell according to claim 6 and recovering the polypeptide.

10. A purified polypeptide resulting from the expression of a sequence according to any one of claims 1, 2, 3, or 4–5.

11. A purified polypeptide comprising a polypeptide selected from the group consisting of the polypeptides SnaA (encoded by SEQ ID no. 2), SnaB (encoded by SEQ ID NO:3), SnaC (encoded by SEQ ID NO:7), SnaD (encoded by SEQ ID NO:8), PapA (encoded by SEQ ID NO:9), PapM (encoded by SEQ ID NO:10), SamS (encoded by SEQ ID NO:4), SnbA (encoded by SEQ ID NO:5), SnbC (encoded by SEQ ID nos. 11 and 12), SnbD (encoded by SEQ ID nos. 13 and 14), SnbE (encoded by SEQ ID nos. 15 and 16), and SnbR (encoded by SEQ ID NO:6).

* * * * *